US007713526B2

(12) United States Patent
Rhee et al.

(10) Patent No.: US 7,713,526 B2

(45) Date of Patent: May 11, 2010

(54) WNT AND FRIZZLED RECEPTORS AS TARGETS FOR IMMUNOTHERAPY IN HEAD AND NECK SQUAMOUS CELL CARCINOMAS

(75) Inventors: Chae-Seo Rhee, Seoul (KR); Malini Sen, San Diego, CA (US); Christina Wu, San Diego, CA (US); Lorenzo M. Leoni, San Diego, CA (US); Maripat Corr, San Diego, CA (US); Dennis A. Carson, Del Mar, CA (US)

(73) Assignee: The Regents of the University of California, Oakland, CA (US)

(*) Notice: Subject to any disclaimer, the term of this patent is extended or adjusted under 35 U.S.C. 154(b) by 1644 days.

(21) Appl. No.: 10/285,976

(22) Filed: Nov. 1, 2002

(65) Prior Publication Data

US 2003/0165500 A1 Sep. 4, 2003

Related U.S. Application Data

(63) Continuation-in-part of application No. PCT/US02/13802, filed on May 1, 2002.

(60) Provisional application No. 60/287,995, filed on May 1, 2001.

(51) Int. Cl.
*A61K 39/395* (2006.01)

(52) U.S. Cl. ............... 424/143.1; 424/155.1; 424/156.1

(58) Field of Classification Search ....................... None
See application file for complete search history.

(56) References Cited

U.S. PATENT DOCUMENTS

| | | | | |
|---|---|---|---|---|
| 5,824,789 | A | 10/1998 | Van Den Berg | |
| 5,851,984 | A | 12/1998 | Matthews et al. | |
| 6,043,053 | A | 3/2000 | Barnes et al. | |
| 6,100,060 | A | 8/2000 | Barnes et al. | |
| 6,133,232 | A | 10/2000 | De Robertis et al. | |
| 6,165,751 | A | 12/2000 | Barnes | |
| 6,171,781 | B1 * | 1/2001 | Crabtree et al. | 435/4 |
| 6,297,030 | B1 | 10/2001 | Barnes et al. | |
| 6,307,019 | B1 | 10/2001 | Constantini et al. | |
| 6,387,657 | B1 | 5/2002 | Botstein et al. | |
| 6,403,325 | B1 | 6/2002 | Kosik et al. | |
| 6,844,422 | B1 * | 1/2005 | Niehrs et al. | 530/350 |
| 6,924,367 | B2 * | 8/2005 | Luyten et al. | 536/23.5 |
| 2002/0187502 | A1 | 12/2002 | Waterman et al. | |
| 2003/0203416 | A1 | 10/2003 | Staudt et al. | |

FOREIGN PATENT DOCUMENTS

| | | |
|---|---|---|
| EP | 1 001 023 A | 5/2000 |
| JP | 2004-051557 A | 2/2004 |
| WO | WO 97/39357 | 10/1997 |
| WO | WO 98/16641 | 4/1998 |
| WO | WO 98/23730 | 6/1998 |
| WO | WO 99/02679 | 1/1999 |
| WO | WO 99/26960 | 6/1999 |
| WO | WO 99/38966 | 8/1999 |
| WO | WO 00/12117 | 3/2000 |
| WO | WO 00/29575 | 5/2000 |
| WO | WO 00/30162 | 5/2000 |
| WO | WO 00/38709 | 7/2000 |
| WO | WO 01/12808 | 2/2001 |
| WO | WO 01/19855 | 3/2001 |
| WO | WO 01/32708 | 5/2001 |
| WO | WO 01/38353 | 5/2001 |
| WO | WO 01/74856 | 10/2001 |
| WO | WO 01/75067 A2 | 10/2001 |
| WO | WO 01/83543 A1 | 11/2001 |
| WO | WO 02/16620 A2 | 2/2002 |
| WO | WO 02/24733 A2 | 3/2002 |
| WO | WO 02/31148 | 4/2002 |
| WO | WO 02/31210 | 4/2002 |
| WO | WO 02/44378 | 6/2002 |
| WO | WO 02/059377 A2 | 8/2002 |
| WO | WO 02/088081 A2 | 11/2002 |

OTHER PUBLICATIONS

Bergstein and Brown, 'Wnt Genes and Breast Cancer', In: Breast Cancer: Molecular genetics, Pathogenesis and Therapeutics, A. Bowcock Ed., Humana Press, 1999, pp. 181-198.*

Morrison et al, 'Complement activation and Fc receptor binding by IgG', In: Protein Engineering of antibody Molecules for Prophylactic and therapeutic applications in Man, 1993, Mike Clark, Ed., pp. 101-113.*

Schlom, 'Monoclonal Antibodies: They're More and Less Than You Think', In: Molecular Foundations of Oncology, 1991, Samuel Broder, Ed, pp. 95-134.*

Abstract of Gao et al, Aizheng, Oct. 2002, vol. 21, pp. 1112-1115.*

Green et al, Immunological Reviews, 2003, vol. 193, pp. 70-81.*

Abstract of Euhus et al, Surgery, Gynecology and Obstetrics, 1992, vol. 175, pp. 89-96.*

Miyoshi et al, Oncogene, 2002, vol. 21, pp. 5548-5556.*

Saitoh et at (International Journal of Oncology, 2002, vol. 20, pp. 117-120).*

Michaelson et al (Oncogene, 2001, vol. 20, pp. 5093-5099).*

(Continued)

*Primary Examiner*—Karen A Canella
(74) *Attorney, Agent, or Firm*—McDermott Will & Emery LLP

(57) ABSTRACT

The diverse receptor-ligand pairs of the Wnt and frizzled (Fzd) families play important roles during embryonic development, and thus may be overexpressed in cancers that arise from immature cells. The mRNA levels and expression levels of 5 Wnt (Wnt-1, 5a, 7a, 10b, 13) and 2 Fzd (Fzd-2, 5) genes in 10 head and neck squamous carcinoma cell lines (HNSCC) were investigated. In addition, anti-Wnt-1 antibodies were used to study the Wnt/Fzd signalling pathway. These results indicate that HNSCC cell lines overexpress one or more Wnt and Fzd genes, and the proliferation and survival of a subset of HNSCC may depend on the Wnt/Fzd pathway. Therefore, the Wnt and Fzd receptors may be useful targets for immunotherapy of this common cancer.

19 Claims, 33 Drawing Sheets

OTHER PUBLICATIONS

Bafico et al (Journal of Biological Chemistry, 1999, vol. 274, pp. 16180-16187).*

Brown, "Wnt signaling in breast cancer: have we come full circle?", *Breast Cancer Research*, 2001, pp. 351-355, vol. 3(6).

Kirikoshi et al., "Molecular Cloning and Genomic Structure of Human *Frizzled*-3 at chromosome 8p21", *Biochemical and Biophysical Research Communications*, 2000, pp. 8-14, vol. 271.

Sakanaka et al., "Bridging of β-catenin and glycogen synthase kinase-3β a by Axin and inhibition of β-catenin-mediated transcription", *PNAS*, 1998, pp. 3020-3023, vol. 95.

Sampson et al., "Negative regulation of the Wnt-β catenin pathway by the transcriptional repressor HBP1", *The EMBO Journal*, 2001, pp. 4500-4511, vol. 20(16).

Tanner et al., "BAALC, the human member of a novel mammalian neuroectoderm gene lineage, is implicated in hematopoiesis and acute leukemia", *PNAS*, 2001, p. 13901-13905, vol. 98(24).

Leethanakul et al., "Distinct pattern of expression of differentiation and growth-related genes in squamous cell carcinomas of the head and neck revealed by the use of laser capture microdissection and cDNA arrays", *Oncogene* 19:3220-3224 (2000).

Wong et al., "Expression of frizzled-related protein and Wnt-signalling molecules in invasive human breast tumours" *J. Pathol.* 196:145-153 (2002).

Lejeune et al., "*Wnt5a* Cloning, Expression, and Up-Regulation in Human Primary Brest Cancers" *Clin. Canc. Res* 1:215-222(1995).

Iozzo et al., "Aberrant Expression of the Growth Factor *Wnt-5A* in Human Malignancy" *Canc. Res.* 55:3495-3499 (1995).

Kirikoshi et al., "*WNT10A* and *WNT6*, Clustered in Human Chromosome 2q35 Region with Head-to-Tail Manner, Are Strongly Coexpressed in SW480 Cells" *BBRC* 283:798-805 (2001).

Bui et al., " A novel human *Wnt* gene, *WNT10B*, maps to 12q13 and is expressed in human breast carcinomas" *Oncogene* 14:1249-1253 (1997).

Katoh et al., Cloning, expression and chromosomal localization of *Wnt-13*, a novel member of the *Wnt* gene family *Oncogene* 13:873-876(1996).

Kirkoshi et al., "Expression of *WNT14* and *WNT14B* mRNAs in human cancer, up-regulation of *WNT14* by IFN and up-regulation of *WNT14B* by β-estradiol" *J. Oncol.* 19:1221-1225 (2001).

Mao et al., "Kremen proteins are Dickkopf receptors that regulate *Wnt/b*-catenin signaling" *Nature* 417:6889:664-667 (2002).

Saitoh et al., "Expression and regulation of *WNT8A* and *WNT8B* mRNAs in human tumor cell lines: Up-regulation of *WNT8B* mRNA by β-estradiol in MCF-7 cells, and down-regulation of *WNT8A* and *WNT8B* mRNAs by retinoic acid in NT2 cells" *J. Oncol.* 20(5):999-1003 (2002).

Shou et al., "Human Dkk-1, a gene encoding a Wnt antagonist, responds to DNA damage and its overexpression sensitizes brain tumor cells to apaptosis following alkylation damage of DNA" *Oncogene* 21:878-889 (2002).

Katoh, Int. "Frequent up-regulation of *WNT2* in primary gastric cancer and colorectal cancer" *J. Oncol.* 19(5):1003-7 (2001).

Kirikoshi et al., "Expression of *WNT10A* in human cancer" *Int. J. Oncol.* 19(5):997-1001 (2001).

Bui et al.,"Expression and hormone regulation of Wnt2, 3, 4, 5a, 7a, 7b and 10b in normal human endometrium and endometrial carcinoma" *Br. J. Canc.* 75(8):1131-1136 (1997).

Kramps et al., "Wnt/Wingless Signaling Requires BCL9/Leglass-Mediated Recruitment of Pygopus to the Nuclear β-Catenin-TCF Complex" *Cell*;:109:4760 (2002).

Aoki et al., "Nuclear endpoint of Wnt signaling: Neoplastic transformation induced by transactivating lymphoid-enhancing factor 1" *Proc. Nat'l Acad. Sci.* USA 96:139-144 (1999).

Rimm et al., "Frequent Nuclear/Cytoplasmic Localization of β-Catenin without Exon 3 Mutations in Malignant Melanoma" *Am J. Pathol* 154:325-329 (1999).

De La Coste et al., "Somatic mutations of the β-catenin gene are frequent in mouse and human hepatocellular carcinomas" *Proc.Nat'l Acad Sci.* USA 95:8847-8851 (1998).

Palacios et al., "Mutations in the β-Catenin Gene (*CTNNB1*) in Endometrioid Ovarian Carcinomas" *Cancer Res.* 58:1344-1347 (1998).

Ikeda, "Mutational analysis of the *CTNNB1* (β-catenin) gene in human endometrial cancer: Frequent mutations at condon 34 that cause nuclear accumulation" *Oncol Rep* 7:323-326 (2000).

Hamilton et al., "The Molecular Basis of Turcot's Syndrome" *N. Engl. J Med.* 332:839-847 (1995).

Chan et al., "A common human skin tumour is caused by activating mutations in β-catenin" *Nat. genetics* 21:410-413 (1999).

Nusse et al., "Many Tumors Induced by the Mouse Mammary Tumor Virus Contain a Provirus Integrated in the Same Region of the Host Genome" *Cell* 31:99-109 (1982).

Cadigan et al., "Wnt signaling: a common theme in animal development" *Genes Dev.* 11:3286-3305 (1997).

Miller et al., "Mechanism and fuction of signal transduction by the Wnt/ β-catenin and Wnt/Ca2+ pathways" *Oncogene* 18:7860-7872 (1999).

Shimizu et al., Transformation by Wnt Family Proteins Correlates with Regulation of β-Catenin *Cell Growth Differ* 8:1349-1358 (1997).

Zhou et al., "Up-Regulation of Human Secreted Frizzled Homolog in Apoptosis and Its Down-Regulation in Breast Tumors" *Int J. Cancer* 78:95-99 (1998).

Sagara et al., "Molecular Cloning, Differential Expression, and Chromosomal Localization of Human *Frizzled-1, Frizzled-2, and Frizzled-7" Biochem Biophys Res Comm* 252:117-122 (1998).

Yang-Snyder et al., A *frizzled* homolog functions in a vertebrate *Wnt* signaling pathway *Curr Biol* 6:1302-1306 (1996).

McWhirter et al., "Oncogenic homeodomain transcription factor E2A-Pbx1 activates a novel WNT gene in pre-B acute lymphoblastoid leukemia" *Proc. Natl., Acad. Sci.* 96:11464-11469 (1999).

Van de Wetering et al., "WNT Signaling and Lymphocyte Development" *Cell* 109:S13-S19 (2002).

Lo Muzio et al., "WNT-1 expression in basal cell carcinoma of head and neck. An immunohistochemical and confocal study with regard to the intracellular distribution of beta-catenin" *Anticancer Res.* 22(2A):565-576 (2002).

Chae-Seo et al., "Wnt and frizzled receptors as potential targets for immunotherapy in head and neck squamous cell carcinomas" *Oncogene* 21:6598-6605 (2002).

Kirkoshi et al., "Expression of *WNT7A* in human normal tissues and cancer, and regulation of *WNT7A* and *WNT7B* in human cancer" *Int. J. Oncol.* 21:895-900 (2002).

Huguet et al., "Differential Expression of Human *WNT* Genes 2, 3, 4, and 7B in Human Breast Cell Lines and Normal Disease States of Human Breast Tissue" *Cancer Research* 54:2615-2621 (1994).

Chen et al., Wnt-1 Signaling Inhibits Apoptosis by Activating β-Catenin/T Cell Factor-mediated Transcription *J Cell Biol* 152:87-96 (2001).

Weeraratna et al., "Wnt5a signaling directly affects cell motility and invasion of metastatic melanoma" *Cancer Cell* 3:279-288 (2002).

Tanaka et al., "A novel frizzled gene identified in human esophageal carcinoma mediates APC/β-catenin signals", *Proc. Natl. Acad. Sci.* 95: 10164-10169 (1998).

"Membrane Receptors: Frizzled and Related Proteins"; *Santa Cruz Biotechnology, Online Catalogue*; Retrieved from the Internet: http://www.scbt.com/catalog/action.lasso?-database=intros2003&-layout=main&-response=toc_ subsection.html&-recordID=38067&-token.order_id=1630401&-search; Retrieved on Nov. 16, 2003.

Malik, J. H. et al.; "Structure and Expression of a Novel Frizzled Gene Isolated from the Developing Mouse Gut"; *Biochemical Journal* 2000; pp. 829-834; vol. 349; Portland Press, London, GB.

Polakis, P. "Wnt Signaling and Cancer"; *Genes and Development*; Aug. 1, 2000; pp. 1837-1851; vol. 14, No. 15; Cold Spring Harbor Press, New York, NY, USA.

Tokuhara, M. et al.; "Molecular Cloning of Human—Frizzled—-6"; *Biochemical and Biophysical Research Communications*; 1998; XP002074753; Academic Press Inc., Orlando, FL, USA.

Van Gijn, Marielle E. et al. "Overexpression of Components of the Frizzled-Dishevelled Cascade Results in Apoptotic Cell Death, Mediated by Beta-Catenin"; *Experimental Cell Research*; Apr. 15, 2001; pp. 46-53; vol. 265, No. 1.

Chung et al., "Regulation of leukemic cell adhesion, proliferation, and survival by beta-catenin," *Blood* 100(3):982-9990 (2002).

Katoh M., "Molecular cloning and characterization of human WNT3," *Int. J. of Oncology* 19(5):977-982 (2001).

Katoh M., "WNT3-WNT14B and WNT3A-WNT14 gene clusters," *Int. J. of Mol. Med.* 9(6):579-584 (2002).

Lu et al., "Activation of the Wnt signaling pathway in chronic lymphocytic leukemia," *PNAS of USA* 101(9):3118-3123 (2004).

Reya et al., "Wnt signaling regulates B lymphocyte proliferation through a LEF-1 dependent mechanism," *Immunity* 13(1):15-24 (2000).

Rhee et al., "Wnt and frizzled receptors as potential targets for immunotherapy in head and neck squamous cell carcinomas," *Oncogene* 21(43):6598-6605 (2002).

Rosenwald et al., "Relation of gene expression phentoype to immunoglobulin mutation genotype in B cell chronic lymphocytic leukemia," *J. of Exp. Med.* 194(11):1639-1647 (2001).

* cited by examiner

Anti-Wnt 1

Anti-Wnt 10b

Figure 6

```
HFZ1  VGQNTSDKGT---PSLLPEFWTSNPQHGGGGHRG---------------------------------GFPGGAG----ASERGKFSCPR
HFZ2  VGQNHSEDGA-----PALLTTAPPPGLQPGAGGTPG---------------------------------GPGGGGAPPRYATLEHPFHC
HFZ3  LVDLNLAG------EPTEGAPV-----------------------------------------------AVQRDYG-----------FWC
HFZ4  CMEGPGD----------EE--------------------------------------------------VPLPHKTPI----------QP
HFZ5  CMDYNRSEATTAPPRPFPAKPTLPG-------------PPGA------------------PASGG-----ECPAGGPFV--------CKC
HFZ6  TFDPHTEF------LGPQKKTE-----------------------------------------------QVQRDIG-----------FWC
HFZ7  VGQNTSDGSGGPGGGPTAYPTAPYLPDLPFTALPPG---------------------------------ASDGRGRPAF------PFSC
HFZ8  CMDYNRTDLTTAAPSPPRRLPPPPP-GEQPPSGSGHGRPPGARPPHRGGGRGGGGGDAAAPPARGGGGGKARPPGGGAAP---CEPGCQC
HFZ9  CMEAPENA-TAGPAEPHKGLGMLPV--------------------------------------------APRPARPPG--------DLGP
HFZ10 NYLCMEAPNN----GSDEPTRGSGLFPP--------------------------------------------LFRPQRPHSAQ----EHP
```

Figure 13A

Primers for real-time PCR

| Genes | Forward Primer | Reverse Primer | Probes |
|---|---|---|---|
| **Wnt family (18)** | | | |
| Wnt1 | CGAACCTGCTTACAGACTCCAA | CAGACGCCGCTGTTTGC | TGCAACTGGTACTCGAGCCCAGTCTG |
| Wnt2 | GGATGACCAAGTGTGGGTGTAAG | GTGCACATCCAGAGCTTCCA | CACTGGTGCTGCGCCGTGC |
| Wnt2b | GGCACGAGTGATCTGTGACAATA | CGCATGATGTCTGGGTAACG | TTTGGTGAGCCGGCAGCGG |
| Wnt3 | CTGGGCCAGCAGTACACATCT | GGCATGATCTCGATGTAATTGC | TGCTCTGCGGCTCCATCCCA |
| Wnt3a | CCCGTGCTGGACAAAGCT | TCTGCACATGAGCGTGTCACT | TTGTCCACGCCATTGCCTCAGC |
| Wnt4 | GGAGGAGACGTGCGAGAAAC | CAGGTTCCGCTTGCACATCT | CAAGGGCCTGATCCAGAGGCAGG |
| Wnt5a | TCTCCTTCGCCCAGGTTGTA | CTTCTGACATCTGAACAGGGTTATTC | TGAAGCCAATTCTTGGTGGTCGCTAGG |
| Wnt5b | CCAACTCCTGGTGGTCATTAGC | TGGGCACCGATGATAAACATC | TTGAACCCGGTGCAGAGACCCG |
| Wnt6 | TCCGCCGCTGGAATTG | AGGCCGTCTCCCGAATGT | AGGCCTTTGGACGCATCCTGCA |
| Wnt7a | GACGCCATCATCGTCATAGGA | GGCCATTGCGGAACTGAA | TCACAAATGGGCCTGGACGAGTGTC |
| Wnt7b | TGAAGCTCGGAGCACTGTCA | GGCCAGGAATCTTGTTGCA | TGGTGGCCCTGGGAGCCAAC |
| Wnt8a | GCAGAGGCGGAACTGATCTT | CGACCCTCTGTGCCATAGATG | CCAGATTACTGTACCTGCAATTCCAGCCTG |
| Wnt8b | AATCGGGAGACAGCATTTGTG | ATCTCCAAGGCTGCAGTTTCTAGT | TGCCATCAGTTCTGCTGGAGTCATGTACA |
| Wnt10a | CTGGGTGCTCCTGTTCTTCCTA | GAGGCGGAGGTCCAGAATG | CTGCCATGCCCAGGTCAGCACC |
| Wnt10b | CCTCGCGGGTCTCCTGTT | AGGCCCAGAATCTCATTGCTTA | CTGGCGTTGTGCAGTCGGGCT |
| Wnt11 | CGTGTGCTATGGCATCAAGTG | GCAGTGTTGCGTCTGGTTCA | TGTCCAAGACACCATCGGCCCTG |
| Wnt14 | GGGCAGACGGTCAAGCAA | CCAGCCTTGATCACCTTCACA | CTGCGAGCCCGTGTGGACTTCC |
| Wnt16 | GCCAATTTGCCGCTGAAC | CGGCAGCAGGTACGGTTT | CCGCCAGAAGGAGCTGTGCAAGA |
| **Fzd family (10)** | | | |
| Fzd1 | CACCTTGTGAGCCGACCAA | CAGCACTGACCAAATGCCAAT | AGGAGCTGCGCTTCTCGCGC |
| Fzd2 | TTTCTGGGCGAGCGTGAT | AAACGCGTCTCCTCCTGTGA | TGCGAACCTGCGCGGCC |
| Fzd3 | TGGCTATGGTGGATGATCAAAG | TGGAGGCTGCCGTGGTA | AGGAAGCATCCACAGCAAAGTGAGCAG |
| Fzd4 | GGCGGCATGTGTCTTTCAGT | GAATTTGCTGCAGTTCAGACTCTCT | AGAGACGCTGTGAACCCGTCCTGAAG |
| Fzd5 | CGCGAGCACAACCACATC | AGAAGTAGACCAGGAGGAAGACGAT | TACGAGACCACGGGCCCTGCAC |
| Fzd6 | ACAAGCTGAAGGTCATTTCCAAA | GCTACTGCAGAAGTGCCATGAT | ATGGGAACCAGCACAGGAGCTACAGC |
| Fzd7 | CAACGGCCTGATGTACTTTAAGG | CATGTCCACCAGGTAGGTGAGA | CTGCGCCTCGACGCTCTTTACCG |
| Fzd8 | GCTCGGTCATCAAGCAACAG | ACGGTGTAGAGCACGGTGAAC | AAGCTGATGATCCGCCTGGGCC |
| Fzd9 | GCGCTCAAGACCATCGTCAT | ATCCGTGCTGGCCACGTA | TGGCGGGTGATGAGCTGACTGG |
| Fzd10 | GCCGCCATCAGCTCCAT | TCATGTTGTAGCCGATGTCCTT | ATGCCAGCCCATCGAGATCCCG |

Figure 13B

| | | | |
|---|---|---|---|
| **Frp family (5)** | | | |
| Frp1 | AGCGAGTACGACTACGTGAGCTT | GCACTGAGGTGGCTTGGTGTA | AGTCGGACATCGGCCCGTACCAG |
| Frp2 | AGACCAAGAGCAAGACCATTTACA | TTGAGCCACAGCACCGATT | CGGTGTGTCCGAAAGGGACCTGA |
| Frp3 | GGGCTATGAAGATGAGGAACGT | CCGAGTCGATCCTTCCACTTC | CCAGATTACTCTTGGTGGAAGGCTCTATAGCTGA |
| Frp4 | CGGAGGATGTTAAGTGGATAGACA | AGGCGTTTACAGTCAACATCAAGA | CACACCAGACATGATGGTACAGGAAAGGC |
| Frp5 | AGCTGATTGGAGCCCAGAAA | TGGTGTCCTTGCGCTTCA | AAGAAGCTGCTCAAGCCGGGCC |
| **Wisp family (3)** | | | |
| Wisp1 | CCTGATGGGCTTGGCTTCT | TGGGATTCCTACAGCTCAGGTT | CCGCCAGGTCCTATGGATTAATGCCT |
| Wisp2 | ACCCACCTCCTGGCCTTCT | AGCAGCCACAGCCATCCA | TCCTCTGCCTCCTCTCAAAGGTGCGTAC |
| Wisp3 | AAAGCTGGCTGGCAGTCACT | AATGGTTCCAGGCTACAGTTTGA | TCTGGAGCTAAAGGTGGAAAGAAGTCTGATCA |
| **DKK family (4)** | | | |
| DKK1 | GGAATAAGTACCAGACCATTGACAAC | GGGACTAGCGCAGTACTCATCA | CAGCCGTACCCGTGCGCAGA |
| DKK2 | CTGATGGTGGAGAGCTCACAGA | CAGAGAGGACTTGATGGAGTTGAGT | CGGCAGTTCGCGGGCCA |
| DKK3 | GGAGGACACGCAGCACAAA | CAGGTTCACTTCTGATGATGCTTT | TGCGCAGCGCGGTGGAAG |
| DKK4 | GGCATAAAGACACTGCTCAAGCT | GCTGGTCAATTGGCTTCGA | CGTTGCGACTGTGGCCCTGGAC |
| **Others** | | | |
| IL-6 | CCTGACCCAACCACAAATGC | GCGCAGAATGAGATGAGTTGTC | CTGACGAAGCTGCAGGCACAGAACC |
| C-Myc | GCCACGTCTCCACACATCAG | TCTTGGCAGCAGGATAGTCCTT | CGCAGCGCCTCCCTCCACTC |
| Fibro | CACCCAATTCCTTGCTGGTATC | CCCAGGCTTCTCATACTTGATGA | AGCCGCCACGTGCCAGGA TTAC |
| Cyc D1 | GGCGGAGGAGAACAAACAGA | TGGCACAAGAGGCAACGA | TCCGCAAACACGCGCAGACC |
| MMP3 | CCATCAGAGGAAATGAGGTACGA | CCTCACGGTTGGAGGGAAA | CTGGATACCCAAGAGGCATCCACACC |
| LRP5 | CGTGATTGCCGACGATCTC | TCCGGCCGCTAGTCTTGTC | ACCCGTTCGGTCTGACGCAGTACAG |

Expression of Wnt's in Normal vs Tumor Tissues

Fold Increase over normal tissues

| Genes | Normal (2) | | BC(DCIS/ALL)(5) | | ΔΔCt | Fold induction |
|---|---|---|---|---|---|---|
| | Mean | SD | Mean | SD | | |
| Wnt | | | | | | |
| Wnt-1 | 11.98 | 0.49 | 14.76 | 1.76 | -2.79 | 0.15 |
| Wnt-2a | 8 02 | 0.34 | 8.17 | 2 20 | -0.16 | 0.90 |
| Wnt-2b | 9 50 | 0.32 | 12.42 | 1 03 | -2.92 | 0.13 |
| Wnt-3 | 10 27 | 0.46 | 18.35 | 1.67 | -8.08 | 0.00 |
| Wnt-3a | 20 34 | 2.16 | 23.68 | 2.72 | -3.34 | 0.10 |
| Wnt-4 | 6 60 | 0.67 | 9 79 | 2.20 | -3.19 | 0.11 |
| Wnt-5a | 12 23 | 0.50 | 8.89 | 1.39 | 3.34 | 10.14 |
| Wnt-5b | 10.96 | 0 55 | 9.89 | 0.55 | 1.07 | 2 10 |
| Wnt-6 | 15.56 | 0.85 | 13.37 | 2.78 | 2.19 | 4.55 |
| Wnt-7a | 9 92 | 0.48 | 14.93 | 1.80 | -5 01 | 0.03 |
| Wnt-7b | 15 70 | 0.57 | 9 86 | 1.58 | 5.83 | 56.95 |
| Wnt-8a | 11.19 | 0.48 | 19.35 | 4.62 | -8.16 | 0.00 |
| Wnt-8b | 11.53 | 0.24 | 15.30 | 1.76 | -3.77 | 0.07 |
| Wnt-10a | 14.90 | 0.58 | 15.53 | 1.45 | -0.63 | 0.65 |
| Wnt-10b | 14.88 | 0.58 | 15.85 | 2.67 | -0.97 | 0.51 |
| Wnt-11 | 14.08 | 0.32 | 12.84 | 2.47 | 1.23 | 2.35 |
| Wnt-14 | 13 92 | 0.38 | 9.97 | 0 73 | 3.96 | 15.52 |
| Wnt-16 | 11.08 | 0.60 | 14.95 | 1.88 | -3.87 | 0.07 |
| Fzd | | | | | | |
| Fzd-1 | 9.89 | 0 42 | 10.37 | 1 72 | -0.48 | 0 72 |
| Fzd-2 | 7.70 | 0 10 | 9.31 | 2.02 | -1.62 | 0.33 |
| Fzd-3 | 5.37 | 0.23 | 7.64 | 0.24 | -2.27 | 0.21 |
| Fzd-4 | 7.89 | 0.64 | 7.01 | 0.76 | 0.88 | 1.84 |
| Fzd-5 | 7.75 | 0.34 | 9.88 | 1.17 | -2.13 | 0.23 |
| Fzd-6 | 5.42 | 0.08 | 7.32 | 1.80 | -1.91 | 0.27 |
| Fzd-7 | 8.96 | 0.19 | 9.39 | 0.50 | -0.43 | 0.74 |
| Fzd-8 | 9.70 | 0.27 | 9.44 | 1.68 | 0.27 | 1.20 |
| Fzd-9 | 9.93 | 0.42 | 12.50 | 1.56 | -2.58 | 0.17 |
| Fzd-10 | 14 24 | 0.51 | 25.83 | 1.66 | -11.59 | 0.00 |
| Frp | | | | | | |
| Frp-1 | 8.59 | 0.13 | 9.49 | 1.19 | -0.91 | 0.53 |
| Frp-2 | 2.33 | 0.20 | 2.46 | 0 79 | -0.13 | 0.91 |
| Frp-3 | 5 86 | 1.64 | 7.59 | 1.72 | -1.73 | 0.30 |
| Frp-4 | 4 43 | 0.32 | 4.92 | 1.38 | -0.49 | 0.71 |
| Frp-5 | 9.96 | 0.27 | 15.48 | 6.48 | -5.53 | 0.02 |
| Wisp | | | | | | |
| Wisp-1 | 9.26 | 0 36 | 10.14 | 1.46 | -0.88 | 0.54 |
| Wisp-2 | 14.79 | 0 25 | 8.01 | 2.00 | 6.78 | 109.64 |
| Wisp-3 | 8.74 | 0 18 | 8.29 | 1 15 | 0.44 | 1.36 |
| DKK | | | | | | |
| DKK-1 | 8.55 | 1.19 | 9.31 | 1.55 | -0.76 | 0.59 |
| DKK-2 | 8.81 | 0 30 | 11.46 | 1.02 | -2.66 | 0.16 |
| DKK-3 | 7.22 | 0.45 | 9.91 | 2 22 | -2.70 | 0.15 |
| DKK-4 | 8 96 | 0.13 | 9.96 | 2 25 | -1.00 | 0 50 |
| IL-6 | 9.36 | 0.14 | 8.09 | 1.23 | 1.27 | 2.41 |
| C_Myc | 2.35 | 0.13 | 5.43 | 0.72 | -3.08 | 0.12 |
| Fibro | 3 22 | 0.24 | 2.21 | 0.81 | 1.01 | 2.01 |
| Cyc D1 | 9.90 | 0.14 | 6 03 | 1.87 | 3.88 | 14.68 |
| MMP3 | 8.01 | 0.57 | 7.57 | 0.84 | 0.44 | 1.35 |
| LBP-5 | 11.68 | 0.08 | 7.21 | 0.44 | 4.47 | 22.15 |

Figure 27

WNT AND FRIZZLED RECEPTORS AS TARGETS FOR IMMUNOTHERAPY IN HEAD AND NECK SQUAMOUS CELL CARCINOMAS

CROSS-REFERENCES TO RELATED APPLICATIONS

This patent application claims the benefit of the filing date of U.S. Provisional Application No. 60/287,995, filed May 1, 2001 and PCT US02/13802, filed May 1, 2002, both of which are incorporated herein by reference. Related applications U.S. Ser. No. 09/847,102 filed May 1, 2001 and PCT/IB02/02887 filed May 1, 2002 are herein incorporated by reference.

STATEMENT AS TO RIGHTS TO INVENTIONS MADE UNDER FEDERALLY SPONSORED RESEARCH OR DEVELOPMENT

This invention was made with U.S. Government support under Grant AR 44850 awarded by the National Institutes of Health. The Government may have certain rights in this invention.

REFERENCE TO A "SEQUENCE LISTING," A TABLE, OR A COMPUTER PROGRAM LISTING APPENDIX SUBMITTED ON A COMPACT DISK.

NOT APPLICABLE

FIELD OF THE INVENTION

This application relates to proteins involved in the Wnt/frizzled signaling pathway. More specifically, it involves the role of these proteins in proliferative disorders.

BACKGROUND OF THE INVENTION

Many cancers arise from differentiated tissues that are slowly dividing. The initial malignant population may have developed from a small, rapidly proliferating population of residual tissue stem cells or cells with a less differentiated subcellular profile. A strategy for targeting tumor cells that are antigenically distinct from mature differentiated cells could be useful in the treatment of cancer, particularly for controlling microscopic spread of disease. Malignant cells may express receptors used in embryonic patterning, which may serve as immunologic targets distinct from mature differentiated tissue.

In embryogenesis body patterning is related to the axial expression of different proteins. The proximal-distal axis is controlled by fibroblast growth factor (Vogel, A. et al., "Involvement of FGF-8 in initiation, outgrowth and patterning of the vertebrate limb," *Development,* 122:1737-1750 (1996); Vogel, A. and Tickle, C., "FGF-4 maintains polarizing activity of posterior limb bud cells in vivo and in vitro," *Development* 119:199-206 (1993); Niswander, L. et al., "FGF-4 replaces the apical ectodermal ridge and directs outgrowth and patterning of the limb," *Cell* 75:579-587 (1993)), anterior-posterior axis by Sonic hedgehog (Riddle, R. D. et al, "Sonic hedgehog mediates the polarizing activity of the ZPA," *Cell* 75:1401-1416 (1993)), and the dorsal ventral axis by wingless (Parr, B. A. et al., "Mouse Wnt genes exhibit discrete domains of expression in the early embryonic CNS and limb buds," *Development* 119:247-261 (1993); Riddle, R. D. et al., "Induction of the LIM homeobox gene Lmx1 by Wnt7a establishes dorsoventral pattern in the vertebrate limb," *Cell* 83:631-640 (1995); Vogel, A. et al., "Dorsal cell fate specified by chick Lmx1 during vertebrate limb development," *Nature* 378:716-720 (1995)). These factors are closely cross-regulated in development. The secretion of Wnt (wingless) is stimulated by Sonic hedgehog (SHH) signaling and conversely the expression of SHH is supported by the continued presence of wingless. SHH in turn influences fibroblast growth factor (FGF) expression (Niswander, L. et al., "A positive feedback loop coordinates growth and patterning in the vertebrate limb," *Nature* 371:609-612 (1994); Niswander, L., et al., "Function of FGF-4 in limb development," *Mol Reprod Dev* 39:83-88; discussion 88-89 (1994); Laufer, E. et al., "Sonic hedgehog and Fgf-4 act through a signaling cascade and feedback loop to integrate growth and patterning of the developing limb bud," *Cell* 79:993-1003 (1994)). Wingless is a ligand for a G-coupled protein receptor named frizzled, which mediates a complex signaling cascade (Vinson, C. R. and Adler, P. N., "Directional non-cell autonomy and the transmission of polarity information by the frizzled gene of Drosophila," *Nature* 329:549-551 (1987)). Transcriptional regulation is also mediated by SHH cell surface interaction with its ligand, Patched. Patched tonically inhibits signaling through Smoothened until it binds to SHH. These pathways are illustrated in FIG. 1, which has been adapted from reviews by others (Hunter, T., "Oncoprotein networks," *Cell* 88:333-346 (1997); Ng, J. K. et al., "Molecular and cellular basis of pattern formation during vertebrate limb development," *Curr Top Dev Biol* 41:37-66 (1999); Ramsdell, A. F. and Yost, H. J., "Molecular mechanisms of vertebrate left-right development," *Trends Genet* 14:459-465 (1998)).

Head and neck squamous cell carcinoma (HNSCC) is the sixth most common cancer in developed countries, and of the 44,000 annual cases reported in the United States approximately 11,000 will result in an unfavorable outcome (Landis, S. H. et al., "Cancer statistics," *CA Cancer J Clin.* 49, 8-31 (1999); Parkin, D. M. et al., "Global cancer statistics," *CA Cancer J Clin.* 49, 33-64 (1999)). Although metastatic HNSCC can respond to chemotherapy and radiotherapy, it is seldom adequately controlled. Therefore, it is important to identify new molecular determinants on HNSCC that may be potential targets for chemotherapy or immunotherapy.

In APC-deficient colon carcinoma, beta-catenin accumulates and is constitutively complexed with nuclear Tcf-4 (Sparks, A. B. et al., "Mutational analysis of the APC/beta-catenin/Tcf pathway in colorectal cancer," *Cancer Res* 58:1130-1134 (1998)). Other colon carcinomas and melanomas also contain constitutive nuclear Tcf-4/beta-catenin complexes as a result of mutations in the N terminus of beta-catenin that render it insensitive to downregulation by APC, and GSK3 beta (Morin, P. J. et al., "Activation of beta-catenin-Tcf signaling in colon cancer by mutations in beta-catenin or APC," *Science* 275:1787-1790 (1997); Rubinfeld, B. et al. "Stabilization of beta-catenin by genetic defects in melanoma cell lines," *Science* 275:1790-1792 (1997)). This results in the unregulated expression of Tcf-4 oncogenic target genes, such as c-myc, cyclin D1, and c-jun (He, T. C. et al., "Identification of C-MYC as a target of the APC pathway," *Science* 281:1509-1512 (1998); Shtutman, M. et al., "The cyclin D1 gene is a target of the beta-catenin/LEF-1 pathway," *Proc. Nat'l. Acad Sci. USA* 96:5522-5527 (1999); Li, L. et al., "Disheveled proteins lead to two signaling pathways. Regulation of LEF-1 and c-Jun N-terminal kinase in mammalian cells," *J Biol Chem* 274:129-134 (1999)). The expression of covalently linked beta-catenin and LEF-1 has been directly demonstrated to result in the oncogenic transformation of chicken fibroblasts (Aoki, M. et al, "Nuclear endpoint of Wnt signaling: neoplastic transformation induced by transactivating lymphoid-enhancing factor 1," *Proc. Nat'l. Acad. Sci. USA* 96:139-144 (1999)). Similar mechanisms leading to deregulation of Tcf target gene activity are likely to be involved in melanoma (Rimm, D. L. et al., "Frequent nuclear/cytoplasmic localization of beta-catenin without exon 3 mutations in malignant melanoma," *Am J Pathol* 154:325-329 (1999)), breast cancer (Bui, T. D. et al., "A novel human Wnt gene, WNT10B, maps to 12q13 and is expressed in human breast carcinomas," *Oncogene* 14:1249-1253 (1997)), heptocellular carcinoma (de La Coste, A. et al., "Somatic mutations of the beta-catenin gene are frequent in mouse and human heptocellular carcinomas," *Proc Nat'l. Acad. Sci. USA* 95:8847-8851 (1998)), ovarian cancer (Palacios, J., and Gamallo, C., "Mutations in the beta-catenin gene (CTNNB1) in endometrioid ovarian carcinomas," *Cancer Res* 58:1344-1347 (1998)), endometrial cancer (Ikeda, T., "Mutational analysis of the CTNNB1 (beta-catenin) gene in human endometrial cancer: frequent mutations at codon 34 that cause nuclear accumulation," *Oncol Rep* 7:323-326 (2000)), medulloblastoma (Hamilton, S. R. et al., "The molecular basis of Turcot's syndrome," *N. Engl J Med* 332: 839-847 (1995)), pilomatricomas (Chan, E. F. et al. "A common human skin tumour is caused by activating mutations in beta-catenin," *Nat. Genet* 21:410-413 (1999)), and prostate cancer (Iozzo, R. V. et al., "Aberrant expression of the growth factor Wnt-5A in human malignancy," *Cancer Res* 55:3495-3499 (1995)).

Other growth regulation pathways in tumors have also attracted recent interest. Many epithelial tumors express excess amounts of epidermal growth factor-receptor tyrosine kinases, particularly epidermal growth factor receptor (EGFR, or ErbB-1), and HER2 (ErbB-2) (Coussens, L. et al, "Tyrosine kinase receptor with extensive homology to EGF receptor shares chromosomal location with neu oncogene," *Science* 230:1132-1139 (1985); King, C. R. et al., "Amplification of a novel v-erbB-related gene in a human mammary carcinoma," *Science* 229:974-976 (1985)). HER2 is transmembrane tyrosine kinase receptor, which dimerizes with another member of the EGFR family to form an active dimeric receptor (Akiyama, T. et al., "The product of the human c-erbB-2 gene: a 185-kilodalton glycoprotein with tyrosine kinase activity," *Science* 232:1644-1646 (1986)). The resulting phosphorylation of tyrosine residues initiates complex signaling pathways that ultimately lead to cell division. HER2 is overexpressed in 25 to 30 percent of breast cancers, usually as a result of gene amplification (Slamon, D. J. et al., "Studies of the HER-2/neu proto-oncogene in human breast and ovarian cancer," *Science* 244:707-712 (1989)). A high level of this protein is associated with an adverse prognosis (Slamon, D. J. et al., "Human breast cancer: correlation of relapse and survival with amplification of the HER-2/neu oncogene," *Science* 235:177-182 (1987); Ravdin, P. M. and Chamness, G. C., "The c-erbB-2 proto-oncogene as a prognostic and predictive marker in breast cancer: a paradigm for the development of other macromolecular markers—a review," *Gene* 159:19-27 (1995)).

In the past decade there has been tremendous progress in identifying genetic and molecular changes that occur during the transformation of malignant cells. Many malignant cells have a less differentiated phenotype, and a higher growth fraction than normal in adult tissues. These basic characteristics are similar to immature or embryonic cells. During the development of the embryo, various cell surface receptors and ligands direct tissue pattern formation, and cellular differentiation (Hunter, T., "Oncoprotein networks," *Cell* 88, 333-346 (1997); Ng, J. K. et al., "Molecular and cellular basis of pattern formation during vertebrate limb development," *Curr Top Dev Biol.* 41, 37-66 (1999); Ramsdell, A. F. and Yost, H. J., "Molecular mechanisms of vertebrate left-right development," *Trends Genet.* 14, 459-465 (1998)). The expression of these receptors and ligands is often no longer required in fully matured adult tissues. Because they are expressed on the cell surface, the receptors and ligands important for morphologic patterning and tissue differentiation could be targets for the immunotherapy of tumors that have arisen from residual immature cells, or that have undergone de-differentiation.

Genes of the wingless (Wnt) and frizzled (Fzd) class have an established role in cell morphogenesis and cellular differentiation (Parr, B. A. et al., "Mouse Wnt genes exhibit discrete domains of expression in the early embryonic CNS and limb buds," *Development,* 119, 247-261 (1993); Riddle, R. D. et al., "Induction of the LIM homeobox gene Lmx1 by WNT7a establishes dorsoventral pattern in the vertebrate limb," *Cell* 83, 631-640 (1995); Vogel, A. et al., (1995) "Dorsal cell fate specified by chick Lmx1 during vertebrate limb development," *Nature* 378, 716-720 (1995)). The Wnt proteins are extracellular ligands for the Fzd receptors, which resemble typical G protein coupled receptors (GPCRs). The first member of the 19 known human Wnt genes, Wnt-1, was initially discovered because of its oncogenic properties (Nusse, R. and Varmus, H. E., "Many tumors induced by the mouse mammary tumor virus contain a provirus integrated in the same region of the host genome," *Cell* 31, 99-109 (1982)). The Wnt glycoproteins bind to one or more of the 10 known, 7 transmembrane domain G-protein coupled Fzd receptors, to initiate a chain of signaling events that often culminates in the stabilization and nuclear translocation of β-catenin, with resultant heterodimerization with one of the four members of the LEF/TCF family of transcription factors (Cadigan, K. M. and Nusse, R., "Wnt signaling: a common theme in animal development," *Genes Dev.,* 11, 3286-3305 (1997); Miller, J. R. et al., "Mechanism and function of signal transduction by the Wnt/β-catenin and Wnt/Ca2+ pathways," *Oncogene* 18, 7860-7872 (1999)). These transcription factor complexes control the activities of specific Wnt target genes, including developmental regulators and other genes involved in coordinating cell proliferation, cell-cell interactions, and cell-matrix interactions (Vogel, A. and Tickle, C., "FGF-4 maintains polarizing activity of posterior limb bud cells in vivo and in vitro," *Development* 119:199-206 (1993)). The overexpression of β-catenin and LEF-1 has been demonstrated to result in the oncogenic transformation of chicken fibroblasts (Aoki, M. et al., "Nuclear endpoint of Wnt signaling: neoplastic transformation induced by transactivating lymphoid-enhancing factor 1," Proc. Nat'l. Acad. Sci. USA 96, 139-144 (1999)).

A recent survey using microarray techniques showed that most HNSCC overexpress mRNAs of the Wnt family (Leethanakul, C. et al., "Distinct pattern of expression of differentiation and growth-related genes in squamous cell carcinomas of the head and neck revealed by the use of laser capture microdissection and cDNA arrays," *Oncogene* 19, 3220-3224 (2000)). However, the various Wnt mRNAs are very homologous, and hybridization in microarrays often cannot distinguish between closely related templates.

A murine monoclonal antibody 4DS binds with high affinity to the extracellular domain of HER2, thereby blocking its function in signal transduction (Hudziak, R. M. et al. "p185HER2 monoclonal antibody has antiproliferative effects in vitro and sensitizes human breast tumor cells to tumor necrosis factor," *Mol Cell Biol* 9:1165-1172 (1989); Fendly, B. M. et al. "Characterization of murine monoclonal antibodies reactive to either the human epidermal growth factor receptor or HER2/neu gene product," *Cancer Res* 50:1550-1558 (1990); Fendly, B. M. et al. "The extracellular domain of HER2/neu is a potential immunogen for active specific immunotherapy of breast cancer," *J Biol Response Mod* 9:449-455 (1990)). In experimental models of breast cancer, it was active in vitro and in vivo, and had greater anti-tumor effects when combined with chemotherapy Hudziak, R. M. et al. "p185HER2 monoclonal antibody has antiproliferative effects in vitro and sensitizes human breast tumor cells to tumor necrosis factor," *Mol Cell Biol* 9:1165-1172 (1989); Pietras, R. J. et al., "Antibody to HER-2/neu receptor blocks DNA repair after cisplatin in human breast and ovarian cancer cells," *Oncogene* 9:1829-1838 (1994). A recently completed phase 3 randomized clinical trial of a humanized form of 4DS monoclonal antibody, trastuzumab (Herceptin; Genentech, Inc, South San Francisco, Calif.), demonstrated efficacy against some forms of breast tumors overexpressing HER2 (Slamon, D. J. et al., "Use of chemotherapy plus a monoclonal antibody against HER2 for metastatic breast cancer that overexpresses HER2," *N Engl J Med* 344:783-792 (2001).

SUMMARY OF THE INVENTION

The present invention provides methods to identify specific Wnt and/or Fzd proteins that are overexpressed in cancer cells. Overexpression can refer to increased levels of particular Wnt and/or Fzd protein levels in cancers cells releative to levels of the same Wnt and/or Fzd protein in non-cancer cells of the same tissue type. Alternatively, overexpression can refer to increased levels of particular Wnt and/or Fzd levels in cancers cells relative to levels of different Wnt and/or Fzd proteins in the same cancer cells. Additionally in some cancers, the Wnt and/or Fzd protein will be overexpressed when compared to both the same Wnt and/or Fzd protein in a non-cancer cells of the same tissue type, and different Wnt and/or Fzd proteins in the same cancer cells.

In one aspect, the present invention provides a method of inhibiting the proliferation or survival of breast cancer cells, in breast cancer cells that overexpress a Wnt protein in a Wnt/Fzd signaling pathway when compared to non-cancer cells. The Wnt protein can be Wnt7b, Wnt-10b, or Wnt-14. The breast cancer cells are contacted with an agent that inhibits the Wnt/Fzd signaling pathway in the cancer cells. In some embodiments, the agent is an antagonist of the Wnt/Fzd signaling pathway. In preferred embodiments, agent is an anti-Wnt antibody that specifically binds Wnt7b, Wnt-10b, or Wnt-14. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

The invention also provides a method of treating a patient with a breast cancer, where the cancer cells overexpress a Wnt protein in a Wnt/Fzd signaling pathway when compared to non-cancer cells. The Wnt protein can be Wnt7b, Wnt-10b, or Wnt-14. The breast cancer cells are contacted with an agent that inhibits the Wnt/Fzd signaling pathway in the cancer cells. In some embodiments, the agent is an antagonist of the Wnt/Fzd signaling pathway. In preferred embodiments, agent is an anti-Wnt antibody that specifically binds Wnt7b, Wnt-10b, or Wnt-14. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

In one aspect, the invention provides a method of inhibiting the proliferation or survival of chronic lymphocytic leukemia cells that overexpress a Wnt protein in a Wnt/Fzd signaling pathway when compared to non-cancer cells. The Wnt protein can be Wnt3 and Wnt-16. The chronic lymphocytic leukemia cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Wnt antibody that specifically binds Wnt3, or Wnt-16. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

The invention also provides, a method of treating a patient with chronic lymphocytic leukemia, where the chronic lymphocytic leukemia cells overexpress a Wnt protein in a Wnt/Fzd signaling pathway when compared to non-cancer cells. The Wnt protein can be Wnt3 and Wnt-16. The chronic lymphocytic leukemia cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Wnt antibody that specifically binds Wnt3, or Wnt-16. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

In one aspect, the invention provides a method of inhibiting the proliferation or survival of mantle zone lymphoma cells that overexpress a Wnt protein in a Wnt/Fzd signaling pathway when compared to non-cancer cells. The Wnt protein can be Wnt-16. The mantle zone lymphoma cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Wnt antibody that specifically binds Wnt-16. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

The invention also provides, a method of treating a patient with mantle zone lymphoma, when the mantle zone lymphoma cells overexpress a Wnt protein in a Wnt/Fzd signaling pathway when compared to non-cancer cells. The Wnt protein can be Wnt-16. The mantle zone lymphoma cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Wnt antibody that specifically binds Wnt-16. In a further embodiment, the anti-Wnt antibody facilitates cellular toxicity or killing by complement. In another aspect of the invention, the Wnt protein is overexpressed when compared to another Wnt protein in the same cancer cells. In a further aspect, the Wnt protein is required for proliferation or survival of the cancer cell.

In one aspect, the present invention provides a method of inhibiting the proliferation or survival of breast cancer cells that overexpress a Fzd protein in a Wnt/Fzd signaling pathway when compared to non-cancer cells. The Fzd protein can be Fzd3, Fzd4, Fzd6, Fzd7, or Fzd10. The breast cancer cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Fzd antibody that specifically binds Fzd3, Fzd4, Fzd6, Fzd7, or Fzd10. In a further embodiment, the anti-Fzd antibody facilitates cellular toxicity or killing by complement. In another aspect, the Fzd protein is overexpressed when compared to another Fzd protein in the same cancer cells. In a further aspect, wherein the Fzd protein is required for proliferation or survival of the cancer cell.

The invention also provides a method of treating a patient with a breast cancer, where the breast cancer cells overexpress a Wnt protein when compared to non-cancer cells. The Fzd protein can be Fzd3, Fzd4, Fzd6, Fzd7, or Fzd10. The breast cancer cells are contacted with an agent that inhibits the Wnt/Fzd signaling pathway in the cancer cells. In some embodiments, the agent is an antagonist of the Wnt/Fzd signaling pathway. In preferred embodiments, the agent is an anti-Fzd antibody that specifically binds Fzd3, Fzd4, Fzd6, Fzd7, or Fzd10. In a further embodiment, the anti-Fzd antibody facilitates cellular toxicity or killing by complement. In another aspect, the Fzd protein is overexpressed when compared to another Fzd protein in the same cancer cells. In a further aspect, wherein the Fzd protein is required for proliferation or survival of the cancer cell.

In one aspect, the invention provides a method of inhibiting the proliferation or survival of chronic lymphocytic leukemia cells that overexpress a Fzd protein in a Wnt/Fzd signaling pathway when compared to non-cancer cells. The Fzd protein can be Fzd3. The chronic lymphocytic leukemia cells are contacted with an agent that inhibits the Wnt/Fzd signaling pathway in the chronic lymphocytic leukemia cells. In some embodiments, the agent is an antagonist of the Wnt/Fzd signaling pathway. In a preferred embodiment, the agent is an anti-Fzd antibody that specifically binds Fzd3. In a further embodiment, the anti-Fzd antibody facilitates cellular toxicity or killing by complement. In another aspect, the Fzd protein is overexpressed when compared to another Fzd protein in the same cancer cells. In a further aspect, wherein the Fzd protein is required for proliferation or survival of the cancer cell.

The invention also provides a method of treating a patient with chronic lymphocytic leukemia, wherein the chronic lymphocytic leukemia cells overexpress a Fzd protein in a Wnt/Fzd signaling pathway when compared to non-cancer cells. The Fzd protein can be Fzd3. The chronic lymphocytic leukemia cells are contacted with an agent that inhibits the Wnt/Fzd signaling pathway in the chronic lymphocytic leukemia cells. In some embodiments, the agent is an antagonist of the Wnt/Fzd signaling pathway. In a preferred embodiment, the agent is an anti-Fzd antibody that specifically binds Fzd3. In a further embodiment, the anti-Fzd antibody facilitates cellular toxicity or killing by complement. In another aspect, the Fzd protein is overexpressed when compared to another Fzd protein in the same cancer cells. In a further aspect, wherein the Fzd protein is required for proliferation or survival of the cancer cell.

In one aspect the present invention provides a method of inhibiting the proliferation or survival of cancer cells that overexpress a Wnt protein when compared to non-cancer cells, and that also overexpress a downstream wnt/fzd regulated gene product compared to non-cancer cells. The cancer cells are contacted with an agent that inhibits the Wnt/Fzd signaling pathway in the cancer cells. In some embodiments, the agent is an antibody directed against the overexpressed Wnt protein. In a further embodiment, the Wnt protein is also overexpressed when compared to another Wnt protein in the same cancer cells. In another embodiment, Wnt protein is required for proliferation or survival of the cancer cell. As an example, the proliferation of breast cancer cells that overexpresses Wnt7b, Wnt-10b, or Wnt-14 and also overexpresses cyclin D1, c-myc, and WISP family member can be inhibited by an antibody that binds specifically to Wnt7b, Wnt-10b, or Wnt-14.

The invention also provides a method of treating a patient with a cancer containing cells that that overexpress a Wnt protein when compared to non-cancer cells, and that also overexpress a downstream wnt/fzd regulated gene product compared to non-cancer cells. The cancer cells are contacted with an agent that inhibits the Wnt/Fzd signaling pathway in the cancer cells. In some embodiments, the agent is an antibody directed against the overexpressed Wnt protein. In a further embodiment, the Wnt protein is also overexpressed when compared to another Wnt protein in the same cancer cells. In another embodiment, Wnt protein is required for proliferation or survival of the cancer cell. As an example, a patient with breast cancer containing cells that overexpresses Wnt7b, Wnt-10b, or Wnt-14 and also overexpresses cyclin D1, c-myc, and WISP family member can be inhibited by an antibody that binds specifically to Wnt7b, Wnt-10b, or Wnt-14.

In one aspect the present invention provides a method of inhibiting the proliferation or survival of cancer cells that overexpress a Fzd protein when compared to non-cancer cells, and that also overexpress a downstream wnt/fzd regulated gene product compared to non-cancer cells. The cancer cells are contacted with an agent that inhibits the Wnt/Fzd signaling pathway in the cancer cells. In some embodiments, the agent is an antibody directed against the overexpressed Fzd protein. In a further embodiment, the Fzd protein is also overexpressed when compared to another Fzd protein in the same cancer cells. In another embodiment, Fzd protein is required for proliferation or survival of the cancer cell. As an example, the proliferation of breast cancer cells that overexpresses Fzd3, Fzd4, Fzd6, Fzd7, or Fzd10 and that also overexpresses cyclin D1, c-myc, and WISP family member can be inhibited by an antibody that binds specifically to Fzd3, Fzd4, Fzd6, Fzd7, or Fzd10.

The invention also provides a method of treating a patient with a cancer containing cells that that overexpress a Fzd protein when compared to non-cancer cells, and that also overexpress a downstream wnt/fzd regulated gene product compared to non-cancer cells. The cancer cells are contacted with an agent that inhibits the Wnt/Fzd signaling pathway in the cancer cells. In some embodiments, the agent is an antibody directed against the overexpressed Fzd protein. In a further embodiment, the Fzd protein is also overexpressed when compared to another Fzd protein in the same cancer cells. In another embodiment, Fzd protein is required for proliferation or survival of the cancer cell. As an example, a patient with breast cancer containing cells that overexpresses Fzd3, Fzd4, Fzd6, Fzd7, or Fzd10 and also overexpresses cyclin D1, c-myc, and WISP family member can be inhibited by an antibody that binds specifically to Fzd3, Fzd4, Fzd6, Fzd7, and Fzd10.

In another aspect, the invention provides an isolated polynucleotide of less than about 100 nucleotides that specifically hybridizes to a Wnt-1 encoding nucleic acid, and specifically hybridizes to the same sequence the polynucleotides: 5'-CGAACCTGCTTACAGACTCCAA-3' (SEQ ID NO:69)

and 5'-CAGACGCCGCTGTTTGC-3' (SEQ ID NO:70). The invention also provides a method of specifically detecting the presence or absence of a nucleic acid encoding Wnt-1 in a biological sample, by contacting the sample with the isolated polynucleotide so that hybridization with the Wnt-1 nucleic acid can be detected.

In another aspect, the invention provides an isolated polynucleotide of less than about 100 nucleotides that specifically hybridizes to a Wnt-2 encoding nucleic acid, and specifically hybridizes to the same sequence as the polynucleotides: 5'-GGATGACCAAGTGTGGGTGTAAG-3' (SEQ ID NO:72) and 5'-GTGCACATCCAGAGCTTCCA-3' (SEQ ID NO:73). The invention also provides a method of specifically detecting the presence or absence of a nucleic acid encoding Wnt-2 in a biological sample, by contacting the sample with the isolated polynucleotide so that hybridization with the Wnt-2 encoding nucleic acid present can be detected.

In another aspect, the invention provides an isolated polynucleotide of less than about 100 nucleotides that specifically hybridizes to a Wnt-2b encoding nucleic acid, and specifically hybridizes to the same sequence as the polynucleotides: 5'-GGCACGAGTGATCTGTGACAATA-3' (SEQ ID NO:75) and 5'-CGCATGATGTCTGGGTAACG-3' (SEQ ID NO:76). The invention also provides a method of specifically detecting the presence or absence of a nucleic acid encoding Wnt-2b in a biological sample, by contacting the sample with the isolated polynucleotide so that specific hybridization with the Wnt-2b encoding nucleic acid present can be detected.

In another aspect, the invention provides an isolated polynucleotide of less than about 100 nucleotides that specifically hybridizes to a Wnt-3 encoding nucleic acid, and specifically hybridizes to the same sequence as the polynucleotides: 5'-CTGGGCCAGCAGTACACATCT-3' (SEQ ID NO:78) and 5'-GGCATGATCTCGATGTAATTGC-3' (SEQ ID NO:79). The invention also provides a method of specifically detecting the presence or absence of a nucleic acid encoding Wnt-3 in a biological sample by contacting the sample with the isolated polynucleotide ao that specific hybridization with the Wnt-3 encoding nucleic acid present can be detected.

In another aspect, the invention provides an isolated polynucleotide of less than about 100 nucleotides that specifically hybridizes to a Wnt-3a encoding nucleic acid, and specifically hybridizes to the same sequence as the polynucleotides: 5'-CCCGTGCTGGACAAAGCT-3' (SEQ ID NO:81) and 5'-TCTGCACATGAGCGTGTCACT-3' (SEQ ID NO:82). The invention also provides a method of specifically detecting the presence or absence of a nucleic acid encoding Wnt-3a in a biological sample, by contacting the sample with the isolated polynucleotide so that specific hybridization with the Wnt-3a encoding nucleic acid present can be detected.

In another aspect, the invention provides an isolated polynucleotide of less than about 100 nucleotides that specifically hybridizes to a Wnt-4 encoding nucleic acid, and specifically hybridizes to the same sequence as the polynucleotides: 5'-GGAGGAGACGTGCGAGAAAC-3' (SEQ ID NO:84) and 5'-CAGGTTCCGCTTGCACATCT-3' (SEQ ID NO:85). The invention also provides a method of specifically detecting the presence or absence of a nucleic acid encoding Wnt-4 in a biological sample, by contacting the sample with the isolated polynucleotide so that specific hybridization with the Wnt-4 encoding nucleic acid present can be detected.

In another aspect, the invention provides an isolated polynucleotide of less than about 100 nucleotides that specifically hybridizes to a Wnt-5a encoding nucleic acid, and specifically hybridizes to the same sequence as the polynucleotides: 5'-TCTCCTTCGCCCAGGTTGTA-3' (SEQ ID NO:87) and 5'-CTTCTGACATCTGAACAGGGTTATTC-3' (SEQ ID NO:88). The invention also provides a method of specifically detecting the presence or absence of a nucleic acid encoding Wnt-5a in a biological sample, by contacting the sample with the isolated polynucleotide so that specific hybridization with the Wnt-5a encoding nucleic acid present can be detected.

In another aspect, the invention provides an isolated polynucleotide of less than about 100 nucleotides that specifically hybridizes to a Wnt-5b encoding nucleic acid, and specifically hybridizes to the same sequence as the polynucleotides: 5'-CCAACTCCTGGTGGTCATTAGC-3' (SEQ ID NO:90) and 5'-TGGGCACCGATGATAAACATC-3' (SEQ ID NO:91). The invention also provides a method of specifically detecting the presence or absence of a nucleic acid encoding Wnt-5b in a biological sample, by contacting the sample with the isolated polynucleotide of claim 99, under conditions to permit so that specific hybridization with the Wnt-5b encoding nucleic acid present can be detected.

In another aspect, the invention provides an isolated polynucleotide of less than about 100 nucleotides that specifically hybridizes to a Wnt-6 encoding nucleic acid, and specifically hybridizes to the same sequence as the polynucleotides: 5'-TCCGCCGCTGGAATTG-3' (SEQ ID NO:93) and 5'-AGGCCGTCTCCCGAATGT-3' (SEQ ID NO:94). The invention also provides a method of specifically detecting the presence or absence of a nucleic acid encoding Wnt-6 in a biological sample, by contacting the sample with the isolated polynucleotide so that specific hybridization with the Wnt-6 encoding nucleic acid present can be detected.

In another aspect, the invention provides an isolated polynucleotide of less than about 100 nucleotides that specifically hybridizes to a Wnt-7a encoding nucleic acid, and specifically hybridizes to the same sequence as the polynucleotides: 5'-GACGCCATCATCGTCATAGGA-3' (SEQ ID NO:96) and 5'-GGCCATTGCGGAACTGAA-3' (SEQ ID NO:97). The invention also provides a method of specifically detecting the presence or absence of a nucleic acid encoding Wnt-7a in a biological sample, by comprising contacting the sample with the isolated polynucleotide so that specific hybridization with the Wnt-7a encoding nucleic acid present can be detected.

In another aspect, the invention provides an isolated polynucleotide of less than about 100 nucleotides that specifically hybridizes to a Wnt-7b encoding nucleic acid, and specifically hybridizes to the same sequence as the polynucleotides: 5'-TGAAGCTCGGAGCACTGTCA-3' (SEQ ID NO:99) and 5'-GGCCAGGAATCTTGTTGCA-3'(SEQ ID NO:100). The invention also provides a method of specifically detecting the presence or absence of a nucleic acid encoding Wnt-7b in a biological sample, by contacting the sample with the isolated polynucleotide so that specific hybridization with the Wnt-7b encoding nucleic acid present can be detected.

In another aspect, the invention provides an isolated polynucleotide of less than about 100 nucleotides that specifically hybridizes to a Wnt-8a encoding nucleic acid, and specifically hybridizes to the same sequence as the polynucleotides: 5'-GCAGAGGCGGAACTGATCTT-3' (SEQ ID NO:102) and 5'-CGACCCTCTGTGCCATAGATG-3' (SEQ ID NO:103). The invention also provides a method of specifically detecting the presence or absence of a nucleic acid encoding Wnt-8a in a biological sample, by contacting the sample with the isolated polynucleotide so that specific hybridization with the Wnt-8a encoding nucleic acid present can be detected.

In another aspect, the invention provides an isolated polynucleotide of less than about 100 nucleotides that specifically hybridizes to a Wnt-8b encoding nucleic acid, and specifically hybridizes to the same sequence as the polynucleotides:

5'-AATCGGGAGACAGCATTTGTG-3' (SEQ ID NO:105) and 5'-ATCTCCAAGGCTGCAGTTTCTAGT-3' (SEQ ID NO:106). The invention also provides a method of specifically detecting the presence or absence of a nucleic acid encoding Wnt-8b in a biological sample, by contacting the sample with the isolated polynucleotide so that specific hybridization with the Wnt-8b encoding nucleic acid present can be detected.

In another aspect, the invention provides an isolated polynucleotide of less than about 100 nucleotides that specifically hybridizes to a Wnt-10a encoding nucleic acid, and specifically hybridizes to the same sequence as the polynucleotides: 5'-CTGGGTGCTCCTGTTCTTCCTA-3' (SEQ ID NO:108) and 5'-GAGGCGGAGGTCCAGAATG-3' (SEQ ID NO:109). The invention also provides a method of specifically detecting the presence or absence of a nucleic acid encoding Wnt-10a in a biological sample, by contacting the sample with the isolated polynucleotide so that specific hybridization with the Wnt-10a encoding nucleic acid present can be detected.

In another aspect, the invention provides an isolated polynucleotide of less than about 100 nucleotides that specifically hybridizes to a Wnt-10b encoding nucleic acid, and specifically hybridizes to the same sequence as the polynucleotides: 5'-CCTCGCGGGTCTCCTGTT-3' (SEQ ID NO:111) and 5'-AGGCCCAGAATCTCATTGCTTA-3' (SEQ ID NO:112). The invention also provides a method of specifically detecting the presence or absence of a nucleic acid encoding Wnt-10b in a biological sample, by contacting the sample with the isolated polynucleotide so that specific hybridization with the Wnt-10b encoding nucleic acid present can be detected.

In another aspect, the invention provides an isolated polynucleotide of less than about 100 nucleotides that specifically hybridizes to a Wnt-11 encoding nucleic acid, and specifically hybridizes to the same sequence as the polynucleotides: 5'-CGTGTGCTATGGCATCAAGTG-3' (SEQ ID NO:114) and 5'-GCAGTGTTGCGTCTGGTTCA-3' (SEQ ID NO:115). The invention also provides a method of specifically detecting the presence or absence of a nucleic acid encoding Wnt-11 in a biological sample, by contacting the sample with the isolated polynucleotide so that specific hybridization with the Wnt-11 encoding nucleic acid present can be detected.

In another aspect, the invention provides an isolated polynucleotide of less than about 100 nucleotides that specifically hybridizes to a Wnt-14 encoding nucleic acid, and specifically hybridizes to the same sequence as the polynucleotides 5'-GGGCAGACGGTCAAGCAA-3' (SEQ ID NO:117) and 5'-CCAGCCTTGATCACCTTCACA-3' (SEQ ID NO:118). The invention also provides a method of specifically detecting the presence or absence of a nucleic acid encoding Wnt-14 in a biological sample, by contacting the sample with the isolated polynucleotides so that specific hybridization with the Wnt-14 encoding nucleic acid present can be detected.

In another aspect, the invention provides an isolated polynucleotide of less than about 100 nucleotides that specifically hybridizes to a Wnt-16 encoding nucleic acid, and specifically hybridizes to the same sequence as the polynucleotides: 5'-GCCAATTTGCCGCTGAAC-3' (SEQ ID NO:120) and 5'-CGGCAGCAGGTACGGTTT-3' (SEQ ID NO:121). The invention also provides a method of specifically detecting the presence or absence of a nucleic acid encoding Wnt-16 in a biological sample, by contacting the sample with the isolated so that specific hybridization with the Wnt-16 encoding nucleic acid present can be detected.

In another aspect, the invention provides an isolated polynucleotide of less than about 100 nucleotides that specifically hybridizes to a Fzd1 encoding nucleic acid, and specifically hybridizes to the same sequence as the polynucleotides: 5'-CACCTTGTGAGCCGACCAA-3' (SEQ ID NO:123) and 5'-CAGCACTGACCAAATGCCAAT-3' (SEQ ID NO:124). The invention also provides a method of specifically detecting the presence or absence of a nucleic acid encoding Fzd1 in a biological sample, by contacting the sample with the isolated polynucleotide so that specific hybridization with the Fzd1 encoding nucleic acid present can be detected.

In another aspect, the invention provides an isolated polynucleotide of less than about 100 nucleotides that specifically hybridizes to a Fzd2 encoding nucleic acid, and specifically hybridizes to the same sequence as the polynucleotides: 5'-TTTCTGGGCGAGCGTGAT-3' (SEQ ID NO:126) and 5'-AAACGCGTCTCCTCCTGTGA-3' (SEQ ID NO:127). The invention also provides a method of specifically detecting the presence or absence of a nucleic acid encoding Fzd2 in a biological sample, by contacting the sample with with the polynucleotide so that specific hybridization with the Fzd2 encoding nucleic acid present can be detected.

In another aspect, the invention provides an isolated polynucleotide of less than about 100 nucleotides that specifically hybridizes to a Fzd3 encoding nucleic acid, and specifically hybridizes to the same sequence as the polynucleotides: 5'-TGGCTATGGTGGATGATCAAAG-3' (SEQ ID NO:129) and 5'-TGGAGGCTGCCGTGGTA-3' (SEQ ID NO:130). The invention also provides a method of specifically detecting the presence or absence of a nucleic acid encoding Fzd3 in a biological sample, by contacting the sample with the isolated polynucleotide so that specific hybridization with the Fzd3 encoding nucleic acid present can be detected.

In another aspect, the invention provides an isolated polynucleotide of less than about 100 nucleotides that specifically hybridizes to a Fzd4 encoding nucleic acid, and specifically hybridizes to the same sequence as the polynucleotides: 5'-GGCGGCATGTGTCTTTCAGT-3' (SEQ ID NO:132) and 5'-GAATTTGCTGCAGTTCAGACTCTCT-3' (SEQ ID NO:133). The invention also provides a method of specifically detecting the presence or absence of a nucleic acid encoding Fzd4 in a biological sample, by contacting the sample with the isolated polynucleotide so that specific hybridization with the Fzd4 encoding nucleic acid present can be detected.

In another aspect, the invention provides an isolated polynucleotide of less than about 100 nucleotides that specifically hybridizes to a Fzd5 encoding nucleic acid, and specifically hybridizes to the same sequence as the polynucleotides: 5'-CGCGAGCACAACCACATC-3' (SEQ ID NO:135) and 5'-AGAAGTAGACCAGGAGGAAGACGAT-3' (SEQ ID NO:136). The invention also provides a method of specifically detecting the presence or absence of a nucleic acid encoding Fzd5 in a biological sample, by contacting the sample with the isolated polynucleotide so that specific hybridization with the Fzd5 encoding nucleic acid present can be detected.

In another aspect, the invention provides an isolated polynucleotide of less than about 100 nucleotides that specifically hybridizes to a Fzd6 encoding nucleic acid, and specifically hybridizes to the same sequence as the polynucleotides: 5'-ACAAGCTGAAGGTCATTTCCAAA-3' (SEQ ID NO:138) and 5'-GCTACTGCAGAAGTGCCATGAT-3' (SEG ID NO:139). The invention also provides a method of specifically detecting the presence or absence of a nucleic acid encoding Fzd6 in a biological sample, by contacting the sample with the isolated polynucleotide so that specific hybridization between Fzd6 encoding nucleic acid present can be detected.

In another aspect, the invention provides an isolated polynucleotide of less than about 100 nucleotides that specifically hybridizes to a Fzd7 encoding nucleic acid, and specifically hybridizes to the same sequence as the polynucleotides: 5'-CAACGGCCTGATGTACTTTAAGG-3' (SEQ ID NO:141) and 5'-CATGTCCACCAGGTAGGTGAGA-3' (SEQ ID NO:142). The invention also provides a method of specifically detecting the presence or absence of a nucleic acid encoding Fzd7 in a biological sample, by contacting the sample with the isolated polynucleotide so that specific hybridization with the Fzd7 encoding nucleic acid present can be detected.

In another aspect, the invention provides an isolated polynucleotide of less than about 100 nucleotides that specifically hybridizes to a Fzd8 encoding nucleic acid, and specifically hybridizes to the same sequence as the polynucleotides: 5'-GCTCGGTCATCAAGCAACAG-3' (SEQ ID NO:144) and 5'-ACGGTGTAGAGCACGGTGAAC-3' (SEQ ID NO:145). The invention also provides a method of specifically detecting the presence or absence of a nucleic acid encoding Fzd8 in a biological sample, by contacting the sample with the isolated polynucleotide so that specific hybridization with the Fzd8 encoding nucleic acid present can be detected.

In another aspect, the invention provides an isolated polynucleotide of less than about 100 nucleotides that specifically hybridizes to a Fzd9 encoding nucleic acid, and specifically hybridizes to the same sequence as the polynucleotides: 5'-GCGCTCAAGACCATCGTCAT-3' (SEQ ID NO:147) and 5'-ATCCGTGCTGGCCACGTA-3' (SEQ ID NO:148). The invention also provides a method of specifically detecting the presence or absence of a nucleic acid encoding Fzd9 in a biological sample, by contacting the sample with the isolated polynucleotide so that specific hybridization with the Fzd9 encoding nucleic acid present can be detected.

In another aspect, the invention provides an isolated polynucleotide of less than about 100 nucleotides that specifically hybridizes to a Fzd10 encoding nucleic acid, and specifically hybridizes to the same sequence as the polynucleotides: 5'-GCCGCCATCAGCTCCAT-3' (SEQ ID NO:150) and 5'-TCATGTTGTAGCCGATGTCCTT-3' (SEQ ID NO:151). The invention also provides a method of specifically detecting the presence or absence of a nucleic acid encoding Fzd10 in a biological sample, by contacting the sample with the isolated polynucleotide so that specific hybridization between Fzd10 encoding nucleic acid present can be detected.

Definitions

The terms "Wnt protein" or "Wnt ligand" refer to a family of mammalian proteins related to the Drosophila segment polarity gene, wingless. In humans, the Wnt family of genes typically encode 38 to 43 kDa cysteine rich glycoproteins having hydrophobic signal sequence, and a conserved asparagine-linked oligosaccharide consensus sequence (see e.g., Shimizu et al *Cell Growth Differ* 8:1349-1358 (1997)). The Wnt family contains at least 19 mammalian members. Exemplary Wnt proteins include Wnt-1, Wnt-2, Wnt-2b (also known as Wnt-13) Wnt-3, Wnt-3A, Wnt-4, Wnt-5A, Wnt-5B, Wnt-6, Wnt-7A, Wnt-7B, Wnt-8A, Wnt-8B, Wnt-10A, Wnt-10B, Wnt-11, Wnt 14, Wnt 15, and Wnt 16. The sequences of exemplary wnt proteins are set forth in the Sequence Listing (SEQ ID NOS:1-38). As explained below, certain cancers are associated with particular Wnt proteins. For example, head and neck squamous cell carcinoma cells are associated with Wnt-5a, Wnt-7a, Wnt-10b, or Wnt-13. Glioblastoma is associated with Wnt-1 or Wnt-10b. Burkitt lymphoma and chronic lymphocytic leukemia are associated with Wnt-1 or Wnt-10b. Malignant lymphocytes overexpress Wnt-6, Wnt-14, or Wnt-16. Breast cancer is associated with overexpression of wnt5a, wnt7b, wnt10b, and wnt14.

The terms "frizzled protein" or "frizzled receptor" refer to a family of mammalian proteins related to the Drosophila frizzled genes, which play a role in the development of tissue polarity. The Frizzled family comprises at least 10 mammalian genes. Exemplary human Frizzled receptors include Frizzled1, Frizzled2, Frizzled3, Frizzled4, Frizzled5, Frizzled6, Frizzled7, Frizzled8, Frizzled9 and Frizzled10. The sequences of exemplary Frizzled receptors are set forth in the Sequence Listing (SEQ ID NOS:39-58). The mammalian homologues of the Drosophila frizzled protein share a number of common structural motifs. The N terminus located at the extracellular membrane surface is followed by a signal sequence, a domain of 120 amino acids with an invariant pattern of 10 cysteine residues, and a highly divergent region of 40-100 largely variable hydrophilic amino acids. Putative hydrophobic segments form seven membrane-spanning helices linked by hydrophilic loops, ending with the C terminus located at the intracellular face of the membrane. The cysteine-rich domains (CRDs) and the transmembrane segments are strongly conserved, suggesting a working model in which an extracellular CRD is tethered by a variable linker region to a bundle of seven membrane-spanning-helices. Frizzled protein receptors are, therefore, involved in a dynamic model of transmembrane signal transduction analogous to G-protein-coupled receptors with amino-terminal ligand binding domains.

In addition to the Wnt ligands, a family of secreted frizzled-related proteins (sFRPs) has been isolated. sFRPs appear to function as soluble endogenous modulators of Wnt signaling by competing with the membrane-spanning frizzled receptors for the binding of secreted Wnt ligands. sFRPs, therefore, modulate apoptosis susceptibility, exerting an antagonistic effect on programmed cell death. sFRPs can either antagonize Wnt function by binding the protein and blocking access to its cell surface signaling receptor, or they can enhance Wnt activity by facilitating the presentation of ligand to the frizzled receptors. To date, sFRPs have not yet been linked causatively to cancer.

The term "agent" or grammatical equivalents as used herein describes any molecule, either naturally occurring or synthetic, e.g., protein (for example an antibody or sFRP), oligopeptide (e.g., from about 5 to about 25 amino acids in length, preferably from about 10 to 20 or 12 to 18 amino acids in length, preferably 12, 15, or 18 amino acids in length), small chemical molecule, polysaccharide, lipid (e.g., a sphingolipid), fatty acid, polynucleotide, oligonucleotide, etc., that directly or indirectly inhibits a Wnt/Fzd signaling pathway.

The terms "antagonists" or "inhibitors" of Wnt signaling or of the wnt/Fzd signaling pathway refer to compounds that, e.g., bind to Wnt or Frizzled proteins, or partially or totally block or inhibit Wnt/Fzd signaling as measured in known assays for Wnt/Fzd signaling (e.g., measurement of β catenin levels, or oncogene expression controlled by Tcf and Lef transcription factors or other downstream wnt/fzd regulated gene products). Inhibitors, include antibodies directed against Wnt or Fzd proteins, and modified versions of Wnt or Frizzled proteins, as well as naturally occurring and synthetic ligands, antagonists, agonists, antibodies, small chemical molecules, and the like. Assays for detecting inhibitors or agaonists of the invention are described in more detail below.

A “cancer cell that overexpresses a Wnt or Frizzled protein” is a cancer cell in which expression of a particular Wnt protein is at least about 2 times, usually at least about 5 times the level of expression in a non-cancer cell from the same tissue type. In some embodiments, wnt and/or fzd expression in a cancer cell is compared to wnt and/or fzd expression in a non-cancer cell of a different tissue-type or a panel of non-cancer cells of a different tissue type. In addition, expression of particular Wnt and/or Frizzled proteins can be compared to other Wnt and/or Frizzled proteins in the same cell. Those proteins that are overexpressed in cancer cells compared to non-cancer cells and that are overexpressed compared to other Wnt and/or Frizzled proteins in the same cancer cell are generally preferred. Methods for determining the level of expression of a particular gene are well known in the art. Such methods include RT-PCR, real time PCR, use of antibodies against the gene products, and the like.

The terms “wnt signaling”, “wnt/fzd” signaling and “fzd signaling” are used interchangeably.

A “Wnt/Fzd signaling pathway” refers to activation of an intracellular signal transduction pathway that is initiated by an interaction between a specific Wnt protein and a specific Fzd protein. Generally, the Wnt/Fzd interaction will be binding of a Wnt protein to a Fzd receptor, leading to activation of a signal transduction pathway. In some instances activation of the Wnt/Fzd signaling pathway will lead to induction of downstream wnt and/or fzd inducible genes. A “downstream wnt/fzd regulated gene product” is a protein or RNA that is upregulated, or otherwise regulated, as a result of signaling by a wnt/fzd transduction pathway.

“Proliferation of a cancer cell” refers to cell division and increase in the number of cancer cells. “Inhibition of proliferation” refers to a decrease in the rate of proliferation (e.g., cellular division), cessation of proliferation (e.g., entry into G0 phase or senescense), or death of a cell, including necrotic cell death.

“Inhibition of survival of a cancer cell” refers to induction or relief of inhibition of a programmed cell death process, e.g., apoptosis.

The term “contact” or “contacting” is used herein interchangeably with the following: combined with, added to, mixed with, passed over, incubated with, flowed over, etc.

“Nucleic acid” refers to deoxyribonucleotides or ribonucleotides and polymers thereof in either single- or double-stranded form. Exemplary wnt and fzd nucleic acids are found in the informal sequence listing. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Thus, the terms “a Wnt encoding nuleic acid” and “a Fzd encoding nucleic acid” include both coding and complementary noncoding sequences. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

As used herein, “antibody” includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term “antibody” also includes antigen binding forms of antibodies, including fragments with antigen-binding capability (e.g., Fab', $F(ab')_2$, Fab, Fv and rIgG. See also, Pierce Catalog and Handbook, 1994-1995 (Pierce Chemical Co., Rockford, Ill.). See also, e.g., Kuby, J., *Immunology,* 3rd Ed., W. H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:*5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as “domains”). Light and heavy chain variable regions contain four “framework” regions interrupted by three hypervariable regions, also called “complementarity-determining regions” or “CDRs”. The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to “$V_H$” or a “VH” refer to the variable region of an immunoglobulin heavy chain of an antibody, including the heavy chain of an Fv, scFv, or Fab. References to “$V_L$” or a “VL” refer to the variable region of an immunoglobulin light chain, including the light chain of an Fv, scFv, dsFv or Fab.

The phrase “single chain Fv” or “scFv” refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., *Nature* 332:323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

"Biological sample" as used herein is a sample of biological tissue or fluid that contains nucleic acids or polypeptides, e.g., of a Wnt protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, wherein the antibodies are specific for the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor & Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of (-sheet and (-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, 3H, 14C, 32P, 35S, or 125I. In some cases, particularly using antibodies against the proteins of the invention, the radioisotopes are used as toxic moieties, as described below. The labels may be incorporated into the nucleic acids, proteins and antibodies at any position. Any method known in the art for conjugating the antibody to the label may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, J. *Histochem. and Cytochem.,* 30:407 (1982). The lifetime of radiolabeled peptides or radiolabeled antibody compositions may be extended by the addition of substances that stablize the radiolabeled peptide or antibody and protect it from degradation. Any substance or combination of substances that stablize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. The antibodies of the invention specifically bind to Wnt or Frizzled proteins or other proteins in a wnt/fzd signaling pathway. By "specifically bind" herein is meant that the antibodies bind to the protein with a $K_D$ of at least about 0.1 mM, more usually at least about 1 μM, preferably at least about 0.1 μM or better, and most preferably, 0.01 μM or better.

Specific binding to an antibody under such conditions requires an antibody that is selected for its specificity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with specific Wnt or specific Frizzled proteins, or other proteins in a wnt/fzd signaling pathway, and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. In the present invention transformation is typically associated with overexpression of Wnt and/or Frizzled proteins. Transformation is associated with other phenotypic changes, such as immortalization of cells, aberrant growth control, nonmorphological changes, and/or malignancy (see, Freshney, Culture of Animal Cells a Manual of Basic Technique (3rd ed. 1994)).

BRIEF DESCRIPTION OF THE DRAWINGS

FIG. 6. Sequence alignment of a portion of the first extracellular region of human Frizzled receptors (SEQ ID NOS: 59-68) is depicted.

FIG. 7A depicts an immunoblot after treatment with Wnt 1 or Wnt 10b antibodies. SNU1076 cells were treated for 72 hrs with 2 μg/ml of anti-Wnt 1, Wnt 10b, or control antibodies. FIG. 7B shows that treatment with Wnt1 antibodies reduces transcription of TCF/LEF gene.

FIG. 8A depicts an RT-PCR amplification for Wnt/FZD families in cancer cell lines. FIG. 8B depicts an RT-PCR amplification for Wnt/FZD families in normal cells.

FIGS. 13A and 13B. Primer and probe sequences for wnt, fzd, and wnt-related gene analysis (SEQ ID NOS:69-206).

FIG. 27. Expression of wnt, fzd, and wnt-related genes in non-tumor cells and breast cancer cells.

DETAILED DESCRIPTION OF FIGURES

Figure 1:
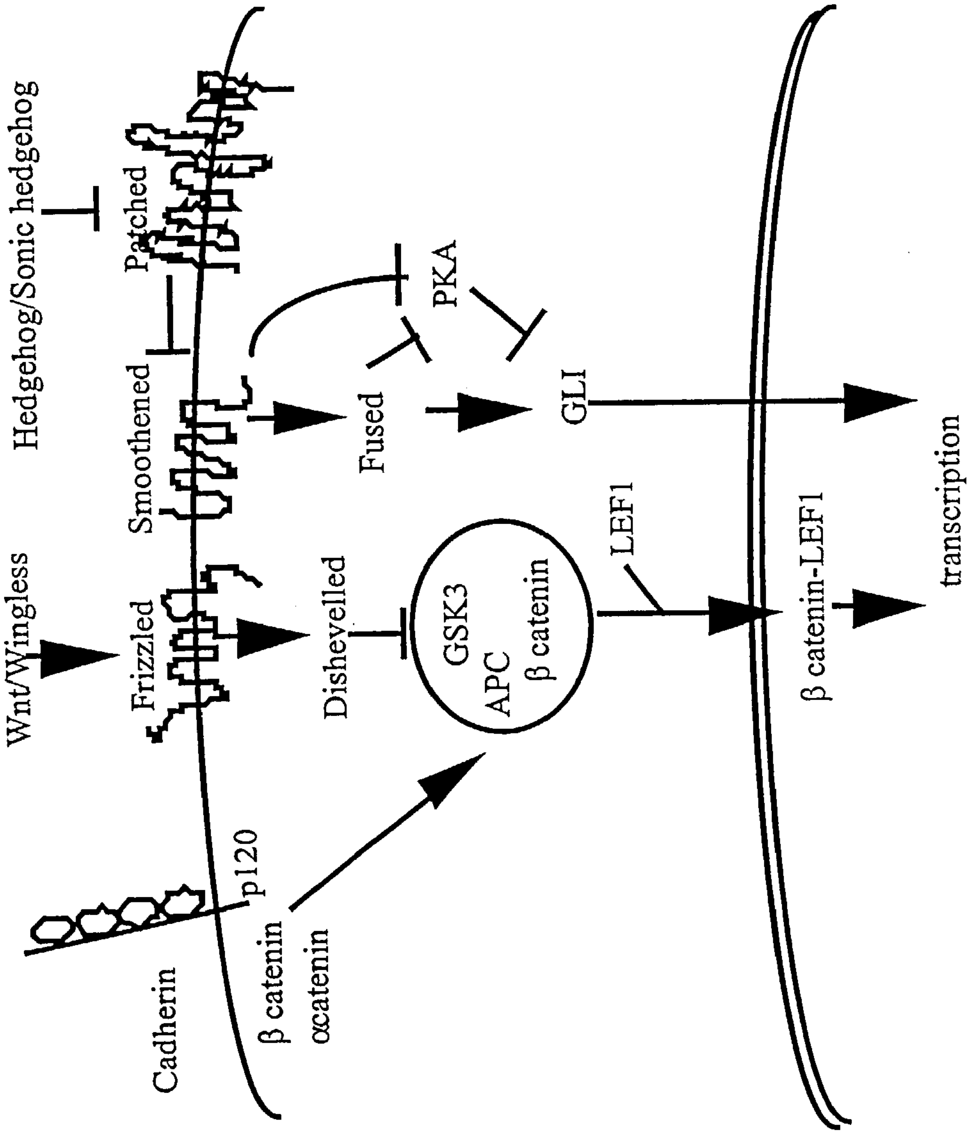
FIG. 1. Several developmental signaling pathways are depicted.

FIG. 1. Schematic of developmental signaling pathways is depicted. The signalling pathways of the Wnt/wingless and Hedehog/Sonic hedgehog are shown. Both sets of ligands interact with a cell surface receptor. Proteins involved in the signaling pathway are shown, for example, LEF1 and GSK3.

Figure 2:
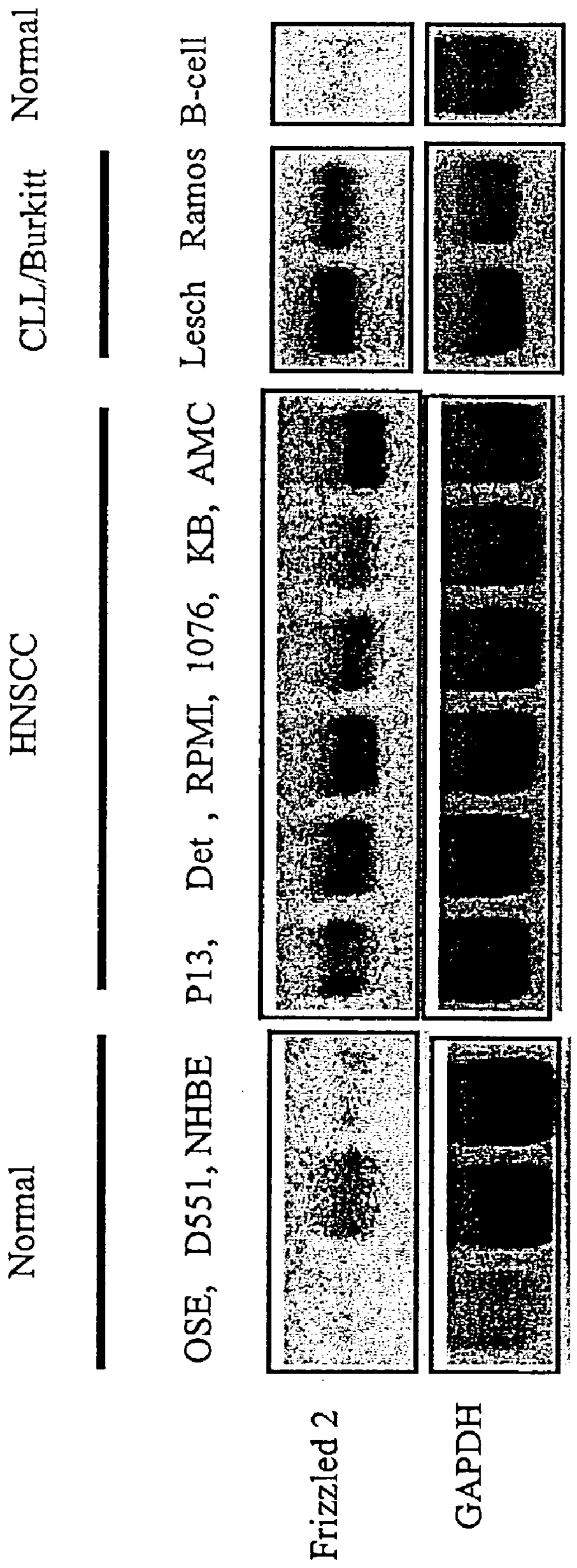
FIG. 2. RT-PCR analysis of a subset of HNSCC and B-cell lines for frizzled 2 mRNA.

FIG. 2. RT-PCR analysis of a subset of HNSCC and B-cell lines for frizzled 2 mRNA. Total RNA was extracted from HNSCC lines (PCI13, Detroit 562, RPMI 2650, SNU1076, KB, AMC4), a CLL line (Lesch), a Burkitt lymphoma line (Ramos), glioma lines (U87MG, and U373MG), normal human bronchial epithelial cell lines (Clonetics, San Diego, Calif.) and normal oral squamous epithelial (OSE) cells using RNAzol (Gibco BRL, Grand Island, N.Y.). Reverse transcription was performed using 1 μg of RNA from each sample and the Superscript™ Preamplification kit (Gibco BRL). Frizzled 2 was amplified with 25 cycles of PCR. G3PDH mRNA was amplified in a separate reaction for each sample.

Figure 3:
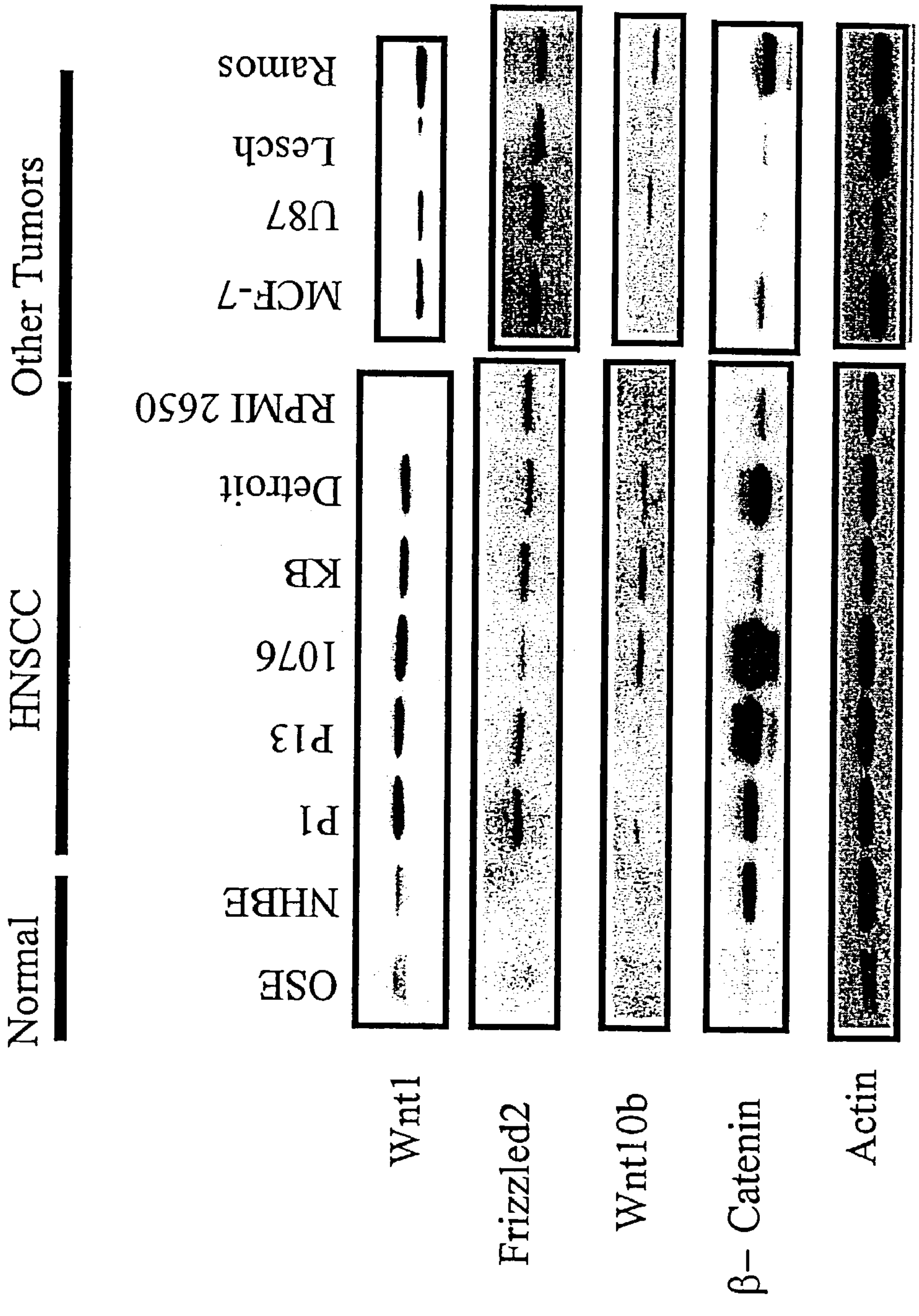
FIG. 3. A western blot analysis of tumor and normal cells for frizzled 2, wnt1 and 10b.

FIG. 3. A sample western blot analysis of tumor and normal cells for frizzled 2, wnt 5A and 10b. Adherent cells in culture were harvested and lysed with a solution containing 25 mM Tris HCl, 150 mM KCl, 5 mM EDTA, 1% NP-40, 0.5% sodium deoxycholic acid, 0.1% sodium dodecyl sulfate, 1 mM $NaVO_3$, 1 mM NaF, 20 mM β-glycerophosphate and protease inhibitors. Twenty μg of protein from each cell line was separated by SDS-PAGE and transferred to a PVDF membrane. The membrane was immersed in 2% I-block, 0.05% Tween X in PBS and then incubated with a 1:500 dilution of polyclonal goat anti-human Wnt 1, Wnt 10b, or frizzled 2 IgG (Santa Cruz Biotechnology, Santa Cruz, Calif.). These primary antibodies were then detected by horseradish peroxidase-conjugated donkey anti-goat IgG (Santa Cruz) and chemiluminescence (ECL detection reagents, Amersham Life Science, Aylesbury, UK). To verify relative amount of protein transferred in each lane, the presence of actin was measured with an actin monoclonal antibody (Chemi-Con International Inc, Temecula, Calif.).

Figure 4A:
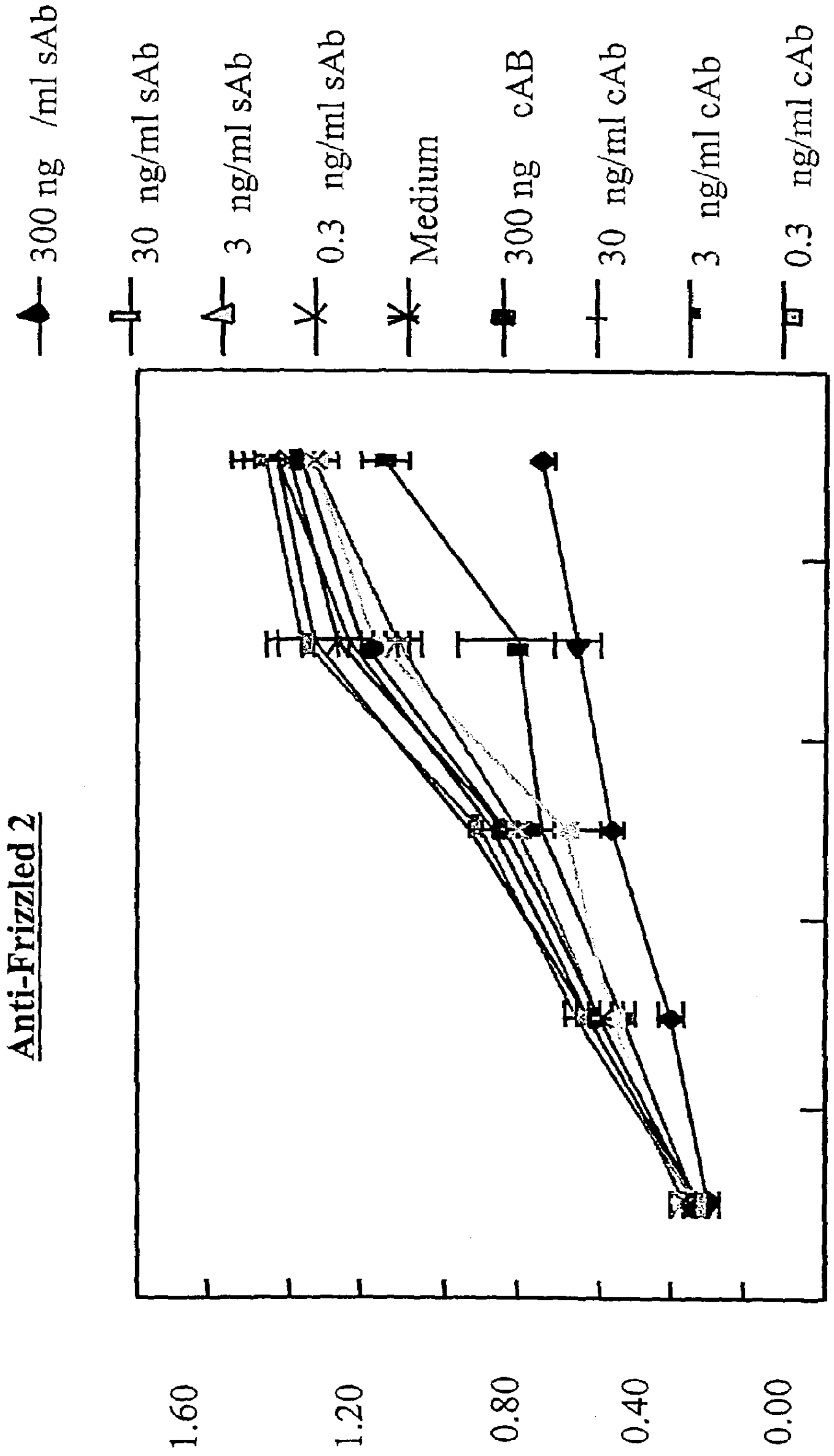
FIGS. 4A, 4B, and 4C. An inhibition of proliferation assay in a HNSCC line is depicted. Specifically, anti-frizzled 2, anti-wnt 1, and anti-wnt 10b are tested for their ability to inhibit proliferation.
Figure 4B:
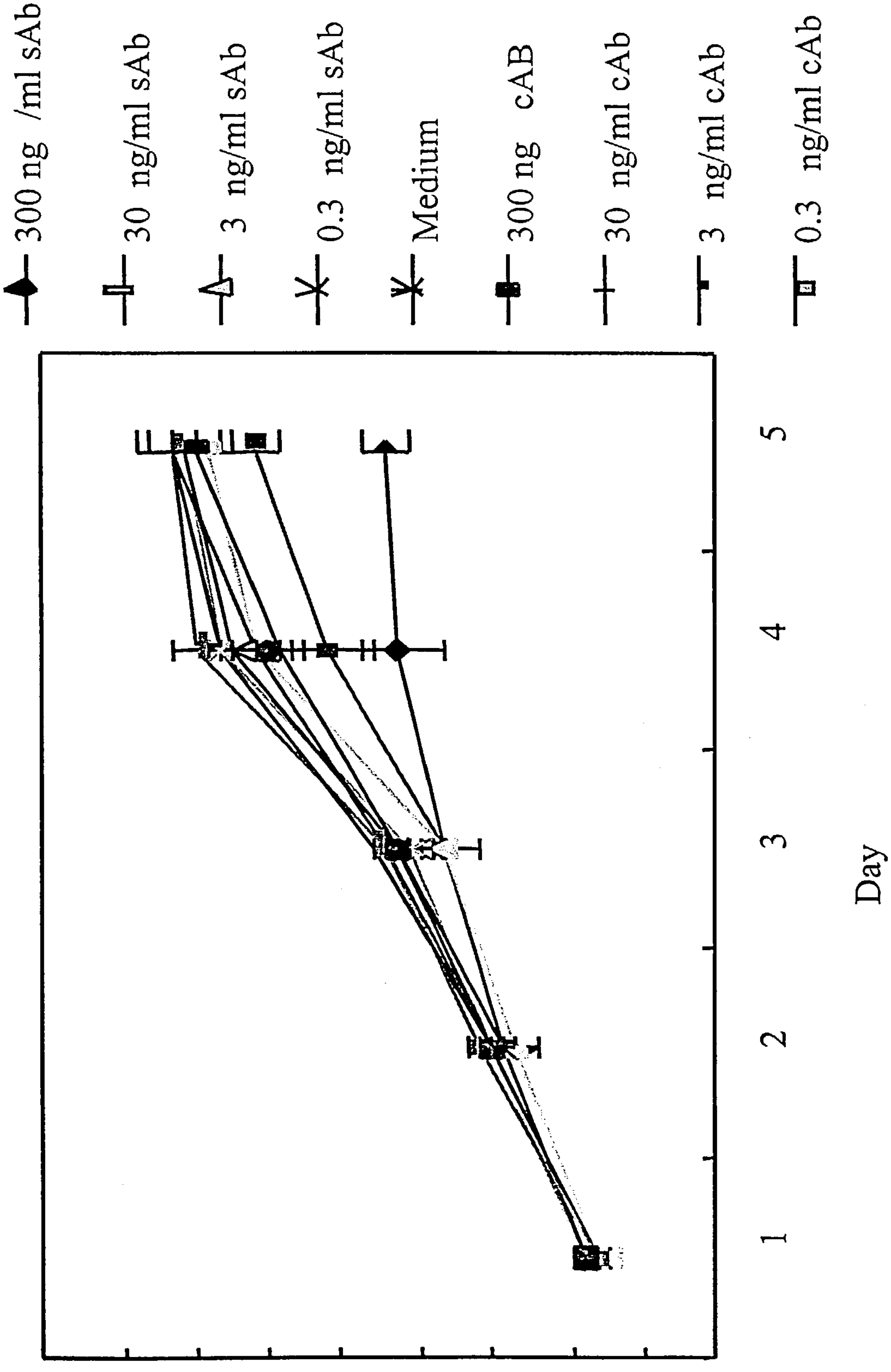
Figure 4C:
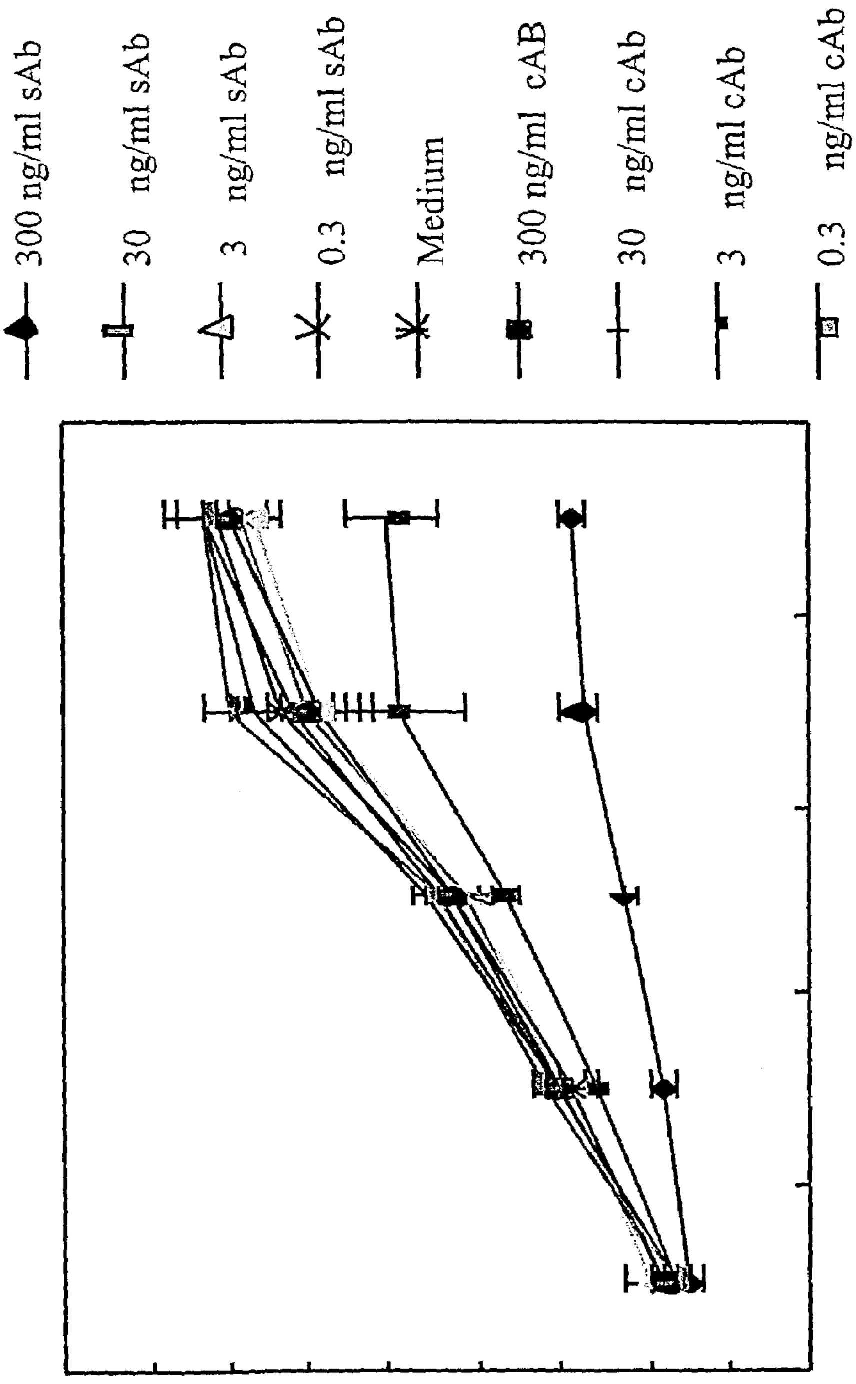

FIGS. 4A, 4B, and 4C. Inhibition of proliferation in a HNSCC line. Briefly, either $7.5\times10^3$ or $10\times10^3$ SNU1076 cells per well were seeded in 96 well plates. After 24 hours, graded amounts of polyclonal goat anti-human frizzled 2, Wnt 1, or Wnt 10b IgG (sAB)(Santa Cruz' Biotechnology, Santa Cruz, Calif.), or control goat anti-human IgG (cAB) (Fisher Scientific, Pittsburgh, Pa.) were added. On days 1, 2, 3, or 4, 20 μl of MTT (3-[4,5-dimethylthiazol-2-yl]-2,5-diphenyl tetrazolium bromide)-based solution was added to wells for four hours prior to lysis with 15% SDS, 0.015 M HCl. Absorbencies of 570 and 650 nm were measured.

Figure 5:
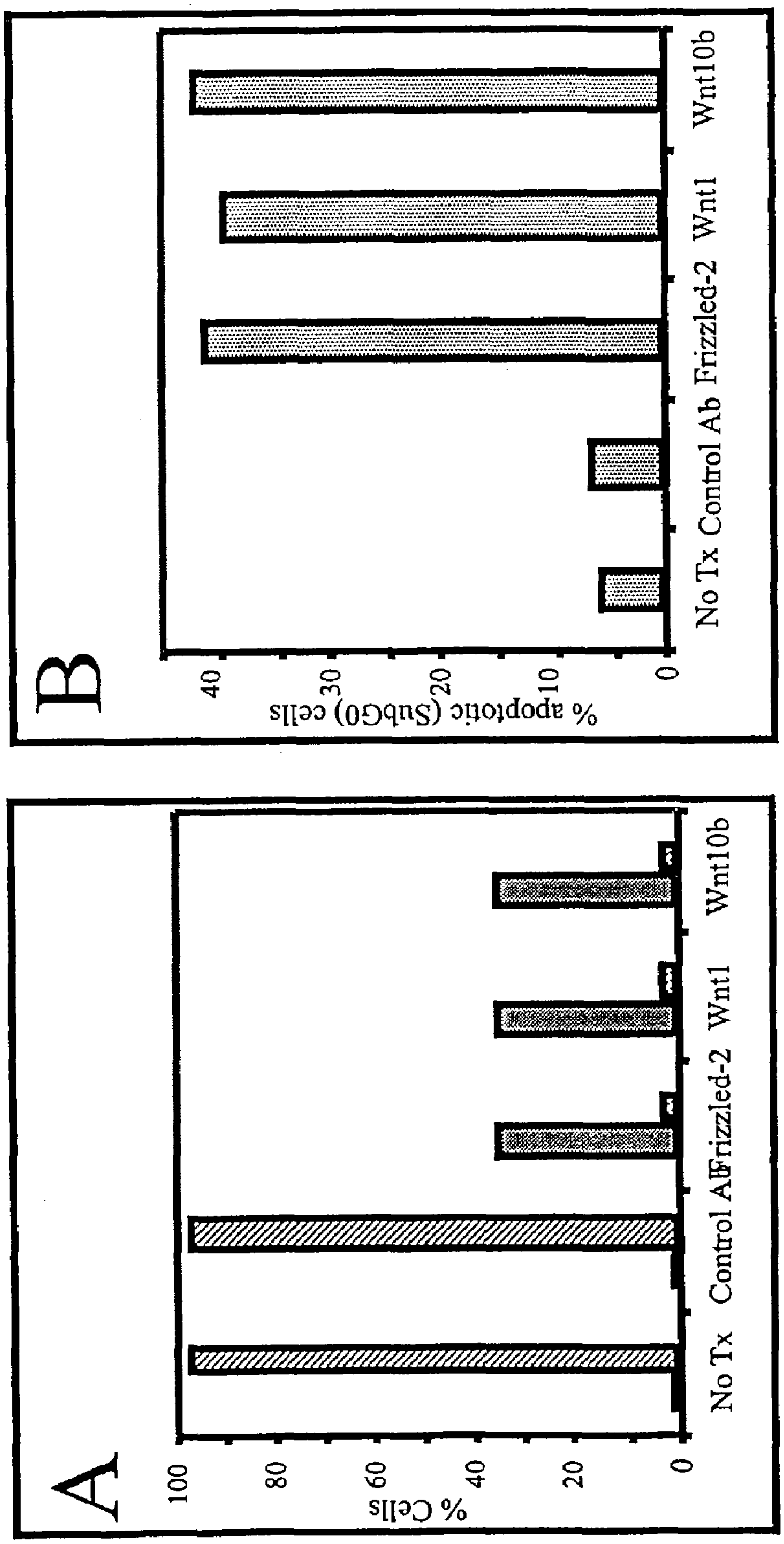
FIG. 5. Apoptotic effects of inhibition of the Wnt/Frizzled signaling pathway in a HNSCC line is depicted.

FIG. 5. Apoptotic effect of inhibition of the Wnt/Frizzled signaling pathway in a HNSCC line. The HNSCC line SNU1076, growing in RPMI-1640 supplemented with 10% FBS, was treated for 72 hrs with 300 ng/ml anti-Frizzled 2, Wnt-1, Wnt10b, or control nonspecific polyclonal antibodies. The cytotoxic effects of these antibodies were assessed by vital dye retention and DNA content. Panel A: cells were detached from the flasks by trypsin treatment and incubated for 10 minutes in growing medium with 5 μg/ml Propidium iodide (PI) and 40 nM $DiOC_6$ and analyzed by flow cytometry. Viable cells (stripes) had high $DiOC_6$ (FL-1) and low PI (FL-3) fluorescence, and apoptotic cells (stippled) had low $DiOC_6$ (FL-1) and low PI (FL-3) fluorescence. Panel B: cells were detached from the flasks by trypsin treatment and incubated overnight in a hypotonic buffer (0.1% citrate, 0.1% SDS) containing 50 μg/ml PI and 100 μg/ml RNase. The amount of DNA was then measured by flow cytometry, and apoptotic cells were defined as having a DNA content lower than the $G_0G_1$ levels (sub-$G_0$ cells).

FIG. 6. Sequence alignment of a portion of the first extracellular region of human Frizzled receptors (SEQ ID NOS: 59-68). Specifically, the amino acid sequences of HFZ1 through HFZ10 are aligned to show similarity.

Figure 7A:
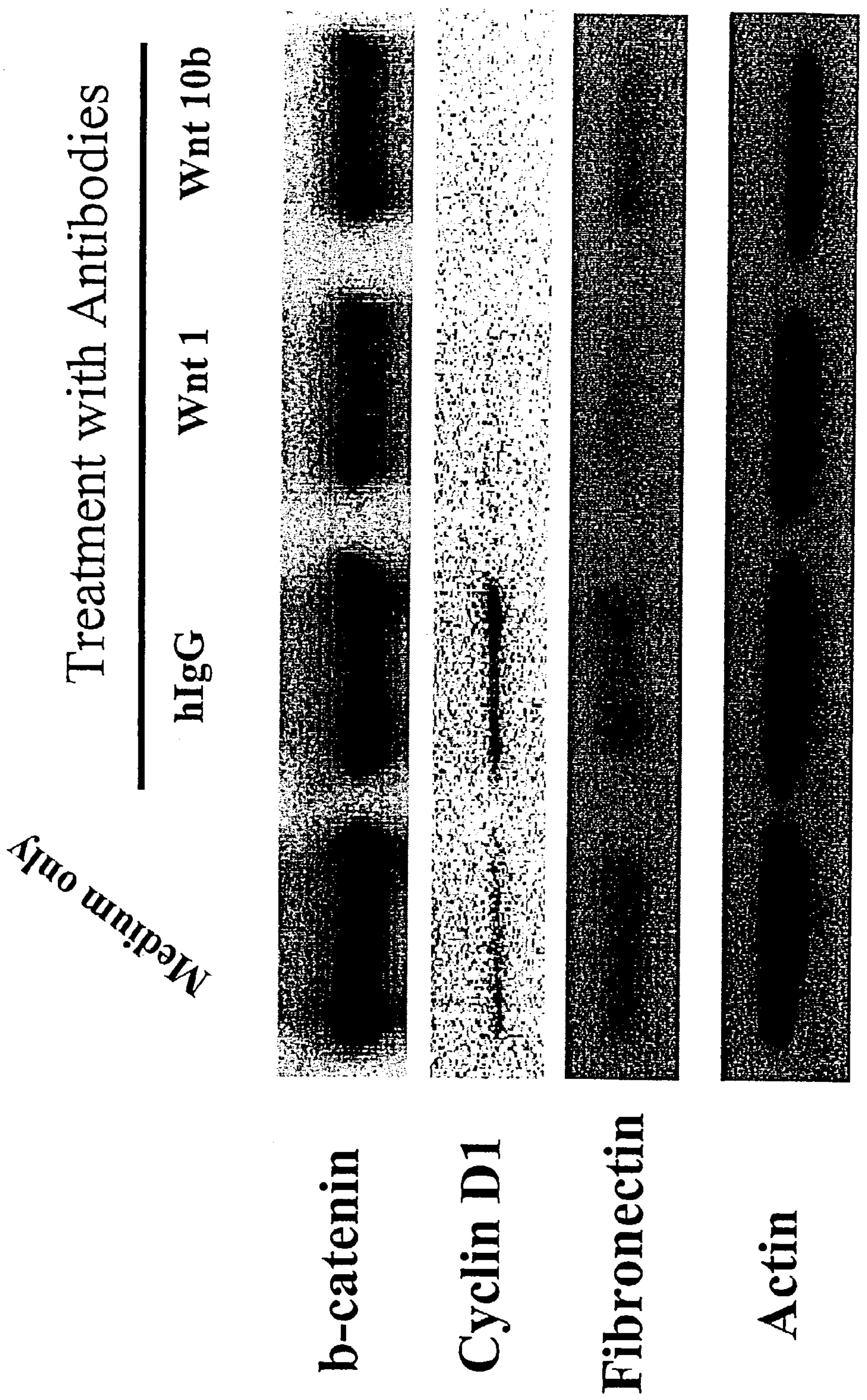
FIGS. 7A and 7B.
Figure 7B:
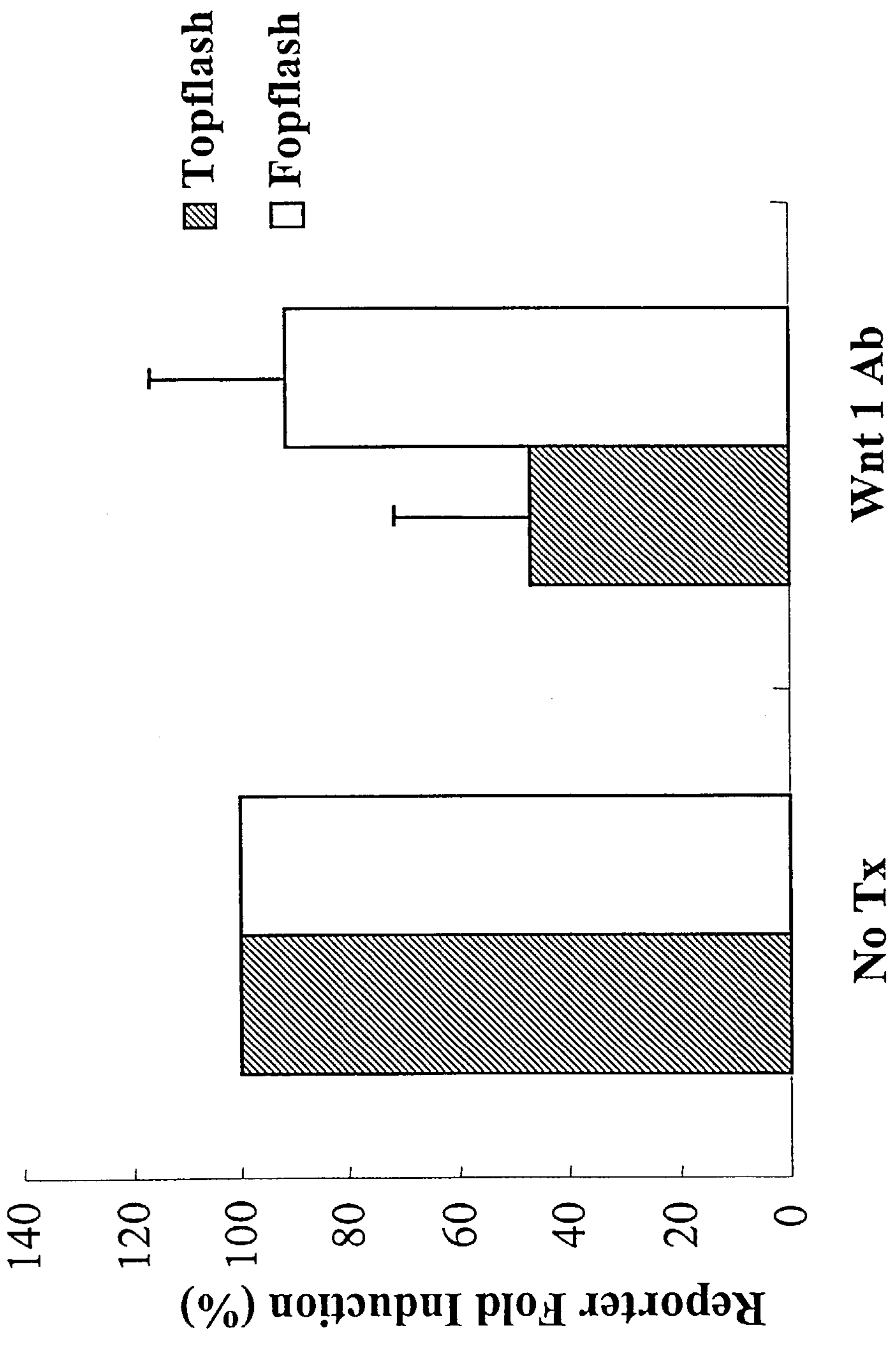

FIGS. 7A and 7B. FIG. 7A: immunoblot after treatment with Wnt 1 or Wnt 10b antibodies. SNU1076 cells were treated for 72 hrs with 2 μg/ml of anti-Wnt 1, Wnt 10b, or control antibodies. Twenty μg of protein from each cell line was separated by SDS-PAGE and transferred to a PVDF membrane. The membrane was immersed in 2% I-block, 0.05% Tween X in PBS and then incubated with a monoclonal anti-human β-catenin, cyclin D1, or fibronectin IgG. These primary antibodies were then detected by horseradish peroxidase-conjugated anti-IgG and chemiluminescence. To verify and compare relative amounts of protein in each lane, PVDF membrane was stripped with Re-Blot™ Western blot recycling kit and reprobed for other antibodies or actin monoclonal antibody. FIG. 7B: treatment with Wnt1 antibodies reduces transcription of TCF/LEF gene. SNU 1076 cells were treated with 2 μg/ml of anti-Wnt-1, or control antibodies for 36 hrs. SNU 1076 cells were cotransfected with 0.5 μg/ml of pTOPFLASH-Luc or pFOPFLASH-Luc-and 0.5 μg/ml of pCMV-βGal. Cells were harvested 24h after transfection, and lysed in lysis buffer. Luciferase and β-galactosidase activities determined using Dual-Light™ reporter gene assay system. Luciferase activities of each of pTOPFLASH-Luc or pFOPFLASH-Luc and β-galactosidase activities of pCMV-βGal were measured in the same sample by luminometer. Transfection efficiency of each sample was normalized by the activity of β-galactosidase activity.

Figure 8A:
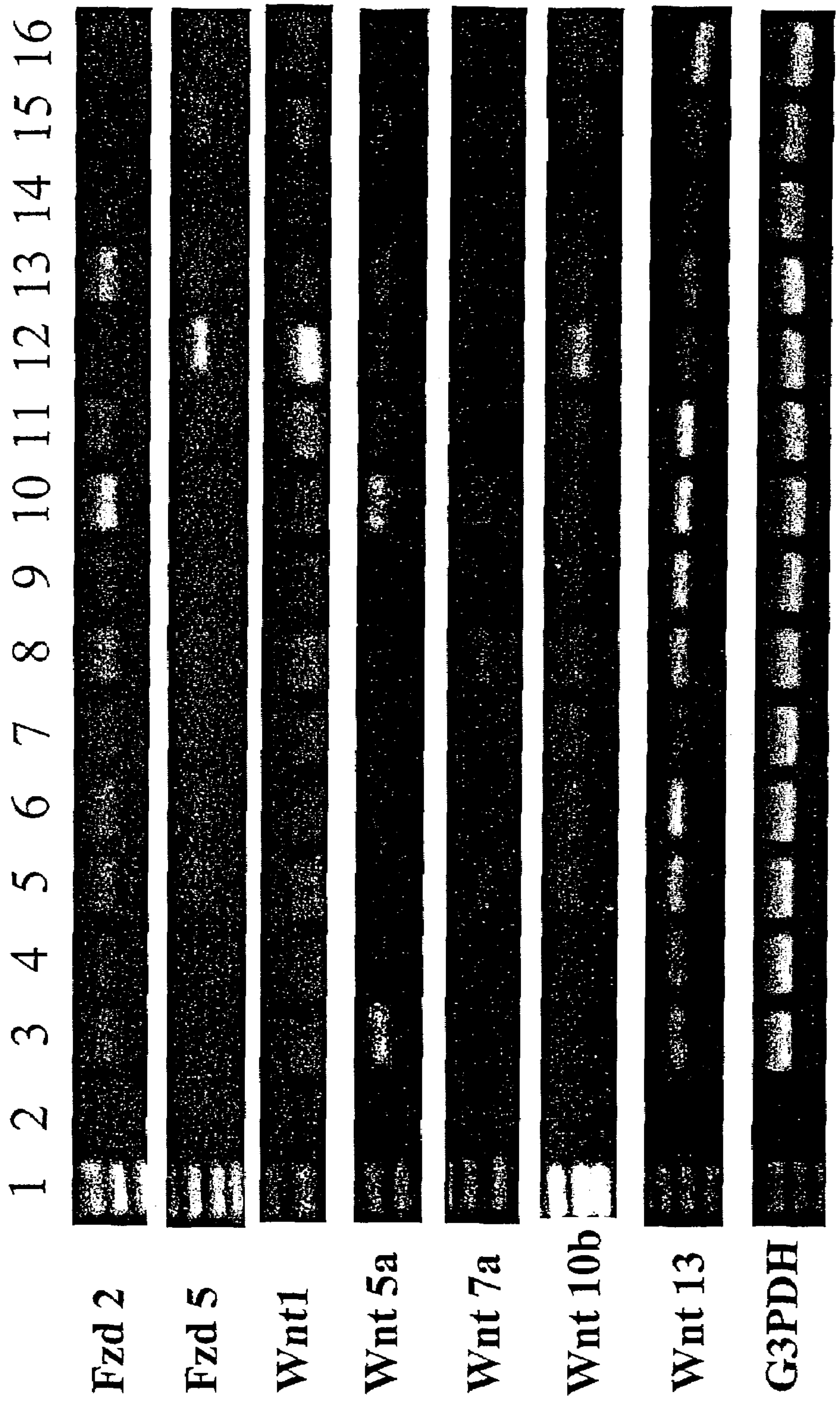
FIGS. 8A and 8B.
Figure 8B:
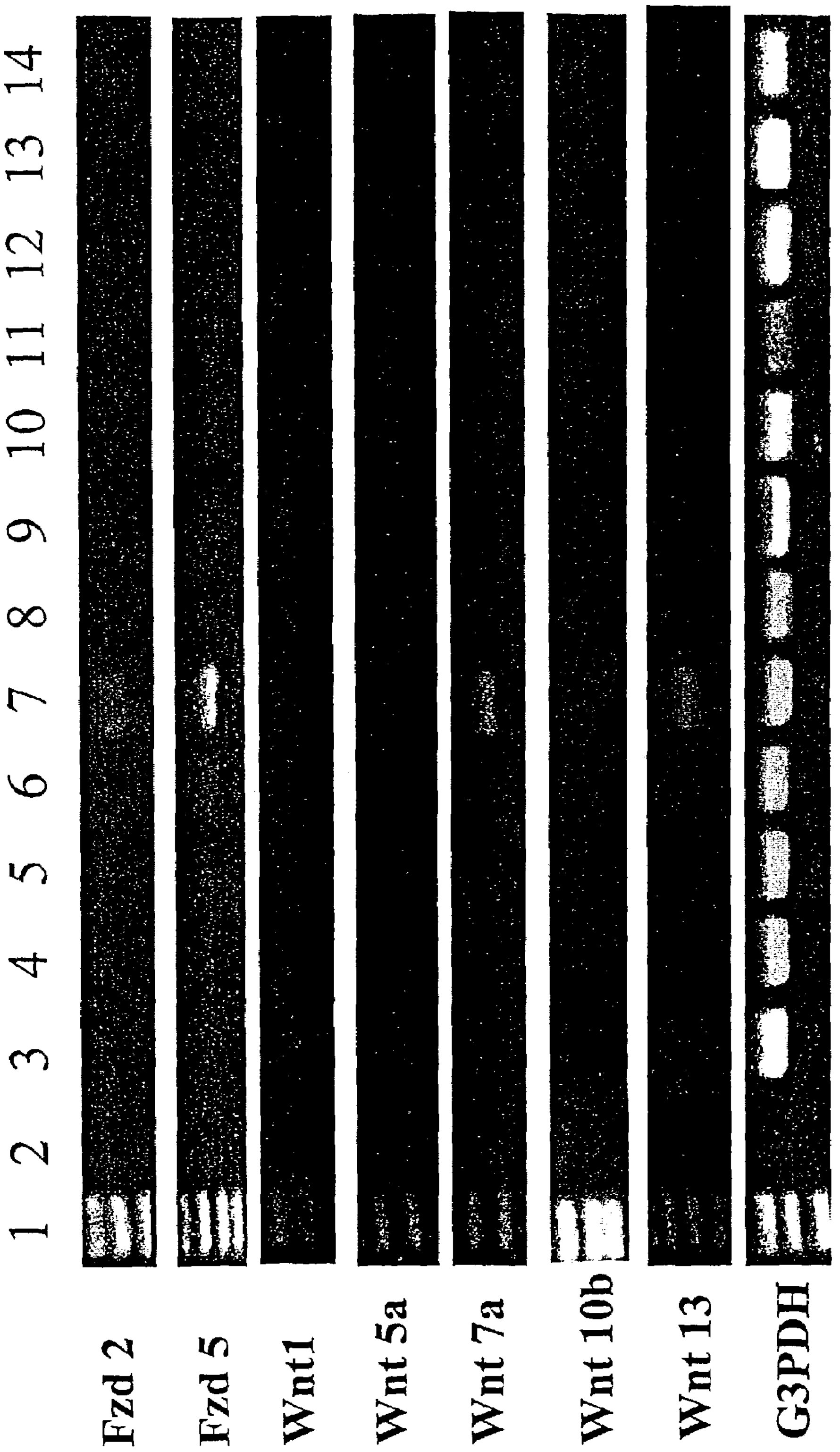

FIGS. 8A and 8B. FIG. 8A: RT-PCR amplification for Wnt/FZD families in cancer cell lines. Lane 1: DNA standard, lane 2: $H_2O$, Lanes 3 and 4: glioblastoma, lanes 5-14: head and neck cancers, lanes 15 and 16: B cell cancers. FIG. 8B: RT-PCR amplification for Wnt/FZD families in normal cells. Lane 1: DNA standard, lane 2: $H_2O$, lanes 7 and 14: normal human bronchial epithelial cell, other lanes: normal oral squamous cells.

Figure 9A:
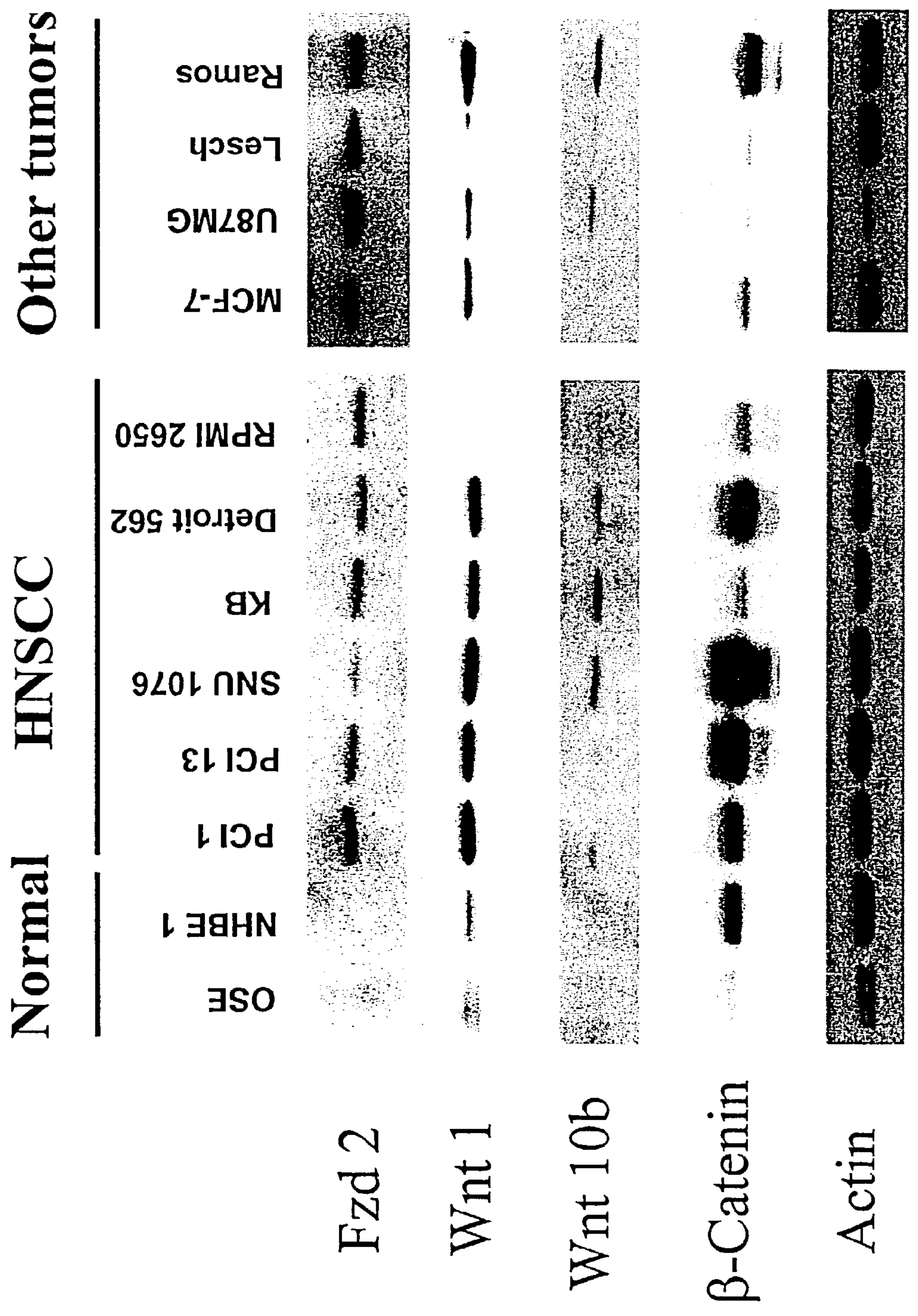
FIGS. 9A and 9B. Protein expression of FZD 2, Wnt 1, Wnt 10b, β-catenin and actin in normal and malignant cells.
Figure 9B:
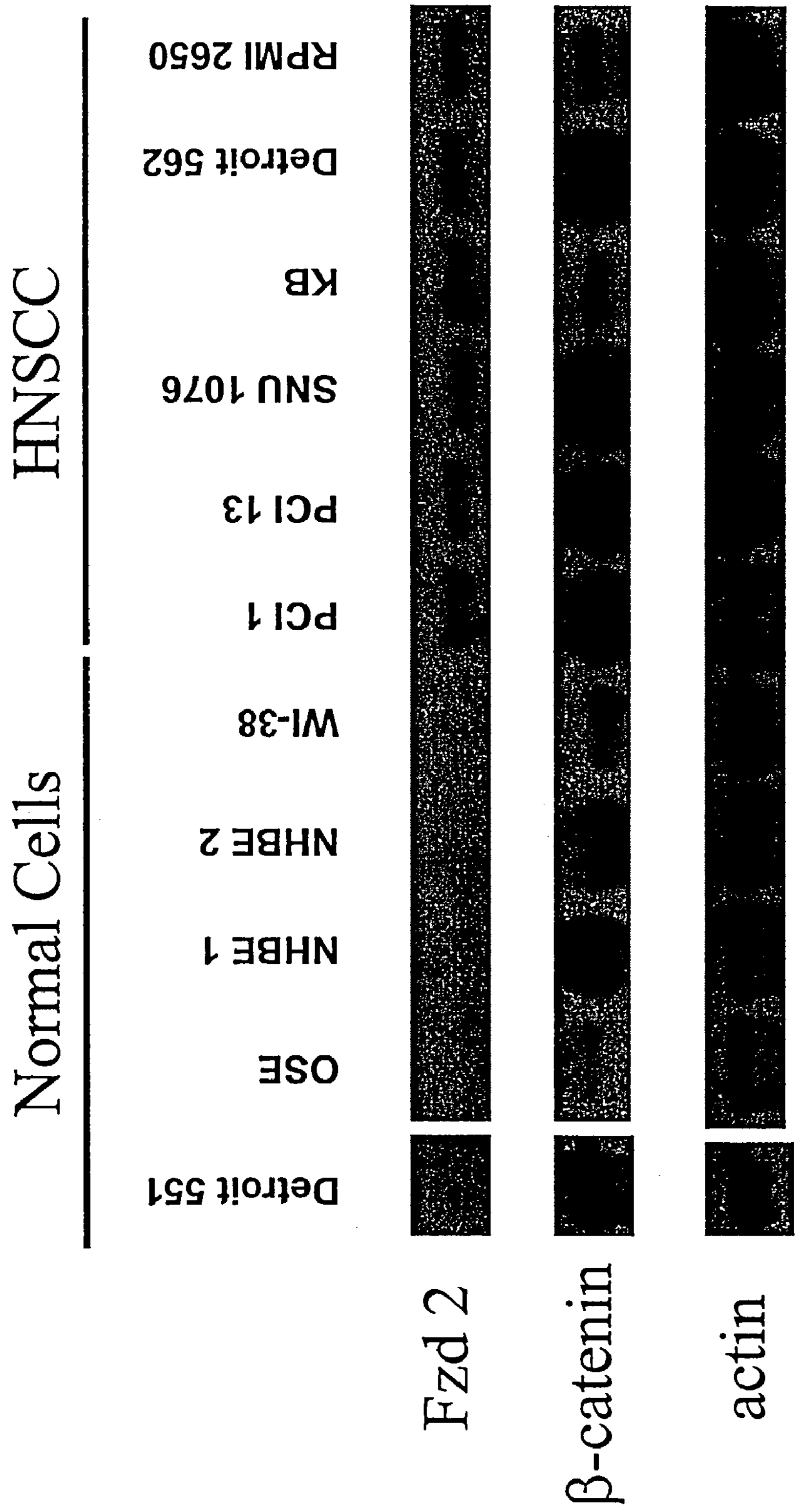

FIGS. 9A and 9B. Protein expression of FZD 2, Wnt 1, Wnt 10b, β-catenin and actin in normal and malignant cells. Normal oral squamous epithelium (OSE), normal human broncheotracheal epithelial cells (NHBE), HNSCC lines, and other solid and B cell tumor lines were lysed, separated by SDS-page, blotted onto PDVF membranes and successively probed with the indicated antibodies.

Figure 10:
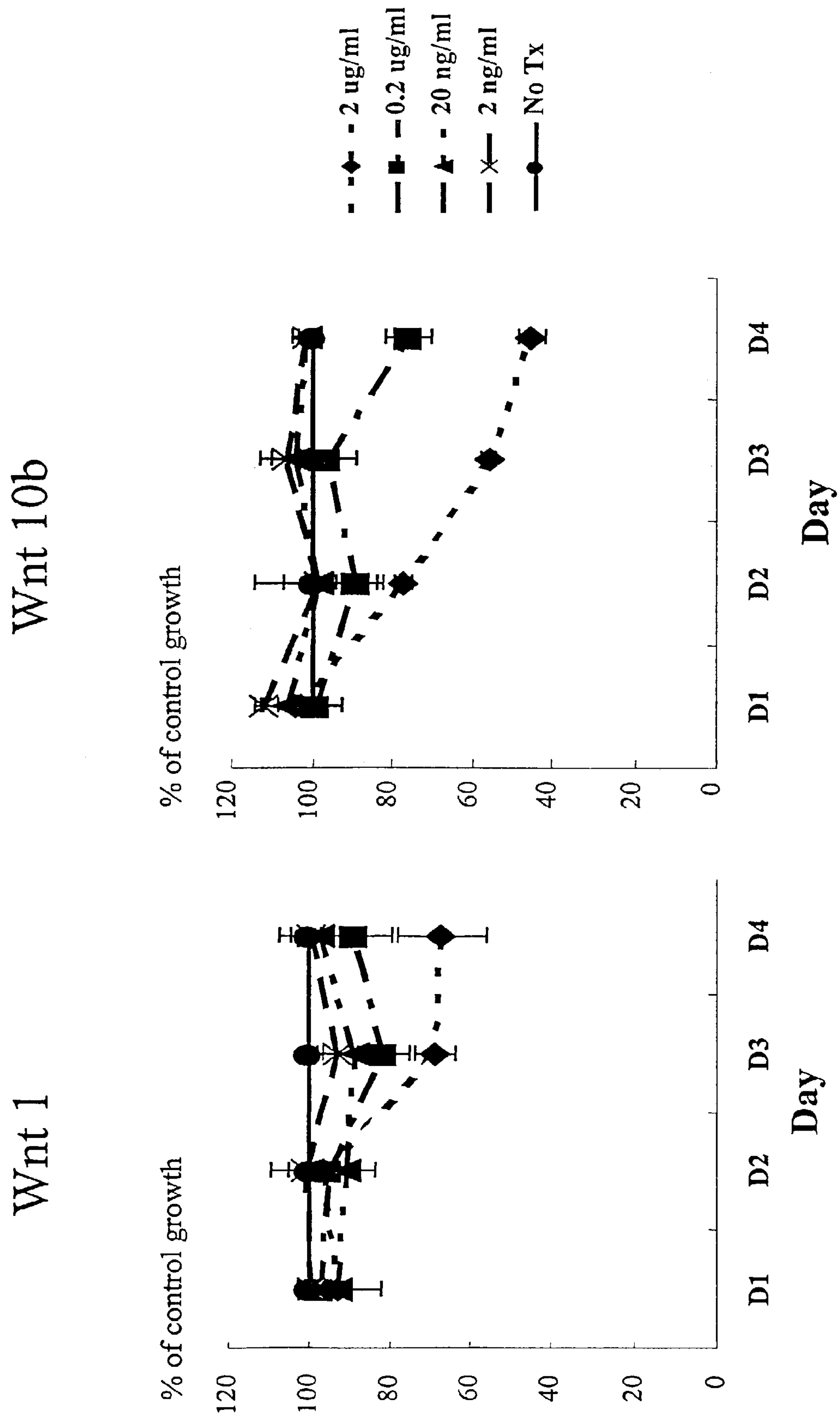
FIG. 10. Inhibition of proliferation of the SNU 1076 cell line Wnt 1 and Wnt 10b.

FIG. 10. Inhibition of proliferation of the SNU 1076 cell line. $7.5\times10^3$ SNU 1076 cells per well were seeded in 96 well plates. After 24 hours, graded amounts of polyclonal goat anti-human Wnt 1, Wnt 10b, or control goat anti-human IgG were added. On days 1, 2, 3, or 4, 20 μL of MTT solution was added to wells for four hours prior to lysis with 15% SDS, 0.015 M HCl. Absorbencies of 570 and 650 nm were measured. Data are expressed as the mean of at least 4 independent experiments±SD.

Figure 11:
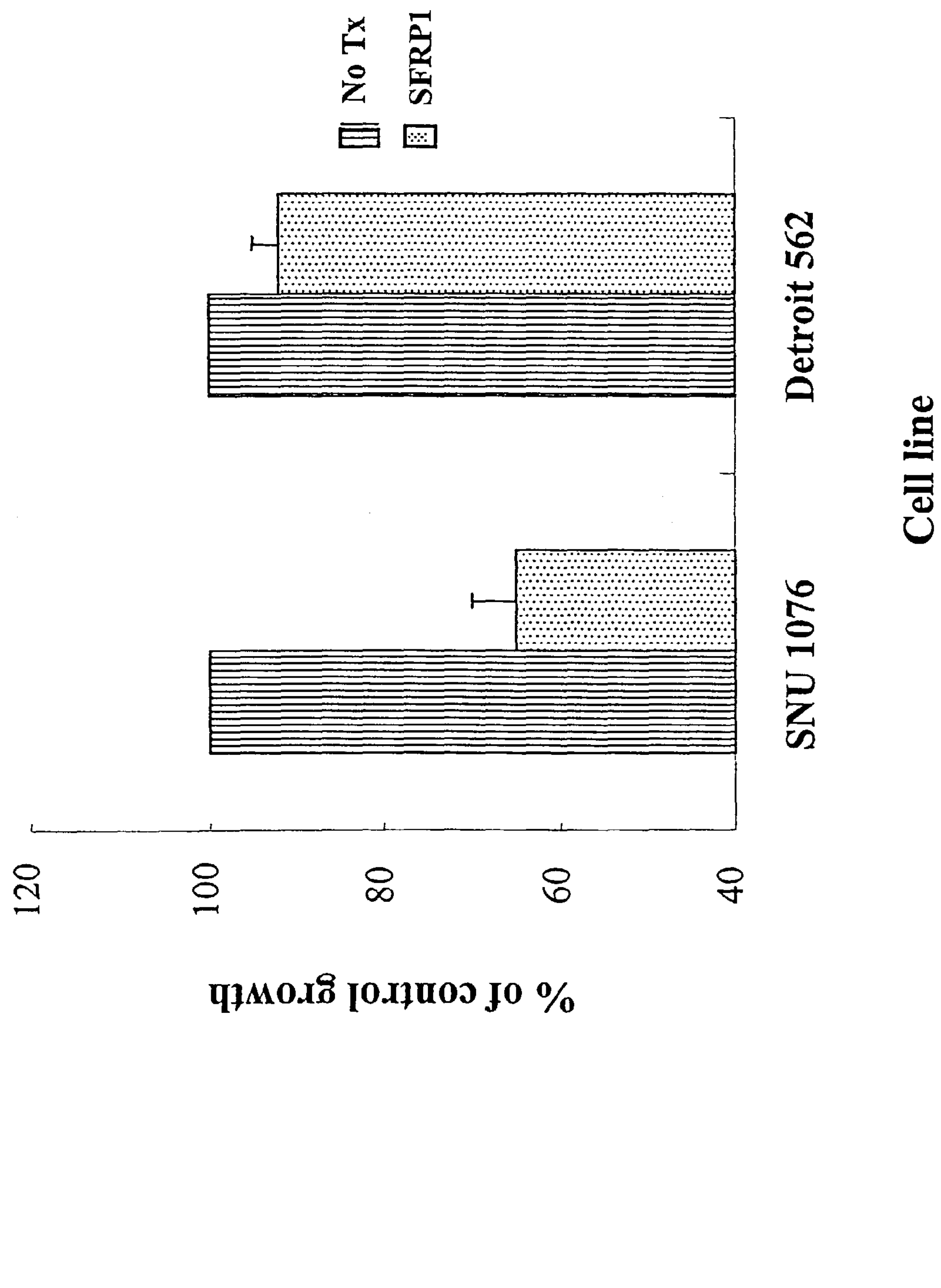
FIG. 11. Growth inhibition with a soluble WNT antagonist, secreted frizzled related protein (SFRP).

FIG. 11. Growth inhibition with a soluble WNT antagonist, secreted frizzled related protein (SFRP). Cell viability of two HNSCC lines was determined with MTT assay 72 hours after addition of 2 μg/ml of recombinant human SFRP 1. Data are expressed as the mean of 2 independent experiments±SD.

Figure 12:
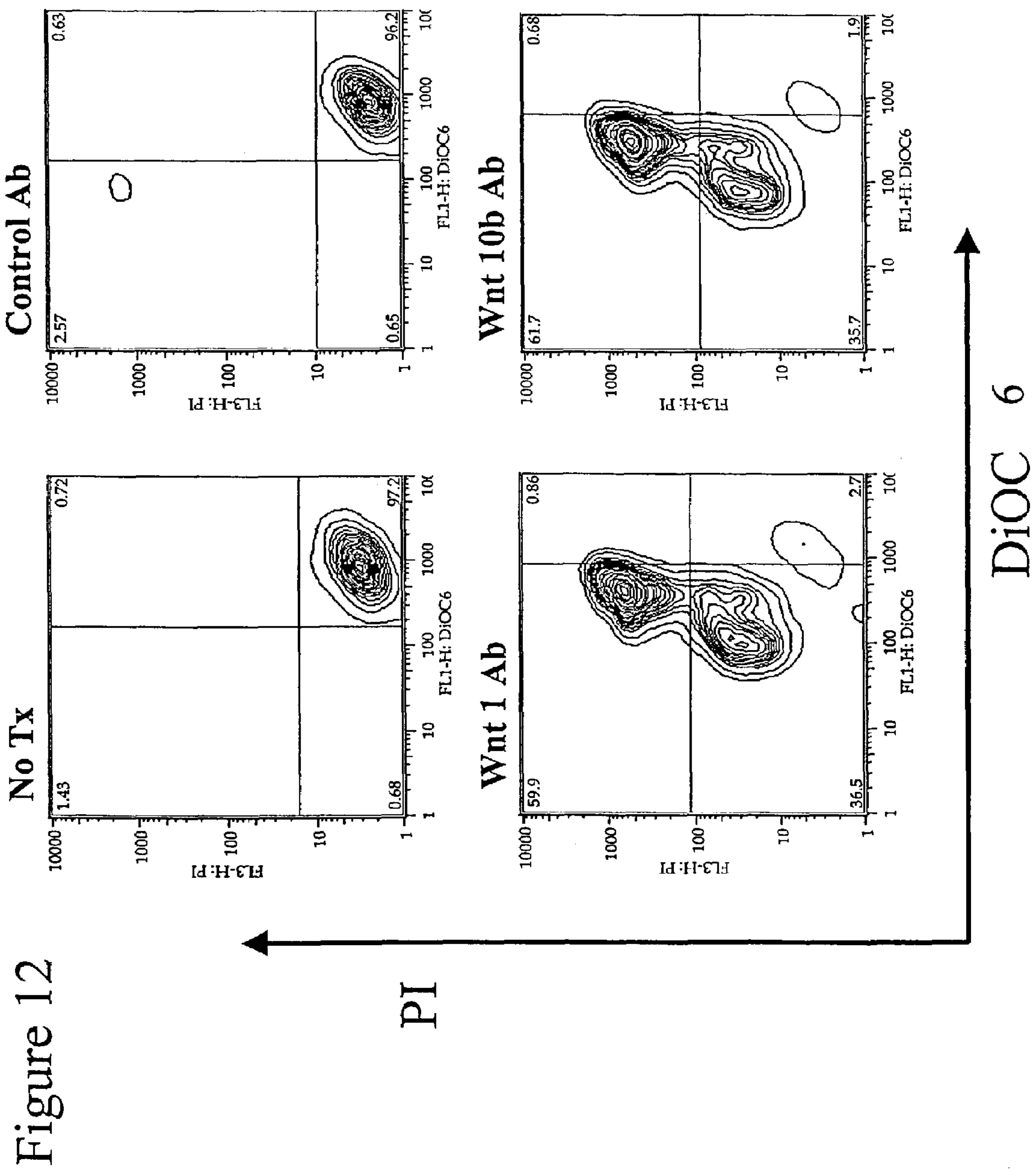
FIG. 12. Apoptotic effect of inhibition of the Wnt/Frizzled signaling pathway in a HNSCC line.

FIG. 12. Apoptotic effect of inhibition of the Wnt/Frizzled signaling pathway in a HNSCC line. SNU1076 was treated for 72 hrs with 2 μg/ml of anti-Wnt 1, Wnt 10b, or control antibodies. The cytotoxic effects of these antibodies were assessed by vital dye retention and DNA content. Cells were detached from the flasks by trypsin treatment and incubated for 10 minutes in growing medium with 5 μg/ml Propidium iodide (PI) and 40 nM $DiOC_6$ and analyzed by flow cytometry. Viable cells had high $DiOC_6$ (FL-1) and low PI (FL-3) fluorescence, and apoptotic cells had low $DiOC_6$ (FL-1) and low PI (FL-3) fluorescence.

FIGS. 13A and 13B. Primer sequences for wnt, fzd, and wnt-related gene analysis. FIG. 13A shows primers and probes used for analysis of wnt and fzd nucleic acid expression (SEQ ID NOS:68-152). FIG. 13B shows primers and probes used for analysis of expression of Frp, WISP, DKK, and other wnt/fzd inducible genes or controls (SEQ ID NOS: 153-206). Levels of wnt fzd and wnt-related genes were determined with real time PCR using the depicted primers and probes.

Figure 14:
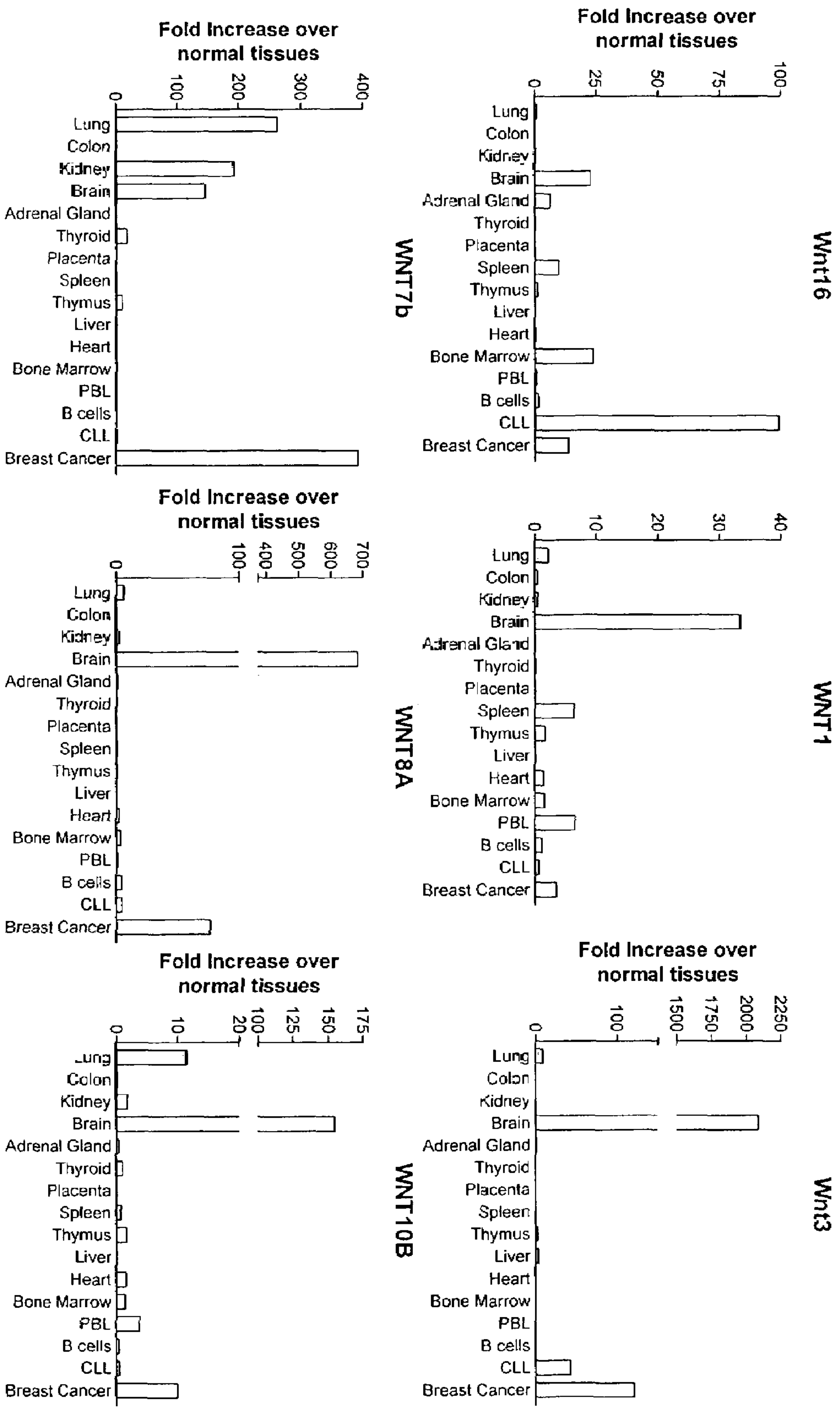
FIG. 14. Expression of wnt's in non-tumor and tumor tissues.

FIG. 14. Expression of wnt's in non-tumor and tumor tissues. Levels of wnt16, wnt1, wnt3, wnt7b, wnt8a, and wnt10b were determined in normal cells from lung, colon, kidney, brain, adrenal gland, thyroid, placenta, spleen, thymus, liver, heart, bone marrow, and peripheral blood lymphocytes. Levels of wnt16, wnt1, wnt3, wnt7b, wnt8a, and wnt10b were also determined in primary CLL cells and in breast cancer tumors. The data in the figures are relative, with the lowest normal tissue level assigned a value of one. Thus, a relative value of 100 in breast cancer or CLL means that the cancer cells had 100 times the values of the lowest normal tissue, as reported by real time PCR.

Figure 15:
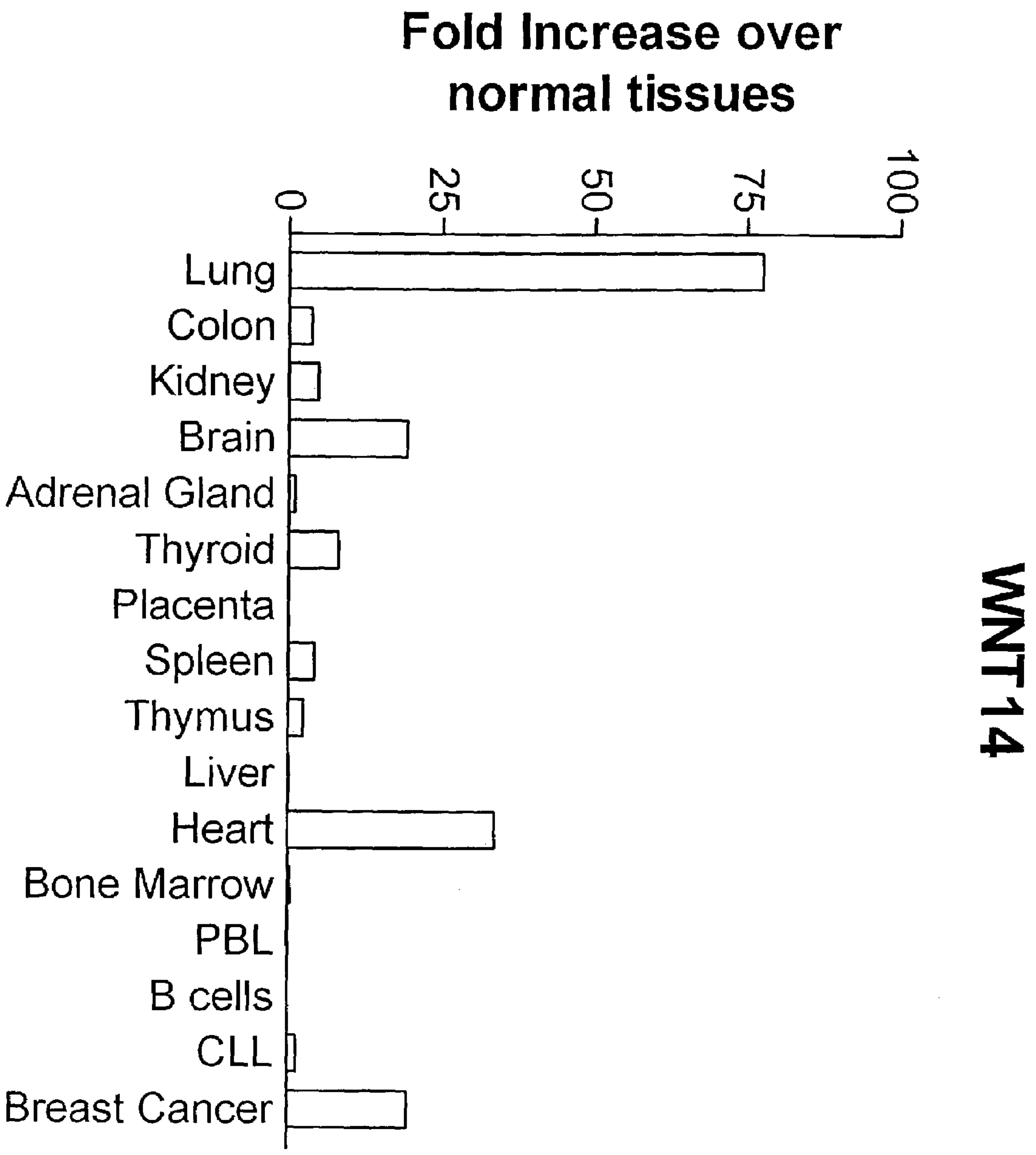
FIG. 15. Expression of wnt 14 in non-tumor and tumor tissues.

FIG. 15. Expression of wnt14 in normal and non-tumor tissues. Levels of wnt 14 were determined in normal cells from lung, colon, kidney, brain, adrenal gland, thyroid, placenta, spleen, thymus, liver, heart, bone marrow, and peripheral blood lymphocytes. Levels of wnt14 were also determined in primary CLL cells and in breast cancer tumors. Data were analyzed as in FIG. 14.

Figure 16:
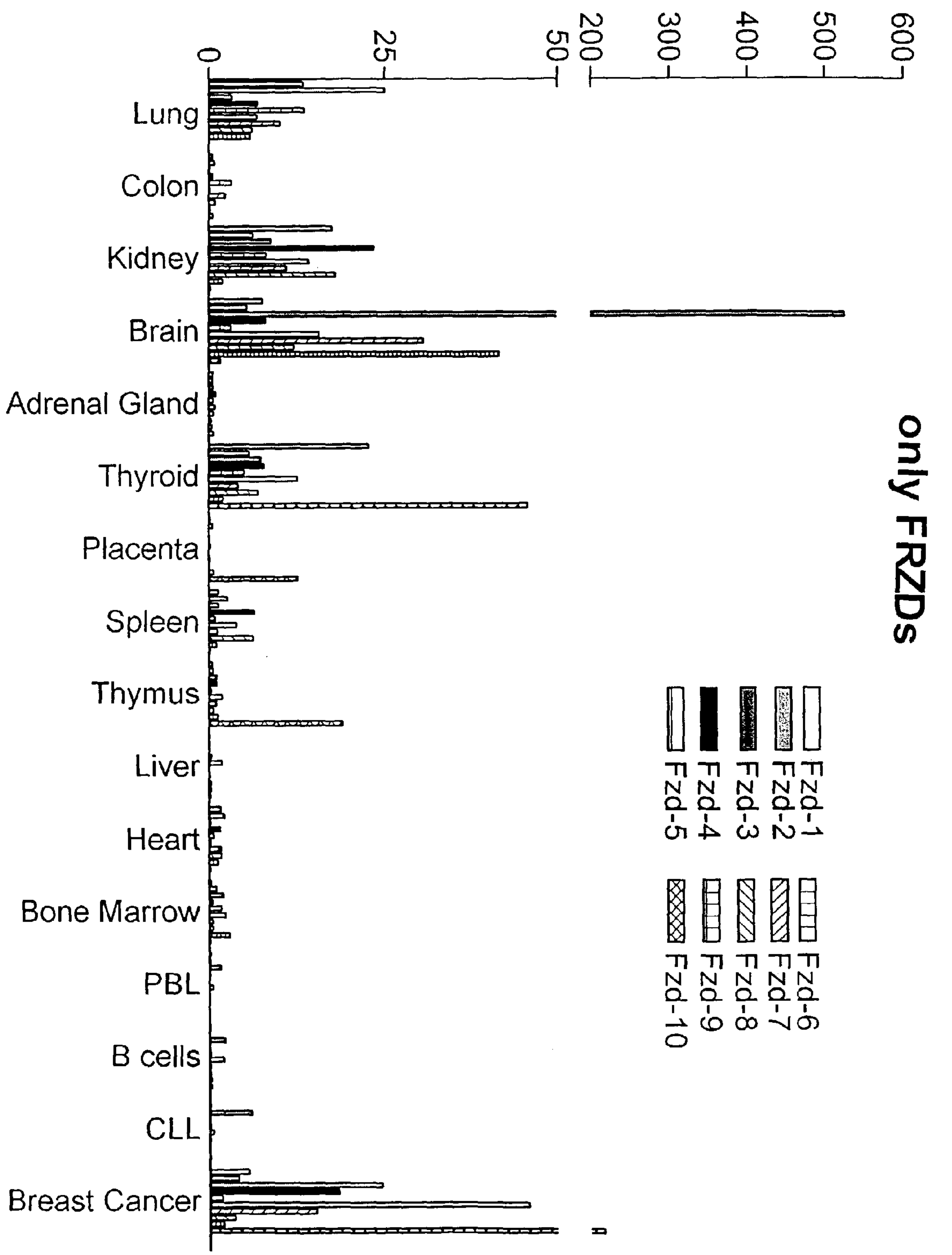
FIG. 16. Expression of fzd's in non-tumor and tumor tissues.

FIG. 16. Expression of fzd's in non-tumor and tumor tissues. Levels of fzd1, fzd2, fzd3, fzd4, fzd5, fzd6, fzd7, fzd8, fzd9, and fzd10 were determined in normal cells from lung, colon, kidney, brain, adrenal gland, thyroid, placenta, spleen, thymus, liver, heart, bone marrow, and peripheral blood lymphocytes. Levels of fzd1, fzd2, fzd3, fzd4, fzd5, fzd6, fzd7, fzd8, fzd9, and fzd10 were also determined in primary CLL cells and in breast cancer tumors. Data were analyzed as in FIG. 14.

Figure 17:
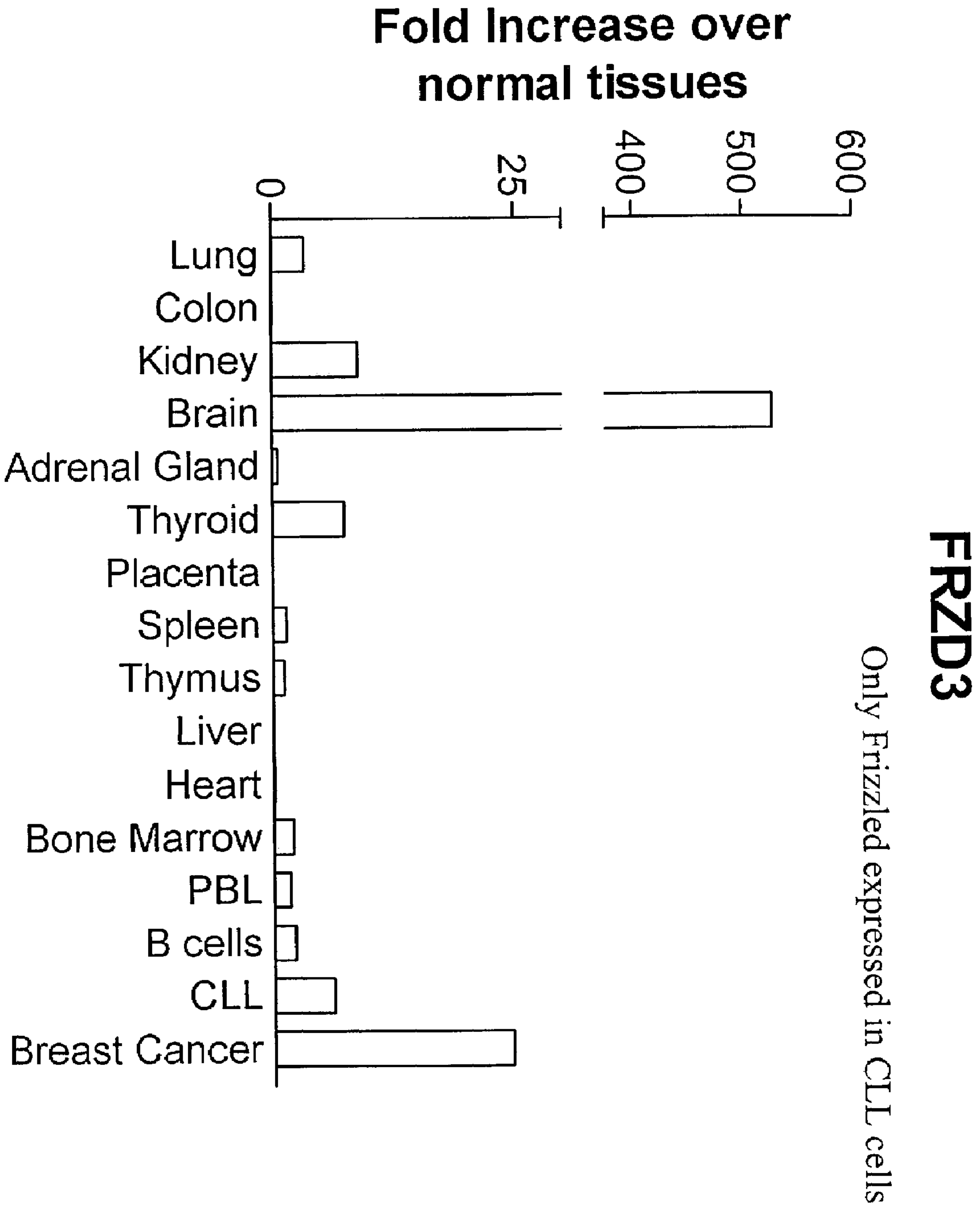
FIG. 17. Expression of fzd3 in non-tumor and tumor tissues.

FIG. 17. Expression of fzd3 in non-tumor and tumor tissues. Levels of fzd3 were determined in normal cells from lung, colon, kidney, brain, adrenal gland, thyroid, placenta, spleen, thymus, liver, heart, bone marrow, and peripheral blood lymphocytes. Levels of fzd3 were also determined in primary CLL cells and in breast cancer tumors. Data were analyzed as in FIG. 14.

Figure 18:
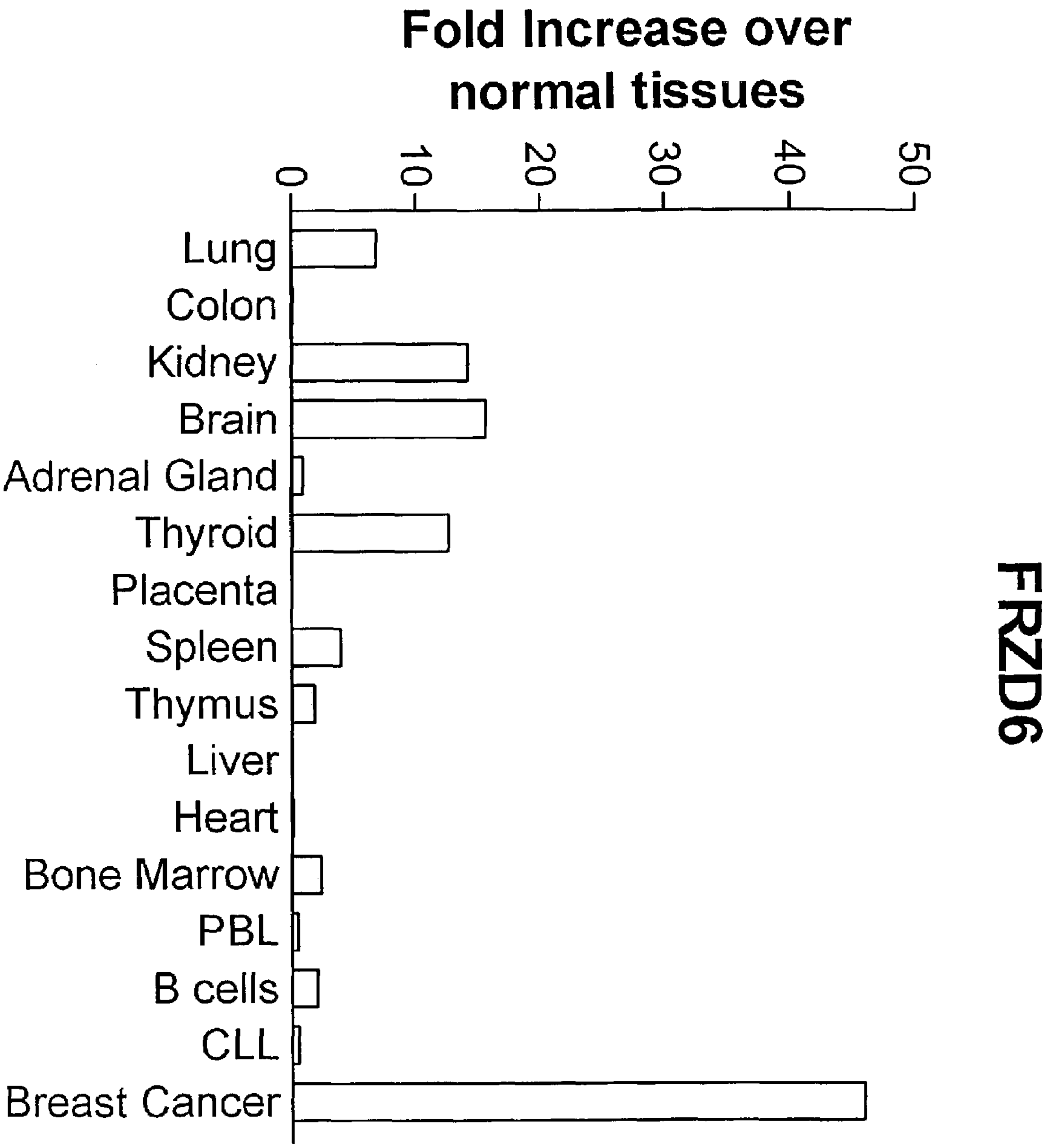
FIG. 18. Expression of fzd6 in non-tumor and tumor tissues.

FIG. 18. Expression of fzd6 in non-tumor and tumor tissues. Levels of fzd6 were determined in normal cells from lung, colon, kidney, brain, adrenal gland, thyroid, placenta, spleen, thymus, liver, heart, bone marrow, and peripheral blood lymphocytes. Levels of fzd6 were also determined in primary CLL cells and in breast cancer tumors. Data were analyzed as in FIG. 14.

Figure 19:
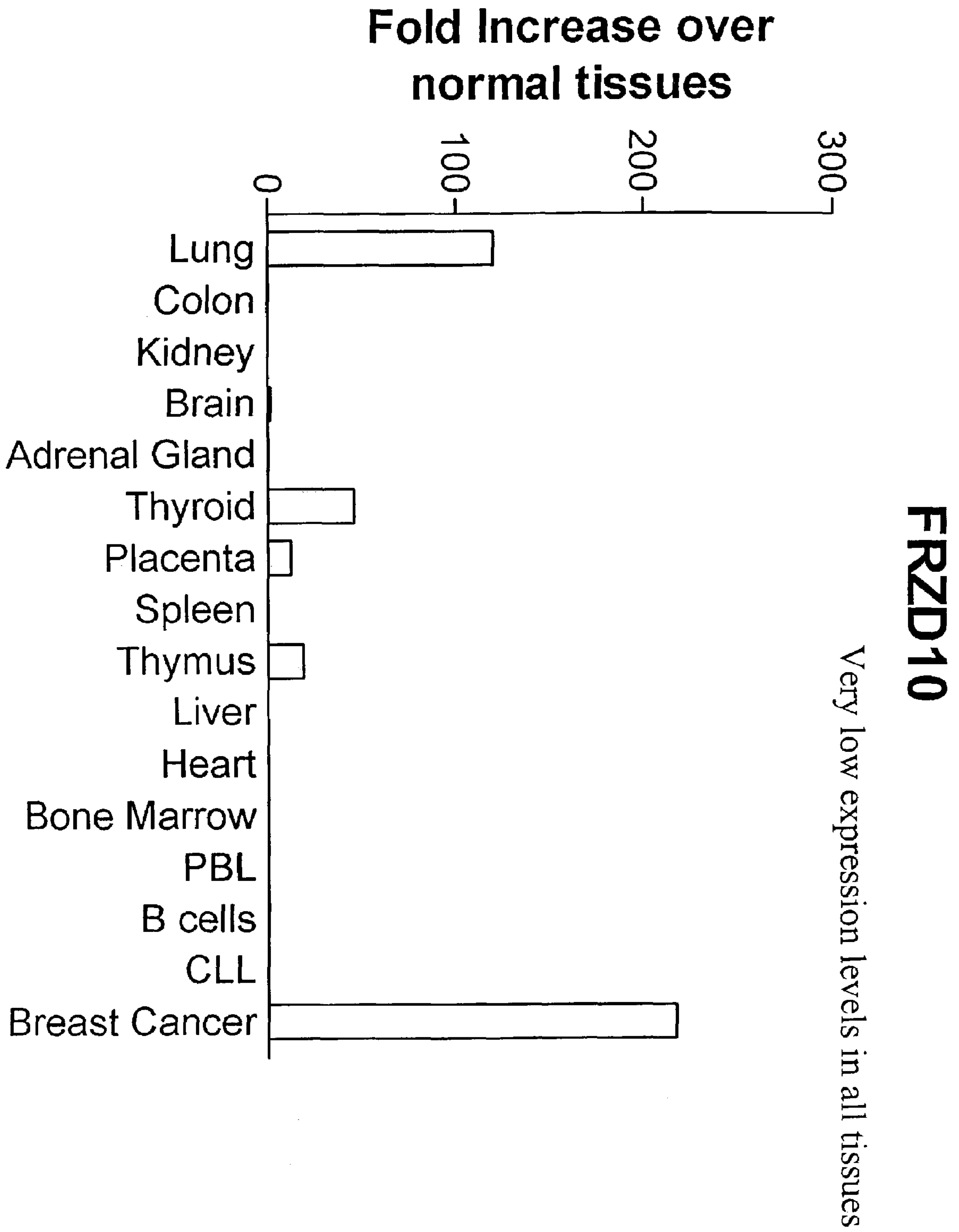
FIG. 19. Expression of fzd10 in non-tumor and tumor tissues.

FIG. 19. Expression of fzd10 in non-tumor and tumor tissues. Levels of fzd10 were determined in normal cells from lung, colon, kidney, brain, adrenal gland, thyroid, placenta, spleen, thymus, liver, heart, bone marrow, and peripheral blood lymphocytes. Levels of fzd10 were also determined in primary CLL cells and in breast cancer tumors. Data were analyzed as in FIG. 14.

Figure 20:
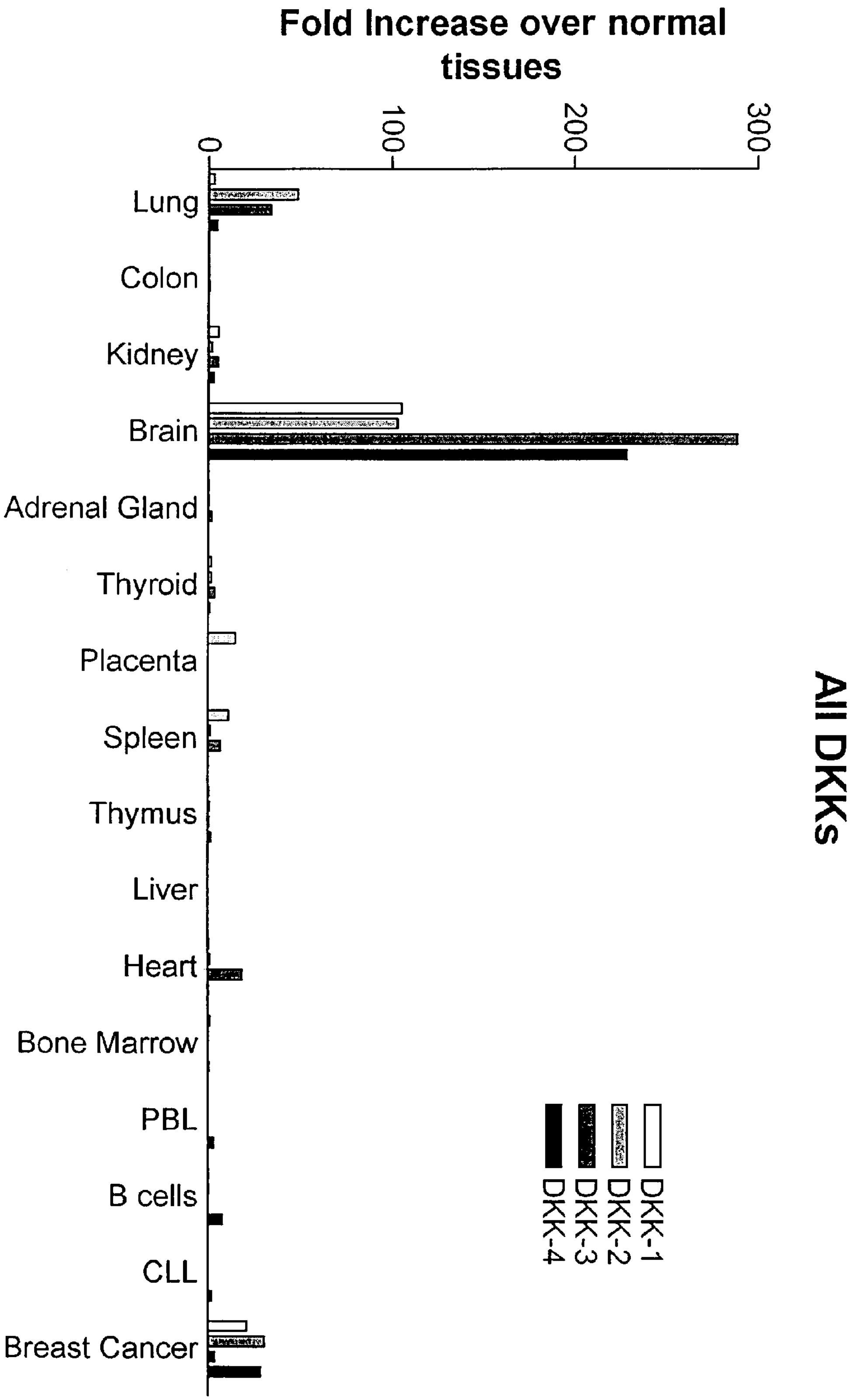
FIG. 20. Expression of DKK's in non-tumor and tumor tissues.

FIG. 20. Expression of DKK's in non-tumor and tumor tissues. Levels of DKK-1, DKK-2, DKK-3, and DKK-4 were determined in normal cells from lung, colon, kidney, brain, adrenal gland, thyroid, placenta, spleen, thymus, liver, heart, bone marrow, and peripheral blood lymphocytes. Levels of DKK-1, DKK-2, DKK-3, and DKK-4, were also determined in primary CLL cells and in breast cancer tumors. Data were analyzed as in FIG. 14.

Figure 21:
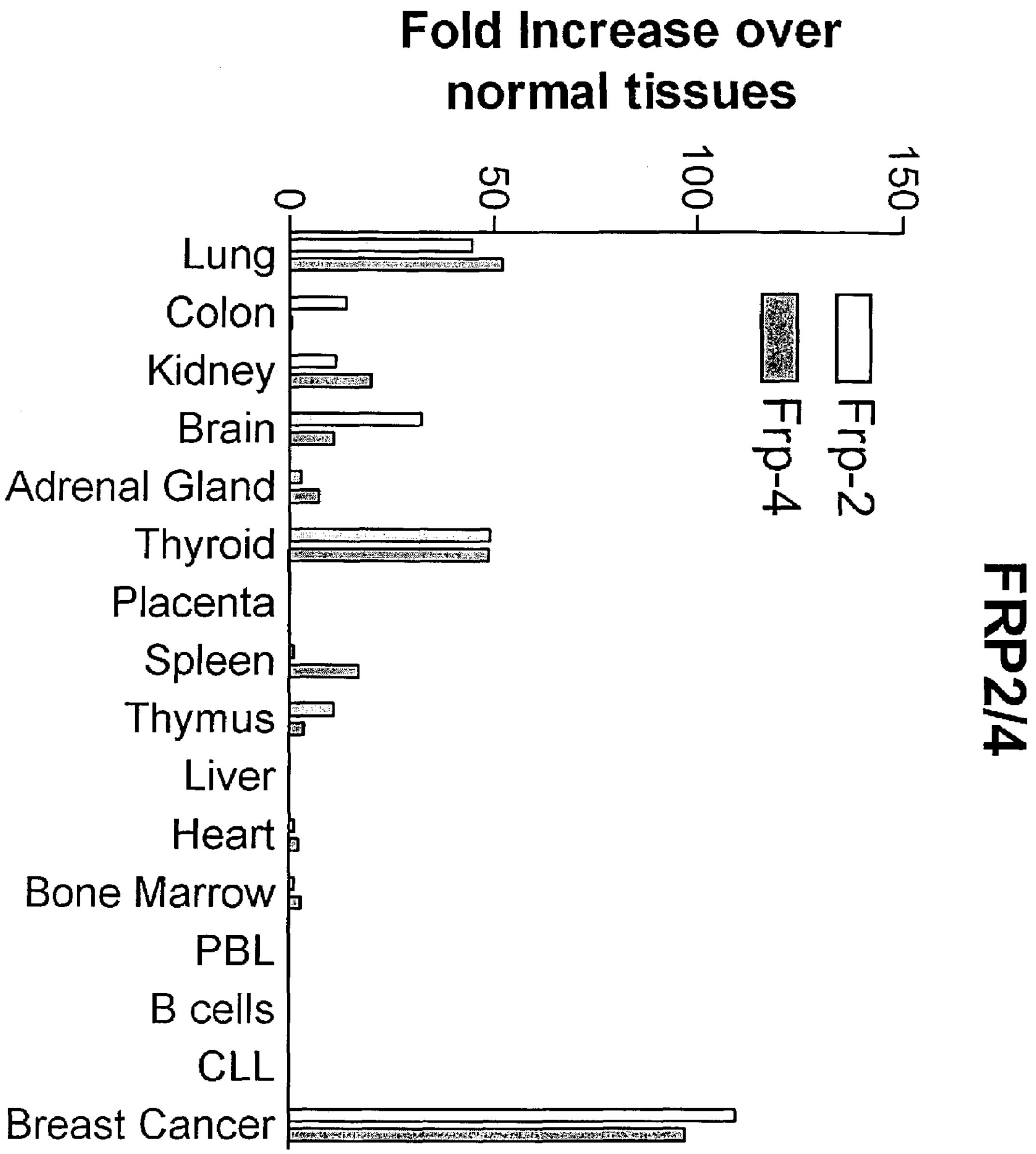
FIG. 21. Expression of FRP2/4 in non-tumor and tumor tissues.

FIG. 21. Expression of FRP2/4 in non-tumor and tumor tissues. Levels of FRP-2 and FRP-4 were determined in normal cells from lung, colon, kidney, brain, adrenal gland, thyroid, placenta, spleen, thymus, liver, heart, bone marrow, and peripheral blood lymphocytes. Levels of FRP-2 and FRP-4 were also determined in primary CLL cells and in breast cancer tumors. Data were analyzed as in FIG. 14.

Figure 22:
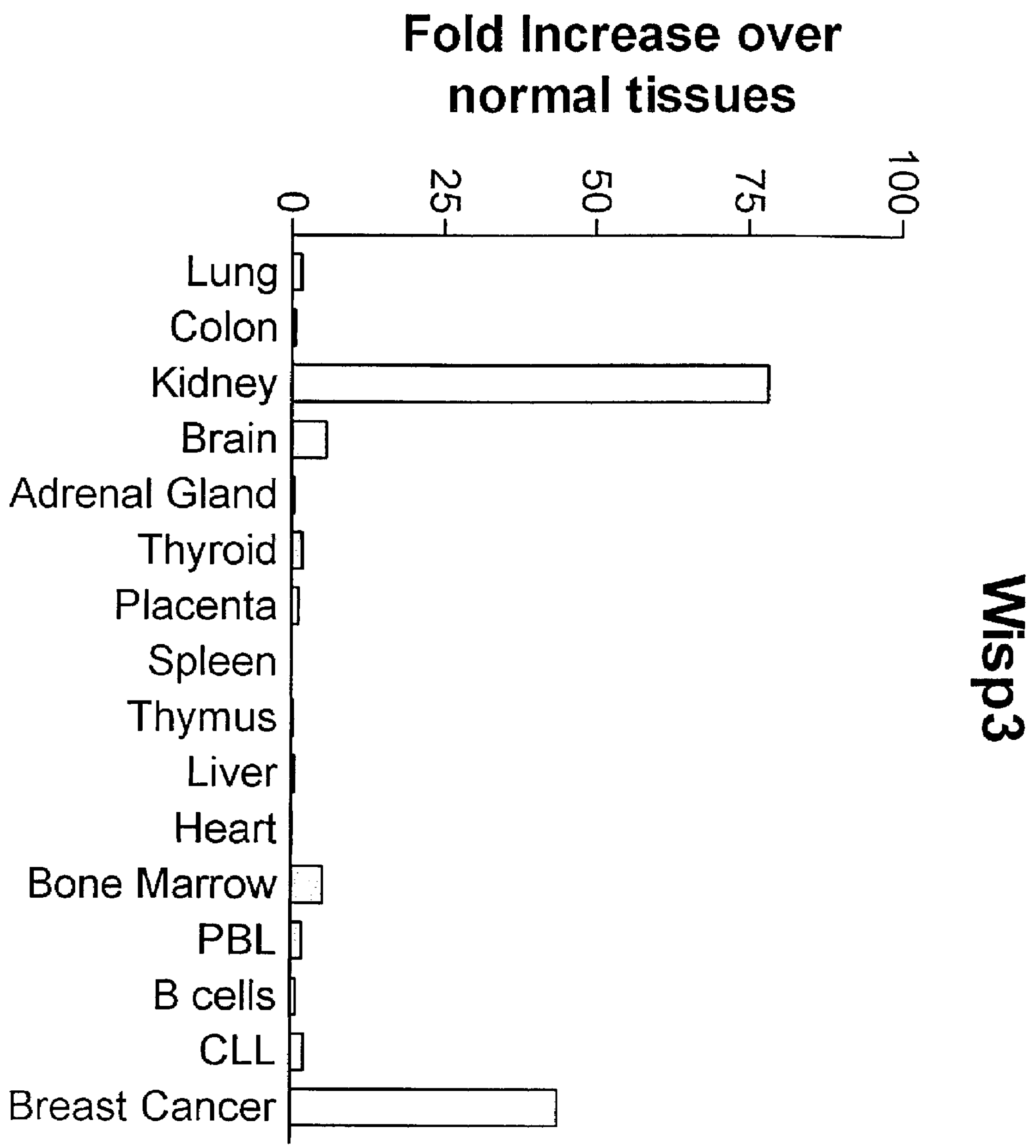
FIG. 22. Expression of WISP3 in non-tumor and tumor tissues.

FIG. 22. Expression of WISP3 in non-tumor and tumor tissues. Levels of WISP3 were determined in normal cells from lung, colon, kidney, brain, adrenal gland, thyroid, placenta, spleen, thymus, liver, heart, bone marrow, and peripheral blood lymphocytes. Levels of WISP3 were also determined in primary CLL cells and in breast cancer tumors. Data were analyzed as in FIG. 14.

Figure 23:
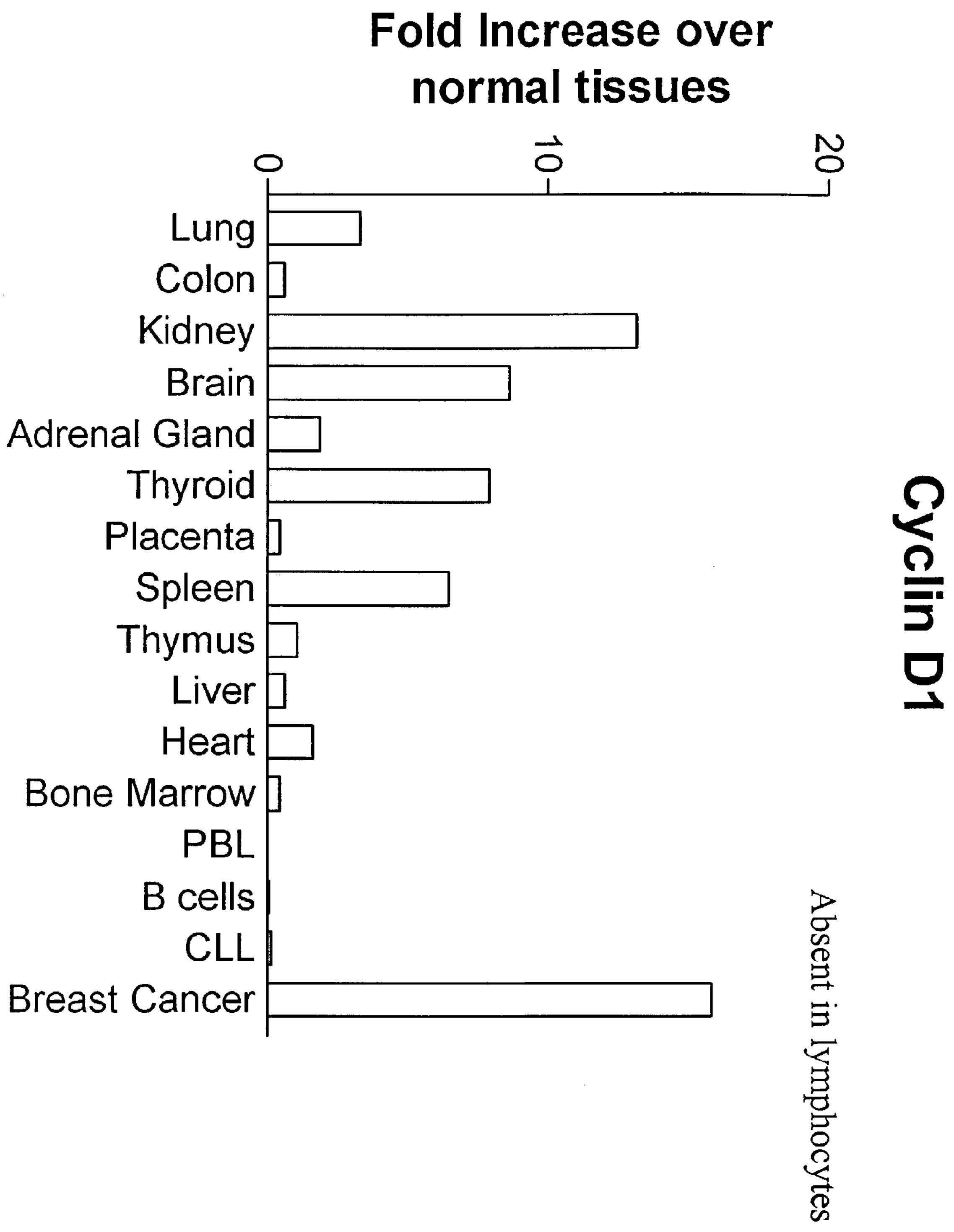
FIG. 23. Expression of cyclin D1 in non-tumor and tumor tissues.

FIG. 23. Expression of cyclin D1 sin non-tumor and tumor tissues. Levels of cyclin D1 were determined in normal cells from lung, colon, kidney, brain, adrenal gland, thyroid, placenta, spleen, thymus, liver, heart, bone marrow, and peripheral blood lymphocytes. Levels of cyclin D1 were also determined in primary CLL cells and in breast cancer tumors. Data were analyzed as in FIG. 14.

Figure 24:
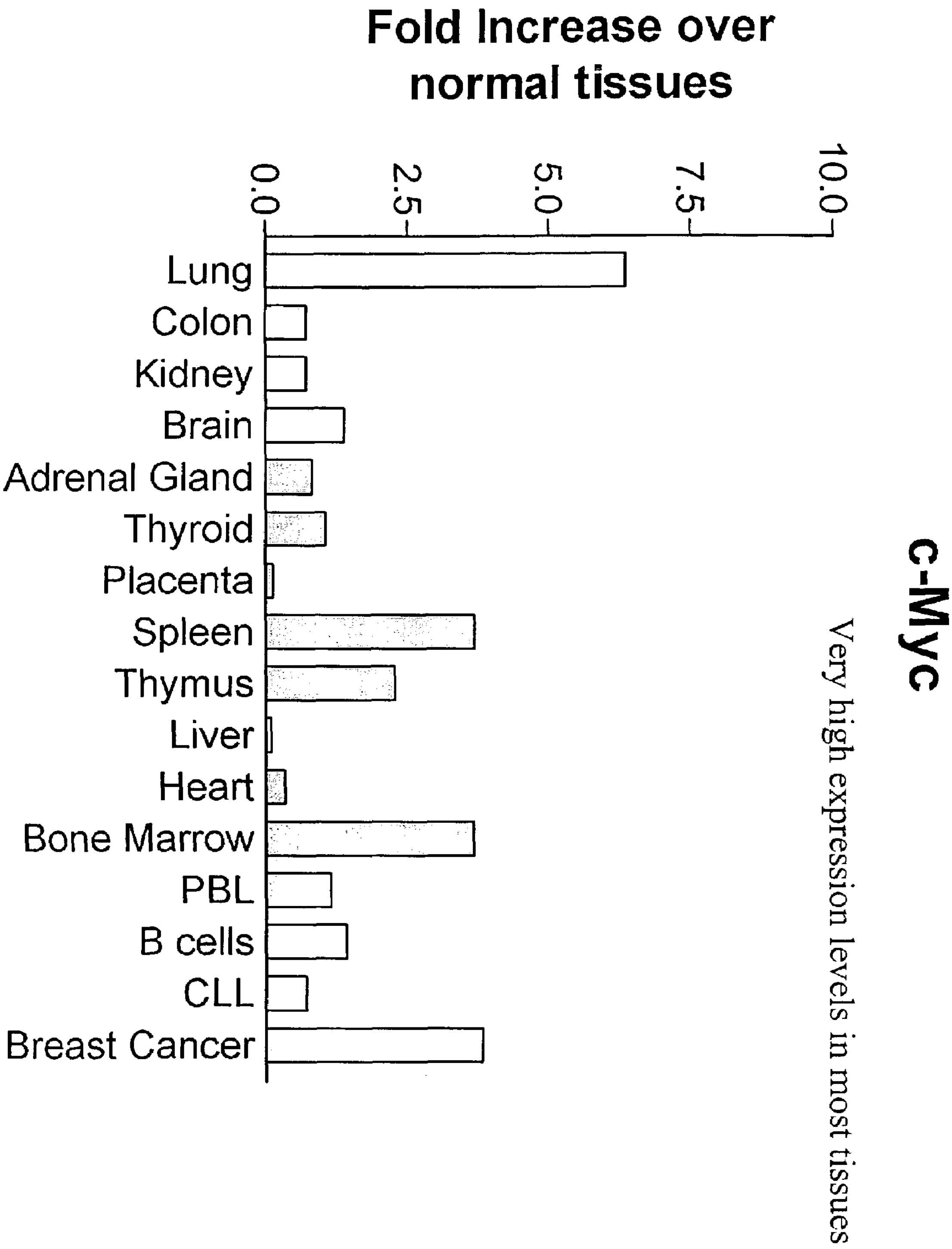
FIG. 24. Expression of c-myc in non-tumor and tumor tissues.

FIG. 24. Expression of c-myc in non-tumor and tumor tissues. Levels of c-myc were determined in normal cells from lung, colon, kidney, brain, adrenal gland, thyroid, placenta, spleen, thymus, liver, heart, bone marrow, and peripheral blood lymphocytes. Levels of c-myc were also determined in primary CLL cells and in breast cancer tumors. Data were analyzed as in FIG. 14.

Figure 25:
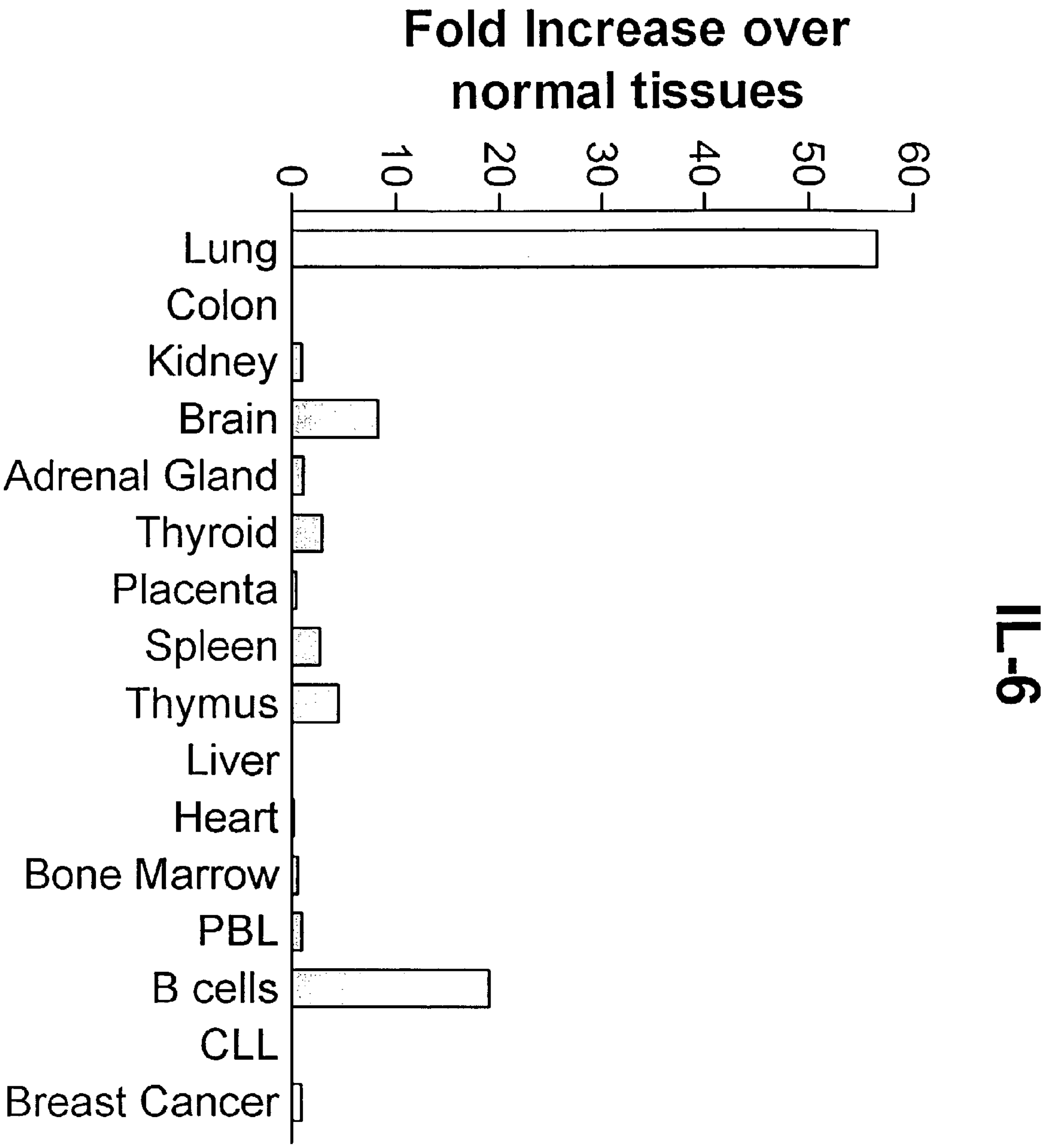
FIG. 25. Expression of IL-6 in non-tumor and tumor tissues.

FIG. 25. Expression of IL-6 in non-tumor and tumor tissues. Levels of IL-6 were determined in normal cells from lung, colon, kidney, brain, adrenal gland, thyroid, placenta, spleen, thymus, liver, heart, bone marrow, and peripheral blood lymphocytes. Levels of IL-6 were also determined in primary CLL cells and in breast cancer tumors. Data were analyzed as in FIG. 14.

Figure 26:
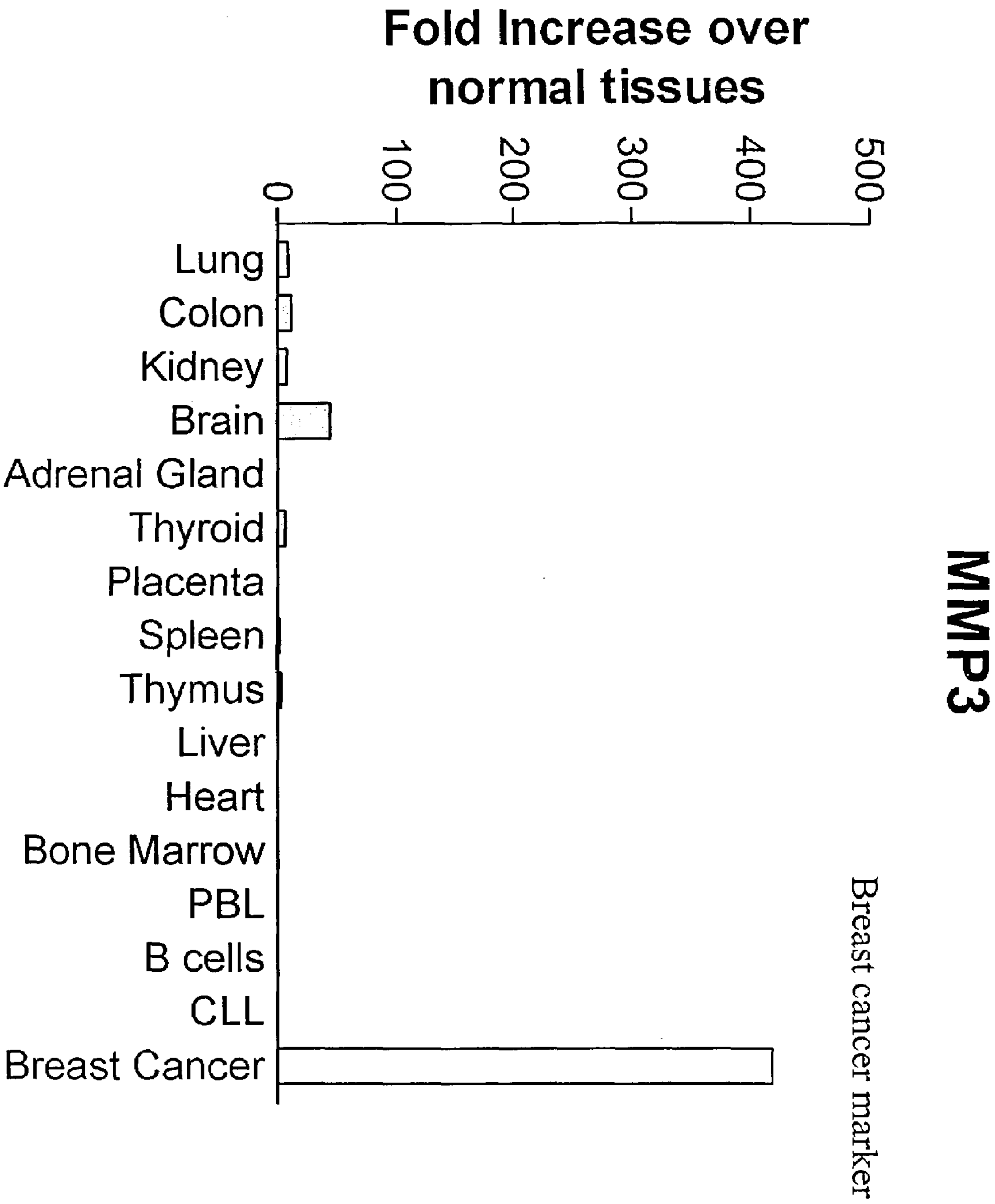
FIG. 26. Expression of MMP3 in non-tumor and tumor tissues.

FIG. 26. Expression of MMP3 in non-tumor and tumor tissues. Levels of MMP3 were determined in normal cells from lung, colon, kidney, brain, adrenal gland, thyroid, placenta, spleen, thymus, liver, heart, bone marrow, and peripheral blood lymphocytes. Levels of MMP3 were also determined in primary CLL cells and in breast cancer tumors. Data were analyzed as in FIG. 14.

FIG. 27. Expression of wnt, fzd, and wnt-related genes in non-tumor cells and breast cancer cells. Levels of wnt, fzd, and wnt-related genes wre determined in normal cells and breast cancer cells. Results are expressed as fold induction. Data were analyzed as in FIG. 14.

DETAILED DESCRIPTION OF THE INVENTION

This invention is based, at least in part, on the discovery that particular Wnt and Frizzled proteins are associated with different cancers. It is known that Wnt proteins often have high level expression in cancer. However, little is known regarding the expression of particular Wnt and Frizzled proteins. The present disclosure provides methods for evaluating the expression of Wnt and Frizzled proteins. Also disclosed are agents useful for treating cancers that overexpress Wnt proteins. The invention is useful for any cancer in which Wnt-Fzd signaling affects cancer cell growth or survival; or in which specific wnt gene products and/or specific fzd gene products are overexpressed. The invention is useful for treating cancers such as head and neck cancer, glioblastoma, chronic lymphocytic leukemia, breast cancer, mantle zone lymphomas, Burkitt's lymphoma, and other lymphocyte malignancies.

Applicants provide novel primers that are useful to assess wnt and/or fzd expression levels in a system of choice. In some embodiments wnt and/or fzd levels are determined in cell lines derived from primary cancer cell, e.g., from a solid tumor or from a hematopoetic cancer. In other embodiments wnt and/or fzd levels are determined in primary tissues, e.g., solid tumors or hematopoetic cancer cells. Cells from normal tissue or from non-transformed cell lines are used as controls. Wnt and/or fzd overexpression can also be determined by using antibodies against the specific wnt or fzd protein to determine expression levels.

Overexpression of a specific wnt or fzd gene product in a cancer cell can be based, inter alia, on two different comparisons. First, a specific wnt and/or fzd gene product can be overexpressed in a cancer cell relative to levels of the specific wnt and/or fzd gene product in a noncancerous cell from the same tissue-type. Alternatively, a specific wnt and/or fzd gene product can be overexpressed in a cancer cell relative to levels of different specific wnt gene product in the same cancer cell. In some embodiments, a specific wnt and/or fzd protein is overexpressed in a cancer cell relative to levels of the specific wnt and/or fzd gene product in a noncancerous cell from the same tissue-type, and relative to levels of different specific wnt gene product in the same cancer cell.

Wnt and/or fzd overexpression can result in at least two different outcomes for the cancer cell. In some embodiments, expression of specific wnt and/or fzd gene products is not required for cancer cell survival, but rather can serve as a marker of the cancer cells. In other embodiments, expression of a specific wnt and/or fzd will be required for proliferation or survival or for inhibition of apoptosis of the cancer cell. (E.g., Blocking wnt/fzd binding or wnt/fzd signaling with, for example a specific antibody or wnt antagonist results in decreased cell proliferation or induction of apoptosis.) Without wishing to be bound by theory, expression of specific wnt and/or fzd gene products can lead to activation of a signal transduction pathway and regulation of downstream wnt and/or fzd inducible genes. In some embodiments, activation of the signal transduction pathway and induction of the downstream genes and gene products are required for proliferation or survival or for inhibition of apoptosis of the cancer cell. For example, in breast cancer cells expression of specific wnt and/or fzd proteins appears to induce required genes including cyclin D1, c-myc, and WISP family genes. In some cells wnt expression appears to activate TCF/LEF transcription factors leading to induction of specific genes. In other embodiments, activation of the signal transduction pathway and induction of the downstream genes and gene products are not required for proliferation or survival or for inhibition of apoptosis of the cancer cell.

At least two therapies can be based on detection of wnt and/or fzd overexpression. For wnt and/or fzd gene products that are required for cell growth, survival or inhibition of apoptosis, specific antibodies that block the wnt/fzd signaling pathway, such as the wnt/fzd interaction, or specific antagonists can be used to kill the cells or to induce apoptosis. For wnt and or/fzd gene products that are overexpressed but not required for cell survival, wnt and or fzd specific antibodies can be radiolabeled or conjugated to toxins or can be used to induce the complement cascade. The overexpressed wnt and/or fzd gene products act as markers to guide the antibodies to the cancer cells. Specific radiolabeled or toxin-conjugated antibodies or induction of the complement cascade can also be used to assist killing of cancer cells that overexpress specific wnts and/or fzds that are required for cell growth.

Wnt and/or fzd expression can be correlated with the expression of wnt/fzd induced genes (e.g., a downstream wnt/fzd regulated gene product). For example, in breast cancer cells expression of specific wnt and fzd proteins appears to induce required genes including cyclin D1, c-myc, and WISP family genes. In lymphocyte cells wnt expression appears to activate TCF/LEF transcription factors leading to induction of specific genes. Thus, different cancers can overexpress different wnt and fzd gene products, as well as different downstream wnt/fzd regulated gene products. Correlation of expression of a specifc wnt and/or fzd gene with a specific downstream gene is an indication that the overexpressed wnt and/or fzd gene product is active. Thus, an assay that detects Wnt overexpression coupled with induced expression of wnt/fzd downstream gene products provides evidence that treatment with an agent that blocks wnt/fzd signaling is appropriate.

Antibodies to WNT and Frizzled Proteins

As noted above, the invention provides methods of inhibiting the wnt/fzd pathway, including Wnt signaling in cancer cells. In some embodiments of the invention, antibodies are used to block the binding between Wnt ligand and the Frizzled receptor, or otherwise block a step in a wnt/fzd signaling pathway. The antibodies can also be used to induce the complement cascade against a target cell expressing the target antigen or can be radiolabeled or toxin-conjugated. This is particularly useful if the antigen is a Frizzled receptor overexpressed on a target cancer cell. The antibodies can be raised against either Wnt or Frizzled proteins, or other proteins in the wnt/fzd pathway in some embodiments. Alternatively, the antibodies could be raised against the Wnt/Frizzled complex on the surface of the cell. Such antibodies will provide more specificity by binding only cells in which the target Wnt and Frizzled proteins are associated and can be used without modification or can be radiolabeled or toxin-conjugated.

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures, or fragment thereof, or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments, a monoclonal antibody is used. The ability of a particular antibody to recognize the same epitope as another antibody is typically determined by the ability of one antibody to competitively inhibit binding of the second antibody to the antigen. Any of a number of competitive binding assays can be used to measure competition between two antibodies to the same antigen. For example, a sandwich ELISA assay can be used for this purpose. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moeity (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

In some embodiments the antibodies to the Wnt or Frizzled proteins are chimeric or humanized antibodies. As noted above, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

Human antibodies can be produced using various techniques known in the art, including phage display libraries (Hoogenboom & Winter, J. Mol. Biol. 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., Nature Biotechnology 14:845-51 (1996); Neuberger, *Nature Biotechnology* 14:826 (1996); Lonberg & Huszar, *Intern. Rev. Immunol.* 13:65-93 (1995).

In some embodiments, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston et al., *Proc. Nat'l Acad. Sci. USA* 8:5879 (1988); Bird et al., *Science* 242:4236 (1988); Glockshuber et al., *Biochemistry* 29:1362 (1990); U.S. Pat. Nos. 4,946,778, 5,132,405 and Stemmer et al., *Biotechniques* 14:256-265 (1993). Generally the peptide linker will have no specific biological activity other than to join the regions or to preserve some minimum distance or other spatial relationship between the $V_H$ and $V_L$. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO:207), preferably 2, 3, 4, 5, or 6 such sequences. However, it is to be appreciated that some amino acid substitutions within the linker can be made. For example, a valine can be substituted for a glycine.

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Regardless of the method of panning chosen, the physical link between genotype and phenotype provided by phage display makes it possible to test every member of a cDNA library for binding to antigen, even with large libraries of clones.

In some embodiments, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for the Wnt or Frizzled protein, the other one is for another cancer antigen. Alternatively, tetramer-type technology may create multivalent reagents.

As noted above, in some embodiments, the antibody is able to fix complement. Alternatively, the antibody is conjugated to an effector moiety. The effector moiety can be any number of molecules, including labeling moieties such as radioactive labels or fluorescent labels, or can be a therapeutic moiety. If the effector moiety is a therapeutic moiety, it will typically be a cytotoxic agent. In this method, targeting the cytotoxic agent to cancer cells, results in direct killing of the target cell. This embodiment is preferably carried out using antibodies against the Frizzled receptor. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies raised against Wnt or Frizzled proteins, or binding of a radionuclide to a chelating agent that has been covalently attached to the antibody.

Identification of Particular WNT/FZD Proteins

As noted above, the invention provides means for determining which Wnt and/or frizzled proteins are overexpressed by a particular cancer cell. In a preferred embodiment, the expression of each Wnt or Frizzled protein expressed in a particular cancer cell is compared to the corresponding expression in non-cancer cells of the same cell type. Wnt or Frizzled proteins that are overexpressed in cancer cells compared to that in non-cancer cells of the same type are selected as targets. In addition, to identify the proteins most likely responsible for cellular proliferation or survival, the Wnt or Frizzled proteins expressed by the cancer cell are also compared. Those proteins that are overexpressed compared to normal cells and those that are overexpressed compared to other Wnt or Frizzled proteins in the cancer cell are selected as targets.

Means for detecting and measuring gene expression or protein activity are well known in the art. Such methods include detecting the gene transcript (e.g. mRNA), measuring the quantity of translated protein, or measuring the gene product activity. In another preferred embodiment, a transcript (e.g., mRNA) can be measured using amplification (e.g. PCR) based methods as described above for directly assessing copy number of DNA. In a preferred embodiment, transcript level is assessed by using reverse transcription PCR (RT-PCR). PCR primers particularly useful for amplification of desired Wnt or Frizzled proteins are provided below.

In another preferred embodiment, transcript level is assessed by using real time PCR. RNA is isolated from a sample of interest. PCR primers are designed to amplify the specific gene of interest. PCR product accumulation is measured using a dual-labeled flourogenic oligonucleotide probe. The probe is labeled with two different flourescent dyes, the 5' terminus reporter dye and the 3' terminus quenching dye. The oligonucleotide probe is selected to be homologous to an internal target sequence present in the PCR amplicon. When the probe is intact, energy transfer occurs between the two flourophors, and the fluorescent emission is quenched. During the extension phase of PCR, the probe is cleaved by 5' nuclease activity of Taq polymerase. Therefore, the reporter is no longer in proximity to the quencher, and the increase in emission intensity is measured. Exemplary PCR primers and hybridization probes for amplification of desired Wnt or Frizzled proteins or downstream wnt/fzd regulated gene products are provided in FIGS. 13A and 13B. The primers can also be used in other methods to amplify DNA, for example RT-PCR. This assay provides a quantitative measure of nucleic acid.

In other embodiments, once the desired amplification products are produced, nucleic acid hybridization techniques can be used to detect and/or quantify the gene transcript, usually after the products are separated on a gel. The probes used in such assays can be full length or less than the full length of the nucleic acid sequence encoding the protein. Shorter probes are empirically tested for specificity. Preferably nucleic acid probes are 20 bases or longer in length, although shorter probes can also be used. Visualization of the hybridized portions allows the qualitative determination of the presence or absence of mRNA.

The "activity" of a Wnt or Frizzled gene can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like. The isolated proteins can also be sequenced according to standard techniques to identify polymorphisms.

The antibodies of the invention can also be used to detect Wnt or Frizzled proteins, or cells expressing them, using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37, Asai, ed. Academic Press, Inc. New York (1993); Basic and Clinical Immunology 7th Edition, Stites & Terr, eds. (1991).

The methods of the invention can also be used for diagnosis. Thus, the present invention provides methods of detecting cells that over-express Wnt or Frizzled proteins in a patient suspected of having a particular cancer. In one method, a biopsy is performed on the subject and the collected tissue is tested in vitro. The tissue or cells from the tissue is then contacted with PCR primers disclosed here to determine the level of expression. Alternatively, an anti-Wnt or anti-Frizzled antibody of the invention can be used. Any immune complexes which result indicate the presence of the target protein in the biopsied sample. To facilitate such detection, the antibody can be radiolabeled or coupled to an effector molecule which is a detectable label, such as a radiolabel. In another method, the cells can be detected in vivo using typical imaging systems. Then, the localization of the label is determined by any of the known methods for detecting the label. A conventional method for visualizing diagnostic imaging can be used. For example, paramagnetic isotopes can be used for MRI. Internalization of the antibody may be important to extend the life within the organism beyond that provided by extracellular binding, which will be susceptible to clearance by the extracellular enzymatic environment coupled with circulatory clearance.

Identification of Inhibitors of WNT Signaling

Wnt or Frizzled proteins (or cells expressing them) can also be used in drug screening assays to identify agents that inhibit a Wnt/Fzd signaling pathway. The present invention thus provides novel methods for screening for compositions which inhibit cancer.

Assays for Wnt/Fzd signaling can be designed to detect and/or quantify any part of the Wnt signaling pathway. For example the ability of an agent to affect intracellular β-catenin levels, or to induce apoptosis, or to decrease or block cellular proliferation in target cells can be measured. Assays suitable for these purposes are described below.

Assays may include those designed to test binding activity to either the Wnt ligand or to the Frizzled receptor. These assays are particularly useful in identifying agents that modulate Wnt activity. Virtually any agent can be tested in such an assay. Such agents include, but are not limited to natural or synthetic polypeptides, antibodies, natural or synthetic small organic molecules, and the like.

As noted above, a family of secreted Frizzled-related proteins (sFRPs) function as soluble endogenous modulators of Wnt signaling by competing with Frizzled receptors for the binding of secreted Wnt ligands. Thus, in some format, test agents are based on natural ligands (e.g., Wnts ligands or sFRPs) of the Frizzled receptor.

Any of the assays for detecting Wnt signaling are amenable to high throughput screening. High throughput assays binding assays and reporter gene assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Other assays useful in the present invention are those designed to test neoplastic phenotypes of cancer cells. These assays include cell growth on soft agar; anchorage dependence; contact inhibition and density limitation of growth; cellular proliferation; cell death (apoptosis); cellular transformation; growth factor or serum dependence; tumor specific marker levels; invasiveness into Matrigel; tumor growth and metastasis in vivo; mRNA and protein expression in cells undergoing metastasis, and other characteristics of cancer cells.

The ability of test agents to inhibit cell growth can also be assessed by introducing the test into an animal model of disease, and assessing the growth of cancer cells in vivo. For example, human tumor cells can be introduced into an immunocompromised animal such as a "nude mouse". The test agent (e.g., a small molecule or an antibody) is administered to the animal and the ability of the tumor cell to form tumors—as assessed by the number and/or size of tumors formed in the animal—is compared to tumor growth in a control animal without the agent.

Kits Used in Diagnostic, Research, and Therapeutic Applications

As noted above, the invention provides evidence of the overexpression of particular Wnt or Frizzled proteins in certain cancers. Thus, kits can be used for the detection of the particular nucleic acids or proteins disclosed here. In diagnostic and research applications such kits may include any or all of the following: assay reagents, buffers, Wnt-specific or Frizzled-specific nucleic acids or antibodies, hybridization probes and/or primers, and the like. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for inhibitors of Wnt signaling. Such kits can be prepared from readily available materials and reagents. For example, such kits can comprise one or more of the following materials: a Wnt or Frizzled polypeptide or polynucleotide, reaction tubes, and instructions for testing the desired Wnt signaling function (e.g., β catenin levels).

Therapeutic Methods

Administration of Inhibitors

The agents that inhibit Wnt signaling (e.g., antibodies) can be administered by a variety of methods including, but not limited to parenteral (e.g., intravenous, intramuscular, intradermal, intraperitoneal, and subcutaneous routes), topical, oral, local, or transdermal administration. These methods can be used for prophylactic and/or therapeutic treatment.

As noted above, inhibitors of the invention can be used to treat cancers associated with Wnt signaling. The compositions for administration will commonly comprise a inhibitor dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 mg to 100 g per patient per day. Dosages from 0.1 mg to 100 g per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington 's Pharmaceutical Science,* 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions containing inhibitors of the invention (e.g., antibodies) can be administered for therapeutic or prophylactic treatments. In therapeutic applications, compositions are administered to a patient suffering from a disease (e.g., breast cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of an inhibitor that is capable of preventing or slowing the development of cancer in a patient is referred to as a "prophylactically effective dose." The particular dose required for a prophylactic treatment will depend upon the medical condition and history of the patient, the particular cancer being prevented, as well as other factors such as age, weight, gender, administration route, efficiency, etc. Such prophylactic treatments may be used, e.g., in a patient who has previously had cancer to prevent a recurrence of the cancer, or in a patient who is suspected of having a significant likelihood of developing cancer.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

Other known cancer therapies can be used in combination with the methods of the invention. For example, inhibitors of Wnt signaling may also be used to target or sensitize the cell to other cancer therapeutic agents such as 5FU, vinblastine, actinomycin D, cisplatin, methotrexate, and the like. In other embodiments, the methods of the invention can be used with radiation therapy and the like.

In some instances the antibody belongs to a sub-type that activates serum complement when complexed with the transmembrane protein thereby mediating cytotoxicity or antigen-dependent cytotoxicity (ADCC). Thus, cancer can be treated by administering to a patient antibodies directed against Wnt or Frizzled proteins on the surface of cancer cells. Antibody-labeling may activate a co-toxin, localize a toxin payload, or otherwise provide means to locally ablate cells. In these embodiments, the antibody is conjugated to an effector moiety. The effector moiety can be any number of molecules, including labeling moieties such as radioactive labels or fluorescent labels, or can be a therapeutic moiety, such as a cytotoxic agent.

Use of Wnt or Frizzled Polypeptides as Vaccines

In addition to administration of inhibitors of wnt signalling, the Wnt or Frizzled proteins or immunogenic fragments of them can be administered as vaccine compositions to stimulate HTL, CTL, and antibody responses against the endogenous proteins. Such vaccine compositions can include, e.g., lipidated peptides (see, e.g., Vitiello, et al. (1995) *J. Clin. Invest.* 95:341-349), peptide compositions encapsulated in poly(D,L-lactide-co-glycolide, "PLG") microspheres (see, e.g., Eldridge, et al. (1991) *Molec. Immunol.* 28:287-294; Alonso, et al. (1994) *Vaccine* 12:299-306; Jones, et al. (1995) *Vaccine* 13:675-681), peptide compositions contained in immune stimulating complexes (ISCOMS; see, e.g., Takahashi, et al. (1990) *Nature* 344:873-875; Hu, et al. (1998) *Clin. Exp. Immunol.* 113:235-243), multiple antigen peptide systems (MAPs; see, e.g., Tam (1988) *Proc. Nat'l Acad. Sci. USA* 85:5409-5413; Tam (1996) *J. Immunol. Methods* 196:17-32); viral delivery vectors (Perkus, et al., p. 379, in Kaufmann (ed. 1996) *Concepts in Vaccine Development* de Gruyter; Chakrabarti, et al. (1986) Nature 320:535-537; Hu, et al. (1986) *Nature* 320:537-540; Kieny, et al. (1986) *AIDS Bio/Technology* 4:790-795; Top, et al. (1971) *J. Infect. Dis.* 124:148-154; Chanda, et al. (1990) *Virology* 175:535-547), particles of viral or synthetic origin (see, e.g., Kofler, et al. (1996) *J. Immunol. Methods* 192:25-35; Eldridge, et al. (1993) *Sem. Hematol.* 30:16-24; Falo, et al. (1995) *Nature Med.* 7:649-653).

Vaccine compositions often include adjuvants. Many adjuvants contain a substance designed to protect the antigen from rapid catabolism, such as aluminum hydroxide or mineral oil, and a stimulator of immune responses, such as lipid A, Bortadella pertussis, or Mycobacterium tuberculosis derived proteins. Certain adjuvants are commercially available as, e.g., Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Vaccines can be administered as nucleic acid compositions wherein DNA or RNA encoding the Wnt or Frizzled polypeptides, or a fragment thereof, is administered to a patient. See, e.g., Wolff et. al. (1990) *Science* 247:1465-1468; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

Methods for the use of genes as DNA vaccines are well known, and include placing the desired gene or portion thereof under the control of a regulatable promoter or a tissue-specific promoter for expression in the patient. The gene used for DNA vaccines can encode full-length Wnt or Frizzled protein, or may encode portions of the proteins.

In a some embodiments, the DNA vaccines include a gene encoding an adjuvant molecule with the DNA vaccine. Such adjuvant molecules include cytokines that increase the immunogenic response to the polypeptide encoded by the DNA vaccine.

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, e.g., as a vector to express nucleotide sequences that encode Wnt or Frizzled polypeptides or polypeptide fragments. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover, et al. (1991) *Nature* 351:456-460. A wide variety of other vectors useful for therapeutic administration or immunization e.g., adeno and adeno-associated virus vectors, retroviral vectors, Salmonella typhi vectors, detoxified anthrax toxin vectors, and the like, will be apparent. See, e.g., Shata, et al. (2000) *Mol. Med. Today* 6:66-71; Shedlock, et al. (2000) *J. Leukoc. Biol.* 68:793-806; and Hipp, et al. (2000) *In Vivo* 14:571-85.

EXAMPLES

Different clonal populations of HNSCC overexpress various receptors of the Wnt and Fzd family because of their immature cell of origin and because of a growth and survival advantage provided by autocrine or paracrine Wnt/Fzd signaling. We examined HNSCC and normal human epithelial cell lines for the expression of 5 Wnt and 2 Fzd genes. The results showed that most HNSCCs did overexpress one or more Wnt and Fzd mRNAs. Moreover, the Wnt/Fzd pathway was functional in some of the HNSCC cells, as indicated by the constitutive expression of a LEF/TCF reporter gene. In the SNU 1076 cell line, anti-Wnt-1 or anti-Wnt-10b antibodies decreased the expression of β-catenin and cyclin D1, inhibited cell growth, and induced apoptosis. Thus, the Wnt and Fzd genes are frequently overexpressed in HNSCC, and are attractive targets for both immunotherapy and drug therapy.

We have examined tumor and normal cell lines for proteins that are involved in embryonic development. These studies suggest that at least one G-coupled protein receptor, frizzled 2, is overexpressed by many tumor cell lines. A broader panel of normal and malignant cells can be studied and immunization strategies can be developed directed towards passive and active immunotherapies against this antigen.

Based on the successful experience of trastuzumab as an adjunctive passive immunotherapy as described above, an evaluation of blocking the Wnt-frizzled signaling pathway on the growth of a HNSCC line with commercially available polyclonal antibodies was performed (FIGS. 4 and 5). Soluble inhibitors of frizzled have been described to induce apoptosis secondary to their inhibition of frizzled signaling (Zhou, Z. J. et al., "Up-regulation of human secreted frizzled homolog in apoptosis and its down-regulation in breast tumors," *Int J Cancer* 78:95-99 (1998)). The antibodies tested appear to have slowed the growth of the tumor line and resulted in apoptosis (FIGS. 4 and 5).

To evaluate Wnt and Fzd receptors as potential tumor associated antigens in head and neck squamous cell cancers (HNSCC), we screened various tumor and normal cell lines by both RT-PCR, and immunoblotting. Initial screening revealed that both frizzled 2 and frizzled 5 are expressed in head and neck squamous cell cancers (HNSCC), glioma, and chronic lymphocytic leukemia (CLL) (FIG. 2). Further, the results revealed that Fzd-2 was overexpressed in many HNSCC cells, compared to normal human bronchoepithelial (NHBE) cells (Table 1). The amino acid sequence of Fzd-2 is very homologous to Fzd-1 and 7 (Sagara, N. et al. "Molecular cloning, differential expression, and chromosomal localization of human frizzled-1, frizzled-2, and frizzled-7," *Biochem Biophys Res Comm* 252, 117-122 (1998)). To confirm that frizzled 2 was specifically amplified in the tumor lines to RT-PCR products from selected reactions were cloned into the TA vector (Invitrogen, Carlsbad, Calif.) and sequenced. There was 100% identity of the inserts with the human frizzled 2 sequence by BLAST search. In addition, immunoblotting showed a lack of detectable Fzd-2 protein in the lysates of NHBE in which there were weakly detectable or undetectable products by RT-PCR. The human Fzd-2 gene originally was isolated by Sagara and colleagues (Sagara 1998, infra). These investigators also found that the mRNA for Fzd-2 was not detectable in any of 15 different normal human adult tissues, with the possible exception of heart. In contrast, embryonic tissues, as well as six of eight malignant cell lines, expressed abundant Fzd-2 mRNA. However, these investigators did not test for the expression of frizzled Fzd-2 protein, and mRNA levels do not necessarily correlate with protein expression. Our studies show that Fzd-2 protein expression is prominent in HNSCC cell lines, when compared to normal NHBE cells. Hence, antibodies against specific determinants of the extracellular domain of Fzd-2 could be used to bind to and target such malignant cells.

Compared to NHBE cells, the HNSCC cell lines expressed much higher message levels of Wnt-1, Wnt-5a, Wnt-10b and Wnt-13. Of these Wnt proteins Wnt-1, 5A, and 10b were exclusively expressed by the malignant cell lines and were not detected in the normal tissues tested. Immunoblotting experiments confirmed the overexpression of Wnt-1 and Wnt-10b protein in several HNSCC cell lines (FIG. 3). Since the tumors had high levels of both the ligands and their Fzd-2 receptors, it was important to determine if Wnt/Fzd signaling was constitutively active in the HNSCC cells. The canonical Wnt/Fzd signaling cascade leads to the accumulation of cytoplasmic β-catenin and its translocation to the nucleus. In the nucleus beta-catenin binds a specific sequence motif at the N terminus of lymphoid-enhancing factor/T cell factor (LEF/TCF) to generate a transcriptionally active complex (Behrens J et al. "Functional interaction of beta-catenin with the transcription factor LEF-1," *Nature* 382, 638-642 (1996)). Experiments using LEF/TCF reporter gene, TOPFLASH, demonstrated that LEF/TCF dependent transcription was active in the SNU 1076 cells.

The Wnt/frizzled pathway has been previously implicated in tumorigenesis. Soluble Wnt glycoproteins have been demonstrated to transmit signal by binding to the seven transmembrane domain G-protein coupled-receptor frizzled (FIG. 1) (Bhanot, P. et al. "A new member of the frizzled family from Drosophila functions as a Wingless receptor," *Nature* 382:225-230 (1996); Yang-Snyder, J. et al. "A frizzled homolog functions in a vertebrate Wnt signaling pathway," *Curr Biol* 6:1302-1306 (1996); Leethanakul, C. et al. "Distinct pattern of expression of differentiation and growth-related genes in squamous cell carcinomas of the head and neck revealed by the use of laser capture microdissection and cDNA arrays," *Oncogene* 19:3220-3224 (2000)). Upon Wnt signaling, a cascade is initiated that results in the accumulation of cytoplasmic beta-catenin and its translocation to the nucleus. In the nucleus beta-catenin binds a specific sequence motif at the N terminus of lymphoid-enhancing factor/T cell factor (LEF/TCF) to generate a transcriptionally active complex (Behrens, J. et al. "Functional interaction of beta-catenin with the transcription factor LEF-1," *Nature* 382:638-642 (1996)). Beta-catenin interacts with multiple other proteins such as cadherin, which it links to the cytoskeleton (Hoschuetzky, H. et al. "Beta-catenin mediates the interaction of the cadherin-catenin complex with epidermal growth factor receptor," *J Cell Biol* 127:1375-1380 (1994); Aberle, H. et al., "Assembly of the cadherin-catenin complex in vitro with recombinant proteins," *J Cell Sci* 107:3655-3663 (1994)). It also associates with the adenomatous polyposis coli (APC) tumor suppressor protein and glycogen synthetase 3 beta (GSK3β) (Rubinfeld, B. et al., "Binding of GSK3beta to the APC-beta-catenin complex and regulation of complex assembly," *Science* 272:1023-1026 (1996)). These proteins function to negatively regulate beta catenin by facilitating phosphorylation near the aminoterminus and thus accelerating its proteolytic degradation (Yost, C. et al, "The axis-inducing activity, stability, and subcellular distribution of beta-catenin is regulated in Xenopus embryos by glycogen synthase kinase 3," *Genes Dev* 10:1443-1454 (1996)).

A panel of tumor cells that can be screened are derived from the panel of 60 lines which are being characterized in the National Institutes of Health Developmental Therapeutics Program. The cell lines that are currently available include: (Non-Small Cell Lung Cancer) A549/ATCC, NCI-11226, NCI-11460, HOP-62, HOP-92, (colon cancer) HT29, HCT-116, (breast cancer) MCF7, NCI/ADR-RES, MDA-MB-231/ATCC, T-47D, (ovarian cancer) OVCAR-3, OVCAR-4, SK-OV-3, (leukemia) CCRF-CEM, K-562, MOLT-4, HL-60 (TB), RPMI-8226, (renal cell) 786-0, TK-10, (prostate cancer) PC-3, DU-145. Normal control cell lines can be purchased from Clonetics.

Although Wnt and Fzd were expressed in HNSCC cells, they may be dispensable for cell growth and survival. Therefore, the effects of antibodies to the extracellular domains of Wnt-1 and Wnt-10b were studied in three HNSCC lines known to express the receptors. When compared to control antibodies, both anti-Wnt antibodies slowed the growth of one of the HNSCC cell lines (SNU 1076) and resulted in apoptosis. Treatment with high levels of SFRP1, a Wnt antagonist, exerted a similar effect. Moreover, interference with Wnt/frizzled signaling in SNU 1076 cells decreased the activity of the LEF/TCF reporter gene, and reduced levels of β-catenin cyclin D1 and fibronectin. These results suggest that continued autocrine or paracrine Wnt/Fzd signaling may be required for the growth and survival of a subset of HNSCC cells.

These results suggest that antibodies against Wnt and frizzled receptors may exert two different effects in HNSCC cancers in vivo. In malignant cells that depend on Wnt/Fzd signaling for survival, the antibodies might directly slow tumor growth and/or induce apoptosis. In HNSCC cells that incidentally overexpress the receptors, but do not require them for proliferation, the antibodies still could potentially target the tumor cells for killing by complement, or antibody dependent cellular toxicity. Based on these data, we believe that passive immunotherapy could be a useful adjunctive therapy in HNSCC that overexpress one or more Wnt and Fzd receptors.

Experimental Methods

Cell lines and culture: Ten HNSCC, 2 B lymphoma, and 2 glioblastoma cell lines were studied. Detroit-562 (pharyngeal cancer), KB (carcinoma in the floor of the mouth), RPMI-2650 (nasal septal) cancer), SCC-25 (tongue cancer), U87MG and U373MG (glioblastoma), Ramos (lymphoma), Detroit-551 (human skin fibroblast-like cells) and WI-38 (human lung fibroblasts) were purchased from the American Type Culture Collection (Manassas, Va.). The PCI-1, 13, and 50 cell lines were kindly provided by Dr. T. Whiteside (Univ. of Pittsburgh, PA) (Whiteside, T. L. et al., "Human tumor antigen-specific T lymphocytes and interleukin-2-activated natural killer cells: comparisons of antitumor effects in vitro and in vivo," *Clin Cancer Res.* 4, 1135-1145 (1998); Yasumura, S. et al., "Human cytotoxic T-cell lines with restricted specificity for squamous cell carcinoma of the head and neck," *Cancer Res.* 53, 1461-1468 (1993)). The HNSCC cell lines SNU 1066, SNU 1076 and AMC 4 cell lines were provided by Dr. J. G. Park (Seoul National University, Korea) and Dr. S. Y. Kim (University of Ulsan, Korea), respectively (Ku, J. L. et al., "Establishment and characterization of human laryngeal squamous cell carcinoma cell lines," *Laryngoscope* 109, 976-82 (1999); Kim, S. Y. et al. "Establishment and characterization of nine new head and neck cancer cell lines," *Acta Otolaryngol.* 117, 775-784 (1997)). Two different normal human tracheobronchial epithelial (NHBE) cells derived from different persons were purchased from Clonetics (San Diego, Calif.). All cancer cell lines were cultured at 37° C. in a humidified atmosphere of 5% $CO_2$, in either RPMI 1640, DMEM (Dulbecco's modified Eagle's medium), or Ham's 12-DMEM medium, as recommended by the suppliers, supplemented with 10% fetal bovine serum. NHBE cells were cultured in the bronchial epithelial cell growth media provided by the company. Normal epithelial cells were obtained from scrapings of the oral mucosa of 10 normal healthy volunteers. All cell lines were found to be free of mycoplasma contamination.

RT-PCR Analyses: Total RNA was extracted by using Trizol® (Gibco BRL, Grand Island, N.Y.), according to the manufacturer's directions. Different pairs of gene-specific primers based on GenBank sequences of cloned human Wnt and Fzd genes were used for reverse transcriptase-PCR (RT-PCR) analysis. Reverse transcription was performed with a Superscript™ Preamplification kit (Gibco BRL). One microgram of RNA was used from each sample, and 25-35 cycles of PCR were carried out. The PCR products were separated by electrophoresis, visualized under ultra violet light, and scanned with a laser densitometer. The intensities of the Wnt and Fzd bands were compared with the amplicon of the housekeeping gene G3PDH. Preliminary experiments confirmed that the PCR amplifications had not reached a plateau for all data reported in the results. The following list summarizes the primer pairs used:

Fzd-2: 5'-cagcgtcttgcccgaccagatcca-3'(reverse) (SEQ ID NO:208); 5'-ctagcgccgctcttcgtgtacctg-3' (forward) (SEQ ID NO:209). Fzd-5: 5'-ttcatgtgcctggtggtgggc-3' (forward) (SEQ ID NO:210); 5'-tacacgtgcgacagggacacc-3' (reverse) (SEQ ID NO:211). Wnt-1:-5'-cacgacctcgtctacttcgac-3' (forward) (SEQ ID NO:212); 5'-acagacactcgtgcagtacgc-3' (reverse) (SEQ ID NO:213). Wnt-5a: 5'-acacctctttccaaacaggcc-3' (forward) (SEQ ID NO:214); 5'-ggattgttaaactcaactctc-3' (reverse) (SEQ ID NO:215. Wnt-7a: 5'-cgcaacaagcggcccaccttc-3' (forward) (SEQ ID NO:216); 5'-tccgtgcgctcgctgcacgtg-3' (reverse) (SEQ ID NO:217). Wnt-10b: 5'-gaatgcgaatccacaacaacag; 3' (forward) (SEQ ID NO:218); 5'-ttgcggttgtgggtatcaatgaa-3'(reverse) (SEQ ID NO:219).Wnt-13: 5'-aagatggtgccaacttcaccg-3' (forward) (SEQ ID NO:220); 5'-ctgccttcttgggggctttgc-3' (reverse) (SEQ ID NO:221). G3PDH: 5'-accacagtccatgccatcac-3' (forward) (SEQ ID NO:222); 5'-tacagcaacagggtggtgga-3' (reverse) (SEQ ID NO:223).

The specificities of the Wnt and Fzd PCR products were confirmed by cloning and sequencing the products, using a TOPO TA Cloning kit and M13 primers (Invitrogen, Carlsbad, Calif.).

Immunoblotting: After removal of medium, cells in logarithmic growth were disrupted in lysis buffer [25 mM Tris HCl, 150 mM KCl, 5 mM EDTA, 1% NP-40, 0.5% sodium deoxycholic acid, 0.1% sodium dodecyl sulfate] including phosphatase and protease inhibitor cocktails. Each lane of an SDS-PAGE gel was loaded with 20 μg-of protein. After electrophoresis, the proteins were transferred to a polyvinylidene difluoride (PVDF) membrane, blocked with 2% I-block™ (Tropix Inc, Bedford, Mass.) containing 0.05% Tween-X in PBS, and then incubated with primary antibody. Horseradish peroxidase-conjugated anti-IgG (Santa Cruz Laboratories, Santa Cruz, Calif.) was used as the secondary antibody. The membranes were developed using a chemiluminescence system (ECL detection reagent: Amersham Life Science, Aylesbury, UK), and scanned with a laser densitometer. The membranes were stripped with Re-Blot™ Western blot recycling kit (Chemi-Con International Inc, Temecula, Calif.) and reprobed using other antibodies and actin monoclonal antibody (Chemi-Con International Inc) as a control. Prestained molecular weight markers (New England Biolabs, Beverly, Mass.) were used as reference.

Antibodies: Polyclonal antibodies specific for the amino terminal extracellular domains of Wnt-1 and Wnt-10b, and for the carboxy terminal region of Fzd-2, were purchased from Santa Cruz Laboratories, and monoclonal antibodies specific for β-catenin and fibronectin were purchased from Transduction Laboratories (Lexington, Ky.). Antibodies to cyclin D1 and actin were purchased from PharMingen (San Diego, Calif.) and Chemi-Con International Inc., respectively. Purified recombinant human soluble frizzled-related protein-1 was prepared in Dr. J. Rubin's laboratory as described previously (Uren, A. et al., "Secreted frizzled-related protein-1 binds directly to Wingless and is a biphasic modulator of Wnt signaling," *J Biol Chem.* 275, 4374-4382 (2000)).

MTT (3-[4,5-dimethylthiazol-2-yl]-2,5-diphenyl tetrazolium bromide)-based cell assay: Cell proliferation was determined by a colorimetric MTT assay. Briefly, either 7.5-10×$10^3$ cells were dispersed in each well of a 96 well plate. Twenty-hours after culture, 4 different concentrations of anti-Wnt-1 or ant-Wnt-10b antibody (2 μg/ml, 0.2 μg/ml, 20 ng/ml, and 2 ng/ml) were added to the cultures. The same concentrations of goat antihuman IgG (Fisher Scientific) were used as an isotype control. The antibodies were dialyzed against tissue culture medium prior to use, to remove preservatives. On 1, 2, 3, or 4 days after incubation, 20 μl of MTT solution was added to each well. Four hours later the cells were lysed, and absorbances at 570 nM and 650 nM were measured and growth, as a percentage of control, was determined from the formula:

$$\%\text{ of control growth}=(B-A)/(C-A)\times 100$$

where A=absorbance at start of incubation, B=absorbance after incubation with antibodies tested, C=absorbance after incubation with control antibody. The assays were performed in triplicate, and the results represent the mean value±standard deviation from four independent experiments.

Flow Cytometry: Cell apoptosis was assayed by propidium iodide (PI) and $DIOC_6$ staining, followed by flow cytometry. The HNSCC line, SNU1076, was treated with 2 μg/ml anti-Wnt-1, anti-Wnt-10, or control IgG for 72 hrs. Cells were detached from the flasks by trypsin treatment and incubated for 10 minutes in medium with 5 μg/ml PI and 40 nM $DiOC_6$, and then were analyzed by flow cytometry in a FACS caliber (Becton-Dickinson, San Jose, Calif.). Viable cells had high $DiOC_6$ (FL-1) and low PI (FL-3) fluorescence, whereas apoptotic cells had low $DiOC_6$ (FL-1) and low PI (FL-3) fluorescence.

Tumor and normal cell lines can be identified that express frizzled 2. Ten cell lines that express frizzled 2 and at least two cell lines that do not can be tested as described above for FIG. 4. The mouse sera that tests for highest titer and specificity will be used in the cell cultures. The cells will be exposed to graded amounts of polyclonal anti-frizzled 2 mouse sera and normal control serum. On days 1, 2, 3, and 4 subsets of the replicate wells will be assayed for proliferative capacity. On successive days 20 μl of MTT (3-[4,5-dimethylthiazol-2-yl]-2,5-diphenyl tetrazolium bromide)-based solution will be added to wells for four hours prior to lysis with 15% SDS, 0.015 M HCl. Absorbencies of 570 and 650 nm will measured. These measurements will be performed in triplicate and statistical relevance will be assessed by Students t test for $P<0.05$.

The selected cell lines will also undergo analysis for DNA content by Propidium iodide (PI) staining. Cell lines treated for 72 hours in the presence of graded concentrations of normal or immunized mouse serum will be trypsinized, incubated for 10 minutes with 5 μg/ml PI and 40 nM $DiOC_6$, and analyzed by flow cytometry. Viable cells will be $DiOC_6$ (FL-1) high and PI (FL-3) low, and apoptotic cells will be $DiOC_6$ (FL-1) low and PI (FL-3) low. Additionally, cells will detached from the flasks with trypsin and incubated overnight in a hypotonic buffer (0.1% citrate, 0.1% SDS) containing 50 μg/ml PI and 100 μg/ml RNase. The amount of DNA will be measured by flow cytometry. Apoptotic cells are defined as having a DNA content lower than the $G_0G_1$ levels (sub-$G_0$ cells).

Transient Luciferase Assays: The pTOPFLASH-Luc reporter gene vector and the pFOPFLASH-Luc control were kindly provided by Dr. Hans Clevers (University Medical Center Utrecht, The Netherlands). For TOPFLASH/FOPFLASH reporter gene assays, SNU 1076 cells were cotransfected with 0.5 μg of pTOPFLASH-Luc or pFOPFLASH-Luc and 0.5 μg of pCMV-βGal, as described previously (Korinek, V. et al., "Constitutive transcriptional activation by a beta-catenin-Tcf complex in APC −/− colon carcinoma," *Science* 275, 1784-1787 (1997)). Cells were harvested 24h after transfection, disrupted in lysis buffer, and luciferase and β-galactosidase activities were determined using the Dual-Light reporter gene assay system (Applied Biosystems, Foster City, Calif.). Luciferase activities of each pTOPFLASH-Luc or pFOPFLASH-Luc transfected culture, and the β-galactosidase activities of pCMV-βGal transfected cells, were measured in the same samples using a luminometer. The transfection efficiencies of the samples were normalized by the activity of β-galactosidase.

Example 1

Immunogenicity of Isolated Non-Homologous Regions of Frizzled 2

The first extracellular domain of frizzled 2 contains a region which based on protein structure is least homologous to the other frizzled protein family members (FIG. 6) (Sagara, N. et al. "Molecular cloning, differential expression, and chromosomal localization of human frizzled-1, frizzled-2, and frizzled-7," *Biochem Biophys Res Commun* 252:117-122 (1998)). This polypeptide sequence may have sufficient ternary structure to generate an antibody response to the native protein. In order to enhance B cell stimulation this epitope will be coupled to T cell epitopes that have been described to generate T cell help.

The overall strategy will be to use the least conserved region of the frizzled protein, attempting to preserve the most native structure possible and to generate the most potent immune response. The most versatile method for designing vaccines of defined regions is naked plasmid DNA. The advantages are that the vectors can be rapidly redesigned to change the length of sequence that is expressed, discontinuous regions of the protein can be co-expressed, and the DNA sequence of the protein can be fused to other epitopes to enhance antigenicity (O'Hem, P. A. et al. "Colinear synthesis of an antigen-specific B-cell epitope with a 'promiscuous' tetanus toxin T-cell epitope: a synthetic peptide immunocontraceptive," *Vaccine* 15:1761-1766 (1997); Paterson, M. et al., "Design and evaluation of a ZP3 peptide vaccine in a homologous primate model," *Mol Hum Reprod* 5:342-352 (1999); Dakappagari, N. K. et al., "Prevention of mammary tumors with a chimeric HER-2 B-cell epitope peptide vaccine," *Cancer Res* 60:3782-3789 (2000)). It affords the versatility of expressing soluble, membrane bound proteins, or small peptide fragments. Also gene transfer by this technique is a powerful tool to introduce multiple protein elements into the same or separate locations. In this system single or multiple proteins can be locally expressed. Injecting a combination of plasmids expressing antigens and costimulators like B7.1 and B7.2 results in enhanced immune responses (Corr, M. et al., "Costimulation provided by DNA immunization enhances antitumor immunity," *J Immunol* 159:4999-5004 (1997); Chan, K. et al., "The roles of mhc class ii, cd40, and b7 costimulation in ctl induction by plasmid dna (DNA?)," *J Immunol* 166:3061-3066 (2001)).

Several plasmids have been constructed which are under the control of the cytomegalovirus (CMV) promoter which has been found to enable high levels of antigen expression in injected muscle. The pCMVint vector includes the cytomegalovirus (CMV) E1 promoter, the simian virus (SV40) t-intron, and the SV-40 polyadenylation site (Corr, M. et al. "Gene vaccination with naked plasmid DNA: mechanism of CTL priming," *J Exp Med* 184:1555-1560 (1996)). The ACB vector has the same elements except the polyadenylation sequence is from the bovine growth hormone gene (Sato, Y. et al "Immunostimulatory DNA sequences necessary for effective intradermal gene immunization," *Science* 273:352-354 (1996)). The first set of plasmid constructs planned will encode the least homologous region of the frizzled 2 between the ninth and tenth cysteines. These cysteines will be preserved in this series of constructs as they may stabilize a configuration that enables antibody binding to the native protein. This polypeptide fragment will be fused at the amino-terminus or the carboxylterminus via a short linker to a tetanus toxin or measles virus fusion (MVF) protein T helper epitopes (see below) (O'Hem, P. A. et al. "Colinear synthesis of an antigen-specific B-cell epitope with a 'promiscuous' tetanus toxin T-cell epitope: a synthetic peptide immunocontraceptive," *Vaccine* 15:1761-1766 (1997); Paterson, M. et al "Design and evaluation of a ZP3 peptide vaccine in a homologous primate model," *Mol Hum Reprod* 5:342-352 (1999); Dakappagari, N. K. et al., "Prevention of mammary tumors with a chimeric HER-2 B-cell epitope peptide vaccine," *Cancer Res* 60:3782-3789 (2000)). These minigenes will be constructed with overlapping oligonucleotides. The oligonucleotides are 5' prime phosphorylated with T4 kinase at room temperature for 30 minutes, annealed by boiling an equimolar admixture of two complementary oligomers and slow cooling. The double stranded oligonucleotides are then ligated 3' to the tissue plasminogen leader (TPA) leader into the EcoR47111 site in frame and into the BamHl site of the pBluescript SKII vector. The minigene is then subcloned into the pCMV and pACB vectors between the Pstl and Xbal sites as previously described (Corr, M. et al., "Costimulation provided by DNA immunization enhances antitumor immunity," *J Immunol* 159:4999-5004 (1997)).

The inserts for the vectors are designed as described above. The frizzled putative B cell epitope is from the published sequence. The tetanus toxin and measles MVF T helper epitopes have been optimized for human codon usage by the most frequently used codon per amino acid. The DNA constructs have an initiating methionine and stop codons added to the 5' and 3' ends respectively. The amino acid and DNA sequences are summarized below with the short GPSL (SEQ ID NO:224) linker sequence in bold and the T cell helper epitope underlined.

Tetanus Toxin Epitope Fused to a Frizzled Domain

```
pFZD2-TT MCVGQNHSEDGAPALLTTAPPPGLQPGAGGTPGGPGGGGAPPRYATLEHPFHC -GPSL-
VDDALINSTKIYSYFPSV-STOP (SEQ ID NO:225)

ATG TGC GTC GGC CAG AAC CAC TCC GAG GAC GGA GCT CCC GCG CTA CTC ACC ACC
GCG CCG CCG CCG GGA CTG CAG CCG GGT GCC GGG GGC ACC CCG GGT GGC CCG GGC
GGC GGC GGC GCT CCC CCG CGC TAC GCC ACG CTG GAG CAC CCC TTC CAC TGC-GGC
CCC AGC CTG- GTG GAC GAC GCC CTG ATC AAC AGC ACC AAG ATC TAC AGC TAC TTT
CCCAGCGTGTAG(SEQ ID NO:226)

pTT-FZD2
MVDDALINSTKIYSYFPSV-GPSL-
CVGQNHSEDGAPALLTTAPPPGLQPGAGGTPGGPGGGGAPPRYATLEHPFHC-STOP
(SEQ ID NO:227)

ATG GTG GAC GAC GCC CTG ATC AAC AGC ACC AAG ATC TAC AGC TAC TTT CCC AGC
GTG-GGC CCC AGC CTG-TGC GTC GGC CAG AAC CAC TCC GAG GAC GGA GCT CCC GCG
CTA CTC ACC ACC GCG CCG CCG CCG GGA CTG CAG CCG GGT GCC GGG GGC ACC CCG
GGT GGC CCG GGC GGC GGC GGC GCT CCC CCG CGC TAC GCC ACG CTG GAG CAC CCC
TTC CAC TGC TAG (SEQ ID NO:228)
```

-

Measles MVF Epitope Fused to a Frizzled Domain

```
PFZD2-MMVF
MCVGQNHSEDGAPALLTTAPPPGLQPGAGGTPGGPGGGGAPPRYATLEHPFHC-GPSL-
KLLSLIKGVIVHRLEGVE-STOP (SEQ ID NO:229)
```

-continued

ATG TGC GTC GGC CAG AAC CAC TCC GAG GAC GGA GCT CCC GCG CTA CTC ACC ACC
GCG CCG CCG CCG GGA CTG CAG CCG GGT GCC GGG GGC ACC CCG GGT GGC CCG GGC
GGC GGC GGC GCT CCC CCG CGC TAC GCC ACG CTG GAG CAC CCC TTC CAC TGC-GGC
CCC AGC CTG- AAG CTG CTG AGC CTG ATC AAG GGC GTG ATC GTG CAC CGC CTG GAG
GGC GTG GAG TAG(SEQ ID NO:230)

PMMVF-FZD2
MKLLSLIKGVIVHRLEGVE-GPSL-
CVGQNHSEDGAPALLTTAPPPGLQPGAGGTPGGPGGGGAPPRYATLEHPFHC-STOP
(SEQ ID NO:231)

ATG AAG CTG CTG AGC CTG ATC AAG GGC GTG ATC GTG CAC CGC CTG GAG GGC GTG
GAG-GGC CCC AGC CTG-TGC GTC GGC CAG AAC CAC TCC GAG GAC GGA GCT CCC GCG
CTA CTC ACC ACC GCG CCG CCG CCG GGA CTG CAG CCG GGT GCC GGG GGC ACC CCG
GGT GGC CCG GGC GGC GGC GGC GCT CCC CCG CGC TAC GCC ACG.CTG GAG CAC CCC
TTC CAC TGC TAG (SEQ ID NO:232)

Plasmid DNA is prepared using Qiagen Maxiprep (Chatsworth, Calif.) kits with the modification of adding one tenth volume 10% Triton X-114 (Sigma, St. Louis, Mo.) to the clarified bacterial lysate prior to applying it to a column. Prior to injection the residual endotoxin level is quantified using a limulus extract clot assay (Associates of Cape Cod, Woods Hole, Mass.). A level of less than or equal to 5 ng endotoxin/μg DNA need be obtained prior to use in an animal (Corr, M. et al. "In vivo priming by DNA injection occurs predominantly by antigen transfer," *J Immunol* 163:4721-4727 (1999)). The DNA is resuspended in a sterile pyrogen free saline solution for injection.

Twenty-eight female mice will be divided into groups of 4 mice each. They will be injected in the dermis of the tail with a combination of 50 pg plasmid encoding a costimulator (B7-1 or B7-2) and 50 μg linker plasmid diluted in normal saline at weeks zero, one and two. A group with empty vector is included as a negative control. The groups are as follows:

| Group | Plasmid 1 | Plasmid 2 |
|---|---|---|
| A | pTT-FZD2 | nCMV |
| B | pTT-FZD2 | nCMVB7-1 |
| C | pTT-FZD2 | nCMVB7-2 |
| D | pFZD2-TT | nCMV |
| E | pFZD2-TT | nCMVB7-1 |
| F | pFZD2-TT | nCMVB7-2 |
| G | — | nCMV |

Another group of mice in similar groups will be immunized using the pMMVF-FZD2 and pFZD2-MMVF set of linked epitope plasmids. The nCMVB7-1 and nCMVB7-2 constructs encode the cDNAs for murine CD80 and CD86, which were kindly provided by G. Freeman (Dana-Farber Cancer Institute, Boston, Mass.) (Corr, M. et al., "Costimulation provided by DNA immunization enhances antitumor immunity," *J Immunol* 159:4999-5004 (1997)).

Mice will be bled prior to the start of the experiment and then every two weeks thereafter. Serum will be separated and stored at −20° C. prior to testing. On week ten (seven weeks after the last injection) mice will be sacrificed. The titers of antibody will be tested by anti-peptide ELISA. Ninety-six well plates (Costar) are coated with 50 μl/well 20 μg/ml peptide in phosphate buffered saline (PBS) overnight at 4° C. The plates are then washed and blocked with 200 μl/well 2% bovine serum albumin (BSA) in PBS. Sera are diluted in 2% BSA in PBS. After overnight incubation at 4° C. the plates are washed. Bound murine IgG is detected by alkaline phosphatase conjugated-goat anti-murine IgG (Jackson Immunoresearch Laboratories) followed by p-nitrophenylphosphate substrate. The titration curves for each sera are compared using DeltaSOFT II v. 3.66 (Biometallics, Princeton, N.J.).

Mice that develop sufficiently high titers of antibody that bind to the peptide will be tested for specificity to frizzled 2 by fluorescent cytometry with cells that express the protein by transfection and known tumor cells that have the mRNA. We will also test the binding by Western blot analysis of cells that express this isoform and to cells that have been found to express other frizzled family members. Briefly, immunoblotting will be performed as described above. Cells are lysed in with a solution containing 25 mM Tris HCl, 150 mM KCl, 5 mM EDTA, 1% NP-40, 0.5% sodium deoxycholic acid, 0.1% sodium dodecyl sulfate, 1 mM $NaVO_3$, 1 mM NaF, 20 mM β-glycerophosphate and protease inhibitors. Twenty μg of protein from each cell line is separated by SDS-PAGE and transferred to a PVDF membrane. The membrane is soaked in 2% I-block, 0.05% Tween X in PBS and then incubated with a 1:500 dilution of polyclonal pre or post immunization mouse serum at 1:500 dilution. Murine antibody binding is then detected by horseradish peroxidase-conjugated rat anti-mouse IgG and chemiluminescence (ECL detection reagents). To verify relative amount of protein transferred in each lane, the blots are then stripped and the presence of actin is measured with an actin monoclonal antibody.

Different immunization strategies are being evaluated for their efficacy in eliciting a humoral immune response. If the antibody response is weak then the vectors can be redesigned with other known potent T helper epitopes. Other vectors can be designed where the polypeptide from frizzled 2 is shorter and does not contain the cysteines, which may be inhibiting the most desirable conformation. Another immunization strategy will be to use a prime boost method. The animals are originally injected with plasmid DNA and then are boosted with peptide or recombinant protein in incomplete Freund's adjuvant. The B-cell epitope in each construct may need to be redesigned until there is no cross-reactivity in the humoral response to other frizzled isoforms.

Example 2

Expression of Wnt and Fzd mRNAs in HNSCC

Ten different HNSCC cell lines, two normal human broncho-epithelial (NHBE) cell lines, and normal oral squamous epithelial cells were tested by RT-PCR for the expression of five Wnts (Wnt-1, Wnt-5a, Wnt-7a, Wnt-10b, Wnt-13), and two Fzds (Fzd-2 and 5). Representative results are illustrated in FIG. 8 and are summarized in Table 1. When compared to the housekeeping gene G3PDH, all the Wnts, as well as Fzd-2, were expressed more frequently in HNSCC than in normal cells, while there was no difference in Fzd-5 gene expression. Of the Wnt genes, Wnt-1, 5a, and 10b were most strongly expressed by the malignant cells, but were barely detectable in the normal tissues tested. We then investigated further Wnt-1 and Wnt-10b, since these Wnts signal through the canonical β-catenin and LEF/TCF, and because antibodies to the extracellular domains were available.

Example 3

Expression of Wnt/Fzd Proteins in HNSCC

Cell lines were lysed and analyzed for Wnt-1, Wnt-10b, Fzd-2, and β-catenin protein expression by immunoblotting (FIG. 9). The normal cells expressed much less of these Wnt or Fzd proteins, when compared to the tested HNSCC, with the exception of RPMI 2650. Of note is the lack of detectable Fzd protein in the lysate of the NHBE cell line that had a weakly detectable product by RT-PCR. Beta-catenin was detected in all the samples, including both HNSCC and NHBE lines.

Example 4

Effects of Anti-Wnt Antibodies and SFRP1

Treatment with antibody against the extracellular domains of Wnt-1 or Wnt-10b decreased the proliferation of the SNU1076 HNSCC cell line (FIG. 10), while little effect was observed in PCI 13 cells (data not shown). The inhibition of cell growth by the antibodies was dependent on the concentration and incubation time. The treatment of the SNU1076 HNSCC cell line with anti-Wnt antibodies, but not control antibody, also induced apoptosis (FIG. 12). Similar to anti-Wnt antibodies, treatment with recombinant SFRPI protein (2 μg/ml), a natural antagonist of Wnt signaling, inhibited growth of SNU 1076 cells (FIG. 11).

To determine if the effects of anti-Wnt antibody on SNU1076 cells were related to inhibition of Wnt signaling, we compared levels of the Wnt regulated genes cyclin D1 and fibronectin (FIG. 7A). The anti-Wnt-1 antibody, but not the control IgG, reduced cyclin D1, fibronectin, and β-catenin levels in the cytosol of SNU 1076 cells. To confirm these results, TOPFLASH-Luc, a reporter plasmid containing TCF/LEF binding sites, or FOPFLASH-Luc, a negative control plasmid having mutant binding sites was introduced into SNU 1076 cells together with the pCMV-β-gal plasmid (to assess transfection efficiency). Luciferase activity was higher in the TOPFLASH than the FOPFLASH transfected cells, indicating that LEF/TCF dependent transcription was constitutively active. Cells transfected with FOPFLASH showed no changes in the low baseline luciferase activity after treatment with anti-Wnt1 antibodies, whereas cells transfected with TOPFLASH displayed decreased luciferase activity (FIG. 7B).

Example 5

Effects of Anti-Frizzled Antibodies

Wnt signaling through frizzled receptors has been described to inhibit apoptosis (Chen, S. et al. "Wnt-1 signaling inhibits apoptosis by activating beta-catenin/T cell factor-mediated transcription," *J Cell Biol* 152:87-96 (2001)). Also some of the genes that are regulated by TCF/beta-catenin are known to be associated with the cell cycle and cellular proliferation. By blocking the binding of Wnt proteins to their receptors via antibodies directed to the extracellular portion of frizzled this pathway can be interrupted. Decreasing the downstream translocation of beta-catenin to the nucleus could result in slower tumor growth or death of the cell.

The immunization strategy that may be useful in terms of raising specific antibodies that delay growth in cell culture will then be tested for potential in vivo efficacy in mice. Previously we have used the H-$2^b$ thymoma line EL4 as a syngeneic tumor in C57B1/6 mice (Corr, M. et al., "Costimulation provided by DNA immunization enhances antitumor immunity," *J Immunol* 159:4999-5004 (1997); (Cho, H. J. et al., "Immunostimulatory DNA-based vaccines induce cytotoxic lymphocyte activity by a T-helper cell-independent mechanism," *Nat Biotechnol* 18:509-514 (2000)). This line will be transfected with a human frizzled 2 expression vector and selected in neomycin. The expression vector will be made by excising the frizzled 2 containing insert from one expression vector with NdeI and BamHI and ligating the insert into pcDNA3 (Invitrogen) which has a CMV promoter and a neomycin selection cassette. Thirty-two female C57B1/6 mice will be divided into groups of 8 mice each. They will be injected in the dermis of the tail with a combination of 50 μg plasmid encoding a costimulator and 50 μg linker plasmid diluted in normal saline at weeks zero, one and two. A group with empty vector is included as a negative control. On day 28 the mice will be injected subcutaneously in the flank with $20\times10^6$ frizzled 2 transfected EL4 cells or untransfected cells (Cho, H. J. et al., "Immunostimulatory DNA-based vaccines induce cytotoxic lymphocyte activity by a T-helper cell-independent mechanism," *Nat Biotechnol* 18:509-514 (2000)). The mice will be monitored three times a week for weight, and tumor growth measured with a caliper. Tumor volume is calculated by $\text{length}\times\text{width}^2\times\pi/6$ as previously described (Radulovic, S. et al., "Inhibition of growth of HT-29 human colon cancer xenografls in nude mice by treatment with bombesin/gastrin releasing peptide antagonist (RC-3095)," *Cancer Res* 51:6006-6009 (1991)). Mice will be sacrificed four weeks post tumor challenge or if the tumor burden reaches approximately 2000 $mm^3$. Inhibition of tumor growth will be determined by ANOVA.

The polyclonal antibodies that are generated by the immunization strategies may exhibit binding, but may not be sufficiently concentrated in the polyclonal serum to have a biologic effect. The serum from several immunization strategies may need to be tested in vitro for their potential therapeutic utility before proceeding with the in vivo active immunization strategy for tumor prevention. The inhibition of tumor growth in the murine model may be due to cellular responses as well as humoral, which will lead to further investigations. These assays may be useful in determining if the frizzled expressing cell lines are susceptible to anti-proliferative activity of polyclonal anti-frizzled IgG.

Example 6

Overexpression of Wnt 14 and 16

Based upon sequences in the public human DNA gene database, we prepared gene-specific primers for all the known human Wnt and frizzled genes. We obtained mRNA from primary human chronic lymphocytic leukemia cells or normal human lymphocytes. Using real time PCR, we then compared the relative expression of the Wnt and frizzled genes in the normal and malignant lymphocytes, compared to the control genes GAPDH and 18S mRNA. We discovered that Wnt 16 was 70-100 fold overexpressed in the malignant lymphocytes. Wnt 14 was 400 fold overexpressed in the malignant lymphocytes. We sequenced the amplicons to determine their identities. Northern blots of normal human tissues confirmed the lack of significant expression of Wnt 16 mRNA in non-lymphoid cells and in peripheral blood lymphocytes. Following the procedures described above, we have confirmed the overexpression of Wnt 16 in the malignant cells using non-crossreactive antibodies and will confirm overexpression of Wnt 14 in a similar fashion. We have tested the effects of the anti-Wnt 16 antibodies on cell survival in vitro, using normal lymphocytes as a control and will test anti-Wnt 14 antibodies in a similar fashion. In addition, upon review of our results, we can develop these antibodies and antigens as therapeutic agents.

Example 7

Regulation of Lymphocyte Survival by Integrins

The survival of lymphocytes requires that they interact with the extracellular matrix proteins produced by stromal cells in their surrounding micro environment. These interactions may render the cells resistant to spontaneous and drug-induced apoptosis. VLA4 integrin-mediated cell adhesion is known to be involved in regulating cell survival in some leukemic cell lines. We are studying integrin effects on the survival of primary blood lymphocytes. Our data show that the α4-CS1 fragment of fibronectin significantly improves the survival of blood lymphocytes. To develop a potential therapeutic strategy that combines integrin antagonists with cytotoxic drugs, we are investigating the mechanism of several integrin α4-specific antagonists. These compounds specifically inhibit the adhesion of B chronic lymphocytic leukemia cells to fibronectin. We are currently studying the signaling events affected by these integrin antagonists in primary human lymphocytes.

Example 8

Wnt Gene Expression in Normal and Malignant Lymphocytes

The secreted proteins of the diverse Wnt gene family are known to play an important role in cell growth and differentiation. Evidence suggests that Wnt signaling may regulate apoptosis. Experiments described below were designed to identify the Wnt genes that are most highly expressed in resting lymphocytes, and then to determine their potential role in cell survival.

Total RNA was prepared and treated with RNase-free DNase. The cDNA was synthesized from 5 μg total RNA using Superscript reverse transcriptase and oligo dT. To assure that there was no genomic DNA contamination, controls in which no reverse transcriptase was added were also carried out. TaqMan real-time PCR was performed using an ABI PRISM 7700 sequence Detector. Primers and probes for 46 Wnt family members and their related genes were designed using Primer Express version 1.0 (Applied Biosystems). The primers are shown in FIGS. 13A and 13B. The reaction conditions were as follows: 2 min at 50° C. (one cycle), 10 min at 95° C. (one cycle), and 15s at 95° C. and 1 min at 60° C. (45 cycles). Two replicates for each gene were performed.

Having developed and validated a TaqMan real-time PCR assay to quantify the gene expression profiles of the wnt family and its related genes, we measured the gene expression profile in three B-CLL, two normal peripheral blood lymphocyte populations, and one purified B cell sample. We found that wnt6, wnt14 and wnt16 were overexpressed in B-CLL, compared to normal PBL or purified B cells. Wnt14 mRNA levels in B-CLL were 16-178 times those of PBL and B cell samples. The concentration of wnt6 mRNA in B-CLL samples was 8-32 fold higher than that in normal PBL and B-CLL samples. Wnt16 mRNA was expressed at 32-178 higher levels in B-CLL than in PBL. For other Wnt-related families, such as Fzd, Frp, Wisp and DKK, we did not observe any significant differences. Thus, the Wnt gene overexpression appears to be unique.

We have established a model system to study the integrin-dependent interaction of primary human lymphocytes with extracellular matrix proteins, and have shown that the binding promotes cell survival. We can now test the effects of integrin antagonists on cell signaling and apoptosis in both normal and malignant cells.

Other experiments revealed three wnt genes that are overexpressed in lymphocytes of patients with B-CLL, compared to normal peripheral blood lymphocytes. Since wnt proteins are secreted, they may function as survival factors for the malignant cells.

The specificities of the feeder cell-lymphocyte interactions that delay senescence and apoptosis are identified by using purified lymphocyte subpopulations (CD4, T cells, CD8, T cells, B cells), co-culturing with different feeder cells (monocytes, dendritic cells, endothelial cells, fibroblasts), and then measuring both spontaneous and drug-induced apoptosis.

The specific surface molecules and/or secreted factors responsible for the extended survival of the lymphocytes are identified by testing the effects of blocking antibodies against surface antigens on the feeder cells and the lymphocytes, determining the effect of neutralizing antibodies against cytokines and growth factors, and generating sense and antisense transfectomas of feeder cells to confirm the roles of the specific interaction revealed in the first two methods described.

The intracellular signaling pathways in quiescent lymphocytes that are altered by contact with feeder cells, and that increase their survival are identified by determining levels and phosphorylation status of proteins in key activation pathways (mitogen activated protein kinase, STATs, NF-Kb, b-catenin), assessing levels and phosphorylation status of proteins that regulate apoptosis (bcl2 family members, caspases, IAPs, SMAC/DIABLO), and testing the effects of pharmacologic inhibitors of signal transduction on the survival of quiescent lymphocytes cultivated with feeder cells, alone or in combination with cytotoxic agents.

Example 9

Expression of Wnt and Fzd Genes in Primary Breast Cancer Tumors and CLL Cells

Wnt and Fzd levels were compared in primary cancer cells from breast cancer tumors and CLL cells. Results are shown in FIGS. 14-27. Primers and hybridization probes are shown in FIGS. 13A and 13B. Gene expression levels were determined using real time PCR. Briefly, total RNA was isolated from microdissected tissues using RNA STAT-60, and reverse transcribed using random hexamer primers and a Superscript Preamplification System. Then real time PCR was performed using 18S RNA as a control gene. PCR was performed in a Taqman Universal PCR MasterMix with initial activation at 95° C. for 15 sec and 60° C. for 10 min, and 40 cycles of 95° C. for 15 sec and 60° C. for 1 min. The fluorescent signal was plotted versus cycle number, and the threshold cycle was determined. Dilutions of cDNA from a pool of 12 normal tissues served as a positive control. The relative message levels were calculated relative to standard calibration curves, which were used in common by the different components of the SCOR, and coordinated by the Research Resources Core. The pairwise comparisons between different sites in the tested tissues were used for statistical analyses. FIGS. 13A and 13B show the primer sets and the Taqman hybridization probes for the analyzed genes. These primers were previously validated in analyses of normal human tissues and unfractionated RA synovial specimens The data in the figures are relative, with the lowest normal tissue level assigned a value of one. Thus, a relative value of 100 in breast cancer tumor or CLL cells means that the cancer cells had 100 times the values of the lowest normal tissue, as reported by real time PCR.

CLL cells have high wnt16 levels, and also over-express wnt3. (FIG. 14.) CLL cells also express Fzd 3. (FIGS. 16-17.)

Breast cancer cells expressed very high wnt7b levels. (FIGS. 14 and 27.) Other specific Wnts that are expressed at levels greater than 5 times normal cell levels in breast tumors include wnt 5a, wnt 10b, and wnt 14. (Id.) Breast cancer tumors also expressed specific Fzd at high levels, including fzd 3, fzd 4, fzd 6, fzd 7, and fzd 10. (FIGS. 16-19)

Expression levels of Wnt downstream signaling genes and Wnt antagonists were also determined in normal cells, CLL cells, and primary breast tumors. The levels of these genes correlate with activity of the expressed wnt genes and proteins. DKKs and FRP 2/4 are antagonists of wnt/fzd signaling pathway that bind either the wnts or the frizzled co-receptor LRP5. DKK levels were increased in some breast cancer tumors. (FIG. 20.) FRP 2/4 were overexpressed in some breast cancer tumors. (FIG. 21.)

Wnt inducible genes include cyclin D1, c-myc, and the WISP's. WISP refers to wnt-inducible serum protein and WISP2 refers to wnt-inducible serum protein 2. WISP2 expression was increased in breast tumor cells. (FIG. 27.) Cyclin D1 and c-myc levels were also high relative to expression levels in normal cells. (FIGS. 23-24 and 27.) Cyclin D1 levels were also elevated in CLL cells relative to normal lymphocytes. (FIGS. 23-24.) This indicates that the specific wnt and fzd expression seen in breast tumors leads to induction of genes and proteins downstream from the wnt/fzd signal. That is, the specific wnt and fzd proteins are active and their expression results in signal transduction. Levels of control gene products IL-6 and MMP3, a breast cancer marker were also determined. (FIGS. 25-27.)

Because some genes induced by a specific wnt/fzd signal are required for proliferation in specific cell types, including cancer cells, blocking a specific wnt/fzd signal by blocking binding of the two molecules can be used to inhibit cellular proliferation. For example, cyclin D1 is required for passage through the G1/S transition in some cells types. Thus, antibodies against a specific wnt or fzd, alone or in combination, can be used to block a specific wnt/fzd interaction resulting in inhibition of cell proliferation or in some case induction of apoptosis.

Levels of wnt 5a, wnt 7b, wnt 10b, and wnt 14 expression are determined in samples from breast cancer tumors. If a wnt gene or protein is highly expressed, antibodies against the overexpressed gene product (e.g., wnt5a, wnt7b, wnt 10b, or wnt 14) are administered to the patient. Administration of the wnt-specific antibody blocks wnt signaling and can result in diminished or no expression of required downstream wnt regulated genes and protein, (e.g., cyclin D1, c-myc, and members of the WISP family), leading to the death of the breast cancer cells. In some instances the wnt-specific antibody is radiolabeled or conjugated to a toxin to facilitate killing of the cancer cells. Induction of the complement cascade or radiolabeled or toxin-conjugated antibodies are used to kill breast cancer cells that overexpress a specific wnt, but do not require on that specific wnt for proliferation or survival or prliferation.

Levels of fzd 3, fzd 4, fzd 6, fzd 7, and fzd 10 expression are determined in samples from breast cancer tumors. If a fzd gene or protein is highly expressed, antibodies against the overexpressed gene product (e.g., fzd 3, fzd 4, fzd 6, fzd 7, and fzd 10) are administered to the patient. Administration of the fzd-specific antibody blocks fzd signaling and can result in diminished or no expression of required downstream fzd regulated genes and protein, (e.g., cyclin D1, c-myc, and members of the WISP family), leading to the death of the breast cancer cells. In some instances the fzd-specific antibody is radiolabeled or conjugated to a toxin to facilitate killing of the cancer cells. Induction of the complement cascade or radiolabeled or toxin-conjugated antibodies are used to kill breast cancer cells that overexpress a specific fzd, but do not rely on that specific fzd for survival.

Levels of wnt16 and wnt3 expression are determined in samples from CLL cells. If a wnt16 or a wnt3 gene or protein is highly expressed, antibodies against the overexpressed gene product (e.g., wnt16 or wnt3) are administered to the patient. Administration of the wnt-specific antibody blocks wnt signaling and can result in diminished or no expression of required downstream wnt regulated genes and protein, leading to the death of the CLL cells. In some instances the wnt-specific antibody is radiolabeled or conjugated to a toxin to facilitate killing of the cancer cells. Induction of the complement cascade or radiolabeled or toxin-conjugated antibodies are used to kill CLL cells that overexpress a specific wnt, but do not rely on that specific wnt for survival.

Levels of Fzd 3 expression are determined in samples from CLL cells. If a Fzd 3 gene or protein is highly expressed, antibodies against the overexpressed gene product (e.g., Fzd 3) are administered to the patient. Administration of the Fzd 3-specific antibody blocks Fzd 3 signaling can result in diminished or no expression of required downstream fzd regulated genes and protein, leading to the death of the CLL cells. In some instances the Fzd 3-specific antibody is radiolabeled or conjugated to a toxin to facilitate killing of the cancer cells. Induction of the complement cascade or radiolabeled or toxin-conjugated antibodies are used to kill CLL cells that overexpress a specific fzd, but do not rely on that specific fzd for survival.

Example 10

Expression of Wnt and Fzd Genes in Human Tonsils and Mantle Zone Lymphomas

Normal human tonsil were stained using the anti-wnt16 antibodies. The antibodies stained mainly the B cells in the mantle zone and the germinal centers, that are thought to be immature or activated B cells. (Data not shown.)

Mantle zone lymphomas are an incurable, aggressive B cell neoplasm, and represent a target for the specific wnt16 antibody. Mantle zone lymphoma cells are assayed for wnt16 expression using real time PCR as described above and using wnt16 specific antibodies. Mantle zone lymphomas that overexpress wnt16 relative to normal B cells or relative to expression of other specific wnts in the mantle zone lymphoma cells. Mantle zone lymphomas that overexpress a specific wnt16 are treated with wnt16 specific antibodies to inhibit proliferation of lymphoma cells that rely on expression of a downstream wnt/fzd induced gene. In some cases the mantle zone lymphoma cells are treated with radiolabeled or toxin-conjugated wnt16 specific antibodies to inhibit cellular proliferation or induce apoptosis of the mantle zone lymphoma cells.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference.

Citation of the above publications or documents is not intended as an admission that any of the foregoing is pertinent prior art, nor does it constitute any admission as to the contents or date of these publications or documents.

What is claimed is:

1. A method of inhibiting the proliferation or survival of breast cancer cells, wherein the cancer cells overexpress a Wnt-14 protein when compared to non-cancer cells, said comprising contacting the cells with an antibody that specifically binds to the Wnt-14 protein and blocks the binding between the Wnt-14 protein and a receptor on the breast cancer cells.

2. The method according to claim 1, wherein the Wnt-14 protein is overexpressed when compared to another Wnt protein in the same cancer cells.

3. The method according to claim 1, wherein the Wnt-14 protein is required for proliferation or survival of the cancer cell.

4. A method of treating a patient with a breast cancer, wherein the cancer cells overexpress a Wnt-14 when compared to non-cancer cells, said method comprising contacting the cancer cells with an antibody that specifically binds to the Wnt-14 protein and blocks the binding between the Wnt-14 protein and a receptor on the breast cancer cells.

5. The method according to claim 4, wherein the Wnt-14 protein is overexpressed when compared to another Wnt protein in the same cancer cells.

6. The method according to claim 4, wherein the Wnt-14 protein is required for proliferation or survival of the cancer cell.

7. The method of claim 1 or 4, wherein the cancer cells overexpress downstream wnt/fzd regulated gene product compared to other cells.

8. A method of inhibiting the proliferation or survival of a breast cancer cell, wherein the breast cancer cell overexpresses a Fzd protein in a Wnt/Fzd signaling pathway when compared to non-cancer cells, and wherein the Fzd protein is selected from the group consisting of Fzd3, Fzd4, Fzd6, Fzd7, or Fzd10, said method comprising contacting the cancer cells with an antibody that specifically binds Fzd3, Fzd4, Fzd6, Fzd7, or Fzd10 and blocks the binding between a wnt protein and a Fzd protein.

9. The method according to claim 8, wherein the antibody is an antagonist of the Wnt/Fzd signaling pathway.

10. The method according to claim 8, wherein the Fzd protein is overexpressed when compared to another Fzd protein in the same cancer cells.

11. The method according to claim 8, wherein the Fzd protein is required for proliferation or survival of the cancer cell.

12. A method of treating a patient with a breast cancer, wherein the cancer cells overexpress a Fzd protein when compared to non-cancer cells, and wherein the Fzd protein is selected from the group consisting of Fzd3, Fzd4, Fzd6, Fzd7, or Fzd 10, said method comprising administering to the patient an antibody that specifically binds Fzd3, Fzd4, Fzd6, Fzd7, or Fzd10 and inhibits the Wnt/Fzd signaling pathway in the cancer cells.

13. The method according to claim 12, wherein the antibody binds to the Fzd protein.

14. The method according to claim 12, wherein the Fzd protein is overexpressed when compared to another Fzd protein in the same cancer cells.

15. The method according to claim 12, wherein the Fzd protein is required for proliferation or survival of the cancer cell.

16. The method of claim 8 or 12, wherein the cancer cells overexpress downstream wnt/fzd regulated gene product compared to other cells.

17. A method of inhibiting the proliferation or survival of breast cancer cells, wherein the breast cancer cells overexpress a Wnt protein when compared to non-cancer cells, and wherein the breast cancer cells overexpress a downstream wnt/fzd regulated gene product compared to non-cancer cells, said method comprising contacting the breast cancer cells with an antibody that inhibits the Wnt/Fzd signaling pathway in the breast cancer cells, wherein said antibody specifically binds a Wnt-14, Fzd3, Fzd4, Fzd6, Fzd7 or Fzd10 protein.

18. A method of inhibiting the proliferation or survival of breast cancer cells, wherein the breast cancer cells overexpress a Fzd protein when compared to non-cancer cells, and wherein the breast cancer cells overexpress a downstream wnt/fzd regulated gene product, said method comprising contacting the breast cancer cells with an antibody that inhibits the Wnt/Fzd signaling pathway in the breast cancer cells, wherein said antibody specifically binds a Wnt-14, Fzd3, Fzd4, Fzd6, Fzd7 or Fzd10 protein.

19. A method of treating a patient with breast cancer, wherein the breast cancer cells overexpress a Wnt protein when compared to non-cancer cells, and wherein the breast cancer cells overexpress a downstream wnt/fzd regulated gene product compared to non-cancer cells, said method comprising administering to the patient an antibody that inhibits the Wnt/Fzd signaling pathway in the breast cancer cells, wherein said antibody specifically binds a Wnt-14, Fzd3, Fzd4, Fzd6, Fzd7 or Fzd10 protein.

* * * * *

SEQUENCE LISTING

```
<160> NUMBER OF SEQ ID NOS: 232

<210> SEQ ID NO 1
<211> LENGTH: 370
<212> TYPE: PRT
<213> ORGANISM: Homo sapiens
<220> FEATURE:
<223> OTHER INFORMATION: human Wnt-1

<400> SEQUENCE: 1

Met Gly Leu Trp Ala Leu Leu Pro Gly Trp Val Ser Ala Thr Leu Leu
  1               5                  10                  15

Leu Ala Leu Ala Ala Leu Pro Ala Ala Leu Ala Ala Asn Ser Ser Gly
             20                  25                  30

Arg Trp Trp Gly Ile Val Asn Val Ala Ser Ser Thr Asn Leu Leu Thr
         35                  40                  45

Asp Ser Lys Ser Leu Gln Leu Val Leu Glu Pro Ser Leu Gln Leu Leu
     50                  55                  60

Ser Arg Lys Gln Arg Arg Leu Ile Arg Gln Asn Pro Gly Ile Leu His
 65                  70                  75                  80

Ser Val Ser Gly Gly Leu Gln Ser Ala Val Arg Glu Cys Lys Trp Gln
                 85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
        115                 120                 125

Ala Ile Thr Ser Ala Gly Val Thr His Ser Val Ala Arg Ser Cys Ser
    130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
            180                 185                 190

Asp Leu Arg Phe Leu Met Asn Leu His Asn Asn Glu Ala Gly Arg Thr
        195                 200                 205

Thr Val Phe Ser Glu Met Arg Gln Glu Cys Lys Cys His Gly Met Ser
    210                 215                 220

Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
            260                 265                 270
```

-continued

```
Arg Leu Glu Pro Glu Asp Pro Ala His Lys Pro Pro Ser Pro His Asp
        275                 280                 285

Leu Val Tyr Phe Glu Lys Ser Pro Asn Phe Cys Thr Tyr Ser Gly Arg
    290                 295                 300

Leu Gly Thr Ala Gly Thr Ala Gly Arg Ala Cys Asn Ser Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
            340                 345                 350

Cys His Val Ser Cys Arg Asn Cys Thr His Thr Arg Val Leu His Glu
        355                 360                 365

Cys Leu
    370


<210> SEQ ID NO 2
<211> LENGTH: 2368
<212> TYPE: DNA
<213> ORGANISM: Homo sapiens
<220> FEATURE:
<223> OTHER INFORMATION: human Wnt-1

<400> SEQUENCE: 2

gcggtgccgc ccgccgtggc cgcctcagcc caccagccgg gaccgcgagc catgctgtcc      60

gccgcccgcc cccagggttg ttaaagccag actgcgaact ctcgccactg ccgccaccgc     120

cgcgtcccgt cccaccgtcg cgggcaacaa ccaaagtcgc cgcaactgca gcacagagcg     180

ggcaaagcca ggcaggccat ggggctctgg gcgctgttgc ctggctgggt ttctgctacg     240

ctgctgctgg cgctggccgc tctgcccgca gccctggctg ccaacagcag tggccgatgg     300

tggggtattg tgaacgtagc ctcctccacg aacctgctta cagactccaa gagtctgcaa     360

ctggtactcg agcccagtct gcagctgttg agccgcaaac agcggcgtct gatacgccaa     420

aatccgggga tcctgcacag cgtgagtggg gggctgcaga gtgccgtgcg cgagtgcaag     480

tggcagttcc ggaatcgccg ctggaactgt cccactgctc cagggcccca cctcttcggc     540

aagatcgtca accgaggctg tcgagaaacg gcgtttatct tcgctatcac ctccgccggg     600

gtcacccatt cggtggcgcg ctcctgctca gaaggttcca tcgaatcctg cacgtgtgac     660

taccggcggc gcggccccgg gggccccgac tggcactggg ggggctgcag cgacaacatt     720

gacttcggcc gcctcttcgg ccgggagttc gtggactccg gggagaaggg gcgggacctg     780

cgcttcctca tgaaccttca caacaacgag gcaggccgta cgaccgtatt ctccgagatg     840

cgccaggagt gcaagtgcca cgggatgtcc ggctcatgca cggtgcgcac gtgctggatg     900

cggctgccca cgctgcgcgc cgtgggcgat gtgctgcgcg accgcttcga cggcgcctcg     960

cgcgtcctgt acggcaaccg cggcagcaac cgcgcttcgc gagcggagct gctgcgcctg    1020

gagccggaag acccggccca caaaccgccc tccccccacg acctcgtcta cttcgagaaa    1080

tcgcccaact tctgcacgta cagcggacgc ctgggcacag caggcacggc agggcgcgcc    1140

tgtaacagct cgtcgcccgc gctggacggc tgcgagctgc tctgctgcgg caggggccac    1200

cgcacgcgca cgcagcgcgt caccgagcgc tgcaactgca ccttccactg gtgctgccac    1260

gtcagctgcc gcaactgcac gcacacgcgc gtactgcacg agtgtctgtg aggcgctgcg    1320

cggactcgcc cccaggaaac gctctcctcg agccctcccc caaacagact cgctagcact    1380

caagacccgg ttattcgccc acccgagtac ctccagtcac actccccgcg gttcatacgc    1440
```

-continued

```
atcccatctc tcccacttcc tcctacctgg ggactcctca aaccacttgc ctggggcggc   1500

atgaaccctc ttgccatcct gatggacctg ccccggacct acctccctcc ctctccgcgg   1560

gagacccctt gttgcactgc cccctgcttg gccaggaggt gagagaagga tgggtcccct   1620

ccgccatggg gtcggctcct gatggtgtca ttctgcctgc tccatcgcgc cagcgacctc   1680

tctgcctctc ttcttcccct ttgtcctgcg ttttctccgg gtcctcctaa gtcccttcct   1740

attctcctgc catgggtgca gaccctgaac ccacacctgg gcatcagggc ctttctcctc   1800

cccacctgta gctgaagcag gaggttacag ggcaaaaggg cagctgtgat gatgtggaaa   1860

tgaggttggg ggaaccagca gaaatgcccc cattctccca gtctctgtcg tggagccatt   1920

gaacagctgt gagccatgcc tccctgggcc acctcctacc ccttcctgtc ctgcctcctc   1980

atcagtgtgt aaataatttg cactgaaacg tggatacaga gccacgagtt tggatgttgt   2040

aaataaaact atttattgtg ctgggtccca gcctggtttg caaagaccac ctccaaccca   2100

acccaatccc tctccactct tctctccttt ctccctgcag ccttttctgg tccctcttct   2160

ctcctcagtt tctcaaagat gcgtttgcct cctggaatca gtatttcctt ccactgtagc   2220

tattagcggc tcctcgcccc caccagtgta gcatcttcct ctgcagaata aaatctctat   2280

ttttatcgat gacttggtgg cttttccttg aatccagaac acaaccttgt ttgtggtgtc   2340

ccctatcctc cccttttacc actcccag                                      2368


<210> SEQ ID NO 3
<211> LENGTH: 360
<212> TYPE: PRT
<213> ORGANISM: Homo sapiens
<220> FEATURE:
<223> OTHER INFORMATION: human Wnt-2

<400> SEQUENCE: 3

Met Asn Ala Pro Leu Gly Gly Ile Trp Leu Trp Leu Pro Leu Leu Leu
  1               5                  10                  15

Thr Trp Leu Thr Pro Glu Val Asn Ser Ser Trp Trp Tyr Met Arg Ala
             20                  25                  30

Thr Gly Gly Ser Ser Arg Val Met Cys Asp Asn Val Pro Gly Leu Val
         35                  40                  45

Ser Ser Gln Arg Gln Leu Cys His Arg His Pro Asp Val Met Arg Ala
     50                  55                  60

Ile Ser Gln Gly Val Ala Glu Trp Thr Ala Glu Cys Gln His Gln Phe
 65                  70                  75                  80

Arg Gln His Arg Trp Asn Cys Asn Thr Leu Asp Arg Asp His Ser Leu
                 85                  90                  95

Phe Gly Arg Val Leu Leu Arg Ser Ser Arg Glu Ser Ala Phe Val Tyr
            100                 105                 110

Ala Ile Ser Ser Ala Gly Val Val Phe Ala Ile Thr Arg Ala Cys Ser
        115                 120                 125

Gln Gly Glu Val Lys Ser Cys Ser Cys Asp Pro Lys Lys Met Gly Ser
    130                 135                 140

Ala Lys Asp Ser Lys Gly Ile Phe Asp Trp Gly Gly Cys Ser Asp Asn
145                 150                 155                 160

Ile Asp Tyr Gly Ile Lys Phe Ala Arg Ala Phe Val Asp Ala Lys Glu
                165                 170                 175

Arg Lys Gly Lys Asp Ala Arg Ala Leu Met Asn Leu His Asn Asn Arg
            180                 185                 190

Ala Gly Arg Lys Ala Val Lys Arg Phe Leu Lys Gln Glu Cys Lys Cys
```

-continued

```
        195                 200                 205

His Gly Val Ser Gly Ser Cys Thr Leu Arg Thr Cys Trp Leu Ala Met
    210                 215                 220

Ala Asp Phe Arg Lys Thr Gly Asp Tyr Leu Trp Arg Lys Tyr Asn Gly
225                 230                 235                 240

Ala Ile Gln Val Val Met Asn Gln Asp Gly Thr Gly Phe Thr Val Ala
                245                 250                 255

Asn Glu Arg Phe Lys Lys Pro Thr Lys Asn Asp Leu Val Tyr Phe Glu
            260                 265                 270

Asn Ser Pro Asp Tyr Cys Ile Arg Asp Arg Glu Ala Gly Ser Leu Gly
        275                 280                 285

Thr Ala Gly Arg Val Cys Asn Leu Thr Ser Arg Gly Met Asp Ser Cys
    290                 295                 300

Glu Val Met Cys Cys Gly Arg Gly Tyr Asp Thr Ser His Val Thr Arg
305                 310                 315                 320

Met Thr Lys Cys Gly Cys Lys Phe His Trp Cys Cys Ala Val Arg Cys
                325                 330                 335

Gln Asp Cys Leu Glu Ala Leu Asp Val His Thr Cys Lys Ala Pro Lys
            340                 345                 350

Asn Ala Asp Trp Thr Thr Ala Thr
        355                 360


<210> SEQ ID NO 4
<211> LENGTH: 2301
<212> TYPE: DNA
<213> ORGANISM: Homo sapiens
<220> FEATURE:
<223> OTHER INFORMATION: human Wnt-2

<400> SEQUENCE: 4

agcagagcgg acgggcgcgc gggaggcgcg cagagctttc gggctgcagg cgctcgctgc      60

cgctggggaa ttgggctgtg ggcgaggcgg tccgggctgg cctttatcgc tcgctgggcc     120

catcgtttga aactttatca gcgagtcgcc actcgtcgca ggaccgagcg gggggcgggg     180

gcgcggcgag gcggcggccg tgacgaggcg ctcccggagc tgagcgcttc tgctctgggc     240

acgcatggcg cccgcacacg gagtctgacc tgatgcagac gcaagggggt taatatgaac     300

gcccctctcg gtggaatctg gctctggctc cctctgctct tgacctggct cacccccgag     360

gtcaactctt catggtggta catgagagct acaggtggct cctccagggt gatgtgcgat     420

aatgtgccag gcctggtgag cagccagcgg cagctgtgtc accgacatcc agatgtgatg     480

cgtgccatta gccagggcgt ggccgagtgg acagcagaat gccagcacca gttccgccag     540

caccgctgga attgcaacac cctggacagg gatcacagcc tttttggcag ggtcctactc     600

cgaagtagtc gggaatctgc ctttgtttat gccatctcct cagctggagt tgtatttgcc     660

atcaccaggg cctgtagcca aggagaagta aaatcctgtt cctgtgatcc aaagaagatg     720

ggaagcgcca aggacagcaa aggcattttt gattggggtg gctgcagtga taacattgac     780

tatgggatca aatttgcccg cgcatttgtg gatgcaaagg aaaggaaagg aaaggatgcc     840

agagccctga tgaatcttca caacaacaga gctggcagga aggctgtaaa gcggttcttg     900

aaacaagagt gcaagtgcca cggggtgagc ggctcatgta ctctcaggac atgctggctg     960

gccatggccg acttcaggaa aacgggcgat tatctctgga ggaagtacaa tggggccatc    1020

caggtggtca tgaaccagga tggcacaggt ttcactgtgg ctaacgagag gtttaagaag    1080

ccaacgaaaa atgacctcgt gtattttgag aattctccag actactgtat cagggaccga    1140
```

-continued

```
gaggcaggct ccctgggtac agcaggccgt gtgtgcaacc tgacttcccg gggcatggac   1200

agctgtgaag tcatgtgctg tgggagaggc tacgacacct cccatgtcac ccggatgacc   1260

aagtgtgggt gtaagttcca ctggtgctgc gccgtgcgct gtcaggactg cctggaagct   1320

ctggatgtgc acacatgcaa ggcccccaag aacgctgact ggacaaccgc tacatgaccc   1380

cagcaggcgt caccatccac cttcccttct acaaggactc cattggatct gcaagaacac   1440

tggacctttg ggttctttct ggggggatat ttcctaaggc atgtggcctt tatctcaacg   1500

gaagcccccct cttcctccct gggggcccca ggatgggggg ccacacgctg cacctaaagc   1560

ctaccctatt ctatccatct cctggtgttc tgcagtcatc tcccctcctg gcgagttctc   1620

tttggaaata gcatgacagg ctgttcagcc gggagggtgg tgggcccaga ccactgtctc   1680

cacccacctt gacgtttctt ctttctagag cagttggcca agcagaaaaa aaagtgtctc   1740

aaaggagctt tctcaatgtc ttcccacaaa tggtcccaat taagaaattc catacttctc   1800

tcagatggaa cagtaaagaa agcagaatca actgcccctg acttaacttt aacttttgaa   1860

aagaccaaga cttttgtctg tacaagtggt tttacagcta ccacccttag ggtaattggt   1920

aattacctgg agaagaatgg ctttcaatac ccttttaagt ttaaaatgtg tatttttcaa   1980

ggcatttatt gccatattaa aatctgatgt aacaaggtgg ggacgtgtgt cctttggtac   2040

tatggtgtgt tgtatctttg taagagcaaa agcctcagaa agggattgct ttgcattact   2100

gtccccttga tataaaaaat ctttagggaa tgagagttcc ttctcactta gaatctgaag   2160

ggaattaaaa agaagatgaa tggtctggca atattctgta actattgggt gaatatggtg   2220

gaaaataatt tagtggatgg aatatcagaa gtatatctgt acagatcaag aaaaaaagga   2280

agaataaaat tcctatatca t                                             2301
```

<210> SEQ ID NO 5
<211> LENGTH: 314
<212> TYPE: PRT
<213> ORGANISM: Homo sapiens
<220> FEATURE:
<223> OTHER INFORMATION: human Wnt-2b

<400> SEQUENCE: 5

```
Met Leu Asp Gly Leu Gly Val Val Ala Ile Ser Ile Phe Gly Ile Gln
  1               5                  10                  15

Leu Lys Thr Glu Gly Ser Leu Arg Thr Ala Val Pro Gly Ile Pro Thr
             20                  25                  30

Gln Ser Ala Phe Asn Lys Cys Leu Gln Arg Tyr Ile Gly Ala Leu Gly
         35                  40                  45

Ala Arg Val Ile Cys Asp Asn Ile Pro Gly Leu Val Ser Arg Gln Arg
     50                  55                  60

Gln Leu Cys Gln Arg Tyr Pro Asp Ile Met Arg Ser Val Gly Glu Gly
 65                  70                  75                  80

Ala Arg Glu Trp Ile Arg Glu Cys Gln His Gln Phe Arg His His Arg
                 85                  90                  95

Trp Asn Cys Thr Thr Leu Arg Gly Asp Phe Asp Trp Gly Gly Cys Ser
            100                 105                 110

Asp Asn Ile His Tyr Gly Val Arg Phe Ala Lys Ala Phe Val Asp Ala
        115                 120                 125

Lys Glu Lys Arg Leu Lys Asp Ala Arg Ala Leu Met Asn Leu His Asn
    130                 135                 140

Asn Arg Cys Gly Arg Thr Ala Val Arg Arg Phe Leu Lys Leu Glu Cys
```

-continued

```
145                 150                 155                 160

Lys Cys His Gly Val Ser Gly Ser Cys Thr Leu Arg Thr Cys Trp Arg
                165                 170                 175

Ala Leu Ser Asp Phe Arg Arg Thr Gly Asp Tyr Leu Arg Arg Arg Tyr
            180                 185                 190

Asp Gly Ala Val Gln Val Met Ala Thr Gln Asp Gly Ala Asn Phe Thr
        195                 200                 205

Ala Ala Arg Gln Gly Tyr Arg Arg Ala Thr Arg Thr Asp Leu Val Tyr
    210                 215                 220

Phe Asp Asn Ser Pro Asp Tyr Cys Val Leu Asp Lys Ala Ala Gly Ser
225                 230                 235                 240

Leu Gly Thr Ala Gly Arg Val Cys Ser Lys Thr Ser Lys Gly Thr Asp
                245                 250                 255

Gly Cys Glu Ile Met Cys Cys Gly Arg Gly Tyr Asp Thr Thr Arg Val
            260                 265                 270

Thr Arg Val Thr Gln Cys Glu Cys Lys Phe His Trp Cys Cys Ala Val
        275                 280                 285

Arg Cys Lys Glu Cys Arg Asn Thr Val Asp Val His Thr Cys Lys Ala
    290                 295                 300

Pro Lys Lys Ala Glu Trp Leu Asp Gln Thr
305                 310


<210> SEQ ID NO 6
<211> LENGTH: 2014
<212> TYPE: DNA
<213> ORGANISM: Homo sapiens
<220> FEATURE:
<223> OTHER INFORMATION: human Wnt-2b

<400> SEQUENCE: 6

aaaccctgaa gagcccaagc aatgtggttg taaaatttgc aaaataagat taaatcttaa     60

ctgcaatctg ttaacactgc tgtctccttt cactctttct cctatatcac actttcccac    120

atgttggatg gccttggagt ggtagccata agcatttttg gaattcaact aaaaactgaa    180

ggatccttga ggacggcagt acctggcata cctacacagt cagcgttcaa caagtgtttg    240

caaaggtaca ttggggcact gggggcacga gtgatctgtg acaatatccc tggtttggtg    300

agccggcagc ggcagctgtg ccagcgttac ccagacatca tgcgttcagt gggcgagggt    360

gcccgagaat ggatccgaga gtgtcagcac caattccgcc accaccgctg gaactgtacc    420

accctggacc gggaccacac cgtctttggc cgtgtcatgc tcagaagtag ccgagaggca    480

gcttttgtat atgccatctc atcagcaggg gtagtccacg ctattactcg cgcctgtagc    540

cagggtgaac tgagtgtgtg cagctgtgac ccctacaccc gtggccgaca ccatgaccag    600

cgtggggact ttgactgggg tggctgcagt gacaacatcc actacggtgt ccgttttgcc    660

aaggccttcg tggatgccaa ggagaagagg cttaaggatg cccgggccct catgaactta    720

cataataacc gctgtggtcg cacggctgtg cggcggtttc tgaagctgga gtgtaagtgc    780

catggcgtga gtggttcctg tactctgcgc acctgctggc gtgcactctc agatttccgc    840

cgcacaggtg attacctgcg gcgacgctat gatggggctg tgcaggtgat ggccacccaa    900

gatggtgcca acttcaccgc agcccgccaa ggctatcgcc gtgccacccg gactgatctt    960

gtctactttg acaactctcc agattactgt gtcttggaca aggctgcagg ttccctaggc   1020

actgcaggcc gtgtctgcag caagacatca aaaggaacag acggttgtga aatcatgtgc   1080

tgtggccgag ggtacgacac aactcgagtc acccgtgtta cccagtgtga gtgcaaattc   1140
```

-continued

```
cactggtgct gtgctgtacg gtgcaaggaa tgcagaaata ctgtggacgt ccatacttgc   1200

aaagcccccca agaaggcaga gtggctggac cagacctgaa cacacagata cctcactcat   1260

ccctccaatt caagcctctc aactcaaaag cacaagatcc ttgcatgcac accttcctcc   1320

accctccacc ctgggctgct accgcttcta tttaaggatg tagagagtaa tccataggga   1380

ccatggtgtc ctggctggtt ccttagccct gggaaggagt tgtcagggga tataagaaac   1440

tgtgcaagct ccctgatttc ccgctctgga gatttgaagg gagagtagaa gagatagggg   1500

gtctttagag tgaaatgagt tgcactaaag tacgtagttg aggctccttt tttctttcct   1560

ttgcaccagc ttcccgacac ttcttggtgt gcaagaggaa gggtacctgt agagagcttc   1620

tttttgtttc tacctggcca aagttagatg ggacaaagat gaatggcatg tcccttctct   1680

gaagtccgtt tgagcagaac tacctggtac cccgaaagaa aaatcttagg ctaccacatt   1740

ctattattga gagcctgaga tgttagccat agtggacaag gttccattca catgctcata   1800

tgtttataaa ctgtgttttg tagaagaaaa agaatcataa caatacaaac acacattcat   1860

tctctctttt tctctctacc attctcaacc tgtattggac agcactgcct cttttgctta   1920

cttgctgcct gttcaaactg aggtggaatg cagtggttcc catgcttaac agatcattaa   1980

aacaccctag aacactccta ggatagatta atgt                               2014
```

<210> SEQ ID NO 7
<211> LENGTH: 355
<212> TYPE: PRT
<213> ORGANISM: Homo sapiens
<220> FEATURE:
<223> OTHER INFORMATION: human Wnt-3

<400> SEQUENCE: 7

```
Met Glu Pro His Leu Leu Gly Leu Leu Leu Gly Leu Leu Leu Gly Gly
  1               5                  10                  15

Thr Arg Val Leu Ala Gly Tyr Pro Ile Trp Trp Ser Leu Ala Leu Gly
             20                  25                  30

Gln Gln Tyr Thr Ser Leu Gly Ser Gln Pro Leu Leu Cys Gly Ser Ile
         35                  40                  45

Pro Gly Leu Val Pro Lys Gln Leu Arg Phe Cys Arg Asn Tyr Ile Glu
     50                  55                  60

Ile Met Pro Ser Val Ala Glu Gly Val Lys Leu Gly Ile Gln Glu Cys
 65                  70                  75                  80

Gln His Gln Phe Arg Gly Arg Arg Trp Asn Cys Thr Thr Ile Asp Asp
                 85                  90                  95

Ser Leu Ala Ile Phe Gly Pro Val Leu Asp Lys Ala Thr Arg Glu Ser
            100                 105                 110

Ala Phe Val His Ala Ile Ala Ser Ala Gly Val Ala Phe Ala Val Thr
        115                 120                 125

Arg Ser Cys Ala Glu Gly Thr Ser Thr Ile Cys Gly Cys Asp Ser His
    130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
        195                 200                 205
```

-continued

```
His Gly Leu Ser Gly Ser Cys Glu Val Lys Thr Cys Trp Trp Ala Gln
    210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
    290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
            340                 345                 350

Thr Cys Lys
        355


<210> SEQ ID NO 8
<211> LENGTH: 1506
<212> TYPE: DNA
<213> ORGANISM: Homo sapiens
<220> FEATURE:
<223> OTHER INFORMATION: human Wnt-3

<400> SEQUENCE: 8

gcgcttctga caagcccgaa agtcatttcc aatctcaagt ggactttgtt ccaactattg     60

ggggcgtcgc tccccctctt catggtcgcg ggcaaacttc ctcctcggcg cctcttctaa    120

tggagcccca cctgctcggg ctgctcctcg gcctcctgct cggtggcacc agggtcctcg    180

ctggctaccc aatttggtgg tccctggccc tgggccagca gtacacatct ctgggctcac    240

agcccctgct ctgcggctcc atcccaggcc tggtccccaa gcaactgcgc ttctgccgca    300

attacatcga gatcatgccc agcgtggccg agggcgtgaa gctgggcatc caggagtgcc    360

agcaccagtt ccggggccgc cgctggaact gcaccaccat agatgacagc ctggccatct    420

ttgggcccgt cctcgacaaa gccacccgcg agtcggcctt cgttcacgcc atcgcctcgg    480

ccggcgtggc cttcgccgtc acccgctcct gcgccgaggg cacctccacc atttgcggct    540

gtgactcgca tcataagggg ccgcctggcg aaggctggaa gtggggcggc tgcagcgagg    600

acgctgactt cggcgtgtta gtgtccaggg agttcgcgga tgcgcgcgag aacaggccgg    660

acgcgcgctc ggccatgaac aagcacaaca acgaggcggg ccgcacgact atcctggacc    720

acatgcacct caaatgcaag tgccacgggc tgtcgggcag ctgtgaggtg aagacctgct    780

ggtgggcgca gcctgacttc cgtgccatcg gtgacttcct caaggacaag tatgacagcg    840

cctcggagat ggtagtagag aagcaccgtg agtcccgagg ctgggtggag accctccggg    900

ccaagtactc gctcttcaag ccacccacgg agagggacct ggtctactac gagaactccc    960

ccaacttttg tgagcccaac ccagagacgg gttcctttgg cacaagggac cggacttgca   1020

atgtcacctc ccacggcatc gatggctgcg atctgctctg ctgtggccgg ggccacaaca   1080

cgaggacgga gaagcggaag gaaaaatgcc actgcatctt ccactggtgc tgctacgtca   1140
```

-continued

```
gctgccagga gtgtattcgc atctacgacg tgcacacctg caagtagggc accagggcgc   1200

tgggaagggg tgaagtgtgt ggctgggcgg attcagcgaa gtctcatggg aagcaggacc   1260

tagagccggg cacagccctc agcgtcagac agcaaggaac tgtcaccagc cgcacgcgtg   1320

gtaaatgacc cagacccaac tcgcctgtgg acggggaggc tctccctctc tctcatctta   1380

catttctcac cctactctgg atggtgtgtg gtttttaaag aagggggctt tctttttagt   1440

tctctagggt ctgataggaa cagacctgag gcttatcttt gcacatgtta aagaaaaaaa   1500

aaaaaa                                                              1506
```

```
<210> SEQ ID NO 9
<211> LENGTH: 352
<212> TYPE: PRT
<213> ORGANISM: Homo sapiens
<220> FEATURE:
<223> OTHER INFORMATION: human Wnt-3a

<400> SEQUENCE: 9

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
```

-continued

```
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350


<210> SEQ ID NO 10
<211> LENGTH: 2932
<212> TYPE: DNA
<213> ORGANISM: Homo sapiens
<220> FEATURE:
<223> OTHER INFORMATION: human Wnt-3a

<400> SEQUENCE: 10

agctcccagg gcccggcccc ccccggcgct cacgctctcg ggcggactc ccggccctcc      60

gcgccctctc gcgcggcgat ggccccactc ggatacttct tactcctctg cagcctgaag     120

caggctctgg gcagctaccc gatctggtgg tcgctggctg ttgggccaca gtattcctcc     180

ctgggctcgc agcccatcct gtgtgccagc atcccgggcc tggtccccaa gcagctccgc     240

ttctgcagga actacgtgga gatcatgccc agcgtggccg agggcatcaa gattggcatc     300

caggagtgcc agcaccagtt ccgcggccgc cggtggaact gcaccaccgt ccacgacagc     360

ctggccatct tcgggcccgt gctggacaaa gctaccaggg agtcggcctt tgtccacgcc     420

attgcctcag ccggtgtggc ctttgcagtg acacgctcat gtgcagaagg cacggccgcc     480

atctgtggct gcagcagccg ccaccagggc tcaccaggca agggctggaa gtggggtggc     540

tgtagcgagg acatcgagtt tggtgggatg gtgtctcggg agttcgccga cgcccgggag     600

aaccggccag atgcccgctc agccatgaac cgccacaaca acgaggctgg gcgccaggcc     660

atcgccagcc acatgcacct caagtgcaag tgccacgggc tgtcgggcag ctgcgaggtg     720

aagacatgct ggtggtcgca acccgacttc cgcgccatcg gtgacttcct caaggacaag     780

tacgacagcg cctcggagat ggtggtggag aagcaccggg agtcccgcgg ctgggtggag     840

accctgcggc cgcgctacac ctacttcaag gtgcccacgg agcgcgacct ggtctactac     900

gaggcctcgc ccaacttctg cgagcccaac cctgagacgg gctccttcgg cacgcgcgac     960

cgcacctgca acgtcagctc gcacggcatc gacggctgcg acctgctgtg ctgcggccgc    1020

ggccacaacg cgcgagcgga gcggcgccgg gagaagtgcc gctgcgtgtt ccactggtgc    1080

tgctacgtca gctgccagga gtgcacgcgc gtctacgacg tgcacacctg caagtaggca    1140

ccggccgcgg ctccccctgg acggggcggg ccctgcctga gggtgggctt ttccctgggt    1200

ggagcaggac tcccacctaa acggggcagt actcctccct gggggcggga ctcctccctg    1260

ggggtggggc tcctacctgg gggcagaact cctacctgaa ggcagggctc ctccctggag    1320

ctagtgtctc ctctctggtg gctgggctgc tcctgaatga ggcggagctc caggatgggg    1380

aggggctctg cgttggcttc tccctgggga cggggctccc ctggacagag gcggggctac    1440

agattgggcg gggcttctct tgggtgggac agggcttctc ctgcgggggc gaggcccctc    1500

ccagtaaggg cgtggctctg ggtgggcggg gcactaggta ggcttctacc tgcaggcggg    1560

gctcctcctg aaggaggcgg ggctctagga tggggcacgg ctctggggta ggctgctccc    1620

tgagggcgga gcgcctcctt aggagtgggg ttttatggtg gatgaggctt cttcctggat    1680

ggggcagagc ttctcctgac cagggcaagg ccccttccac gggggctgtg gctctgggtg    1740
```

-continued

```
ggcgtggcct gcataggctc cttcctgtgg gtggggcttc tctgggacca ggctccaatg   1800

gggcggggct tctctccgcg ggtgggactc ttccctggga accgccctcc tgattaaggc   1860

gtggcttctg caggaatccc ggctccagag caggaaattc agcccaccag ccacctcatc   1920

cccaaccccc tgtaaggttc catccacccc tgcgtcgagc tgggaaggtt ccatgaagcg   1980

agtcgggtcc ccaacccgtg cccctgggat ccgagggccc ctctccaagc gcctggcttt   2040

ggaatgctcc aggcgcgccg acgcctgtgc cacccccttcc tcagcctggg gtttgaccac  2100

ccacctgacc aggggcccta cctggggaaa gcctgaaggg cctcccagcc cccaacccca   2160

agaccaagct tagtcctggg agaggacagg gacttcgcag aggcaagcga ccgaggccct   2220

cccaaagagg cccgccctgc ccgggctccc acaccgtcag gtactcctgc cagggaactg   2280

gcctgctgcg ccccaggccc cgcccgtctc tgctctgctc agctgcgccc ccttctttgc   2340

agctgcccag cccctcctcc ctgccctcgg gtctccccac ctgcactcca tccagctaca   2400

ggagagatag aagcctctcg tcccgtccct ccctttcctc cgcctgtcca cagcccctta   2460

agggaaaggt aggaagagag gtccagcccc ccaggctgcc cagagctgct ggtctcattt   2520

gggggcgttc gggaggtttg gggggcatca accccccgac tgtgctgctc gcgaaggtcc   2580

cacagccctg agatgggccg gcccccttcc tggcccctca tggcgggact ggagaaatgg   2640

tccgctttcc tggagccaat ggcccggccc ctcctgactc atccgcctgg cccgggaatg   2700

aatggggagg ccgctgaacc cacccggccc atatccctgg ttgcctcatg gccagcgccc   2760

ctcagcctct gccactgtga accggctccc accctcaagg tgcggggaga agaagcggcc   2820

aggcggggcg ccccaagagc ccaaaagagg gcacaccgcc atcctctgcc tcaaattctg   2880

cgtttttggt tttaatgtta tatctgatgc tgctatatcc actgtccaac gg           2932
```

<210> SEQ ID NO 11
<211> LENGTH: 351
<212> TYPE: PRT
<213> ORGANISM: Homo sapiens
<220> FEATURE:
<223> OTHER INFORMATION: human Wnt-4

<400> SEQUENCE: 11

```
Met Ser Pro Arg Ser Cys Leu Arg Ser Leu Arg Leu Leu Val Phe Ala
  1               5                  10                  15

Val Phe Ser Ala Ala Ala Ser Asn Trp Leu Tyr Leu Ala Lys Leu Ser
            20                  25                  30

Ser Val Gly Ser Ile Ser Glu Glu Glu Thr Cys Glu Lys Leu Lys Gly
        35                  40                  45

Leu Ile Gln Arg Gln Val Gln Met Cys Lys Arg Asn Leu Glu Val Met
     50                  55                  60

Asp Ser Val Arg Arg Gly Ala Gln Leu Ala Ile Glu Glu Cys Gln Tyr
 65                  70                  75                  80

Gln Phe Arg Asn Arg Arg Trp Asn Cys Ser Thr Leu Asp Ser Leu Pro
                 85                  90                  95

Val Phe Gly Lys Val Val Thr Gln Gly Thr Arg Glu Ala Ala Phe Val
            100                 105                 110

Tyr Ala Ile Ser Ser Ala Gly Val Ala Phe Ala Val Thr Arg Ala Cys
        115                 120                 125

Ser Ser Gly Glu Leu Glu Lys Cys Gly Cys Asp Arg Thr Val His Gly
    130                 135                 140

Val Ser Pro Gln Gly Phe Gln Trp Ser Gly Cys Ser Asp Asn Ile Ala
145                 150                 155                 160
```

-continued

```
Tyr Gly Val Ala Phe Ser Gln Ser Phe Val Asp Val Arg Glu Arg Ser
                165                 170                 175

Lys Gly Ala Ser Ser Ser Arg Ala Leu Met Asn Leu His Asn Asn Glu
            180                 185                 190

Ala Gly Arg Lys Ala Ile Leu Thr His Met Arg Val Glu Cys Lys Cys
        195                 200                 205

His Gly Val Ser Gly Ser Cys Glu Val Lys Thr Cys Trp Arg Ala Val
    210                 215                 220

Pro Pro Phe Arg Gln Val Gly His Ala Leu Lys Glu Lys Phe Asp Gly
225                 230                 235                 240

Ala Thr Glu Val Glu Pro Arg Arg Val Gly Ser Ser Arg Ala Leu Val
                245                 250                 255

Pro Arg Asn Ala Gln Phe Lys Pro His Thr Asp Glu Asp Leu Val Tyr
            260                 265                 270

Leu Glu Pro Ser Pro Asp Phe Cys Glu Gln Asp Met Arg Ser Gly Val
        275                 280                 285

Leu Gly Thr Arg Gly Arg Thr Cys Asn Lys Thr Ser Lys Ala Ile Asp
    290                 295                 300

Gly Cys Glu Leu Leu Cys Cys Gly Arg Gly Phe His Thr Ala Gln Val
305                 310                 315                 320

Glu Leu Ala Glu Arg Cys Ser Cys Lys Phe His Trp Cys Cys Phe Val
                325                 330                 335

Lys Cys Arg Gln Cys Gln Arg Leu Val Glu Leu His Thr Cys Arg
            340                 345                 350


<210> SEQ ID NO 12
<211> LENGTH: 1198
<212> TYPE: DNA
<213> ORGANISM: Homo sapiens
<220> FEATURE:
<223> OTHER INFORMATION: human Wnt-4

<400> SEQUENCE: 12

gcggccgcag ccgctgcccc gggccgggcg cccgcggcgg caccatgagt ccccgctcgt     60

gcctgcgttc gctgcgcctc ctcgtcttcg ccgtcttctc agccgccgcg agcaactggc    120

tgtacctggc caagctgtcg tcggtgggga gcatctcaga ggaggagacg tgcgagaaac    180

tcaagggcct gatccagagg caggtgcaga tgtgcaagcg gaacctggaa gtcatggact    240

cggtgcgccg cggtgcccag ctggccattg aggagtgcca gtaccagttc cggaaccggc    300

gctggaactg ctccacactc gactccttgc ccgtcttcgg caaggtggtg acgcaaggga    360

ctcgggaggc ggccttcgtg tacgccatct cttcggcagg tgtggccttt gcagtgacgc    420

gggcgtgcag cagtggggag ctggagaagt gcggctgtga caggacagtg catggggtca    480

gcccacaggg cttccagtgg tcaggatgct ctgacaacat cgcctacggt gtggccttct    540

cacagtcgtt tgtggatgtg cgggagagaa gcaagggggc ctcgtccagc agagccctca    600

tgaacctcca caacaatgag gccggcagga aggccatcct gacacacatg cgggtggaat    660

gcaagtgcca cggggtgtca ggctcctgtg aggtaaagac gtgctggcga gccgtgccgc    720

ccttccgcca ggtgggtcac gcactgaagg agaagtttga tggtgccact gaggtggagc    780

cacgccgcgt gggctcctcc agggcactgg tgccacgcaa cgcacagttc aagccgcaca    840

cagatgagga cctggtgtac ttggagccta gccccgactt ctgtgagcag gacatgcgca    900

gcggcgtgct gggcacgagg ggccgcacat gcaacaagac gtccaaggcc atcgacggct    960
```

-continued

```
gtgagctgct gtgctgtggc cgcggcttcc acacggcgca ggtggagctg gctgaacgct   1020

gcagctgcaa attccactgg tgctgcttcg tcaagtgccg gcagtgccag cggctcgtgg   1080

agttgcacac gtgccgatga ccgcctgcct agccctgcgc cggcaaccac ctagtggccc   1140

agggaaggcc gataatttaa acagtctccc accacctacc ccaagagata ctggttgt     1198


<210> SEQ ID NO 13
<211> LENGTH: 365
<212> TYPE: PRT
<213> ORGANISM: Homo sapiens
<220> FEATURE:
<223> OTHER INFORMATION: human Wnt-5a

<400> SEQUENCE: 13

Met Ala Gly Ser Ala Met Ser Ser Lys Phe Phe Leu Val Ala Leu Ala
  1               5                  10                  15

Ile Phe Phe Ser Phe Ala Gln Val Val Ile Glu Ala Asn Ser Trp Trp
             20                  25                  30

Ser Leu Gly Met Asn Asn Pro Val Gln Met Ser Glu Val Tyr Ile Ile
         35                  40                  45

Gly Ala Gln Pro Leu Cys Ser Gln Leu Ala Gly Leu Ser Gln Gly Gln
     50                  55                  60

Lys Lys Leu Cys His Leu Tyr Gln Asp His Met Gln Tyr Ile Gly Glu
 65                  70                  75                  80

Gly Ala Lys Thr Gly Ile Lys Glu Cys Gln Tyr Gln Phe Arg His Arg
                 85                  90                  95

Arg Trp Asn Cys Ser Thr Val Asp Asn Thr Ser Val Phe Gly Arg Val
            100                 105                 110

Met Gln Ile Gly Ser Arg Glu Thr Ala Phe Thr Tyr Ala Val Ser Ala
        115                 120                 125

Ala Gly Val Val Asn Ala Met Ser Arg Ala Cys Arg Glu Gly Glu Leu
    130                 135                 140

Ser Thr Cys Gly Cys Ser Arg Ala Ala Arg Pro Lys Asp Leu Pro Arg
145                 150                 155                 160

Asp Trp Leu Trp Gly Gly Cys Gly Asp Asn Ile Asp Tyr Gly Tyr Arg
                165                 170                 175

Phe Ala Lys Glu Phe Val Asp Ala Arg Glu Arg Glu Arg Ile His Ala
            180                 185                 190

Lys Gly Ser Tyr Glu Ser Ala Arg Ile Leu Met Asn Leu His Asn Asn
        195                 200                 205

Glu Ala Gly Arg Arg Thr Val Tyr Asn Leu Ala Asp Val Ala Cys Lys
    210                 215                 220

Cys His Gly Val Ser Gly Ser Cys Ser Leu Lys Thr Cys Trp Leu Gln
225                 230                 235                 240

Leu Ala Asp Phe Arg Lys Val Gly Asp Ala Leu Lys Glu Lys Tyr Asp
                245                 250                 255

Ser Ala Ala Ala Met Arg Leu Asn Ser Arg Gly Lys Leu Val Gln Val
            260                 265                 270

Asn Ser Arg Phe Asn Ser Pro Thr Thr Gln Asp Leu Val Tyr Ile Asp
        275                 280                 285

Pro Ser Pro Asp Tyr Cys Val Arg Asn Glu Ser Thr Gly Ser Leu Gly
    290                 295                 300

Thr Gln Gly Arg Leu Cys Asn Lys Thr Ser Glu Gly Met Asp Gly Cys
305                 310                 315                 320

Glu Leu Met Cys Cys Gly Arg Gly Tyr Asp Gln Phe Lys Thr Val Gln
```

-continued

```
                325                 330                 335

Thr Glu Arg Cys His Cys Lys Phe His Trp Cys Cys Tyr Val Lys Cys
            340                 345                 350

Lys Lys Cys Thr Glu Ile Val Asp Gln Phe Val Cys Lys
        355                 360                 365


<210> SEQ ID NO 14
<211> LENGTH: 4428
<212> TYPE: DNA
<213> ORGANISM: Homo sapiens
<220> FEATURE:
<223> OTHER INFORMATION: human Wnt-5a

<400> SEQUENCE: 14

ttaaggaaat ccgggctgct cttccccatc tggaagtggc tttccccaca tcggctcgta     60

aactgattat gaaacatacg atgttaattc ggagctgcat ttcccagctg ggcactctcg    120

cgcgctggtc cccggggcct cgccccccac cccctgccct tccctcccgc gtcctgcccc    180

catcctccac cccccgcgct ggccaccccg cctccttggc agcctctggc ggcagcgcgc    240

tccactcgcc tcccgtgctc ctctcgccca tggaattaat tctggctcca cttgttgctc    300

ggcccaggtt ggggagagga cggagggtgg ccgcagcggg ttcctgagtg aattacccag    360

gagggactga gcacagcacc aactagagag gggtcagggg gtgcgggact cgagcgagca    420

ggaaggaggc agcgcctggc accagggctt tgactcaaca gaattgagac acgtttgtaa    480

tcgctggcgt gccccgcgca caggatccca gcgaaaatca gatttcctgg tgaggttgcg    540

tgggtggatt aatttggaaa aagaaactgc ctatatcttg ccatcaaaaa actcacggag    600

gagaagcgca gtcaatcaac agtaaactta agagaccccc gatgctcccc tggtttaact    660

tgtatgcttg aaaattatct gagagggaat aaacatcttt tccttcttcc ctctccagaa    720

gtccattgga atattaagcc caggagttgc tttggggatg gctggaagtg caatgtcttc    780

caagttcttc ctagtggctt tggccatatt tttctccttc gcccaggttg taattgaagc    840

caattcttgg tggtcgctag gtatgaataa ccctgttcag atgtcagaag tatatattat    900

aggagcacag cctctctgca gccaactggc aggactttct caaggacaga agaaactgtg    960

ccacttgtat caggaccaca tgcagtacat cggagaaggc gcgaagacag gcatcaaaga   1020

atgccagtat caattccgac atcgacggtg gaactgcagc actgtggata acacctctgt   1080

ttttggcagg gtgatgcaga taggcagccg cgagacggcc ttcacatacg ccgtgagcgc   1140

agcaggggtg gtgaacgcca tgagccgggc gtgccgcgag ggcgagctgt ccacctgcgg   1200

ctgcagccgc gccgcgcgcc ccaaggacct gccgcgggac tggctctggg gcggctgcgg   1260

cgacaacatc gactatggct accgctttgc caaggagttc gtggacgccc gcgagcggga   1320

gcgcatccac gccaagggct cctacgagag tgctcgcatc ctcatgaacc tgcacaacaa   1380

cgaggccggc cgcaggacgg tgtacaacct ggctgatgtg gcctgcaagt gccatggggt   1440

gtccggctca tgtagcctga agacatgctg gctgcagctg gcagacttcc gcaaggtggg   1500

tgatgccctg aaggagaagt acgacagcgc ggcggccatg cggctcaaca gccggggcaa   1560

gttggtacag gtcaacagcc gcttcaactc gcccaccaca caagacctgg tctacatcga   1620

ccccagccct gactactgcg tgcgcaatga gagcaccggc tcgctgggca cgcagggccg   1680

cctgtgcaac aagacgtcgg agggcatgga tggctgcgag ctcatgtgct gcggccgtgg   1740

gtacgaccag ttcaagaccg tgcagacgga gcgctgccac tgcaagttcc actggtgctg   1800

ctacgtcaag tgcaagaagt gcacggagat cgtggaccag tttgtgtgca agtagtgggt   1860
```

-continued

```
gccacccagc actcagcccc gctcccagga cccgcttatt tatagaaagt acagtgattc   1920
tggtttttgg tttttagaaa tattttttat ttttccccaa gaattgcaac cggaaccatt   1980
tttttcctg ttaccatcta agaactctgt ggtttattat taatattata attattattt   2040
ggcaataatg ggggtgggaa ccacgaaaaa tatttatttt gtggatcttt gaaaaggtaa   2100
tacaagactt cttttggata gtatagaatg aagggggaaa taacacatac cctaacttag   2160
ctgtgtggga catggtacac atccagaagg taaagaaata cattttcttt ttctcaaata   2220
tgccatcata tgggatgggt aggttccagt tgaaagaggg tggtagaaat ctattcacaa   2280
ttcagcttct atgaccaaaa tgagttgtaa attctctggt gcaagataaa aggtcttggg   2340
aaaacaaaac aaaacaaaac aaacctccct tccccagcag ggctgctagc ttgctttctg   2400
cattttcaaa atgataattt acaatggaag gacaagaatg tcatattctc aaggaaaaaa   2460
ggtatatcac atgtctcatt ctcctcaaat attccatttg cagacagacc gtcatattct   2520
aatagctcat gaaatttggg cagcagggag gaaagtcccc agaaattaaa aaatttaaaa   2580
ctcttatgtc aagatgttga tttgaagctg ttataagaat tgggattcca gatttgtaaa   2640
aagaccccca atgattctgg acactagatt ttttgtttgg ggaggttggc ttgaacataa   2700
atgaaatatc ctgtattttc ttagggatac ttggttagta aattataata gtagaaataa   2760
tacatgaatc ccattcacag gtttctcagc ccaagcaaca aggtaattgc gtgccattca   2820
gcactgcacc agagcagaca acctatttga ggaaaaacag tgaaatccac cttcctcttc   2880
acactgagcc ctctctgatt cctccgtgtt gtgatgtgat gctggccacg tttccaaacg   2940
gcagctccac tgggtcccct ttggttgtag gacaggaaat gaaacattag gagctctgct   3000
tggaaaacag ttcactactt agggattttt gtttcctaaa acttttattt tgaggagcag   3060
tagttttcta tgttttaatg acagaacttg gctaatggaa ttcacagagg tgttgcagcg   3120
tatcactgtt atgatcctgt gtttagatta tccactcatg cttctcctat tgtactgcag   3180
gtgtacctta aaactgttcc cagtgtactt gaacagttgc atttataagg ggggaaatgt   3240
ggtttaatgg tgcctgatat ctcaaagtct tttgtacata acatatatat atatatacat   3300
atatataaat ataaatataa atatatctca ttgcagccag tgatttagat ttacagctta   3360
ctctggggtt atctctctgt ctagagcatt gttgtccttc actgcagtcc agttgggatt   3420
attccaaaag tttttgagt cttgagcttg ggctgtggcc ccgctgtgat catacccctga   3480
gcacgacgaa gcaacctcgt ttctgaggaa gaagcttgag ttctgactca ctgaaatgcg   3540
tgttgggttg aagatatctt tttttctttt ctgcctcacc cctttgtctc caacctccat   3600
ttctgttcac tttgtggaga gggcattact tgttcgttat agacatggac gttaagagat   3660
attcaaaact cagaagcatc agcaatgttt ctcttttctt agttcattct gcagaatgga   3720
aacccatgcc tattagaaat gacagtactt attaattgag tccctaagga atattcagcc   3780
cactacatag atagcttttt tttttttttt tttttttaa taaggacacc tctttccaaa   3840
caggccatca aatatgttct tatctcagac ttacgttgtt ttaaaagttt ggaaagatac   3900
acatcttttc atacccccc ttaggaggtt gggctttcat atcacctcag ccaactgtgg   3960
ctcttaattt attgcataat gatatccaca tcagccaact gtggctcttt aatttattgc   4020
ataatgatat tcacatcccc tcagttgcag tgaattgtga gcaaaagatc ttgaaagcaa   4080
aaagcactaa ttagtttaaa atgtcacttt tttggttttt attatacaaa aaccatgaag   4140
tacttttttt atttgctaaa tcagattgtt cctttttagt gactcatgtt tatgaagaga   4200
```

-continued

```
gttgagttta acaatcctag cttttaaaag aaactattta atgtaaaata ttctacatgt   4260

cattcagata ttatgtatat cttctagcct ttattctgta cttttaatgt acatatttct   4320

gtcttgcgtg atttgtatat ttcactggtt taaaaaacaa acatcgaaag gcttattcca   4380

aatggaagat agaatataaa ataaaacgtt acttgtaaaa aaaaaaaa                4428


<210> SEQ ID NO 15
<211> LENGTH: 359
<212> TYPE: PRT
<213> ORGANISM: Homo sapiens
<220> FEATURE:
<223> OTHER INFORMATION: human Wnt-5b

<400> SEQUENCE: 15

Met Pro Ser Leu Leu Leu Leu Phe Thr Ala Ala Leu Leu Ser Ser Trp
  1               5                  10                  15

Ala Gln Leu Leu Thr Asp Ala Asn Ser Trp Trp Ser Leu Ala Leu Asn
             20                  25                  30

Pro Val Gln Arg Pro Glu Met Phe Ile Ile Gly Ala Gln Pro Val Cys
         35                  40                  45

Ser Gln Leu Pro Gly Leu Ser Pro Gly Gln Arg Lys Leu Cys Gln Leu
     50                  55                  60

Tyr Gln Glu His Met Ala Tyr Ile Gly Glu Gly Ala Lys Thr Gly Ile
 65                  70                  75                  80

Lys Glu Cys Gln His Gln Phe Arg Gln Arg Arg Trp Asn Cys Ser Thr
                 85                  90                  95

Ala Asp Asn Ala Ser Val Phe Gly Arg Val Met Gln Ile Gly Ser Arg
            100                 105                 110

Glu Thr Ala Phe Thr His Ala Val Ser Ala Ala Gly Val Val Asn Ala
        115                 120                 125

Ile Ser Arg Ala Cys Arg Glu Gly Glu Leu Ser Thr Cys Gly Cys Ser
    130                 135                 140

Arg Thr Ala Arg Pro Lys Asp Leu Pro Arg Asp Trp Leu Trp Gly Gly
145                 150                 155                 160

Cys Gly Asp Asn Val Glu Tyr Gly Tyr Arg Phe Ala Lys Glu Phe Val
                165                 170                 175

Asp Ala Arg Glu Arg Glu Lys Asn Phe Ala Lys Gly Ser Glu Glu Gln
            180                 185                 190

Gly Arg Val Leu Met Asn Leu Gln Asn Asn Glu Ala Gly Arg Arg Ala
        195                 200                 205

Val Tyr Lys Met Ala Asp Val Ala Cys Lys Cys His Gly Val Ser Gly
    210                 215                 220

Ser Cys Ser Leu Lys Thr Cys Trp Leu Gln Leu Ala Glu Phe Arg Lys
225                 230                 235                 240

Val Gly Asp Arg Leu Lys Glu Lys Tyr Asp Ser Ala Ala Ala Met Arg
                245                 250                 255

Val Thr Arg Lys Gly Arg Leu Glu Leu Val Asn Ser Arg Phe Thr Gln
            260                 265                 270

Pro Thr Pro Glu Asp Leu Val Tyr Val Asp Pro Ser Pro Asp Tyr Cys
        275                 280                 285

Leu Arg Asn Glu Ser Thr Gly Ser Leu Gly Thr Gln Gly Arg Leu Cys
    290                 295                 300

Asn Lys Thr Ser Glu Gly Met Asp Gly Cys Glu Leu Met Cys Cys Gly
305                 310                 315                 320

Arg Gly Tyr Asn Gln Phe Lys Ser Val Gln Val Glu Arg Cys His Cys
```

-continued

```
            325                 330                 335

Lys Phe His Trp Cys Cys Phe Val Arg Cys Lys Lys Cys Thr Glu Ile
        340                 345                 350

Val Asp Gln Tyr Ile Cys Lys
        355


<210> SEQ ID NO 16
<211> LENGTH: 2251
<212> TYPE: DNA
<213> ORGANISM: Homo sapiens
<220> FEATURE:
<223> OTHER INFORMATION: human Wnt-5b

<400> SEQUENCE: 16

gaccattagc aggcacccag gcctgtcttt ggctcggaaa cggtggcccc caatgtagcc      60

tagtttgaac ctaggaactg caggaccaga gagattccac tggagcctga tggacgggtg     120

acagagggaa ccctactctg gaaactgtca gtcccagggc actggggagg gctgaggccg     180

accatgccca gcctgctgct gctgttcacg gctgctctgc tgtccagctg ggctcagctt     240

ctgacagacg ccaactcctg gtggtcatta gctttgaacc cggtgcagag acccgagatg     300

tttatcatcg gtgcccagcc cgtgtgcagt cagcttcccg ggctctcccc tggccagagg     360

aagctgtgcc aattgtacca ggagcacatg gcctacatag gggagggagc caagactggc     420

atcaaggaat gccagcacca gttccggcag cggcggtgga attgcagcac agcggacaac     480

gcatctgtct ttgggagagt catgcagata ggcagccgag agaccgcctt cacccacgcg     540

gtgagcgccg cgggcgtggt caacgccatc agccgggcct gccgcgaggg cgagctctcc     600

acctgcggct gcagccggac ggcgcggccc aaggacctgc cccgggactg gctgtggggc     660

ggctgtgggg acaacgtgga gtacggctac cgcttcgcca aggagtttgt ggatgcccgg     720

gagcgagaga agaactttgc caaaggatca gaggagcagg gccgggtgct catgaacctg     780

caaaacaacg aggccggtcg cagggctgtg tataagatgg cagacgtagc ctgcaaatgc     840

cacggcgtct cggggtcctg cagcctcaag acctgctggc tgcagctggc cgagttccgc     900

aaggtcgggg accggctgaa ggagaagtac gacagcgcgg ccgccatgcg cgtcacccgc     960

aagggccggc tggagctggt caacagccgc ttcacccagc ccaccccgga ggacctggtc    1020

tatgtggacc ccagccccga ctactgcctg cgcaacgaga gcacgggctc cctgggcacg    1080

cagggccgcc tctgcaacaa gacctcggag ggcatggatg gctgtgagct catgtgctgc    1140

gggcgtggct acaaccagtt caagagcgtg caggtggagc gctgccactg caagttccac    1200

tggtgctgct tcgtcaggtg taagaagtgc acggagatcg tggaccagta catctgtaaa    1260

tagcccggag ggcctgctcc cggccccccct gcactctgcc tcacaaaggt ctatattata    1320

taaatctata taaatctatt ttatatttgt ataagtaaat gggtgggtgc tatacaatgg    1380

aaagatgaaa atggaaagga agagcttatt taagagacgc tggagatctc tgaggagtgg    1440

actttgctgg ttctctcctc ttggtgggtg ggagacaggg ctttttctct ccctctggcg    1500

aggactctca ggatgtaggg acttggaaat atttactgtc tgtccaccac ggcctggagg    1560

agggaggttg tggttggatg gaggagatga tcttgtctgg aagtctagag tctttgttgg    1620

ttagaggact gcctgtgatc ctggccacta ggccaagagg ccctatgaag gtggcgggaa    1680

ctcagcttca acctcgatgt cttcagggtc ttgtccagaa tgtagatggg ttccgtaaga    1740

ggcctggtgc tctcttactc tttcatccac gtgcacttgt gcggcatctg cagtttacag    1800

gaacggctcc ttccctaaaa tgagaagtcc aaggtcatct ctggcccagt gaccacagag    1860
```

-continued

```
agatctgcac ctcccggact tcaggcctgc ctttccagcg agaattcttc atcctccacg   1920

gttcactagc tcctacctga agaggaaagg gggccatttg acctgacatg tcaggaaagc   1980

cctaaactga atgtttgcgc ctgggctgca gaagccaggg tgcatgacca ggctgcgtgg   2040

acgttatact gtcttccccc acccccgggg aggggaagct tgagctgctg ctgtcactcc   2100

tccaccgagg gaggcctcac aaaccacagg acgctgcaac gggtcaggct ggcgggcccg   2160

gcgtgctcat catctctgcc ccaggtgtac ggtttctctc tgacattaaa tgcccttcat   2220

ggaaaaaaaa aaaaaaaaaa aaaaaaaaaa a                                  2251


<210> SEQ ID NO 17
<211> LENGTH: 365
<212> TYPE: PRT
<213> ORGANISM: Homo sapiens
<220> FEATURE:
<223> OTHER INFORMATION: human Wnt-6

<400> SEQUENCE: 17

Met Leu Pro Pro Leu Pro Ser Arg Leu Gly Leu Leu Leu Leu Leu Leu
  1               5                  10                  15

Leu Cys Pro Ala His Val Gly Gly Leu Trp Trp Ala Val Gly Ser Pro
             20                  25                  30

Leu Val Met Asp Pro Thr Ser Ile Cys Arg Lys Ala Arg Arg Leu Ala
         35                  40                  45

Gly Arg Gln Ala Glu Leu Cys Gln Ala Glu Pro Glu Val Val Ala Glu
     50                  55                  60

Leu Ala Arg Gly Ala Arg Leu Gly Val Arg Glu Cys Gln Phe Gln Phe
 65                  70                  75                  80

Arg Phe Arg Arg Trp Asn Cys Ser Ser His Ser Lys Ala Phe Gly Arg
                 85                  90                  95

Ile Leu Gln Gln Asp Ile Arg Glu Thr Ala Phe Val Phe Ala Ile Thr
            100                 105                 110

Ala Ala Gly Ala Ser His Ala Val Thr Gln Ala Cys Ser Met Gly Glu
        115                 120                 125

Leu Leu Gln Cys Gly Cys Gln Ala Pro Arg Gly Arg Ala Pro Pro Arg
    130                 135                 140

Pro Ser Gly Leu Pro Gly Thr Pro Gly Pro Pro Gly Pro Ala Gly Ser
145                 150                 155                 160

Pro Glu Gly Ser Ala Ala Trp Glu Trp Gly Gly Cys Gly Asp Asp Val
                165                 170                 175

Asp Phe Gly Asp Glu Lys Ser Arg Leu Phe Met Asp Ala Arg His Lys
            180                 185                 190

Arg Gly Arg Gly Asp Ile Arg Ala Leu Val Gln Leu His Asn Asn Glu
        195                 200                 205

Ala Gly Arg Leu Ala Val Arg Ser His Thr Arg Thr Glu Cys Lys Cys
    210                 215                 220

His Gly Leu Ser Gly Ser Cys Ala Leu Arg Thr Cys Trp Gln Lys Leu
225                 230                 235                 240

Pro Pro Phe Arg Glu Val Gly Ala Arg Leu Leu Glu Arg Phe His Gly
                245                 250                 255

Ala Ser Arg Val Met Gly Thr Asn Asp Gly Lys Ala Leu Leu Pro Ala
            260                 265                 270

Val Arg Thr Leu Lys Pro Pro Gly Arg Ala Asp Leu Leu Tyr Ala Ala
        275                 280                 285
```

-continued

```
Asp Ser Pro Asp Phe Cys Ala Pro Asn Arg Arg Thr Gly Ser Pro Gly
    290                 295                 300

Thr Arg Gly Arg Ala Cys Asn Ser Ser Ala Pro Asp Leu Ser Gly Cys
305                 310                 315                 320

Asp Leu Leu Cys Cys Gly Arg Gly His Arg Gln Glu Ser Val Gln Leu
                325                 330                 335

Glu Glu Asn Cys Leu Cys Arg Phe His Trp Cys Cys Val Val Gln Cys
            340                 345                 350

His Arg Cys Arg Val Arg Lys Glu Leu Ser Leu Cys Leu
        355                 360                 365
```

<210> SEQ ID NO 18
<211> LENGTH: 1726
<212> TYPE: DNA
<213> ORGANISM: Homo sapiens
<220> FEATURE:
<223> OTHER INFORMATION: human Wnt-6

<400> SEQUENCE: 18

```
ggcacgagcg caggagacac aggcgctggc tgccccgtcc gctctccgcc tccgccgcgc     60

cctcctcgcc cgggatgggc ccccccgccg ccgccggatc cctcgcctcc cggccgccgc    120

cgttgcgctc gccgcgctcg cactgaagcc cgggccctcg cgcgccgcgg ttcgccccgc    180

agcctcgccc cctgcccacc cgggcggccg tagggcggtc acgatgctgc cgcccttacc    240

ctcccgcctc gggctgctgc tgctgctgct cctgtgcccg gcgcacgtcg gcggactgtg    300

gtgggctgtg ggcagcccct tggttatgga ccctaccagc atctgcagga aggcacggcg    360

gctggccggg cggcaggccg agttgtgcca ggctgagccg gaagtggtgg cagagctagc    420

tcggggcgcc cggctcgggg tgcgagagtg ccagttccag ttccgcttcc gccgctggaa    480

ttgctccagc cacagcaagg cctttggacg catcctgcaa caggacattc gggagacggc    540

cttcgtgttc gccatcactg cggccggcgc cagccacgcc gtcacgcagg cctgttctat    600

gggcgagctg ctgcagtgcg gctgccaggc gccccgcggg cgggcccctc cccggccctc    660

cggcctgccc ggcacccccg gacccccctgg ccccgcgggc tccccggaag gcagcgccgc    720

ctgggagtgg ggaggctgcg gcgacgacgt ggacttcggg gacgagaagt cgaggctctt    780

tatggacgcg cggcacaagc ggggacgcgg agacatccgc gcgttggtgc aactgcacaa    840

caacgaggcg ggcaggctgg ccgtgcggag ccacacgcgc accgagtgca aatgccacgg    900

gctgtcggga tcatgcgcgc tgcgcacctg ctggcagaag ctgcctccat ttcgcgaggt    960

gggcgcgcgg ctgctggagc gcttccacgg cgcctcacgc gtcatgggca ccaacgacgg   1020

caaggccctg ctgcccgccg tccgcacgct caagccgccg ggccgagcgg acctcctcta   1080

cgccgccgat tcgcccgact tttgcgcccc caaccgacgc accggctccc ccggcacgcg   1140

cggtcgcgcc tgcaatagca gcgccccgga cctcagcggc tgcgacctgc tgtgctgcgg   1200

ccgcgggcac cgccaggaga gcgtgcagct cgaagagaac tgcctgtgcc gcttccactg   1260

gtgctgcgta gtacagtgcc accgttgccg tgtgcgcaag gagctcagcc tctgcctgtg   1320

acccgccgcc cggccgctag actgacttcg cgcagcggtg gctcgcacct gtgggacctc   1380

agggcaccgg caccgggcgc ctctcgccgc tcgagcccag cctctccctg ccaaagccca   1440

actcccaggg ctctggaaat ggtgaggcga ggggcttgag aggaacgccc acccacgaag   1500

gcccagggcg ccagacggcc ccgaaaaggc gctcggggag cgtttaaagg acactgtaca   1560

ggccctccct ccccttggcc tctaggagga aacagttttt tagactggaa aaaagccagt   1620
```

-continued

```
ctaaaggcct ctggatactg ggctccccag aactgctggc cacaggatgg tgggtgaggt   1680

tagtatcaat aaagatattt aaaccaaaaa aaaaaaaaaa aaaaaa                  1726


<210> SEQ ID NO 19
<211> LENGTH: 349
<212> TYPE: PRT
<213> ORGANISM: Homo sapiens
<220> FEATURE:
<223> OTHER INFORMATION: human Wnt-7a

<400> SEQUENCE: 19

Met Asn Arg Lys Ala Arg Arg Cys Leu Gly His Leu Phe Leu Ser Leu
  1               5                  10                  15

Gly Met Val Tyr Leu Arg Ile Gly Gly Phe Ser Ser Val Val Ala Leu
             20                  25                  30

Gly Ala Ser Ile Ile Cys Asn Lys Ile Pro Gly Leu Ala Pro Arg Gln
         35                  40                  45

Arg Ala Ile Cys Gln Ser Arg Pro Asp Ala Ile Ile Val Ile Gly Glu
     50                  55                  60

Gly Ser Gln Met Gly Leu Asp Glu Cys Gln Phe Gln Phe Arg Asn Gly
 65                  70                  75                  80

Arg Trp Asn Cys Ser Ala Leu Gly Glu Arg Thr Val Phe Gly Lys Glu
                 85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345
```

-continued

<210> SEQ ID NO 20
<211> LENGTH: 1736
<212> TYPE: DNA
<213> ORGANISM: Homo sapiens
<220> FEATURE:
<223> OTHER INFORMATION: human Wnt-7a

<400> SEQUENCE: 20
gagggagggg cgggggctgg aggcagcagc gcccccgcac tccccgcgtc tcgcacactt 60
gcaccggtcg ctcgcgcgca gcccggcgtc gccccacgcc gcgctcgctc ctccctccct 120
cctcccgctc cgtggctccc gtgctcctgg cgaggctcag gcgcggagcg cgcggacggg 180
cgcaccgaca gacggccccg gggacgcctc ggctcgcgcc tcccgggcgg gctatgttga 240
ttgccccgcc ggggccggcc cgcgggatca gcacagcccg gcccgcggcc ccggcggcca 300
atcgggacta tgaaccggaa agcgcggcgc tgcctgggcc acctctttct cagcctgggc 360
atggtctacc tccggatcgg tggcttctcc tcagtggtag ctctgggcgc aagcatcatc 420
tgtaacaaga tcccaggcct ggctcccaga cagcgggcga tctgccagag ccggcccgac 480
gccatcatcg tcataggaga aggctcacaa atgggcctgg acgagtgtca gtttcagttc 540
cgcaatggcc gctggaactg ctctgcactg ggagagcgca ccgtcttcgg gaaggagctc 600
aaagtgggga gccgggaggc tgcgttcacc tacgccatca ttgccgccgg cgtggcccac 660
gccatcacag ctgcctgtac ccagggcaac ctgagcgact gtggctgcga caaagagaag 720
caaggccagt accaccggga cgagggctgg aagtggggtg gctgctctgc cgacatccgc 780
tacggcatcg gcttcgccaa ggtctttgtg gatgcccggg agatcaagca gaatgcccgg 840
actctcatga acttgcacaa caacgaggca ggccgaaaga tcctggagga gaacatgaag 900
ctggaatgta agtgccacgg cgtgtcaggc tcgtgcacca ccaagacgtg ctggaccaca 960
ctgccacagt ttcgggagct gggctacgtg ctcaaggaca agtacaacga ggccgttcac 1020
gtggagcctg tgcgtgccag ccgcaacaag cggcccacct tcctgaagat caagaagcca 1080
ctgtcgtacc gcaagcccat ggacacggac ctggtgtaca tcgagaagtc gcccaactac 1140
tgcgaggagg acccggtgac cggcagtgtg ggcacccagg gccgcgcctg caacaagacg 1200
gctccccagg ccagcggctg tgacctcatg tgctgtgggc gtggctacaa cacccaccag 1260
tacgcccgcg tgtggcagtg caactgtaag ttccactggt gctgctatgt caagtgcaac 1320
acgtgcagcg agcgcacgga gatgtacacg tgcaagtgag ccccgtgtgc acaccaccct 1380
cccgctgcaa gtcagattgc tgggaggact ggaccgtttc caagctgcgg gctccctggc 1440
aggatgctga gcttgtcttt tctgctgagg agggtacttt tcctgggttt cctgcaggca 1500
tccgtggggg aaaaaaaatc tctcagagcc ctcaactatt ctgttccaca cccaatgctg 1560
ctccaccctc ccccagacac agcccaggtc cctccgcggc tggagcgaag ccttctgcag 1620
caggaactct ggacccctgg gcctcatcac agcaatattt aacaatttat tctgataaaa 1680
ataatattaa tttatttaat taaaaagaat tcttccacaa aaaaaaaaaa aaaaaa 1736

<210> SEQ ID NO 21
<211> LENGTH: 349
<212> TYPE: PRT
<213> ORGANISM: Homo sapiens
<220> FEATURE:
<223> OTHER INFORMATION: human Wnt-7b

<400> SEQUENCE: 21

-continued

```
Met His Arg Asn Phe Arg Lys Trp Ile Phe Tyr Val Phe Leu Cys Phe
  1               5                  10                  15

Gly Val Leu Tyr Val Lys Leu Gly Ala Leu Ser Ser Val Val Ala Leu
            20                  25                  30

Gly Ala Asn Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ala Gln Met Gly Ile Asn Glu Cys Gln Tyr Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345
```

```
<210> SEQ ID NO 22
<211> LENGTH: 2250
<212> TYPE: DNA
<213> ORGANISM: Homo sapiens
<220> FEATURE:
<223> OTHER INFORMATION: human Wnt-7b

<400> SEQUENCE: 22

gagtctgccc gcagccccct ggcccctgcc cggccctgcg tgcccgcgcg tccctccggc      60

cgcgctgtct atggcgcagc ccccctccct ggatcatgca cagaaacttt cgcaagtgga     120
```

-continued

```
ttttctacgt gtttctctgc tttggcgtcc tgtacgtgaa gctcggagca ctgtcatccg    180
tggtggccct gggagccaac atcatctgca acaagattcc tggcctagcc ccgcggcagc    240
gtgccatctg ccagagtcgg cccgatgcca tcattgtgat tggggagggg gcgcagatgg    300
gcatcaacga gtgccagtac cagttccgct tcggacgctg gaactgctct gccctcggcg    360
agaagaccgt cttcgggcaa gagctccgag tagggagccg tgaggctgcc ttcacgtacg    420
ccatcaccgc ggctggcgtg gcgcacgccg tcaccgctgc ctgcagccaa gggaacctga    480
gcaactgcgg ctgcgaccgc gagaagcagg gctactacaa ccaagccgag ggctggaagt    540
ggggcggctg ctcggccgac gtgcgttacg gcatcgactt ctcccggcgc ttcgtggacg    600
ctcgggagat caagaagaac gcgcggcgcc tcatgaacct gcataacaat gaggccggca    660
ggaaggttct agaggaccgg atgcagctgg agtgcaagtg ccacggcgtg tctggctcct    720
gcaccaccaa aacctgctgg accacgctgc ccaagttccg agaggtgggc cacctgctga    780
aggagaagta caacgcggcc gtgcaggtgg aggtggtgcg ggccagccgt ctgcggcagc    840
ccaccttcct gcgcatcaaa cagctgcgca gctatcagaa gcccatggag acagacctgg    900
tgtacattga gaagtcgccc aactactgcg aggaggacgc ggccacgggc agcgtgggca    960
cgcagggccg tctctgcaac cgcacgtcgc ccggcgcgga cggctgtgac accatgtgct   1020
gcggccgagg ctacaacacc caccagtaca ccaaggtgtg gcagtgcaac tgcaaattcc   1080
actggtgctg cttcgtcaag tgcaacacct gcagcgagcg caccgaggtc ttcacctgca   1140
agtgaggcca ggcccggagg cggccgcggg caccctggaa cccggcggca ttttgcacat   1200
ccactcctca ccttccctgc cttggtgctg ccagcagcag acatagacgg gtgcagaagc   1260
ggggagctcc aggtgcagga gggcaccggc cggggcccac gccctctgcc cgcctccctg   1320
gggctccttc ctgccacctc ctcccatcac ctcctgcggc agaacagcac ccgtgaccca   1380
cccagagagc aaggccaggg gtcttggtgc tccccgacgg ggcccggcaa gttctctttc   1440
ttctctctgg gaaaatgaac gtccaggaca cacctgtatc ccagagagca aagtgatgag   1500
gagactgagc gtccccagcc ccacctggcg gcatggacac agaaaagcta cgccggctgg   1560
cctctccaga ccagttccca ggctgggtct gccgctgggc cctggggcgg tggggacaga   1620
tgttgacaca aattatttat gttttcttag tatcagaaga ggattctcgg cactaacaca   1680
tagccagtcc taactccgta ctctgtgtca gcccatcccc tagacaccct ctgtttcctt   1740
tcccggcccc acctggccgg ccctctgccc ctgcagagct gaggcagcct ggggttgatg   1800
gggaccacgc ggtgcctgca ggtcctagaa gtgagctggg caggggctct tcagaccaca   1860
cagccctgac cgggccttgg aggagagcca tggacaggct cctccatgcc gtctttcctt   1920
cttttgaaaa tcctatcaat ggctgggcgc ggtggctcac acctgtaatc ccagcacttt   1980
gggagaccga ggcaggtgga tcacctgagg tcaggagttc gagaccagcc tggccaacgt   2040
ggtgaaaccc tgtctctact aaaaatacaa aaattagctg ggcgtggtgg cgtgcacctg   2100
taatcccagc tactcaggag gctgagacag gacacttgct tgaacccggg aggtggaggt   2160
tgcaatgagc caagattgtg ccactgtatt ccaacttggg tgacagagca cgactctgtc   2220
tcaaaaaaaa aaaaaaaaaa aaaaaaaaaa                                    2250
```

<210> SEQ ID NO 23
<211> LENGTH: 355
<212> TYPE: PRT
<213> ORGANISM: Homo sapiens
<220> FEATURE:

-continued

<223> OTHER INFORMATION: human Wnt-8a

<400> SEQUENCE: 23

```
Met Gly Asn Leu Phe Met Leu Trp Ala Ala Leu Gly Ile Cys Cys Ala
  1               5                  10                  15

Ala Phe Ser Ala Ser Ala Trp Ser Val Asn Asn Phe Leu Ile Thr Gly
             20                  25                  30

Pro Lys Ala Tyr Leu Thr Tyr Thr Thr Ser Val Ala Leu Gly Ala Gln
         35                  40                  45

Ser Gly Ile Glu Glu Cys Lys Phe Gln Phe Ala Trp Glu Arg Trp Asn
     50                  55                  60

Cys Pro Glu Asn Ala Leu Gln Leu Ser Thr His Asn Arg Leu Arg Ser
 65                  70                  75                  80

Ala Thr Arg Glu Thr Ser Phe Ile His Ala Ile Ser Ser Ala Gly Val
                 85                  90                  95

Met Tyr Ile Ile Thr Lys Asn Cys Ser Met Gly Asp Phe Glu Asn Cys
            100                 105                 110

Gly Cys Asp Gly Ser Asn Asn Gly Lys Thr Gly Gly His Gly Trp Ile
        115                 120                 125

Trp Gly Gly Cys Ser Asp Asn Val Glu Phe Gly Glu Arg Ile Ser Lys
    130                 135                 140

Leu Phe Val Asp Ser Leu Glu Lys Gly Lys Asp Ala Arg Ala Leu Met
145                 150                 155                 160

Asn Leu His Asn Asn Arg Ala Gly Arg Leu Ala Val Arg Ala Thr Met
                165                 170                 175

Lys Arg Thr Cys Lys Cys His Gly Ile Ser Gly Ser Cys Ser Ile Gln
            180                 185                 190

Thr Cys Trp Leu Gln Leu Ala Glu Phe Arg Glu Met Gly Asp Tyr Leu
        195                 200                 205

Lys Ala Lys Tyr Asp Gln Ala Leu Lys Ile Glu Met Asp Lys Arg Gln
    210                 215                 220

Leu Arg Ala Gly Asn Ser Ala Glu Gly His Trp Val Pro Ala Glu Ala
225                 230                 235                 240

Phe Leu Pro Ser Ala Glu Ala Glu Leu Ile Phe Leu Glu Glu Ser Pro
                245                 250                 255

Asp Tyr Cys Thr Cys Asn Ser Ser Leu Gly Ile Tyr Gly Thr Glu Gly
            260                 265                 270

Arg Glu Cys Leu Gln Asn Ser His Asn Thr Ser Arg Trp Glu Arg Arg
        275                 280                 285

Ser Cys Gly Arg Leu Cys Thr Glu Cys Gly Leu Gln Val Glu Glu Arg
    290                 295                 300

Lys Thr Glu Val Ile Ser Ser Cys Asn Cys Lys Phe Gln Trp Cys Cys
305                 310                 315                 320

Thr Val Lys Cys Asp Gln Cys Arg His Val Val Ser Lys Tyr Tyr Cys
                325                 330                 335

Ala Arg Ser Pro Gly Ser Ala Gln Ser Leu Gly Arg Val Trp Phe Gly
            340                 345                 350

Val Tyr Ile
        355
```

<210> SEQ ID NO 24
<211> LENGTH: 1597
<212> TYPE: DNA
<213> ORGANISM: Homo sapiens
<220> FEATURE:

-continued

<223> OTHER INFORMATION: human Wnt-8a

<400> SEQUENCE: 24

```
cagaattttc tcacataaat actgaggaag accctgccct ctcctcactc ctctggactt     60
ggccctgagc tggacctggt ccactggggt aggcagggcg atggggaacc tgtttatgct    120
ctgggcagct ctgggcatat gctgtgctgc attcagtgcc tctgcctggt cagtgaacaa    180
tttcctgata acaggtccca aggcctatct gacctacacg actagtgtgg ccttgggtgc    240
ccagagtggc atcgaggagt gcaagttcca gtttgcttgg gaacgctgga actgccctga    300
aaatgctctt cagctctcca cccacaacag gctgagaagt gctaccagag agacttcctt    360
catacatgct atcagctctg ctggagtcat gtacatcatc accaagaact gtagcatggg    420
tgacttcgaa aactgtggct gtgatgggtc aaacaatgga aaaacaggag gccatggctg    480
gatctgggga ggctgcagcg acaatgtgga atttggggaa aggatctcca aactctttgt    540
ggacagtttg gagaagggga aggatgccag agccctgatg aatcttcaca acaacagggc    600
cggcagactg gcagtgagag ccaccatgaa aaggacatgc aaatgtcatg gcatctctgg    660
gagctgcagc atacagacat gctggctgca gctggctgaa ttccgggaga tgggagacta    720
cctaaaggcc aagtatgacc aggcgctgaa aattgaaatg gataagcggc agctgagagc    780
tgggaacagc gccgagggcc actgggtgcc cgctgaggcc ttccttccta gcgcagaggc    840
ggaactgatc tttttagagg aatcaccaga ttactgtacc tgcaattcca gcctgggcat    900
ctatggcaca gagggtcgtg agtgcctaca gaacagccac aacacatcca ggtgggagcg    960
acgtagctgt gggcgcctgt gcactgagtg tgggctgcag gtggaagaga ggaaaactga   1020
ggtcataagc agctgtaact gcaaattcca gtggtgctgt acggtcaagt gtgaccagtg   1080
taggcatgtg gtgagcaagt attactgcgc acgctcccca ggcagtgccc agtccctggg   1140
gagagtttgg tttggggtct atatctagag ggaccttcaa agtatttgtt cctttaaatt   1200
tcagaccatg tccaacccag ctgtgctgct gggaatcagg agaatagaag caaaaaacga   1260
aagagttctg ttcagacttc tgaagagcag cctgtggcta caaatctatg ctgataaatg   1320
agattgagaa ctcaactgta ttttgccata aatgcttcta agatatatcc agctgggact   1380
tctattactc cctttggaaa ccttaagatc aaaaagggaa taagaaaccc ttcttctgta   1440
tcccaataat ccaccaggat aaaggagaaa ctagaaatat gcaactccct tgatttcagt   1500
gtttggcagg taacaaaaaa ttgagaccca gacactggtc aacaggaaaa caatacagac   1560
tcccagaatt agaaagtgtt attttaatgc aacctag                            1597
```

<210> SEQ ID NO 25
<211> LENGTH: 351
<212> TYPE: PRT
<213> ORGANISM: Homo sapiens
<220> FEATURE:
<223> OTHER INFORMATION: human Wnt-8b

<400> SEQUENCE: 25

```
Met Phe Leu Ser Lys Pro Ser Val Tyr Ile Cys Leu Phe Thr Cys Val
1               5                   10                  15

Leu Gln Leu Ser His Ser Trp Ser Val Asn Asn Phe Leu Met Thr Gly
            20                  25                  30

Pro Lys Ala Tyr Leu Ile Tyr Ser Ser Ser Val Ala Ala Gly Ala Gln
        35                  40                  45

Ser Gly Ile Glu Glu Cys Lys Tyr Gln Phe Ala Trp Asp Arg Trp Asn
    50                  55                  60
```

-continued

```
Cys Pro Glu Arg Ala Leu Gln Leu Ser Ser His Gly Gly Leu Arg Ser
 65                  70                  75                  80

Ala Asn Arg Glu Thr Ala Phe Val His Ala Ile Ser Ser Ala Gly Val
                 85                  90                  95

Met Tyr Thr Leu Thr Arg Asn Cys Ser Leu Gly Asp Phe Asp Asn Cys
            100                 105                 110

Gly Cys Asp Asp Ser Arg Asn Gly Gln Leu Gly Gly Gln Gly Trp Leu
        115                 120                 125

Trp Gly Gly Cys Ser Asp Asn Val Gly Phe Gly Glu Ala Ile Ser Lys
    130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
                165                 170                 175

Lys Arg Thr Cys Lys Cys His Gly Val Ser Gly Ser Cys Thr Thr Gln
            180                 185                 190

Thr Cys Trp Leu Gln Leu Pro Glu Phe Arg Glu Val Gly Ala His Leu
        195                 200                 205

Lys Glu Lys Tyr His Ala Ala Leu Lys Val Asp Leu Leu Gln Gly Ala
    210                 215                 220

Gly Asn Ser Ala Ala Ala Arg Gly Ala Ile Ala Asp Thr Phe Arg Ser
225                 230                 235                 240

Ile Ser Thr Arg Glu Leu Val His Leu Glu Asp Ser Pro Asp Tyr Cys
                245                 250                 255

Leu Glu Asn Lys Thr Leu Gly Leu Leu Gly Thr Glu Gly Arg Glu Cys
            260                 265                 270

Leu Arg Arg Gly Arg Ala Leu Gly Arg Trp Glu Leu Arg Ser Cys Arg
        275                 280                 285

Arg Leu Cys Gly Asp Cys Gly Leu Ala Val Glu Glu Arg Arg Ala Glu
    290                 295                 300

Thr Val Ser Ser Cys Asn Cys Lys Phe His Trp Cys Cys Ala Val Arg
305                 310                 315                 320

Cys Glu Gln Cys Arg Arg Arg Val Thr Lys Tyr Phe Cys Ser Arg Ala
                325                 330                 335

Glu Arg Pro Arg Gly Gly Ala Ala His Lys Pro Gly Arg Lys Pro
            340                 345                 350


<210> SEQ ID NO 26
<211> LENGTH: 2117
<212> TYPE: DNA
<213> ORGANISM: Homo sapiens
<220> FEATURE:
<223> OTHER INFORMATION: human Wnt-8b

<400> SEQUENCE: 26

tccgcttaca caccaaggaa agttgggctt tgaagaattc catccccatg gccactggag     60

gaagaatatt tctccgtctt gcttacccat ctcccagttt tttggaattt tctctagctg    120

ttactccaga ggattatgtt tctttcaaag ccttctgtgt acatctgtct tttcacctgt    180

gtcctccaac tcagccacag ctggtcggtg aacaatttcc tgatgactgg tccaaaggct    240

tacctgattt actccagcag tgtggcagct ggtgcccaga gtggtattga agaatgcaag    300

tatcagtttg cctgggaccg ctggaactgc cctgagagag ccctgcagct gtccagccat    360

ggtgggcttc gcagtgccaa tcgggagaca gcatttgtgc atgccatcag ttctgctgga    420
```

-continued

```
gtcatgtaca ccctgactag aaactgcagc cttggagatt ttgataactg tggctgtgat    480

gactcccgca acgggcaact gggggggacaa ggctggctgt ggggaggctg cagtgacaat    540

gtgggcttcg gagaggcgat ttccaagcag tttgtcgatg ccctggaaac aggacaggat    600

gcacgggcag ccatgaacct gcacaacaac gaggctggcc gcaaggcggt gaagggcacc    660

atgaaacgca cgtgtaagtg ccatggcgtg tctggcagct gcaccacgca gacctgttgg    720

ctgcagctgc ccgagttccg cgaggtgggc gcgcacctga aggagaagta ccacgcagca    780

ctcaaggtgg acctgctgca gggtgctggc aacagcgcgg ccgcccgcgg cgccatcgcc    840

gacacctttc gctccatctc tacccgggag ctggtgcacc tggaggactc cccggactac    900

tgcctggaga acaaaacgct agggctgctg ggcaccgaag gccgagagtg cctaaggcgc    960

gggcgggccc tgggtcgctg ggaactccgc agctgccgcc ggctctgcgg ggactgcggg   1020

ctggcggtgg aggagcgccg ggccgagacc gtgtccagct gcaactgcaa gttccactgg   1080

tgctgtgcag tccgctgcga gcagtgccgc cggagggtca ccaagtactt ctgtagccgc   1140

gcagagcggc cgcggggggg cgctgcgcac aaacccggga gaaaacccta agggtttcct   1200

ctgcccccct cttttcccac tggttcttgg cttcctttag agaccccggt aattgtggaa   1260

cctagggaat ggggaacccg ctctcccaga cctagggatc ctgaaaggga aaaactgcaa   1320

tttctccaaa gcttgccact ttccagcctg tttccccaat tcctctgtgc tctcctaaag   1380

ctctgtctga atcctcgcag ccacacctag gtctgaaaac tcaggctttg agttactgat   1440

cttccttgga ttaggaaaac aggtgttcct cctcccctct cctatcagcc ctaatctctg   1500

acctagccta tcaaccctta ggcgctggaa aaaccttctc atacacgcag gacccaggtt   1560

aactcaaagc tttgcccttt tgcccactgt ctgctaccag ggctcaccc tctgctgcac    1620

ctctcttctg cacagctcct cccctgctac tgctgaccaa attcccagga atcttgaatg   1680

ctttctctcc tcttctccct ttcctttccc aaaaaaaact gaggaaactg gccccggaaa   1740

agcatgtctt tggggttggt tcctagaggc agaggttgaa gatggaagag ggagctctgg   1800

agtgctaact tgaacaccaa gggtgctact catccctatg gtatcatatc atgaatggac   1860

tttactagtg gggcaatgac tttcctagac aataacccga gggactccag atacataccc   1920

cgaaggtcta ggaaatacgt taagggcaga ttacagtcat ttcctaccct ttaaaggtaa   1980

cttctccctt ctcctgacct acttcctcct agcaaccaac tttacctctt cttctccaaa   2040

ggatctttgt tcctctgagc caagactgag gtaaataaag ccactttcct cttcagatcc   2100

tggtctgcac ctctaga                                                  2117
```

<210> SEQ ID NO 27
<211> LENGTH: 417
<212> TYPE: PRT
<213> ORGANISM: Homo sapiens
<220> FEATURE:
<223> OTHER INFORMATION: human Wnt-10a

<400> SEQUENCE: 27

```
Met Gly Ser Ala His Pro Arg Pro Trp Leu Arg Leu Arg Pro Gln Pro
  1               5                  10                  15

Gln Pro Arg Pro Ala Leu Trp Val Leu Leu Phe Phe Leu Leu Leu Leu
             20                  25                  30

Ala Ala Ala Met Pro Arg Ser Ala Pro Asn Asp Ile Leu Asp Leu Arg
         35                  40                  45

Leu Pro Pro Glu Pro Val Leu Asn Ala Asn Thr Val Cys Leu Thr Leu
     50                  55                  60
```

-continued

```
Pro Gly Leu Ser Arg Arg Gln Met Glu Val Cys Val Arg His Pro Asp
 65                  70                  75                  80

Val Ala Ala Ser Ala Ile Gln Gly Ile Gln Ile Ala Ile His Glu Cys
                 85                  90                  95

Gln His Gln Phe Arg Asp Gln Arg Trp Asn Cys Ser Ser Leu Glu Thr
            100                 105                 110

Arg Asn Lys Ile Pro Tyr Glu Ser Pro Ile Phe Ser Arg Gly Phe Arg
        115                 120                 125

Glu Ser Ala Phe Ala Tyr Ala Ile Ala Ala Ala Gly Val Val His Ala
    130                 135                 140

Val Ser Asn Ala Cys Ala Leu Gly Lys Leu Lys Ala Cys Gly Cys Asp
145                 150                 155                 160

Ala Ser Arg Arg Gly Asp Glu Glu Ala Phe Arg Arg Lys Leu His Arg
                165                 170                 175

Leu Gln Leu Asp Ala Leu Gln Arg Gly Lys Gly Leu Ser His Gly Val
            180                 185                 190

Pro Glu His Pro Ala Leu Pro Thr Ala Ser Pro Gly Leu Gln Asp Ser
        195                 200                 205

Trp Glu Trp Gly Gly Cys Ser Pro Asp Met Gly Phe Gly Glu Arg Phe
    210                 215                 220

Ser Lys Asp Phe Leu Asp Ser Arg Glu Pro His Arg Asp Ile His Ala
225                 230                 235                 240

Arg Met Arg Leu His Asn Asn Arg Val Gly Arg Gln Ala Val Met Glu
                245                 250                 255

Asn Met Arg Arg Lys Cys Lys Cys His Gly Thr Ser Gly Ser Cys Gln
            260                 265                 270

Leu Lys Thr Cys Trp Gln Val Thr Pro Glu Phe Arg Thr Val Gly Ala
        275                 280                 285

Leu Leu Arg Ser Arg Phe His Arg Ala Thr Leu Ile Arg Pro His Asn
    290                 295                 300

Arg Asn Gly Gly Gln Leu Glu Pro Gly Pro Ala Gly Ala Pro Ser Pro
305                 310                 315                 320

Ala Pro Gly Ala Pro Gly Pro Arg Arg Arg Ala Ser Pro Ala Asp Leu
                325                 330                 335

Val Tyr Phe Glu Lys Ser Pro Asp Phe Cys Glu Arg Glu Pro Arg Leu
            340                 345                 350

Asp Ser Ala Gly Thr Val Gly Arg Leu Cys Asn Lys Ser Ser Ala Gly
        355                 360                 365

Ser Asp Gly Cys Gly Ser Met Cys Cys Gly Arg Gly His Asn Ile Leu
    370                 375                 380

Arg Gln Thr Arg Ser Glu Arg Cys His Cys Arg Phe His Trp Cys Cys
385                 390                 395                 400

Phe Val Val Cys Glu Glu Cys Arg Ile Thr Glu Trp Val Ser Val Cys
                405                 410                 415

Lys
```

<210> SEQ ID NO 28
<211> LENGTH: 2375
<212> TYPE: DNA
<213> ORGANISM: Homo sapiens
<220> FEATURE:
<223> OTHER INFORMATION: human Wnt-10a

<400> SEQUENCE: 28

-continued

```
acagtcactt actctacagg cagtggggcc cgacacagac agcgccgccc ccgccagcca     60
gcctcgcacg ccctcggaag cgcaggctcc cggcgctgcg ctggagggtt ccccggcacc    120
ccagcctccc gtccccagcc cgctgcacct ccgggccccc cttacccttg agaggcaccg    180
ggagttgtcg cgggggggcc tcgggaaatt ccccggaccc ctgtgccagg aggtgcccgg    240
ttcgcccgct cttcaccccc cgcccccccc gagggcggtg cccgggggtg ctgccccatg    300
gagcggggag gcgggcgccg tctgctccgg gagccctgac ccgagtcgga gctgtgtgtc    360
gcagccgccc cgaccccccg ccgatcatgc gccggcgccc ctggctctcc agtcccactg    420
ggctgtgagc cccccactcc cagcccgtca gggcctgcgc gccatgggca gcgcccaccc    480
tcgcccctgg ctgcggctcc gaccccagcc ccagccgcgg ccagcgctct gggtgctcct    540
gttcttccta ctgctgctgg ctgctgccat gcccaggtca gcacccaatg acattctgga    600
cctccgcctc cccccggagc ccgtgctcaa tgccaacaca gtgtgcctaa cattgccagg    660
cctgagccgg cggcagatgg aggtgtgtgt gcgtcaccct gatgtggctg cctcagccat    720
acagggcatc cagatcgcca tccacgaatg ccaacaccaa ttcagggacc agcgctggaa    780
ctgctcaagc ctggagactc gcaacaagat cccctatgag agtcccatct tcagcagagg    840
tttccgagag agcgcttttg cctacgccat cgcagcagct ggcgtggtgc acgccgtgtc    900
caatgcgtgt gccctgggca aactgaaggc ctgtggctgt gatgcgtccc ggcgagggga    960
cgaggaggcc ttccgtagga agctgcaccg cttacaactg gatgcactgc agcgtggtaa   1020
gggcctgagc catggggtcc cggaacaccc agccctgccc acagccagcc caggcctgca   1080
ggactcctgg gagtggggcg gctgcagccc cgacatgggc ttcggggagc gcttttctaa   1140
ggactttctg gactcccggg agcctcacag agacatccac gcgagaatga ggcttcacaa   1200
caaccgagtt gggaggcagg cagtgatgga gaacatgcgg cggaagtgca agtgccacgg   1260
cacgtcaggc agctgccagc tcaagacgtg ctggcaggtg acgcccgagt tccgcaccgt   1320
gggggcgctg ctgcgcagcc gcttccaccg cgccacgctc atccggccgc acaaccgcaa   1380
cggcggccag ctggagccgg gcccagcggg ggcaccctcg ccggctccgg gcgctcccgg   1440
gccgcgccga cgggccagcc ccgccgacct ggtctacttc gaaaagtctc ccgacttctg   1500
cgagcgcgag ccgcgcctgg actcggcggg caccgtgggc cgcctgtgca acaagagcag   1560
cgccggctcg gatggctgcg gcagcatgtg ctgcggccgc ggccacaaca tcctgcgcca   1620
gacgcgcagc gagcgctgcc actgccgctt ccactggtgc tgtttcgtgg tctgcgaaga   1680
gtgccgcatc accgagtggg tcagcgtctg caagtgagcg gcccggggtc ccctgggccc   1740
tgatcgaggt cccctcctgg agcctggccc tctgaggctt acggtcttgg caaggcagca   1800
tcgccttggc tcttgggaag aggagattgg accacatgat cttataggaa cccctcagct   1860
ctgaggtctg tgatcgccgg acagtccagg cctgtctgaa ccccaccact cacttctgtg   1920
ggctctagga ctgactgggt tcttcctccc tccccgaagc ccagacagtt cagttgggct   1980
gggggttgct ccacacccta aaacaagcct cagccaggca acccgtcagt ctgtctccat   2040
cctttcaccc cttccctgga gatgggaggt ggggaatgaa tggaagctga cgggcagaga   2100
gaggaggatt aaaaaaaaga aatagacata actgagctga agtaattcca taaagggccc   2160
agacagcctc ctccaccatt cccttcatca ttcatttaac aaatatttat tttgcactct   2220
ctttgcggca ctctgggggc ggtggggtgc gtgggggtgg caatgcaagg cactgaggcc   2280
acagatgtga gtaagcgaga cacaacactt gtcctcttgg aggttacatt cttgctgggg   2340
ggaggcatgg gcaataaaca agtaaatata caaac                              2375
```

-continued

<210> SEQ ID NO 29
<211> LENGTH: 389
<212> TYPE: PRT
<213> ORGANISM: Homo sapiens
<220> FEATURE:
<223> OTHER INFORMATION: human Wnt-10b

<400> SEQUENCE: 29

```
Met Leu Glu Glu Pro Arg Pro Arg Pro Pro Pro Ser Gly Leu Ala Gly
  1               5                  10                  15

Leu Leu Phe Leu Ala Leu Cys Ser Arg Ala Leu Ser Asn Glu Ile Leu
             20                  25                  30

Gly Leu Lys Leu Pro Gly Glu Pro Pro Leu Thr Ala Asn Thr Val Cys
         35                  40                  45

Leu Thr Leu Ser Gly Leu Ser Lys Arg Gln Leu Gly Leu Cys Leu Arg
     50                  55                  60

Asn Pro Asp Val Thr Ala Ser Ala Leu Gln Gly Leu His Ile Ala Val
 65                  70                  75                  80

His Glu Cys Gln His Gln Leu Arg Asp Gln Arg Trp Asn Cys Ser Ala
                 85                  90                  95

Leu Glu Gly Gly Gly Arg Leu Pro His His Ser Ala Ile Leu Lys Arg
            100                 105                 110

Gly Phe Arg Glu Ser Ala Phe Ser Phe Ser Met Leu Ala Ala Gly Val
        115                 120                 125

Met His Ala Val Ala Thr Ala Cys Ser Leu Gly Lys Leu Val Ser Cys
    130                 135                 140

Gly Cys Gly Trp Lys Gly Ser Gly Glu Gln Asp Arg Leu Arg Ala Lys
145                 150                 155                 160

Leu Leu Gln Leu Gln Ala Leu Ser Arg Gly Lys Ser Phe Pro His Ser
                165                 170                 175

Leu Pro Ser Pro Gly Pro Gly Ser Ser Pro Ser Pro Gly Pro Gln Asp
            180                 185                 190

Thr Trp Glu Trp Gly Gly Cys Asn His Asp Met Asp Phe Gly Glu Lys
        195                 200                 205

Phe Ser Arg Asp Phe Leu Asp Ser Arg Glu Ala Pro Arg Asp Ile Gln
    210                 215                 220

Ala Arg Met Arg Ile His Asn Asn Arg Val Gly Arg Gln Val Val Thr
225                 230                 235                 240

Glu Asn Leu Lys Arg Lys Cys Lys Cys His Gly Thr Ser Gly Ser Cys
                245                 250                 255

Gln Phe Lys Thr Cys Trp Arg Ala Ala Pro Glu Phe Arg Ala Val Gly
            260                 265                 270

Ala Ala Leu Arg Glu Arg Leu Gly Arg Ala Ile Phe Ile Asp Thr His
        275                 280                 285

Asn Arg Asn Ser Gly Ala Phe Gln Pro Arg Leu Arg Pro Arg Arg Leu
    290                 295                 300

Ser Gly Glu Leu Val Tyr Phe Glu Lys Ser Pro Asp Phe Cys Glu Arg
305                 310                 315                 320

Asp Pro Thr Met Gly Ser Pro Gly Thr Arg Gly Arg Ala Cys Asn Lys
                325                 330                 335

Thr Ser Arg Leu Leu Asp Gly Cys Gly Ser Leu Cys Cys Gly Arg Gly
            340                 345                 350

His Asn Val Leu Arg Gln Thr Arg Val Glu Arg Cys His Cys Arg Phe
        355                 360                 365
```

-continued

His Trp Cys Cys Tyr Val Leu Cys Asp Glu Cys Lys Val Thr Glu Trp
370 375 380

Val Asn Val Cys Lys
385

<210> SEQ ID NO 30
<211> LENGTH: 2288
<212> TYPE: DNA
<213> ORGANISM: Homo sapiens
<220> FEATURE:
<223> OTHER INFORMATION: human Wnt-10b

<400> SEQUENCE: 30
ggggctgcag ctccgtcagc ccggcagagc caccctgagc tcggtgagag caaagccaga 60
gcccccagtc ctttgctcgc cggcttgcta tctctctcga tcactccctc ccttcctccc 120
tcccttcctc ccggcggccg cggcggcgct ggggaagcgg tgaagaggag tggcccggcc 180
ctggaagaat gcggctctga caaggggaca gaacccagcg cagtctcccc acggtttaag 240
cagcactagt gaagcccagg caacccaacc gtgcctgtct cggaccccgc acccaaacca 300
ctggaggtcc tgatcgatct gcccaccgga gcctccgggc ttcgacatgc tggaggagcc 360
ccggccgcgg cctccgccct cgggcctcgc gggtctcctg ttcctggcgt tgtgcagtcg 420
ggctctaagc aatgagattc tgggcctgaa gttgcctggc gagccgccgc tgacggccaa 480
caccgtgtgc ttgacgctgt ccggcctgag caagcggcag ctaggcctgt gcctgcgcaa 540
ccccgacgtg acggcgtccg cgcttcaggg tctgcacatc gcggtccacg agtgtcagca 600
ccagctgcgc gaccagcgct ggaactgctc cgcgcttgag ggcggcggcc gcctgccgca 660
ccacagcgcc atcctcaagc gcggtttccg agaaagtgct tttccttct ccatgctggc 720 tgctggggtc atgcacgcag tagccacggc ctgcagcctg ggcaagctgg tgagctgtgg 780
ctgtggctgg aagggcagtg gtgagcagga tcggctgagg gccaaactgc tgcagctgca 840
ggcactgtcc cgaggcaaga gtttccccca ctctctgccc agccctggcc ctggctcaag 900
ccccagccct ggcccccagg acacatggga atggggtggc tgtaaccatg acatggactt 960
tggagagaag ttctctcggg atttcttgga ttccagggaa gctccccggg acatccaggc 1020
acgaatgcga atccacaaca acagggtggg gcgccaggtg gtaactgaaa acctgaagcg 1080
gaaatgcaag tgtcatggca catcaggcag ctgccagttc aagacatgct ggagggcggc 1140
cccagagttc cgggcagtgg gggcggcgtt gagggagcgg ctgggccggg ccatcttcat 1200
tgatacccac aaccgcaatt ctggagcctt ccagccccgt ctgcgtcccc gtcgcctctc 1260
aggagagctg gtctactttg agaagtctcc tgacttctgt gagcgagacc ccactatggg 1320
ctccccaggg acaaggggcc gggcctgcaa caagaccagc cgcctgttgg atggctgtgg 1380
cagcctgtgc tgtggccgtg ggcacaacgt gctccggcag acacgagttg agcgctgcca 1440
ttgccgcttc cactggtgct gctatgtgct gtgtgatgag tgcaaggtta cagagtgggt 1500
gaatgtgtgt aagtgagggt cagccttacc ttggggctgg ggaagaggac tgtgtgagag 1560
gggcgccttt tcagcccttt gctctgattt ccttccaagg tcactcttgg tccctggaag 1620
cttaaagtat ctacctggaa acagctttag ggtggtgggg ggtcaggtgg actctgggat 1680
gtgtagcctt ctccccaaca attggagggt cttgagggga agctgccacc cctcttctgc 1740
tccttagaca cctgaatgga ctaagatgaa atgcactgta ttgctcctcc cacttctcaa 1800
ctccagagcc cctttaaccc tgattcatac tccttttggc tggggagtcc ctatagtttc 1860

-continued

```
accactcctc tcccttgagg gataacccca ggcactgttt ggagccataa gatctgtatc   1920

tagaaagaga tcacccactc ctatgtacta tccccaaact cctttactgc agcctgggct   1980

ccctcttgtg ggataatggg agacagtggt agagaggttt ttcttgggaa agagacagag   2040

tgctgagggg cactctcccc tgaatcctca gagagttgtc tgtccaggcc cttagggaag   2100

ttgtctcctt ccattcagat gttaatgggg accctccaaa ggaaggggtt ttcccatgac   2160

tcttggagcc tctttttcct tcttcagcag gaagggtggg aagggataat ttatcatact   2220

gagacttgtt cttggttcct gtttgaaact aaaataaatt aagttactgg aaaaaaaaaa   2280

aaaaaaaa                                                            2288


<210> SEQ ID NO 31
<211> LENGTH: 354
<212> TYPE: PRT
<213> ORGANISM: Homo sapiens
<220> FEATURE:
<223> OTHER INFORMATION: human Wnt-11

<400> SEQUENCE: 31

Met Arg Ala Arg Pro Gln Val Cys Glu Ala Leu Leu Phe Ala Leu Ala
  1               5                  10                  15

Leu Gln Thr Gly Val Cys Tyr Gly Ile Lys Trp Leu Ala Leu Ser Lys
             20                  25                  30

Thr Pro Ser Ala Leu Ala Leu Asn Gln Thr Gln His Cys Lys Gln Leu
         35                  40                  45

Glu Gly Leu Val Ser Ala Gln Val Gln Leu Cys Arg Ser Asn Leu Glu
     50                  55                  60

Leu Met His Thr Val Val His Ala Ala Arg Glu Val Met Lys Ala Cys
 65                  70                  75                  80

Arg Arg Ala Phe Ala Asp Met Arg Trp Asn Cys Ser Ser Ile Glu Leu
                 85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ala Ile Ser His Ala Ile Ala Arg
        115                 120                 125

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285
```

-continued

Val Gly Ser His Gly Thr Gln Asp Arg Gln Cys Asn Lys Thr Ser Asn
290 295 300

Gly Ser Asp Ser Cys Asp Leu Met Cys Cys Gly Arg Gly Tyr Asn Pro
305 310 315 320

Tyr Thr Asp Arg Val Val Glu Arg Cys His Cys Lys Tyr His Trp Cys
325 330 335

Cys Tyr Val Thr Cys Arg Arg Cys Glu Arg Thr Val Glu Arg Tyr Val
340 345 350

Cys Lys

<210> SEQ ID NO 32
<211> LENGTH: 1927
<212> TYPE: DNA
<213> ORGANISM: Homo sapiens
<220> FEATURE:
<223> OTHER INFORMATION: human Wnt-11

<400> SEQUENCE: 32
taacccgccg cctccgctct ccccggctgc aggcggcgtg caggaccagc ggcggccgtg 60
caggcggagg acttcggcgc ggctcctcct gggtgtgacc ccgggcgcgc ccgccgcgcg 120
acgatgaggg cgcggccgca ggtctgcgag gcgctgctct tcgccctggc gctccagacc 180
ggcgtgtgct atggcatcaa gtggctggcg ctgtccaaga caccatcggc cctggcactg 240
aaccagacgc aacactgcaa gcagctggag ggtctggtgt ctgcacaggt gcagctgtgc 300
cgcagcaacc tggagctcat gcacacggtg gtgcacgccg cccgcgaggt catgaaggcc 360
tgtcgccggg cctttgccga catgcgctgg aactgctcct ccattgagct cgcccccaac 420
tatttgcttg acctggagag agggacccgg gagtcggcct tcgtgtatgc gctgtcggcc 480
gccgccatca gccacgccat cgcccgggcc tgcacctccg gcgacctgcc cggctgctcc 540
tgcggccccg tcccaggtga gccacccggg cccgggaacc gctggggagg atgtgcggac 600
aacctcagct acgggctcct catgggggcc aagttttccg atgctcctat gaaggtgaaa 660
aaaacaggat cccaagccaa taaactgatg cgtctacaca acagtgaagt ggggagacag 720
gctctgcgcg cctctctgga aatgaagtgt aagtgccatg ggtgtctggg ctcctgctcc 780
atccgcacct gctggaaggg gctgcaggag ctgcaggatg tggctgctga cctcaagacc 840
cgatacctgt cggccaccaa ggtagtgcac cgacccatgg gcacccgcaa gcacctggtg 900
cccaaggacc tggatatccg gcctgtgaag gactcggaac tcgtctatct gcagagctca 960
cctgacttct gcatgaagaa tgagaaggtg ggctcccacg ggacacaaga caggcagtgc 1020
aacaagacat ccaacggaag cgacagctgc gaccttatgt gctgcgggcg tggctacaac 1080
ccctacacag accgcgtggt cgagcggtgc cactgtaagt accactggtg ctgctacgtc 1140
acctgccgca ggtgtgagcg taccgtggag cgctatgtct gcaagtgagg ccctgccctc 1200
cgccccacgc aggagcgagg actctgctca aggaccctca gcaactgggg ccaggggcct 1260
ggagacactc catggagctc tgcttgtgaa ttccagatgc caggcatggg aggcggcttg 1320
tgctttgcct tcacttggaa gccaccagga acagaaggtc tggccaccct ggaaggaggg 1380
caggacatca aaggaaaccg acaagattaa aaataacttg gcagcctgag gctctggagt 1440
gcccacaggc tggtgtaagg agcggggctt gggatcggtg agactgatac agacttgacc 1500
tttcagggcc acagagacca gcctccggga aggggtctgc ccgccttctt cagaatgttc 1560
tgcgggaccc cctggcccac cctggggtct gagcctgctg ggcccaccac atggaatcac 1620

-continued

```
tagcttgggt tgtaaatgtt ttcttttgtt ttttgctttt tcttcctttg ggatgtggaa   1680

gctacagaaa tatttataaa acatagcttt ttctttgggg tggcacttct caattcctct   1740

ttatatattt tatatatata aatatatatg tatatatata atgatctcta ttttaaaact   1800

agctttttaa gcagctgtat gaaataaatg ctgagtgagc cccagcccgc ccctgcagtt   1860

cccggcctcg tcaagtgaac tcggcagacc ctggggctgg cagagggagc tctccagttt   1920

ccaggca                                                             1927


<210> SEQ ID NO 33
<211> LENGTH: 365
<212> TYPE: PRT
<213> ORGANISM: Homo sapiens
<220> FEATURE:
<223> OTHER INFORMATION: human Wnt-14

<400> SEQUENCE: 33

Met Leu Asp Gly Ser Pro Leu Ala Arg Trp Leu Ala Ala Ala Phe Gly
  1               5                  10                  15

Leu Thr Leu Leu Leu Ala Ala Leu Arg Pro Ser Ala Ala Tyr Phe Gly
             20                  25                  30

Leu Thr Gly Ser Glu Pro Leu Thr Ile Leu Pro Leu Thr Leu Glu Pro
         35                  40                  45

Glu Ala Ala Ala Gln Ala His Tyr Lys Ala Cys Asp Arg Leu Lys Leu
     50                  55                  60

Glu Arg Lys Gln Arg Arg Met Cys Arg Arg Asp Pro Gly Val Ala Glu
 65                  70                  75                  80

Thr Leu Val Glu Ala Val Ser Met Ser Ala Leu Glu Cys Gln Phe Gln
                 85                  90                  95

Phe Arg Phe Glu Arg Trp Asn Cys Thr Leu Glu Gly Arg Tyr Arg Ala
            100                 105                 110

Ser Leu Leu Lys Arg Gly Phe Lys Glu Thr Ala Phe Leu Tyr Ala Ile
        115                 120                 125

Ser Ser Ala Gly Leu Thr His Ala Leu Ala Lys Ala Cys Ser Ala Gly
    130                 135                 140

Arg Met Glu Arg Cys Thr Cys Asp Glu Ala Pro Asp Leu Glu Asn Arg
145                 150                 155                 160

Glu Ala Trp Gln Trp Gly Gly Cys Gly Asp Asn Leu Lys Tyr Ser Ser
                165                 170                 175

Lys Phe Val Lys Glu Phe Leu Gly Arg Arg Ser Ser Lys Asp Leu Arg
            180                 185                 190

Ala Arg Val Asp Phe His Asn Asn Leu Val Gly Val Lys Val Ile Lys
        195                 200                 205

Ala Gly Val Glu Thr Thr Cys Lys Cys His Gly Val Ser Gly Ser Cys
    210                 215                 220

Thr Val Arg Thr Cys Trp Arg Gln Leu Ala Pro Phe His Glu Val Gly
225                 230                 235                 240

Lys His Leu Lys His Lys Tyr Glu Thr Ala Leu Lys Val Gly Ser Thr
                245                 250                 255

Thr Asn Glu Ala Ala Gly Glu Ala Gly Ala Ile Ser Pro Pro Arg Gly
            260                 265                 270

Arg Ala Ser Gly Ala Gly Gly Ser Asp Pro Leu Pro Arg Thr Pro Glu
        275                 280                 285

Leu Val His Leu Asp Asp Ser Pro Ser Phe Cys Leu Ala Gly Arg Phe
    290                 295                 300
```

-continued

```
Ser Pro Gly Thr Ala Gly Arg Arg Cys His Arg Glu Lys Asn Cys Glu
305                 310                 315                 320

Ser Ile Cys Cys Gly Arg Gly His Asn Thr Gln Ser Arg Val Val Thr
                325                 330                 335

Arg Pro Cys Gln Cys Gln Val Arg Trp Cys Cys Tyr Val Glu Cys Arg
            340                 345                 350

Gln Cys Thr Gln Arg Glu Glu Val Tyr Thr Cys Lys Gly
        355                 360                 365


<210> SEQ ID NO 34
<211> LENGTH: 1631
<212> TYPE: DNA
<213> ORGANISM: Homo sapiens
<220> FEATURE:
<223> OTHER INFORMATION: human Wnt-14

<400> SEQUENCE: 34

ggcgcggcaa gatgctggat gggtccccgc tggcgcgctg gctggccgcg gccttcgggc     60

tgacgctgct gctcgccgcg ctgcgccctt cggccgccta cttcgggctg acgggcagcg    120

agcccctgac catcctcccg ctgaccctgg agccagaggc ggccgcccag gcgcactaca    180

aggcctgcga ccggctgaag ctggagcgga agcagcggcg catgtgccgc cgggacccgg    240

gcgtggcaga gacgctggtg gaggccgtga gcatgagtgc gctcgagtgc cagttccagt    300

tccgctttga gcgctggaac tgcacgctgg agggccgcta ccgggccagc ctgctcaagc    360

gaggcttcaa ggagactgcc ttcctctatg ccatctcctc ggctggcctg acgcacgcac    420

tggccaaggc gtgcagcgcg ggccgcatgg agcgctgtac ctgcgatgag gcacccgacc    480

tggagaaccg tgaggcctgg cagtgggggg gctgcggaga caaccttaag tacagcagca    540

agttcgtcaa ggaattcctg ggcagacggt caagcaagga tctgcgagcc cgtgtggact    600

tccacaacaa cctcgtgggt gtgaaggtga tcaaggctgg ggtggagacc acctgcaagt    660

gccacggcgt gtcaggctca tgcacggtgc ggacctgctg gcggcagttg gcgcctttcc    720

atgaggtggg caagcatctg aagcacaagt atgagacggc actcaaggtg ggcagcacca    780

ccaatgaagc tgccggcgag gcaggtgcca tctccccacc acggggccgt gcctcggggg    840

caggtggcag cgacccgctg ccccgcactc cagagctggt gcacctggat gactcgccta    900

gcttctgcct ggctggccgc ttctccccgg gcaccgctgg ccgtaggtgc caccgtgaga    960

agaactgcga gagcatctgc tgtggccgcg gccataacac acagagccgg gtggtgacaa   1020

ggccctgcca gtgccaggtg cgttggtgct gctatgtgga gtgcaggcag tgcacgcagc   1080

gtgaggaggt ctacacctgc aagggctgag ttcccaggcc ctgccagccc tgctgcacag   1140

ggtgcaggca ttgcacacgg tgtgaagggt ctacacctgc acaggctgag ttcctgggct   1200

cgaccagccc agctgcgtgg ggtacaggca ttgcacacag tgtgaatggg tctacacctg   1260

catgggctga gtccctgggc tcagacctag cagcgtgggg tagtccctgg gctcagtcct   1320

agctgcatgg ggtgcaggca ttgcacagag catgaatggg cctacacctg ccaaggctga   1380

atccctgggc ccagccagcc ctgctgcaca tggcacaggc attgcacacg gtgtgaggag   1440

tgtacacctg caagggctga ggccctgggc ccagtcagcc ctgctgctca gagtgcaggc   1500

attgcacatg gtgtgagaag gtctacacct gcaagggacg agtccccggg cctggccaac   1560

cctgctgtgc agggtgaggg ccatgcatgc tagtatgagg ggtctacacc tgcaaggact   1620

gagaggcttt t                                                         1631
```

-continued

<210> SEQ ID NO 35
<211> LENGTH: 357
<212> TYPE: PRT
<213> ORGANISM: Homo sapiens
<220> FEATURE:
<223> OTHER INFORMATION: human Wnt-15

<400> SEQUENCE: 35

```
Met Arg Pro Pro Pro Ala Leu Ala Leu Ala Gly Leu Cys Leu Leu Ala
  1               5                  10                  15

Leu Pro Ala Ala Ala Ala Ser Tyr Phe Gly Leu Thr Gly Arg Glu Val
             20                  25                  30

Leu Thr Pro Phe Pro Gly Leu Gly Thr Ala Ala Ala Pro Ala Gln Gly
         35                  40                  45

Gly Ala His Leu Lys Gln Cys Asp Leu Leu Lys Leu Ser Arg Arg Gln
     50                  55                  60

Lys Gln Leu Cys Arg Arg Glu Pro Gly Leu Ala Glu Thr Leu Arg Asp
 65                  70                  75                  80

Ala Ala His Leu Gly Leu Leu Glu Cys Gln Phe Gln Phe Arg His Glu
                 85                  90                  95

Arg Trp Asn Cys Ser Leu Glu Gly Arg Met Gly Leu Leu Lys Arg Gly
            100                 105                 110

Phe Lys Glu Thr Ala Phe Leu Tyr Ala Val Ser Ser Ala Ala Leu Thr
        115                 120                 125

His Thr Leu Ala Arg Ala Cys Ser Ala Gly Arg Met Glu Arg Cys Thr
    130                 135                 140

Cys Asp Asp Ser Pro Gly Leu Glu Ser Arg Gln Ala Trp Gln Trp Gly
145                 150                 155                 160

Val Cys Gly Asp Asn Leu Lys Tyr Ser Thr Lys Phe Leu Ser Asn Phe
                165                 170                 175

Leu Gly Ser Lys Arg Gly Asn Lys Asp Leu Arg Ala Arg Ala Asp Ala
            180                 185                 190

His Asn Thr His Val Gly Ile Lys Ala Val Lys Ser Gly Leu Arg Thr
        195                 200                 205

Thr Cys Lys Cys His Gly Val Ser Gly Ser Cys Ala Val Arg Thr Cys
    210                 215                 220

Trp Lys Gln Leu Ser Pro Phe Arg Glu Thr Gly Gln Val Leu Lys Leu
225                 230                 235                 240

Arg Tyr Asp Ser Ala Val Lys Val Ser Ser Ala Thr Asn Glu Ala Leu
                245                 250                 255

Gly Arg Leu Glu Leu Trp Ala Pro Ala Arg Gln Gly Ser Leu Thr Lys
            260                 265                 270

Gly Leu Ala Pro Arg Ser Gly Asp Leu Val Tyr Met Glu Asp Ser Pro
        275                 280                 285

Ser Phe Cys Arg Pro Ser Lys Tyr Ser Pro Gly Thr Ala Gly Arg Val
    290                 295                 300

Cys Ser Arg Glu Ala Ser Cys Ser Ser Leu Cys Cys Gly Arg Gly Tyr
305                 310                 315                 320

Asp Thr Gln Ser Arg Leu Val Ala Phe Ser Cys His Cys Gln Val Gln
                325                 330                 335

Trp Cys Cys Tyr Val Glu Cys Gln Gln Cys Val Gln Glu Glu Leu Val
            340                 345                 350

Tyr Thr Cys Lys His
        355
```

-continued

<210> SEQ ID NO 36
<211> LENGTH: 1464
<212> TYPE: DNA
<213> ORGANISM: Homo sapiens
<220> FEATURE:
<223> OTHER INFORMATION: human Wnt-15

<400> SEQUENCE: 36
gcgaggagat gctagagggc gcagcgccgc cagcaccatg cgcccccgc ccgcgctggc 60 cctggccggg ctctgcctgc tggcgctgcc cgccgccgcc gcctcctact tcggcctgac 120
cgggcgggaa gtcctgacgc ccttcccagg attgggcact gcggcagccc cggcacaggg 180
cggggcccac ctgaagcagt gtgacctgct gaagctgtcc cggcggcaga agcagctctg 240
ccggagggag cccggcctgg ctgagaccct gagggatgct gcgcacctcg gcctgcttga 300
gtgccagttt cagttccggc atgagcgctg gaactgtagc ctggagggca ggatgggcct 360
gctcaagaga ggcttcaaag agacagcttt cctgtacgcg gtgtcctctg ccgccctcac 420
ccacaccctg gcccgggcct gcagcgctgg gcgcatggag cgctgcacct gtgatgactc 480
tccggggctg gagagccggc aggcctggca gtggggcgtg tgcggtgaca acctcaagta 540
cagcaccaag tttctgagca acttcctggg gtccaagaga ggaaacaagg acctgcgggc 600
acgggcagac gcccacaata cccacgtggg catcaaggct gtgaagagtg gcctcaggac 660
cacgtgtaag tgccatggcg tatcaggctc ctgtgccgtg cgcacctgct ggaagcagct 720
ctccccgttc cgtgagacgg gccaggtgct gaaactgcgc tatgactcgg ctgtcaaggt 780
gtccagtgcc accaatgagg ccttgggccg cctagagctg tgggcccctg ccaggcaggg 840
cagcctcacc aaaggcctgg ccccaaggtc tggggacctg gtgtacatgg aggactcacc 900
cagcttctgc cggcccagca agtactcacc tggcacagca ggtagggtgt gctcccggga 960
ggccagctgc agcagcctgt gctgcgggcg gggctatgac acccagagcc gcctggtggc 1020
cttctcctgc cactgccagg tgcagtggtg ctgctacgtg gagtgccagc aatgtgtgca 1080
ggaggagctt gtgtacacct gcaagcacta ggcctactgc ccagcaagcc agtctggcac 1140
tgccaggacc tcctgtggca cccttcaagc tgcccagccg gccctctggg cagactgtca 1200
tcacatgcat gcataaaccg gcatgtgtgc caatgcacac gagtgtgcca ctcaccacca 1260
ttccttggcc agccttttgc ctccctcgat actcaacaaa gagaagcaaa gcctcctccc 1320
ttaacccaag catccccaac cttgttgagg acttggagag gagggcagag tgagaaagac 1380
atggagggaa ataagggaga ccaagagcac agcaggactg aaattttgga cgggagagag 1440
gggctattcc atcttgcttc ctgg 1464

<210> SEQ ID NO 37
<211> LENGTH: 365
<212> TYPE: PRT
<213> ORGANISM: Homo sapiens
<220> FEATURE:
<223> OTHER INFORMATION: human Wnt-16

<400> SEQUENCE: 37

Met Asp Arg Ala Ala Leu Leu Gly Leu Ala Arg Leu Cys Ala Leu Trp
1 5 10 15

Ala Ala Leu Leu Val Leu Phe Pro Tyr Gly Ala Gln Gly Asn Trp Met
20 25 30

Trp Leu Gly Ile Ala Ser Phe Gly Val Pro Glu Lys Leu Gly Cys Ala
35 40 45

Asn Leu Pro Leu Asn Ser Arg Gln Lys Glu Leu Cys Lys Arg Lys Pro

-continued

```
     50                  55                  60

Tyr Leu Leu Pro Ser Ile Arg Glu Gly Ala Arg Leu Gly Ile Gln Glu
 65                  70                  75                  80

Cys Gly Ser Gln Phe Arg His Glu Arg Trp Asn Cys Met Ile Thr Ala
                 85                  90                  95

Ala Ala Thr Thr Ala Pro Met Gly Ala Ser Pro Leu Phe Gly Tyr Glu
            100                 105                 110

Leu Ser Ser Gly Thr Lys Glu Thr Ala Phe Ile Tyr Ala Val Met Ala
        115                 120                 125

Ala Gly Leu Val His Ser Val Thr Arg Ser Cys Ser Ala Gly Asn Met
    130                 135                 140

Thr Glu Cys Ser Cys Asp Thr Thr Leu Gln Asn Gly Gly Ser Ala Ser
145                 150                 155                 160

Glu Gly Trp His Trp Gly Gly Cys Ser Asp Asp Val Gln Tyr Gly Met
                165                 170                 175

Trp Phe Ser Arg Lys Phe Leu Asp Phe Pro Ile Gly Asn Thr Thr Gly
            180                 185                 190

Lys Glu Asn Lys Val Leu Leu Ala Met Asn Leu His Asn Asn Glu Ala
        195                 200                 205

Gly Arg Gln Ala Val Ala Lys Leu Met Ser Val Asp Cys Arg Cys His
    210                 215                 220

Gly Val Ser Gly Ser Cys Ala Val Lys Thr Cys Trp Lys Thr Met Ser
225                 230                 235                 240

Ser Phe Glu Lys Ile Gly His Leu Leu Lys Asp Lys Tyr Glu Asn Ser
                245                 250                 255

Ile Gln Ile Ser Asp Lys Thr Lys Arg Lys Met Arg Arg Arg Glu Lys
            260                 265                 270

Asp Gln Arg Lys Ile Pro Ile His Lys Asp Asp Leu Leu Tyr Val Asn
        275                 280                 285

Lys Ser Pro Asn Tyr Cys Val Glu Asp Lys Lys Leu Gly Ile Pro Gly
    290                 295                 300

Thr Gln Gly Arg Glu Cys Asn Arg Thr Ser Glu Gly Ala Asp Gly Cys
305                 310                 315                 320

Asn Leu Leu Cys Cys Gly Arg Gly Tyr Asn Thr His Val Val Arg His
                325                 330                 335

Val Glu Arg Cys Glu Cys Lys Phe Ile Trp Cys Cys Tyr Val Arg Cys
            340                 345                 350

Arg Arg Cys Glu Ser Met Thr Asp Val His Thr Cys Lys
        355                 360                 365


<210> SEQ ID NO 38
<211> LENGTH: 3132
<212> TYPE: DNA
<213> ORGANISM: Homo sapiens
<220> FEATURE:
<223> OTHER INFORMATION: human Wnt-16

<400> SEQUENCE: 38

cccgcatctc ctgcacatct ccacccctgc gcaggaggag atccccaggc tgctctctcc      60

atctctccta cagctccctg caaacgaggg ggaagctgct gagagtccct atcactgctg     120

gccttttaat gttgtatgca aggaggaaga gggcgaggga taacttggtg ctggacaact     180

gacctgcggc ccgaagggcc tctggggagg gggtgcaaaa gaggagcggc tgggctgggg     240

gactccatgc gggggcgatg gacagggcgg cgctcctggg actggcccgc ttgtgcgcgc     300
```

-continued

```
tgtgggcagc cctgctcgtg ctgttcccct acggagccca aggaaactgg atgtggttgg    360
gcattgcctc cttcggggtt ccagagaagc tgggctgcgc caatttgccg ctgaacagcc    420
gccagaagga gctgtgcaag aggaaaccgt acctgctgcc gagcatccga gagggcgccc    480
ggctgggcat tcaggagtgc gggagccagt tcagacacga gagatggaac tgcatgatca    540
ccgccgccgc cactaccgcc ccgatgggcg ccagcccccct ctttggctac gagctgagca    600
gcggcaccaa agagacagca tttatttatg ctgtgatggc tgcaggcctg gtgcattctg    660
tgaccaggtc atgcagtgca ggcaacatga cagagtgttc ctgtgacacc accttgcaga    720
acggcggctc agcaagtgaa ggctggcact ggggggggctg ctccgatgat gtccagtatg    780
gcatgtggtt cagcagaaag ttcctagatt tccccatcgg aaacaccacg ggcaaagaaa    840
acaaagtact attagcaatg aacctacata acaatgaagc tggaaggcag gctgtcgcca    900
agttgatgtc agtagactgc cgctgccacg gagtttccgg ctcctgtgct gtgaaaacat    960
gctggaaaac catgtcttct tttgaaaaga ttggccattt gttgaaggat aaatatgaaa   1020
acagtatcca gatatcagac aaaacaaaga ggaaaatgcg caggagagaa aaagatcaga   1080
ggaaaatacc aatccataag gatgatctgc tctatgttaa taagtctccc aactactgtg   1140
tagaagataa gaaactggga atcccaggga cacaaggcag agaatgcaac cgtacatcag   1200
agggtgcaga tggctgcaac ctcctctgct gtggccgagg ttacaacacc catgtggtca   1260
ggcacgtgga gaggtgtgag tgtaagttca tctggtgctg ctatgtccgt tgcaggaggt   1320
gtgaaagcat gactgatgtc cacacttgca agtaaccact ccatccagcc ttgggcaaga   1380
tgcctcagca atatacaatg gcattgcaac cagagaggtg cccatccctg tgcagcgcta   1440
gtaaagttga ctcttgcagt ggaatcccta gaaccttgga cctgagagtt tcccttacct   1500
gatcgacata ttttccttta tctgatcaac ccatcaatca tgtggatttc ttgggattct   1560
aatgttgaaa aggtttatat tcaccttttg atgatttggg gaatatatat tgacatacaa   1620
ggaagataat ctgtttccta agcaagaaat aacaggaaag atcccttatg ccaggaggcc   1680
tgccatactc aggataagat ccttgaatat ggaacttagt tacaggactc aataatggtg   1740
ggtgaacatt agtcattttt aaaagacacc tcttatagca ataaggagac attaacatga   1800
atctcattta ttctctcagt attttaactg aagaaattat actgtttgtg tgtggataga   1860
agatgttgaa aagttaacat aagcattggg tgctgactta cccttttcatg tacttccaaa   1920
gaaaggtaat caaaaagaat cttcttaagt gatataatat ccctaaaaaa atgatcatta   1980
cagatgttta gtgacaaaga atcaatatgt aaaaagtata atgaatgatt tagattttaa   2040
gtgccttttc actgggagaa tctggaaaaa cctccataag gtatatagca atctttgatc   2100
tttagattca tacttttatc acagatcagt ttcaactgtt aaaaacccac ctctgagata   2160
ctgggggggag gatcctgaaa catgcgggaa aaggagaggt aaacagtgga ggtaaaaata   2220
taatttcata cattgtaaag aaaagcaccc tttaaatgtg taaagacagt gttttgtaaa   2280
gaattttgtt taaaaagttt ctattttgta aatacagtac ttaagttata tgatttatat   2340
taaaacattt attgacaaag cctaagagct aaggcagtaa aattatctca taaataatat   2400
tagcttattt tttttcatac tattaatgct attttttttgg acatcgaaga gaatttaact   2460
tagcagttag ttatatggat gtgtatttct tgctaaaatg acagttttat atgttataga   2520
ttaaaatatg ttgcaaaata tcaaaaattt gtgttatttc agcagtaaga ttaattgaat   2580
tctcttttca cattagttat gcttaactca taaggttatt ataataaatt atattagtaa   2640
aagtcttaac tggaaaaaag aatctaaatc agaatagtga tcaatttgtg gatttgatat   2700
```

-continued

```
cctggatatt tattatattt tatgtaatgc tgcatttcta tttgaatgtt aagtggtctt   2760

tcttgttttt aatattcatg catgtatatt catcatattt tacaaggttc ctggtaaaaa   2820

ttacagggct ctatttaagg atgtatttta atgtaaatgc ttatgttttt tatgaattgt   2880

taaatatttc agtattatat agaaaaaaat agatttttaa aattcagaat ggacaaagag   2940

aatattcatt ttcttattaa taagataaag aaatgtttcc ctgccccaca gtcttcattc   3000

tatttctctt taattttatt cactgaggca gagaaacaat ttttgaaaaa gagcaaaccc   3060

atggaaaatg tctcagatct aatattaaaa tcaagactaa gcatttaact gtgaaaaaaa   3120

aaaaaaaaaa aa                                                         3132
```

```
<210> SEQ ID NO 39
<211> LENGTH: 647
<212> TYPE: PRT
<213> ORGANISM: Homo sapiens
<220> FEATURE:
<223> OTHER INFORMATION: human frizzled1 (Fzd1)

<400> SEQUENCE: 39

Met Ala Glu Glu Glu Ala Pro Lys Lys Ser Arg Ala Ala Gly Gly Gly
  1               5                  10                  15

Ala Ser Trp Glu Leu Cys Ala Gly Ala Leu Ser Ala Arg Leu Ala Glu
             20                  25                  30

Glu Gly Ser Gly Asp Ala Gly Gly Arg Arg Arg Pro Pro Val Asp Pro
         35                  40                  45

Arg Arg Leu Ala Arg Gln Leu Leu Leu Leu Leu Trp Leu Leu Glu Ala
     50                  55                  60

Pro Leu Leu Leu Gly Val Arg Ala Gln Ala Ala Gly Gln Gly Pro Gly
 65                  70                  75                  80

Gln Gly Pro Gly Pro Gly Gln Gln Pro Pro Pro Pro Pro Gln Gln Gln
                 85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
    210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
                245                 250                 255

Gly His Arg Gly Gly Phe Pro Gly Gly Ala Gly Ala Ser Glu Arg Gly
            260                 265                 270

Lys Phe Ser Cys Pro Arg Ala Leu Lys Val Pro Ser Tyr Leu Asn Tyr
```

-continued

```
        275                 280                 285

His Phe Leu Gly Glu Lys Asp Cys Gly Ala Pro Cys Glu Pro Thr Lys
    290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
                325                 330                 335

Thr Val Leu Thr Tyr Leu Val Asp Met Arg Arg Phe Ser Tyr Pro Glu
            340                 345                 350

Arg Pro Ile Ile Phe Leu Ser Gly Cys Tyr Thr Ala Val Ala Val Ala
        355                 360                 365

Tyr Ile Ala Gly Phe Leu Leu Glu Asp Arg Val Val Cys Asn Asp Lys
    370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
                405                 410                 415

Ser Ile Trp Trp Val Ile Leu Ser Leu Thr Trp Phe Leu Ala Ala Gly
            420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
    450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
                485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
    530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
                565                 570                 575

Tyr Ala Ile Pro Cys Pro His Leu Gln Ala Gly Gly Gly Ala Pro Pro
            580                 585                 590

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
    610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645
```

<210> SEQ ID NO 40
<211> LENGTH: 4350
<212> TYPE: DNA
<213> ORGANISM: Homo sapiens
<220> FEATURE:
<223> OTHER INFORMATION: human frizzled1 (Fzd1)

-continued

<400> SEQUENCE: 40

```
agttgaggga ttgacacaaa tggtcaggcg gcggcggcgg agaaggaggc ggaggcgcag     60
gggggagccg agcccgctgg gctgcggaga gttgcgctct ctacggggcc gcggccacta    120
gcgcggcgcc gccagccggg agccagcgag ccgagggcca ggaaggcggg acacgacccc    180
ggcgcgccct agccacccgg gttctccccg ccgcccgcgc ttcatgaatc gcaagtttcc    240
gcggcggcgg cggctgcggt acgcagaaca ggagccgggg gagcgggccg aaagcggctt    300
gggctcgacg gagggcaccc gcgcagaggt ctccctggcc gcagggggag ccgccgccgg    360
ccgtgcccct ggcagcccca gcggagcggc gccaagagag gagccgagaa agtatggctg    420
aggaggaggc gcctaagaag tcccgggccg ccggcggtgg cgcgagctgg gaactttgtg    480
ccggggcgct ctcggcccgg ctggcggagg agggcagcgg ggacgccggt ggccgccgcc    540
gcccgccagt tgacccccgg cgattggcgc gccagctgct gctgctgctt tggctgctgg    600
aggctccgct gctgctgggg gtccgggccc aggcggcggg ccaggggcca ggccaggggc    660
ccgggccggg gcagcaaccg ccgccgccgc ctcagcagca acagagcggg cagcagtaca    720
acggcgagcg gggcatctcc gtcccggacc acggctattg ccagcccatc tccatcccgc    780
tgtgcacgga catcgcgtac aaccagacca tcatgcccaa cctgctgggc cacacgaacc    840
aggaggacgc gggcctggag gtgcaccagt tctaccctct agtgaaagtg cagtgttccg    900
ctgagctcaa gttcttcctg tgctccatgt acgcgcccgt gtgcaccgtg ctagagcagg    960
cgctgccgcc ctgccgctcc ctgtgcgagc gcgcgcgcca gggctgcgag gcgctcatga   1020
acaagttcgg cttccagtgg ccagacacgc tcaagtgtga gaagttcccg gtgcacggcg   1080
ccggcgagct gtgcgtgggc cagaacacgt ccgacaaggg caccccgacg ccctcgctgc   1140
ttccagagtt ctggaccagc aaccctcagc acggcggcgg agggcaccgt ggcggcttcc   1200
cgggggggcgc cggcgcgtcg gagcgaggca agttctcctg cccgcgcgcc ctcaaggtgc   1260
cctcctacct caactaccac ttcctggggg agaaggactg cggcgcacct tgtgagccga   1320
ccaaggtgta tgggctcatg tacttcgggc ccgaggagct gcgcttctcg cgcacctgga   1380
ttggcatttg gtcagtgctg tgctgcgcct ccacgctctt cacggtgctt acgtacctgg   1440
tggacatgcg gcgcttcagc tacccggagc ggcccatcat cttcttgtcc ggctgttaca   1500
cggccgtggc cgtggcctac atcgccggct tcctcctgga agaccgagtg gtgtgtaatg   1560
acaagttcgc cgaggacggg gcacgcactg tggcgcaggg caccaagaag gagggctgca   1620
ccatcctctt catgatgctc tacttcttca gcatggccag ctccatctgg tgggtgatcc   1680
tgtcgctcac ctggttcctg gcggctggca tgaagtgggg ccacgaggcc atcgaagcca   1740
actcacagta ttttcacctg gccgcctggg ctgtgccggc catcaagacc atcaccatcc   1800
tggcgctggg ccaggtggac ggcgatgtgc tgagcggagt gtgcttcgtg gggcttaaca   1860
acgtggacgc gctgcgtggc ttcgtgctgg cgcccctctt cgtgtacctg tttatcggca   1920
cgtcctttct gctggccggc tttgtgtcgc tcttccgcat ccgcaccatc atgaagcacg   1980
atggcaccaa gaccgagaag ctggagaagc tcatggtgcg cattggcgtc ttcagcgtgc   2040
tgtacactgt gccagccacc atcgtcatcg cctgctactt ctacgagcag gccttccggg   2100
accagtggga acgcagctgg gtggcccaga gctgcaagag ctacgctatc ccctgccctc   2160
acctccaggc gggcggaggc gccccgccgc acccgcccat gagcccggac ttcacggtct   2220
tcatgattaa gtaccttatg acgctgatcg tgggcatcac gtcgggcttc tggatctggt   2280
ccggcaagac cctcaactcc tggaggaagt tctacacgag gctcaccaac agcaaacaag   2340
```

-continued

```
gggagactac agtctgagac ccggggctca gcccatgccc aggcctcggc cggggcgcag   2400
cgatccccca aagccagcgc cgtggagttc gtgccaatcc tgacatctcg aggtttcctc   2460
actagacaac tctctttcgc aggctccttt gaacaactca gctcctgcaa aagcttccgt   2520
ccctgaggca aaaggacacg agggcccgac tgccagaggg aggatggaca gacctcttgc   2580
cctcacactc tggtaccagg actgttcgct tttatgattg taaatagcct gtgtaagatt   2640
tttgtaagta tatttgtatt taaatgacga ccgatcacgc gtttttcttt ttcaaaagtt   2700
tttaattatt tagggcggtt taaccatttg aggcttttcc ttcttgccct tttcggagta   2760
ttgcaaagga gctaaaactg gtgtgcaacc gcacagcgct cctggtcgtc ctcgcgcgcc   2820
tctccctacc acgggtgctc gggacggctg ggcgccagct ccggggcgag ttcagcactg   2880
cggggtgcga ctagggctgc gctgccaggg tcacttcccg cctcctcctt ttgcccccctc   2940
cccctccttc tgtcccctcc ctttctttcc tggcttgagg taggggctct taaggtacag   3000
aactccacaa accttccaaa tctggaggag ggccccccata cattacaatt cctcccttgc   3060
tcggcggtgg attgcgaagg cccgtccctt cgacttcctg aagctggatt tttaactgtc   3120
cagaactttc ctccaacttc atgggggccc acgggtgtgg gcgctggcag tctcagcctc   3180
cctccacggt caccttcaac gcccagacac tcccttctcc caccttagtt ggttacaggg   3240
tgagtgagat aaccaatgcc aaactttttg aagtctaatt tttgaggggt gagctcattt   3300
cattctctag tgtctaaaac ctggtatggg tttggccagc gtcatggaaa gatgtggtta   3360
ctgagatttg ggaagaagca tgaagctttg tgtgggttgg aagagactga agatatgggt   3420
tataaaatgt taattctaat tgcatacgga tgcctggcaa ccttgccttt gagaatgaga   3480
cagcctgcgc ttagatttta ccggtctgta aaatggaaat gttgaggtca cctggaaagc   3540
tttgttaagg agttgatgtt tgctttcctt aacaagacag caaaacgtaa acagaaattg   3600
aaaacttgaa ggatatttca gtgtcatgga cttcctcaaa atgaagtgct attttcttat   3660
ttttaatcaa ataactagac atatatcaga aactttaaaa tgtaaaagtt gtacactttc   3720
aacattttat tacgattatt attcagcagc acattctgag gggggaacaa ttcacaccac   3780
caataataac ctggtaagat ttcaggaggt aaagaaggtg gaataattga cggggagata   3840
gcgcctgaaa taaacaaaat atgggcatgc atgctaaagg gaaaatgtgt gcaggtctac   3900
tgcattaaat cctgtgtgct cctcttttgg atttacagaa atgtgtcaaa tgtaaatctt   3960
tcaaagccat ttaaaaatat tcactttagt tctctgtgaa gaagaggaga aaagcaatcc   4020
tcctgattgt attgttttaa actttaagaa tttatcaaaa tgccggtact taggacctaa   4080
atttatctat gtctgtcata cgctaaaatg atattggtct ttgaatttgg tatacattta   4140
ttctgttcac tatcacaaaa tcatctatat ttatagagga atagaagttt atatatatat   4200
aataccatat ttttaatttc acaaataaaa aattcaaagt tttgtacaaa attatatgga   4260
ttttgtgcct gaaaataata gagcttgagc tgtctgaact attttacatt ttatggtgtc   4320
tcatagccaa tcccacagtg taaaaattca                                    4350
```

<210> SEQ ID NO 41
<211> LENGTH: 565
<212> TYPE: PRT
<213> ORGANISM: Homo sapiens
<220> FEATURE:
<223> OTHER INFORMATION: human frizzled2 (Fzd2)

<400> SEQUENCE: 41

-continued

```
Met Arg Pro Arg Ser Ala Leu Pro Arg Leu Leu Leu Pro Leu Leu Leu
  1               5                  10                  15

Leu Pro Ala Ala Gly Pro Ala Gln Phe His Gly Glu Lys Gly Ile Ser
             20                  25                  30

Ile Pro Asp His Gly Phe Cys Gln Pro Ile Ser Ile Pro Leu Cys Thr
         35                  40                  45

Asp Ile Ala Tyr Asn Gln Thr Ile Met Pro Asn Leu Leu Gly His Thr
     50                  55                  60

Asn Gln Glu Asp Ala Gly Leu Glu Val His Gln Phe Tyr Pro Leu Val
 65                  70                  75                  80

Lys Val Gln Cys Ser Pro Glu Leu Arg Phe Phe Leu Cys Ser Met Tyr
                 85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
    130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Pro Gly Leu Gln Pro Gly Ala
                165                 170                 175

Gly Gly Thr Pro Gly Gly Pro Gly Gly Gly Gly Ala Pro Pro Arg Tyr
            180                 185                 190

Ala Thr Leu Glu His Pro Phe His Cys Pro Arg Val Leu Lys Val Pro
        195                 200                 205

Ser Tyr Leu Ser Tyr Lys Phe Leu Gly Glu Arg Asp Cys Ala Ala Pro
    210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr Trp Ser Val Leu Cys Cys
                245                 250                 255

Ala Ser Thr Phe Phe Thr Val Thr Thr Tyr Leu Val Asp Met Gln Arg
            260                 265                 270

Phe Arg Tyr Pro Glu Arg Pro Ile Ile Phe Leu Ser Gly Cys Tyr Thr
        275                 280                 285

Met Val Ser Val Ala Tyr Ile Ala Gly Phe Val Leu Gln Glu Arg Val
    290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
                325                 330                 335

Phe Ser Met Ala Ser Ser Ile Trp Trp Val Ile Leu Ser Leu Thr Trp
            340                 345                 350

Phe Leu Ala Ala Gly Met Lys Trp Gly His Glu Ala Ile Glu Ala Asn
        355                 360                 365

Ser Gln Tyr Phe His Leu Ala Ala Trp Ala Val Pro Ala Val Lys Thr
    370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
```

-continued

```
            420                 425                 430

Ala Gly Phe Val Ser Leu Phe Arg Ile Arg Thr Ile Met Lys His Asp
        435                 440                 445

Gly Thr Lys Thr Glu Lys Leu Glu Arg Leu Met Val Arg Ile Gly Val
    450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
                485                 490                 495

Gln His Cys Lys Ser Leu Ala Ile Pro Cys Pro Ala His Tyr Thr Pro
            500                 505                 510

Arg Met Ser Pro Asp Phe Thr Val Tyr Met Ile Lys Tyr Leu Met Thr
        515                 520                 525

Leu Ile Val Gly Ile Thr Ser Gly Phe Trp Ile Trp Ser Gly Lys Thr
    530                 535                 540

Leu His Ser Trp Arg Lys Phe Tyr Thr Arg Leu Thr Asn Ser Arg His
545                 550                 555                 560

Gly Glu Thr Thr Val
                565


<210> SEQ ID NO 42
<211> LENGTH: 1983
<212> TYPE: DNA
<213> ORGANISM: Homo sapiens
<220> FEATURE:
<223> OTHER INFORMATION: human frizzled2 (Fzd2)

<400> SEQUENCE: 42

cgagtaaagt ttgcaaagag gcgcgggagg cggcagccgc agcgaggagg cggcggggaa     60

gaagcgcagt ctccgggttg ggggcggggg cggggggggc gccaaggagc cgggtggggg    120

gcggcggcca gcatgcggcc ccgcagcgcc ctgccccgcc tgctgctgcc gctgctgctg    180

ctgcccgccg ccgggccggc ccagttccac ggggagaagg gcatctccat cccggaccac    240

ggcttctgcc agcccatctc catcccgctg tgcacggaca tcgcctacaa ccagaccatc    300

atgcccaacc ttctgggcca cacgaaccag gaggacgcag gcctagaggt gcaccagttc    360

tatccgctgg tgaaggtgca gtgctcgccc gaactgcgct tcttcctgtg ctccatgtac    420

gcacccgtgt gcaccgtgct ggaacaggcc atcccgccgt gccgctctat ctgtgagcgc    480

gcgcgccagg gctgcgaagc cctcatgaac aagttcggtt ttcagtggcc cgagcgcctg    540

cgctgcgagc acttcccgcg ccacggcgcc gagcagatct gcgtcggcca gaaccactcc    600

gaggacggag ctcccgcgct actcaccacc gcgccgccgc cgggactgca gccgggtgcc    660

gggggcaccc cgggtggccc gggcggcggc ggcgctcccc cgcgctacgc cacgctggag    720

cacccctcc actgcccgcg cgtcctcaag gtgccatcct atctcagcta caagtttctg     780

ggcgagcgtg attgtgctgc gccctgcgaa cctgcgcggc ccgatggttc catgttcttc    840

tcacaggagg agacgcgttt cgcgcgcctc tggatcctca cctggtcggt gctgtgctgc    900

gcttccacct tcttcactgt caccacgtac ttggtagaca tgcagcgctt ccgctaccca    960

gagcggccta tcatttttct gtcgggctgc tacaccatgg tgtcggtggc ctacatcgcg   1020

ggcttcgtgc tccaggagcg cgtggtgtgc aacgagcgct tctccgagga cggttaccgc   1080

acggtggtgc agggcaccaa gaaggagggc tgcaccatcc tcttcatgat gctctacttc   1140

ttcagcatgg ccagctccat ctggtgggtc atcctgtcgc tcacctggtt cctggcagcc   1200
```

-continued

```
ggcatgaagt ggggccacga ggccatcgag gccaactctc agtacttcca cctggccgcc   1260

tgggccgtgc cggccgtcaa gaccatcacc atcctggcca tgggccagat cgacggcgac   1320

ctgctgagcg gcgtgtgctt cgtaggcctc aacagcctgg acccgctgcg gggcttcgtg   1380

ctagcgccgc tcttcgtgta cctgttcatc ggcacgtcct tcctcctggc cggcttcgtg   1440

tcgctcttcc gcatccgcac catcatgaag cacgacggca ccaagaccga aaagctggag   1500

cggctcatgg tgcgcatcgg cgtcttctcc gtgctctaca cagtgcccgc caccatcgtc   1560

atcgcttgct acttctacga gcaggccttc cgcgagcact gggagcgctc gtgggtgagc   1620

cagcactgca agagcctggc catcccgtgc ccggcgcact acacgccgcg catgtcgccc   1680

gacttcacgg tctacatgat caaatacctc atgacgctca tcgtgggcat cacgtcgggc   1740

ttctggatct ggtcgggcaa gacgctgcac tcgtggagga agttctacac tcgcctcacc   1800

aacagccgac acggtgagac caccgtgtga gggacgcccc caggccggaa ccgcgcggcg   1860

ctttcctccg cccggggtgg ggcccctaca gactccgtat tttatttttt taaataaaaa   1920

acgatcgaaa ccatttcact tttaggttgc tttttaaaag agaactctct gcccaacacc   1980

ccc                                                                1983


<210> SEQ ID NO 43
<211> LENGTH: 666
<212> TYPE: PRT
<213> ORGANISM: Homo sapiens
<220> FEATURE:
<223> OTHER INFORMATION: human frizzled3 (Fzd3)

<400> SEQUENCE: 43

Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
            20                  25                  30

Leu Arg Met Cys Gln Asp Leu Pro Tyr Asn Thr Thr Phe Met Pro Asn
        35                  40                  45

Leu Leu Asn His Tyr Asp Gln Gln Thr Ala Ala Leu Ala Met Glu Pro
    50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110

Leu Met Glu Met Phe Gly Val Pro Trp Pro Glu Asp Met Glu Cys Ser
        115                 120                 125

Arg Phe Pro Asp Cys Asp Glu Pro Tyr Pro Arg Leu Val Asp Leu Asn
    130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr Phe Ile Gly Leu
        195                 200                 205

Ile Ser Ile Ile Cys Leu Ser Ala Thr Leu Phe Thr Phe Leu Thr Phe
    210                 215                 220
```

-continued

```
Leu Ile Asp Val Thr Arg Phe Arg Tyr Pro Glu Arg Pro Ile Ile Phe
225                 230                 235                 240

Tyr Ala Val Cys Tyr Met Met Val Ser Leu Ile Phe Phe Ile Gly Phe
                245                 250                 255

Leu Leu Glu Asp Arg Val Ala Cys Asn Ala Ser Ile Pro Ala Gln Tyr
            260                 265                 270

Lys Ala Ser Thr Val Thr Gln Gly Ser His Asn Lys Ala Cys Thr Met
        275                 280                 285

Leu Phe Met Ile Leu Tyr Phe Phe Thr Met Ala Gly Ser Val Trp Trp
    290                 295                 300

Val Ile Leu Thr Ile Thr Trp Phe Leu Ala Ala Val Pro Lys Trp Gly
305                 310                 315                 320

Ser Glu Ala Ile Glu Lys Lys Ala Leu Leu Phe His Ala Ser Ala Trp
                325                 330                 335

Gly Ile Pro Gly Thr Leu Thr Ile Ile Leu Leu Ala Met Asn Lys Ile
            340                 345                 350

Glu Gly Asp Asn Ile Ser Gly Val Cys Phe Val Gly Leu Tyr Asp Val
        355                 360                 365

Asp Ala Leu Arg Tyr Phe Val Leu Ala Pro Leu Cys Leu Tyr Val Val
    370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
                405                 410                 415

Phe Met Ile Arg Ile Gly Val Phe Ser Ile Leu Tyr Leu Val Pro Leu
            420                 425                 430

Leu Val Val Ile Gly Cys Tyr Phe Tyr Glu Gln Ala Tyr Arg Gly Ile
        435                 440                 445

Trp Glu Thr Thr Trp Ile Gln Glu Arg Cys Arg Glu Tyr His Ile Pro
    450                 455                 460

Cys Pro Tyr Gln Val Thr Gln Met Ser Arg Pro Asp Leu Ile Leu Phe
465                 470                 475                 480

Leu Met Lys Tyr Leu Met Ala Leu Ile Val Gly Ile Pro Ser Val Phe
                485                 490                 495

Trp Val Gly Ser Lys Lys Thr Cys Phe Glu Trp Ala Ser Phe Phe His
            500                 505                 510

Gly Arg Arg Lys Lys Glu Ile Val Asn Glu Ser Arg Gln Val Leu Gln
        515                 520                 525

Glu Pro Asp Phe Ala Gln Ser Leu Leu Arg Asp Pro Asn Thr Pro Ile
    530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
                565                 570                 575

Ser Ile His Ser Lys Val Ser Ser Tyr His Gly Ser Leu His Arg Ser
            580                 585                 590

Arg Asp Gly Arg Tyr Thr Pro Cys Ser Tyr Arg Gly Met Glu Glu Arg
        595                 600                 605

Leu Pro His Gly Ser Met Ser Arg Leu Thr Asp His Ser Arg His Ser
    610                 615                 620

Ser Ser His Arg Leu Asn Glu Gln Ser Arg His Ser Ser Ile Arg Asp
625                 630                 635                 640
```

-continued

```
Leu Ser Asn Asn Pro Met Thr His Ile Thr His Gly Thr Ser Met Asn
                645                 650                 655

Arg Val Ile Glu Glu Asp Gly Thr Ser Ala
            660                 665


<210> SEQ ID NO 44
<211> LENGTH: 3933
<212> TYPE: DNA
<213> ORGANISM: Homo sapiens
<220> FEATURE:
<223> OTHER INFORMATION: human frizzled3 (Fzd3)

<400> SEQUENCE: 44

gccgctccgg gtacctgagg gacgcgcggc cgcccgcggc aggcggtgca gcccccccac      60

cccttggagc caggcgccgg ggtctgagga tagcatttct caagacctga cttatggagc     120

acttgtaacc tgagatattt cagttgaagg aagaaatagc tcttctccta agatggaatc     180

tgtggtttgg gaatgtggtt gatcaacttg atatgttggc caaatgtgcc ccatgtaata     240

aaatgaaaag aagagacaag atgatgtcat tttcccatat tgtgaaacca aaaacaaacg     300

ccttttgtga gaccaagcta acaaacctct gacggtgcga agagtattta actgtttgaa     360

gaatttaaca gtaagataca gaagaagtac cttcgagctg agacctgcag gtgtataaat     420

atctaaaata catattgaat aggcctgatc atctgaatct ccttcagacc caggaaggat     480

ggctatgact tggattgtct tctctctttg gcccttgact gtgttcatgg ggcatatagg     540

tgggcacagt ttgttttctt gtgaacctat taccttgagg atgtgccaag atttgcctta     600

taatactacc ttcatgccta atcttctgaa tcattatgac caacagacag cagctttggc     660

aatggagcca ttccacccta tggtgaatct ggattgttct cgggatttcc ggccttttct     720

ttgtgcactc tacgctccta tttgtatgga atatggacgt gtcacacttc cctgtcgtag     780

gctgtgtcag cgggcttaca gtgagtgttc gaagctcatg gagatgtttg gtgttccttg     840

gcctgaagat atggaatgca gtaggttccc agattgtgat gagccatatc ctcgacttgt     900

ggatctgaat ttagctggag aaccaactga aggagcccca gtggcagtgc agagagacta     960

tggtttttgg tgtccccgag agttaaaaat tgatcctgat ctgggttatt cttttctgca    1020

tgtgcgtgat tgttcacctc cttgtccaaa tatgtacttc agaagagaag aactgtcatt    1080

tgctcgctat ttcataggat tgatttcaat catttgcctc tcggccacat tgtttacttt    1140

tttaactttt ttgattgatg tcacaagatt ccgttatcct gaaaggccta ttatatttta    1200

tgcagtctgc tacatgatgg tatccttaat ttcttcattg ggatttttgc ttgaagatcg    1260

agtagcctgc aatgcatcca tccctgcaca atataaggct tccacagtga cacaaggatc    1320

tcataataaa gcctgtacca tgcttttat gatactctat tttttacta tggctggcag    1380

tgtatggtgg gtaattctta ccatcacatg gtttttagca gctgtgccaa agtggggtag    1440

tgaagctatt gagaagaaag cattgctgtt tcacgccagt gcatggggca tccccggaac    1500

tctaaccatc atccttttag cgatgaataa aattgaaggt gacaatatta gtggcgtgtg    1560

ttttgttggc ctctacgatg ttgatgcatt gagatatttt gttcttgctc ccctctgcct    1620

gtatgtggta gttggggttt ctctcctctt agctggcatt atatccctaa acagagttcg    1680

aattgagatt ccattagaaa aggagaacca agataaatta gtgaagttta tgatccggat    1740

cggtgttttc agcattcttt atctcgtacc actcttggtt gtaattggat gctacttttta   1800

tgagcaagct taccggggca tctgggaaac aacgtggata caagaacgct gcagagaata    1860

tcacattcca tgtccatatc aggttactca aatgagtcgt ccagacttga ttctctttct    1920
```

-continued

```
gatgaaatac ctgatggctc tcatagttgg cattccctct gtattttggg ttggaagcaa   1980
aaagacatgc tttgaatggg ccagtttttt tcatggtcgt aggaaaaaag agatagtgaa   2040
tgagagccga caggtactcc aggaacctga ttttgctcag tctctcctga gggatccaaa   2100
tactcctatc ataagaaagt caaggggaac ttccactcaa ggaacatcca cccatgcttc   2160
ttcaactcag ctggctatgg tggatgatca aagaagcaaa gcaggaagca tccacagcaa   2220
agtgagcagc taccacggca gcctccacag atcacgtgat ggcaggtaca cgccctgcag   2280
ttacagagga atggaggaga gactacctca tggcagcatg tcacgactaa cagatcactc   2340
caggcatagt agttctcatc ggctcaatga acagtcacga catagcagca tcagagatct   2400
cagtaataat cccatgactc atatcacaca tggcaccagc atgaatcggg ttattgaaga   2460
agatggaacc agtgcttaat ttgtcttgtc taaggtggaa atcttgtgct gtttaaaaag   2520
cagattttat tctttgcctt ttgcatgact gatagctgta actcacagtt aacatgcttt   2580
cagtcaagta cagattgtgt ccactggaaa ggtaaatgat tgcttttttta tattgcatca   2640
aacttggaac atcaaggcat ccaaaacact aagaattcta tcatcacaaa aataattcgt   2700
ctttctaggt tatgaagaga taattatttg tctggtaagc atttttataa acccactcat   2760
tttatattta gaaaaatcct aaatgtgtgg tgactgcttt gtagtgaact ttcatatact   2820
ataaactagt tgtgagataa cattctggta gctcagttaa taaaacaatt tcagaattaa   2880
agaaattttc tatgcaaggt ttacttctca gatgaacagt aggactttgt agttttattt   2940
ccactaagtg aaaaaagaac tgtgttttta aactgtagga gaatttaata aatcagcaag   3000
ggtattttag ctaatagaat aaaagtgcaa cagaagaatt tgattagtct atgaaaggtt   3060
ctcttaaaat tctatcgaaa taatcttcat gcagagatat tcagggtttg gattagcagt   3120
ggaataaaga gatgggcatt gtttccccta taattgtgct gtttttataa cttttgtaaa   3180
tattactttt tctggctgtg tttttataac ttatccatat gcatgatgga aaaattttaa   3240
tttgtagcca tcttttccca tgtaatagta ttgattcata gagaacttaa tgttcaaaat   3300
ttgctttgtg gaggcatgta ataagataaa catcatacat tataaggtaa ccacaattac   3360
aaaatggcaa aacattttct ctgtattcat tgttgtattt ttctacagtg agatgtgatc   3420
ttgccaaagc caccagacct tggcttccag gccctcctgt agtgagttga ttgtctgcac   3480
ttgccttgcc caatagccag taggctacag cttttgcccc acacccttat tttcagattc   3540
tggatcattc ttgtttacaa ctgaaatata tataacctca gtccaaagtg gtgattgatt   3600
tgagtatttg aaaattgttg tagctaaatg aagcatgatt agtcttagta tgaatatcat   3660
ttaatcttta aaaaatcaag taaaaatgtt tatctgataa tgtttaaata atttacaata   3720
taaactgtaa aacttattag gcatgaaatc aatcagaaga gaaagaaaaa tgctggaaca   3780
tgcttgatgt attatgtaaa aagcatattt aaacaagggt cctcaaccct gactgcagat   3840
aagaatcact tgggttactt cagatgccta acaccttcct ctcatacaaa taagaattgg   3900
tagctttctt aaaaaaaaaa aaaaaaaaaa aaa                                 3933
```

<210> SEQ ID NO 45
<211> LENGTH: 537
<212> TYPE: PRT
<213> ORGANISM: Homo sapiens
<220> FEATURE:
<223> OTHER INFORMATION: human frizzled4 (Fzd4)

<400> SEQUENCE: 45

-continued

```
Met Ala Trp Arg Gly Ala Gly Pro Ser Val Pro Gly Ala Pro Gly Gly
1               5                   10                  15

Val Gly Leu Ser Leu Gly Leu Leu Leu Gln Leu Leu Leu Leu Leu Gly
            20                  25                  30

Pro Ala Arg Gly Phe Gly Asp Glu Glu Glu Arg Arg Cys Asp Pro Ile
        35                  40                  45

Arg Ile Ser Met Cys Gln Asn Leu Gly Tyr Asn Val Thr Lys Met Pro
    50                  55                  60

Asn Leu Val Gly His Glu Leu Gln Thr Asp Ala Glu Leu Gln Leu Thr
65                  70                  75                  80

Thr Phe Thr Pro Leu Ile Gln Tyr Gly Cys Ser Ser Gln Leu Gln Phe
                85                  90                  95

Phe Leu Cys Ser Val Tyr Val Pro Met Cys Thr Glu Lys Ile Asn Ile
            100                 105                 110

Pro Ile Gly Pro Cys Gly Gly Met Cys Leu Ser Val Lys Arg Arg Cys
        115                 120                 125

Glu Pro Val Leu Lys Glu Phe Gly Phe Ala Trp Pro Glu Ser Leu Asn
    130                 135                 140

Cys Ser Lys Phe Pro Pro Gln Asn Asp His Asn His Met Cys Met Glu
145                 150                 155                 160

Gly Pro Gly Asp Glu Glu Val Pro Leu Pro His Lys Thr Pro Ile Gln
                165                 170                 175

Pro Gly Glu Glu Cys His Ser Val Gly Thr Asn Ser Asp Gln Tyr Ile
            180                 185                 190

Trp Val Lys Arg Ser Leu Asn Cys Val Leu Lys Cys Gly Tyr Asp Ala
        195                 200                 205

Gly Leu Tyr Ser Arg Ser Ala Lys Glu Phe Thr Asp Ile Trp Met Ala
    210                 215                 220

Val Trp Ala Ser Leu Cys Phe Ile Ser Thr Ala Phe Thr Val Leu Thr
225                 230                 235                 240

Phe Leu Ile Asp Ser Ser Arg Phe Ser Tyr Pro Glu Arg Pro Ile Ile
                245                 250                 255

Phe Leu Ser Met Cys Tyr Asn Ile Tyr Ser Ile Ala Tyr Ile Val Arg
            260                 265                 270

Leu Thr Val Gly Arg Glu Arg Ile Ser Cys Asp Phe Glu Glu Ala Ala
        275                 280                 285

Glu Pro Val Leu Ile Gln Glu Gly Leu Lys Asn Thr Gly Cys Ala Ile
    290                 295                 300

Ile Phe Leu Leu Met Tyr Phe Phe Gly Met Ala Ser Ser Ile Trp Trp
305                 310                 315                 320

Val Ile Leu Thr Leu Thr Trp Phe Leu Ala Ala Gly Leu Lys Trp Gly
                325                 330                 335

His Glu Ala Ile Glu Met His Ser Ser Tyr Phe His Ile Ala Ala Trp
            340                 345                 350

Ala Ile Pro Ala Val Lys Thr Ile Val Ile Leu Ile Met Arg Leu Val
        355                 360                 365

Asp Ala Asp Glu Leu Thr Gly Leu Cys Tyr Val Gly Asn Gln Asn Leu
    370                 375                 380

Asp Ala Leu Thr Gly Phe Val Val Ala Pro Leu Phe Thr Tyr Leu Val
385                 390                 395                 400

Ile Gly Thr Leu Phe Ile Ala Ala Gly Leu Val Ala Leu Phe Lys Ile
                405                 410                 415

Arg Ser Asn Leu Gln Lys Asp Gly Thr Lys Thr Asp Lys Leu Glu Arg
```

-continued

```
            420                 425                 430

Leu Met Val Lys Ile Gly Val Phe Ser Val Leu Tyr Thr Val Pro Ala
        435                 440                 445

Thr Cys Val Ile Ala Cys Tyr Phe Tyr Glu Ile Ser Asn Trp Ala Leu
    450                 455                 460

Phe Arg Tyr Ser Ala Asp Asp Ser Asn Met Ala Val Glu Met Leu Lys
465                 470                 475                 480

Ile Phe Met Ser Leu Leu Val Gly Ile Thr Ser Gly Met Trp Ile Trp
                485                 490                 495

Ser Ala Lys Thr Leu His Thr Trp Gln Lys Cys Ser Asn Arg Leu Val
            500                 505                 510

Asn Ser Gly Lys Val Lys Arg Glu Lys Arg Gly Asn Gly Trp Val Lys
        515                 520                 525

Pro Gly Lys Gly Ser Glu Thr Val Val
    530                 535


<210> SEQ ID NO 46
<211> LENGTH: 7391
<212> TYPE: DNA
<213> ORGANISM: Homo sapiens
<220> FEATURE:
<223> OTHER INFORMATION: human frizzled4 (Fzd4)

<400> SEQUENCE: 46

gctgcgcagc gctggctgct ggctggcctc gcggagacgc cgaacggacg cggccggcgc     60

cggcttgtgg gctcgccgcc tgcagccatg accctcgcag cctgtccctc ggcctcggcc    120

cgggacgtct aaaatcccac acagtcgcgc gcagctgctg gagagccggc cgctgccccc    180

tcgtcgccgc atcacactcc cgtcccggga gctgggagca gcgcgggcag ccggcgcccc    240

cgtgcaaact gggggtgtct gccagagcag ccccagccgc tgccgctgct acccccgatg    300

ctggccatgg cctggcgggg cgcagggccg agcgtcccgg gggcgcccgg gggcgtcggt    360

ctcagtctgg ggttgctcct gcagttgctg ctgctcctgg ggccggcgcg gggcttcggg    420

gacgaggaag agcggcgctg cgaccccatc cgcatctcca tgtgccagaa cctcggctac    480

aacgtgacca agatgcccaa cctggttggg cacgagctgc agacggacgc cgagctgcag    540

ctgacaactt tcacaccgct catccagtac ggctgctcca gccagctgca gttcttcctt    600

tgttctgttt atgtgccaat gtgcacagag aagatcaaca tccccattgg cccatgcggc    660

ggcatgtgtc tttcagtcaa gagacgctgt gaacccgtcc tgaaggaatt tggatttgcc    720

tggccagaga gtctgaactg cagcaaattc ccaccacaga acgaccacaa ccacatgtgc    780

atggaagggc caggtgatga agaggtgccc ttacctcaca aaaccccccat ccagcctggg   840

gaagagtgtc actctgtggg aaccaattct gatcagtaca tctgggtgaa aaggagcctg    900

aactgtgtgc tcaagtgtgg ctatgatgct ggcttataca gccgctcagc caaggagttc    960

actgatatct ggatggctgt gtgggccagc ctgtgtttca tctccactgc cttcacagta   1020

ctgaccttcc tgatcgattc ttctaggttt tcctaccctg agcgccccat catatttctc   1080

agtatgtgct ataatattta tagcattgct tatattgtca ggctgactgt aggccgggaa   1140

aggatatcct gtgattttga agaggcagca gaacctgttc tcatccaaga aggacttaag   1200

aacacaggat gtgcaataat tttcttgctg atgtactttt ttggaatggc cagctccatt   1260

tggtgggtta ttctgacact cacttggttt ttggcagcag gactcaaatg gggtcatgaa   1320

gccattgaaa tgcacagctc ttatttccac attgcagcct gggccatccc cgcagtgaaa   1380
```

-continued

```
accattgtca tcttgattat gagactggtg gatgcagatg aactgactgg cttgtgctat   1440
gttggaaacc aaaatctcga tgccctcacc gggttcgtgg tggctcccct ctttacttat   1500
ttggtcattg gaactttgtt cattgctgca ggtttggtgg ccttgttcaa aattcggtca   1560
aatcttcaaa aggatgggac aaagacagac aagttagaaa gactgatggt caagattggg   1620
gtgttctcag tactgtacac agttcctgca acgtgtgtga ttgcctgtta tttttatgaa   1680
atctccaact gggcactttt tcggtattct gcagatgatt ccaacatggc tgttgaaatg   1740
ttgaaaattt ttatgtcttt gttggtgggc atcacttcag gcatgtggat ttggtctgcc   1800
aaaactcttc acacgtggca gaagtgttcc aacagattgg tgaattctgg aaaggtaaag   1860
agagagaaga gaggaaatgg ttgggtgaag cctggaaaag gcagtgagac tgtggtataa   1920
ggctagtcag cctccatgct ttcttcattt tgaagggggg aatgccagca ttttggagga   1980
aattctacta aaagttttat gcagtgaatc tcagtttgaa caaactagca acaattaagt   2040
gacccccgtc aacccactgc ctcccacccc gaccccagca tcaaaaaacc aatgattttg   2100
ctgcagactt tggaatgatc caaaatggaa aagccagtta gaggctttca aagctgtgaa   2160
aaatcaaaac gttgatcact ttagcaggtt gcagcttgga gcgtggaggt cctgcctaga   2220
ttccaggaag tccagggcga tactgttttc ccctgcaggg tgggatttga gctgtgagtt   2280
ggtaactagc agggagaaat attaactttt ttaacccttt accattttaa atactaactg   2340
ggtctttcag atagcaaagc aatctataaa cactggaaac gctgggttca gaaaagtgtt   2400
acaagagttt tatagtttgg ctgatgtaac ataaacatct tctgtggtgc gctgtctgct   2460
gtttagaact ttgtggactg cactcccaag aagtggtgtt agaatctttc agtgcctttg   2520
tcataaaaca gttatttgaa caaacaaaag tactgtactc acacacataa ggtatccagt   2580
ggatttttct tctctgtctt cctctcttaa atttcaacat ctctcttctt ggctgctgct   2640
gttttcttca ttttatgtta atgactcaaa aaaggtattt ttatagaatt tttgtactgc   2700
agcatgctta aagaggggaa aaggaagggt gattcacttt ctgacaatca cttaattcag   2760
aggaaaatga gatttactaa gttgacttac ctgacggacc ccagagacct attgcattga   2820
gcagtgggga cttaatatat tttacttgtg tgattgcatc tatgcagacg ccagtctgga   2880
agagctgaaa tgttaagttt cttggcaact ttgcattcac acagattagc tgtgtaattt   2940
ttgtgtgtca attacaatta aaagcacatt gttggaccat gacatagtat actcaactga   3000
ctttaaaact atggtcaact tcaacttgca ttctcagaat gatagtgcct ttaaaaattt   3060
ttttattttt taaagcataa gaatgttatc agaatctggt ctacttagga caatggagac   3120
tttttcagtt ttataaaggg aactgaggac agctaatcca actacttggt gcgtaattgt   3180
ttcctagtaa ttggcaaagg ctccttgtaa gatttcactg gaggcagtgt ggcctggagt   3240
atttatatgg tgcttaatga atctccagaa tgccagccag aagcctgatt ggttagtagg   3300
gaataaagtg tagaccatat gaaatgaact gcaaactcta atagcccagg tcttaattgc   3360
ctttagcaga ggtatccaaa gcttttaaaa tttatgcata cgttcttcac aagggggtac   3420
ccccagcagc ctctcgaaaa ttgcacttct cttaaaactg taactggcct ttctcttacc   3480
ttgccttagg ccttctaatc atgagatctt ggggacaaat tgactatgtc acaggttgct   3540
ctccttgtaa ctcatacctg tctgcttcag caactgcttt gcaatgacat ttatttatta   3600
attcatgcct taaaaaaata ggaagggaag cttttttttt tctttttttt tttttcaatc   3660
acactttgtg gaaaaacatt tccagggact caaaattcca aaaaggtggt caaattctgg   3720
aagtaagcat ttcctctttt ttaaaaattt ggtttgagcc ttatgcccat agtttgacat   3780
```

-continued

```
ttccctttct tctttccttt ttgtttttgt gtggttcttg agctctctga catcaagatg   3840
catgtaaagt cgattgtatg ttttggaagg caaagtcttg gcttttgaga ctgaagttaa   3900
gtgggcacag gtggcccctg ctgctgtgcc cagtctgagt accttggcta gactctaggt   3960
caggctccag gagcatgaga attgatcccc agaagaacca ttttaactcc atctgatact   4020
ccattgccta tgaaatgtaa aatgtgaact ccctgtgctg cttgtagaca gttcccataa   4080
ctgtccacgg ccctggagca cgcacccagg ggcagagcct gcccttactc acgctctgct   4140
ctggtgtctt gggagttgtg cagggactct ggcccaggca ggggaaggaa gaccaggcgg   4200
taggggactg gtcttgctgt tagagtatag aggtttgtaa tgcagttttc ttcataatgt   4260
gtcagtgatt gtgtgaccaa ggcagcatct agcagaaagc caggcatgga gtaggtgatc   4320
gatacttgtc aatgactaaa taataacaat aaaagagcac ttgggtgaat ctgggcacct   4380
gatttctgag ttttgagttc tggagctagt gttttgacaa tgctttgggt tttgacatgc   4440
cttttccaca aatctcttgc cttttcaggg caaagtgtat ttgatcagaa gtggccattt   4500
ggattagtag ccttagcaat gctacagggt tataggcctc tcctttcaca ttccagacaa   4560
tggagagtgt ttatggtttc aggaaaagaa ctttgtggct gaggggtcag ttaccagtga   4620
ccttcaatca actccatcac ttcttaaatc ggtatttgtt aaaaaaatca gttattttat   4680
ttattgagtg ccgactgtag taaagccctg aaatagataa tctctgttct tctaactgat   4740
ctaggatggg gacgcaccca ggtctgctga actttactgt tcctctggga aaggagcagg   4800
gacctctgga attcccatct gtttcactgt ctccattcca taaatctctt cctgtgtgag   4860
ccaccacacc cagcctgggt ctctctactt ttaacacatc tctcatccct ttcccaggat   4920
tccttccaag tcagttacag gtggttttaa cagaaagcat cagctctgct tcgtgacagt   4980
ctctggagaa atcccttagg aagactatga gagtaggcca caaggacatg ggcccacaca   5040
tctgctttgg ctttgccggc aattcagggc ttggggtatt ccatgtgact tgtataggta   5100
tatttgagga cagcatcttg ctagagaaaa ggtgagggtt gtttttcttt ctctgaaacc   5160
tacagtaaat gggtatgatt gtagcttcct cagaaatccc ttggcctcca gagattaaac   5220
atggtgcaat ggcacctctg tccaacctcc tttctggtag attcctttct cctgcttcat   5280
ataggccaaa cctcagggca agggaacatg ggggtagagt ggtgctggcc agaaccatct   5340
gcttgagcta cttggttgat tcatatcctc tttcctttat ggagacccat ttcctgatct   5400
ctgagactgt tgctgaactg gcaacttact tgggcctgaa actggagaag gggtgacatt   5460
tttttaattt cagagatgct ttctgatttt cctctcccag gtcactgtct cacctgcact   5520
ctccaaactc aggttccggg aagcttgtgt gtctagatac tgaattgaga ttctgttcag   5580
caccttttag ctctatactc tctggctccc ctcatcctca tggtcactga attaaatgct   5640
tattgtattg agaaccaaga tgggacctga ggacacaaag atgagctcaa cagtctcagc   5700
cctagaggaa tagactcagg gatttcacca ggtcggtgca gtatttgatt tctggtgagg   5760
tgaccacagc tgcagttagg gaagggagcc attgagcaca gactttggaa ggaacctttt   5820
ttttgttgtt tgtttgtttg tttgtttgtt tgtttgtttg agacagggtc ttgctctgtc   5880
acccaggctg gggcgcaatg gcacgatctt ggctcactgc aacctctgcc tcctgggttc   5940
aagtgattct cctgccacag cctcctgagg agctgggact acaggtgcgt gctaccacgc   6000
ccagctactt ctgtattttt agtagagacg ggtttcact gtgttggcca ggctggtctc   6060
gaactcctga cctcatgatc tgcccgcctc agcctcccaa agtgctggga ttacaagtgt   6120
```

-continued

```
gagccaccac acctggcctg gaaggaacct cttaaaatca gtttacgtct tgtattttgt   6180

tctgtgatgg aggacactgg agagagttgc tattccagtc aatcatgtcg agtcactgga   6240

ctctgaaaat cctattggtt cctttatttt atttgagttt agagttccct tctgggtttg   6300

tattatgtct ggcaaatgac ctgggttatc acttttcctc cagggttaga tcatagatct   6360

tggaaactcc ttagagagca ttttgctcct accaaggatc agatactgga gccccacata   6420

atagatttca tttcactcta gcctacatag agctttctgt tgctgtctct tgccatgcac   6480

ttgtgcggtg attacacact tgacagtacc aggagacaaa tgacttacag atcccccgac   6540

atgcctcttc cccttggcaa gctcagttgc cctgatagta gcatgtttct gtttctgatg   6600

taccttttt ctcttcttct ttgcatcagc caattcccag aatttcccca ggcaatttgt   6660

agaggacctt tttggggtcc tatatgagcc atgtcctcaa agcttttaaa cctccttgct   6720

ctcctacaat attcagtaca tgaccactgt catcctagaa ggcttctgaa aagaggggca   6780

agagccactc tgcgccacaa aggttgggtc catcttctct ccgaggttgt gaaagttttc   6840

aaattgtact aataggctgg ggccctgact tggctgtggg ctttgggagg ggtaagctgc   6900

tttctagatc tctcccagtg aggcatggag gtgtttctga attttgtcta cctcacaggg   6960

atgttgtgag gcttgaaaag gtcaaaaaat gatggcccct tgagctcttt gtaagaaagg   7020

tagatgaaat atcggatgta atctgaaaaa aagataaaat gtgacttccc ctgctctgtg   7080

cagcagtcgg gctggatgct ctgtggcctt tcttgggtcc tcatgccacc ccacagctcc   7140

aggaaccttg aagccaatct gggggacttt cagatgtttg acaaagaggt accaggcaaa   7200

cttcctgcta cacatgccct gaatgaattg ctaaatttca aaggaaatgg accctgcttt   7260

taaggatgta caaaagtatg tctgcatcga tgtctgtact gtaaatttct aatttatcac   7320

tgtacaaaga aaaccccttg ctatttaatt ttgtattaaa ggaaaataaa gttttgtttg   7380

ttaaaaaaaa a                                                        7391


<210> SEQ ID NO 47
<211> LENGTH: 585
<212> TYPE: PRT
<213> ORGANISM: Homo sapiens
<220> FEATURE:
<223> OTHER INFORMATION: human frizzled5 (Fzd5)

<400> SEQUENCE: 47

Met Ala Arg Pro Asp Pro Ser Ala Pro Pro Ser Leu Leu Leu Leu Leu
  1               5                  10                  15

Leu Ala Gln Leu Val Gly Arg Ala Ala Ala Ala Ser Lys Ala Pro Val
             20                  25                  30

Cys Gln Glu Ile Thr Val Pro Met Cys Arg Gly Ile Gly Tyr Asn Leu
         35                  40                  45

Thr His Met Pro Asn Gln Phe Asn His Asp Thr Gln Asp Glu Ala Gly
     50                  55                  60

Leu Glu Val His Gln Phe Trp Pro Leu Val Glu Ile Gln Cys Ser Pro
 65                  70                  75                  80

Asp Leu Arg Phe Phe Leu Cys Thr Met Tyr Thr Pro Ile Cys Leu Pro
                 85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
```

-continued

```
    130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Thr Val Ala Thr
                245                 250                 255

Phe Leu Ile Asp Met Asp Thr Phe Arg Tyr Pro Glu Arg Pro Ile Ile
            260                 265                 270

Phe Leu Ser Ala Cys Tyr Leu Cys Val Ser Leu Gly Phe Leu Val Arg
        275                 280                 285

Leu Val Val Gly His Ala Ser Val Ala Cys Ser Arg Glu His Asn His
    290                 295                 300

Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
                325                 330                 335

Ser Leu Thr Trp Phe Leu Ala Ala Ala Met Lys Trp Gly Asn Glu Ala
            340                 345                 350

Ile Ala Gly Tyr Gly Gln Tyr Phe His Leu Ala Ala Trp Leu Ile Pro
        355                 360                 365

Ser Val Lys Ser Ile Thr Ala Leu Ala Leu Ser Ser Val Asp Gly Asp
    370                 375                 380

Pro Val Ala Gly Ile Cys Tyr Val Gly Asn Gln Asn Leu Asn Ser Leu
385                 390                 395                 400

Arg Arg Phe Val Leu Gly Pro Leu Val Leu Tyr Leu Leu Val Gly Thr
                405                 410                 415

Leu Phe Leu Leu Ala Gly Phe Val Ser Leu Phe Arg Ile Arg Ser Val
            420                 425                 430

Ile Lys Gln Gly Gly Thr Lys Thr Asp Lys Leu Glu Lys Leu Met Ile
        435                 440                 445

Arg Ile Gly Ile Phe Thr Leu Leu Tyr Thr Val Pro Ala Ser Ile Val
    450                 455                 460

Val Ala Cys Tyr Leu Tyr Glu Gln His Tyr Arg Glu Ser Trp Glu Ala
465                 470                 475                 480

Ala Leu Thr Cys Ala Cys Pro Gly His Asp Thr Gly Gln Pro Arg Ala
                485                 490                 495

Lys Pro Glu Tyr Trp Val Leu Met Leu Lys Tyr Phe Met Cys Leu Val
            500                 505                 510

Val Gly Ile Thr Ser Gly Val Trp Ile Trp Ser Gly Lys Thr Val Glu
        515                 520                 525

Ser Trp Arg Arg Phe Thr Ser Arg Cys Cys Cys Arg Pro Arg Arg Gly
    530                 535                 540

His Lys Ser Gly Gly Ala Met Ala Ala Gly Asp Tyr Pro Glu Ala Ser
545                 550                 555                 560
```

-continued

```
Ala Ala Leu Thr Gly Arg Thr Gly Pro Pro Gly Pro Ala Ala Thr Tyr
                565                 570                 575

His Lys Gln Val Ser Leu Ser His Val
            580                 585
```

<210> SEQ ID NO 48
<211> LENGTH: 2334
<212> TYPE: DNA
<213> ORGANISM: Homo sapiens
<220> FEATURE:
<223> OTHER INFORMATION: human frizzled5 (Fzd5)

<400> SEQUENCE: 48

```
acccagggac ggaggaccca ggctggcttg ggactgtct gctcttctcg gcgggagccg      60

tggagagtcc tttccctgga atccgagccc taaccgtctc tccccagccc tatccggcga     120

ggagcggagc gctgccagcg gaggcagcgc cttcccgaag cagtttatct ttggacggtt     180

ttctttaaag gaaaaacgaa ccaacaggtt gccagccccg gcgccacaca cgagacgccg     240

gagggagaag ccccggcccg gattcctctg cctgtgtgcg tccctcgcgg gctgctggag     300

gcgaggggag ggagggggcg atggctcggc ctgacccatc cgcgccgccc tcgctgttgc     360

tgctgctcct ggcgcagctg gtgggccggg cggccgccgc gtccaaggcc ccggtgtgcc     420

aggaaatcac ggtgcccatg tgccgcggca tcggctacaa cctgacgcac atgcccaacc     480

agttcaacca cgacacgcag gacgaggcgg gcctggaggt gcaccagttc tggccgctgg     540

tggagatcca atgctcgccg gacctgcgct tcttcctatg cactatgtac acgcccatct     600

gtctgcccga ctaccacaag ccgctgccgc cctgccgctc ggtgtgcgag cgcgccaagg     660

ccggctgctc gccgctgatg cgccagtacg gcttcgcctg gcccgagcgc atgagctgcg     720

accgcctccc ggtgctgggc cgcgacgccg aggtcctctg catggattac aaccgcagcg     780

aggccaccac ggcgcccccc aggcctttcc cagccaagcc cacccttcca ggcccgccag     840

gggcgccggc ctcgggggc gaatgccccg ctgggggccc gttcgtgtgc aagtgtcgcg     900

agcccttcgt gcccattctg aaggagtcac acccgctcta caacaaggtg cggacgggcc     960

aggtgcccaa ctgcgcggta ccctgctacc agccgtcctt cagtgccgac gagcgcacgt    1020

tcgccacctt ctggataggc ctgtggtcgg tgctgtgctt catctccacg tccaccacag    1080

tggccacctt cctcatcgac atggacacgt tccgctatcc tgagcgcccc atcatcttcc    1140

tgtcagcctg ctacctgtgc gtgtcgctgg gcttcctggt gcgtctggtc gtgggccatg    1200

ccagcgtggc ctgcagccgc gagcacaacc acatccacta cgagaccacg ggccctgcac    1260

tgtgcaccat cgtcttcctc ctggtctact tcttcggcat ggccagctcc atctggtggg    1320

tcatcctgtc gctcacctgg ttcctggccg ccgcgatgaa gtggggcaac gaggccatcg    1380

cgggctacgg ccagtacttc cacctggctg cgtggctcat ccccagcgtc aagtccatca    1440

cggcactggc gctgagctcc gtggacgggg acccagtggc cggcatctgc tacgtgggca    1500

accagaacct gaactcgctg cggcgcttcg tgctgggccc gctggtgctc tacctgctgg    1560

tgggcacgct cttcctgctg gcgggcttcg tgtcgctctt ccgcatccgc agcgtcatca    1620

agcagggcgg caccaagacg gacaagctgg agaagctcat gatccgcatc ggcatcttca    1680

cgctgctcta cacggtcccc gccagcattg tggtggcctg ctacctgtac gagcagcact    1740

accgcgagag ctgggaggcg gcgctcacct gcgcctgccc gggccacgac accggccagc    1800

cgcgcgccaa gcccgagtac tgggtgctca tgctcaagta cttcatgtgc ctggtggtgg    1860
```

-continued

```
gcatcacgtc gggcgtctgg atctggtcgg gcaagacggt ggagtcgtgg cggcgtttca   1920

ccagccgctg ctgctgccgc ccgcggcgcg gccacaagag cgggggcgcc atggccgcag   1980

gggactaccc cgaggcgagc gccgcgctca caggcaggac cgggccgccg ggccccgccg   2040

ccacctacca caagcaggtg tccctgtcgc acgtgtagga ggctgccgcc gagggactcg   2100

gccggagagc tgaggggagg ggggcgtttt gtttggtagt tttgccaagg tcacttccgt   2160

ttaccttcat ggtgctgttg ccccctcccg cggcgacttg gagagaggga agaggggcgt   2220

tttcgaggaa gaacctgtcc caggtcttct ccaaggggcc cagctcacgt gtattctatt   2280

ttgcgtttct tacctgcctt ctttatggga accctctttt taatttatat gtat         2334


<210> SEQ ID NO 49
<211> LENGTH: 706
<212> TYPE: PRT
<213> ORGANISM: Homo sapiens
<220> FEATURE:
<223> OTHER INFORMATION: human frizzled6 (Fzd6)

<400> SEQUENCE: 49

Met Glu Met Phe Thr Phe Leu Leu Thr Cys Ile Phe Leu Pro Leu Leu
  1               5                  10                  15

Arg Gly His Ser Leu Phe Thr Cys Glu Pro Ile Thr Val Pro Arg Cys
             20                  25                  30

Met Lys Met Ala Tyr Asn Met Thr Phe Phe Pro Asn Leu Met Gly His
         35                  40                  45

Tyr Asp Gln Ser Ile Ala Ala Val Glu Met Glu His Phe Leu Pro Leu
     50                  55                  60

Ala Asn Leu Glu Cys Ser Pro Asn Ile Glu Thr Phe Leu Cys Lys Ala
 65                  70                  75                  80

Phe Val Pro Thr Cys Ile Glu Gln Ile His Val Val Pro Pro Cys Arg
                 85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
        115                 120                 125

Cys Asp Glu Thr Val Pro Val Thr Phe Asp Pro His Thr Glu Phe Leu
    130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile Phe
        195                 200                 205

Cys Leu Cys Ala Thr Leu Phe Thr Phe Leu Thr Phe Leu Ile Asp Val
    210                 215                 220

Arg Arg Phe Arg Tyr Pro Glu Arg Pro Ile Ile Tyr Tyr Ser Val Cys
225                 230                 235                 240

Tyr Ser Ile Val Ser Leu Met Tyr Phe Ile Gly Phe Leu Leu Gly Asp
                245                 250                 255

Ser Thr Ala Cys Asn Lys Ala Asp Glu Lys Leu Glu Leu Gly Asp Thr
            260                 265                 270

Val Val Leu Gly Ser Gln Asn Lys Ala Cys Thr Val Leu Phe Met Leu
        275                 280                 285
```

-continued

```
Leu Tyr Phe Phe Thr Met Ala Gly Thr Val Trp Trp Val Ile Leu Thr
    290                 295                 300

Ile Thr Trp Phe Leu Ala Ala Gly Arg Lys Trp Ser Cys Glu Ala Ile
305                 310                 315                 320

Glu Gln Lys Ala Val Trp Phe His Ala Val Ala Trp Gly Thr Pro Gly
                325                 330                 335

Phe Leu Thr Val Met Leu Leu Ala Leu Asn Lys Val Glu Gly Asp Asn
            340                 345                 350

Ile Ser Gly Val Cys Phe Val Gly Leu Tyr Asp Leu Asp Ala Ser Arg
        355                 360                 365

Tyr Phe Val Leu Leu Pro Leu Cys Leu Cys Val Phe Val Gly Leu Ser
    370                 375                 380

Leu Leu Leu Ala Gly Ile Ile Ser Leu Asn His Val Arg Gln Val Ile
385                 390                 395                 400

Gln His Asp Gly Arg Asn Gln Glu Lys Leu Lys Lys Phe Met Ile Arg
                405                 410                 415

Ile Gly Val Phe Ser Gly Leu Tyr Leu Val Pro Leu Val Thr Leu Leu
            420                 425                 430

Gly Cys Tyr Val Tyr Glu Gln Val Asn Arg Ile Thr Trp Glu Ile Thr
        435                 440                 445

Trp Val Ser Asp His Cys Arg Gln Tyr His Ile Pro Cys Pro Tyr Gln
    450                 455                 460

Ala Lys Ala Lys Ala Arg Pro Glu Leu Ala Leu Phe Met Ile Lys Tyr
465                 470                 475                 480

Leu Met Thr Leu Ile Val Gly Ile Ser Ala Val Phe Trp Val Gly Ser
                485                 490                 495

Lys Lys Thr Cys Thr Glu Trp Ala Gly Phe Phe Lys Arg Asn Arg Lys
            500                 505                 510

Arg Asp Pro Ile Ser Glu Ser Arg Arg Val Leu Gln Glu Ser Cys Glu
        515                 520                 525

Phe Phe Leu Lys His Asn Ser Lys Val Lys His Lys Lys Lys His Tyr
    530                 535                 540

Lys Pro Ser Ser His Lys Leu Lys Val Ile Ser Lys Ser Met Gly Thr
545                 550                 555                 560

Ser Thr Gly Ala Thr Ala Asn His Gly Thr Ser Ala Val Ala Ile Thr
                565                 570                 575

Ser His Asp Tyr Leu Gly Gln Glu Thr Leu Thr Glu Ile Gln Thr Ser
            580                 585                 590

Pro Glu Thr Ser Met Arg Glu Val Lys Ala Asp Gly Ala Ser Thr Pro
        595                 600                 605

Arg Leu Arg Glu Gln Asp Cys Gly Glu Pro Ala Ser Pro Ala Ala Ser
    610                 615                 620

Ile Ser Arg Leu Ser Gly Glu Gln Val Asp Gly Lys Gly Gln Ala Gly
625                 630                 635                 640

Ser Val Ser Glu Ser Ala Arg Ser Glu Gly Arg Ile Ser Pro Lys Ser
                645                 650                 655

Asp Ile Thr Asp Thr Gly Leu Ala Gln Ser Asn Asn Leu Gln Val Pro
            660                 665                 670

Ser Ser Ser Glu Pro Ser Ser Leu Lys Gly Ser Thr Ser Leu Leu Val
        675                 680                 685

His Pro Val Ser Gly Val Arg Lys Glu Gln Gly Gly Gly Cys His Ser
    690                 695                 700
```

-continued

Asp Thr
705

<210> SEQ ID NO 50
<211> LENGTH: 3342
<212> TYPE: DNA
<213> ORGANISM: Homo sapiens
<220> FEATURE:
<223> OTHER INFORMATION: human frizzled6 (Fzd6)

<400> SEQUENCE: 50
gcagctccag tcccggacgc aaccccggag ccgtctcagg tccctggggg gaacggtggg 60
ttagacgggg acgggaaggg acagcggcct tcgaccgccc cccgagtaat tgacccagga 120
ctcattttca ggaaagcctg aaaatgagta aaatagtgaa atgaggaatt tgaacatttt 180
atctttggat ggggatcttc tgaggatgca aagagtgatt catccaagcc atgtggtaaa 240
atcaggaatt tgaagaaaat ggagatgttt acatttttgt tgacgtgtat tttctaccc 300 ctcctaagag ggcacagtct cttcacctgt gaaccaatta ctgttcccag atgtatgaaa 360
atggcctaca acatgacgtt tttccctaat ctgatgggtc attatgacca gagtattgcc 420
gcggtggaaa tggagcattt tcttcctctc gcaaatctgg aatgttcacc aaacattgaa 480
actttcctct gcaaagcatt tgtaccaacc tgcatagaac aaattcatgt ggttccacct 540
tgtcgtaaac tttgtgagaa agtatattct gattgcaaaa aattaattga cacttttggg 600
atccgatggc ctgaggagct tgaatgtgac agattacaat actgtgatga gactgttcct 660
gtaacttttg atccacacac agaatttctt ggtcctcaga agaaaacaga acaagtccaa 720
agagacattg gattttggtg tccaaggcat cttaagactt ctgggggaca aggatataag 780
tttctgggaa ttgaccagtg tgcgcctcca tgccccaaca tgtattttaa aagtgatgag 840
ctagagtttg caaaaagttt tattggaaca gtttcaatat tttgtctttg tgcaactctg 900
ttcacattcc ttactttttt aattgatgtt agaagattca gatacccaga gagaccaatt 960
atatattact ctgtctgtta cagcattgta tctcttatgt acttcattgg atttttgctg 1020
ggcgatagca cagcctgcaa taaggcagat gagaagctag aacttggtga cactgttgtc 1080
ctaggctctc aaaataaggc ttgcaccgtt ttgttcatgc ttttgtattt tttcacaatg 1140
gctggcactg tgtggtgggt gattcttacc attacttggt tcttagctgc aggaagaaaa 1200
tggagttgtg aagccatcga gcaaaaagca gtgtggtttc atgctgttgc atggggaaca 1260
ccaggtttcc tgactgttat gcttcttgct ctgaacaaag ttgaaggaga caacattagt 1320
ggagtttgct ttgttggcct ttatgacctg gatgcttctc gctactttgt actcttgcca 1380
ctgtgccttt gtgtgtttgt tgggctctct cttcttttag ctggcattat ttccttaaat 1440
catgttcgac aagtcataca acatgatggc cggaaccaag aaaaactaaa gaaatttatg 1500
attcgaattg gagtcttcag cggcttgtat cttgtgccat tagtgacact tctcggatgt 1560
tacgtctatg agcaagtgaa caggattacc tgggagataa cttgggtctc tgatcattgt 1620
cgtcagtacc atatcccatg tccttatcag gcaaaagcaa aagctcgacc agaattggct 1680
ttatttatga taaaatacct gatgacatta attgttggca tctctgctgt cttctgggtt 1740
ggaagcaaaa agacatgcac agaatgggct gggtttttta aacgaaatcg caagagagat 1800
ccaatcagtg aaagtcgaag agtactacag gaatcatgtg agtttttctt aaagcacaat 1860
tctaaagtta aacacaaaaa gaagcactat aaaccaagtt cacacaagct gaaggtcatt 1920
tccaaatcca tgggaaccag cacaggagct acagcaaatc atggcacttc tgcagtagca 1980

-continued

```
attactagcc atgattacct aggacaagaa actttgacag aaatccaaac ctcaccagaa   2040

acatcaatga gagaggtgaa agcggacgga gctagcaccc ccaggttaag agaacaggac   2100

tgtggtgaac ctgcctcgcc agcagcatcc atctccagac tctctgggga acaggtcgac   2160

gggaagggcc aggcaggcag tgtatctgaa agtgcgcgga gtgaaggaag gattagtcca   2220

aagagtgata ttactgacac tggcctggca cagagcaaca atttgcaggt ccccagttct   2280

tcagaaccaa gcagcctcaa aggttccaca tctctgcttg ttcacccagt ttcaggagtg   2340

agaaaagagc agggaggtgg ttgtcattca gatacttgaa gaacattttc tctcgttact   2400

cagaagcaaa tttgtgttac actggaagtg acctatgcac tgttttgtaa gaatcactgt   2460

tacgttcttc ttttgcactt aaagttgcat tgcctactgt tatactggaa aaaatagagt   2520

tcaagaataa tatgactcat ttcacacaaa ggttaatgac aacaatatac ctgaaaacag   2580

aaatgtgcag gttaataata tttttttaat agtgtgggag gacagagtta gaggaatctt   2640

ccttttctat ttatgaagat tctactcttg gtaagagtat tttaagatgt actatgctat   2700

tttacctttt tgatataaaa tcaagatatt tctttgctga agtatttaaa tcttatcctt   2760

gtatcttttt atacatattt gaaaataagc ttatatgtat ttgaactttt ttgaaatcct   2820

attcaagtat ttttatcatg ctattgtgat attttagcac tttggtagct tttacactga   2880

atttctaaga aaattgtaaa atagtcttct tttatactgt aaaaaaagat ataccaaaaa   2940

gtcttataat aggaatttaa ctttaaaaac ccacttattg ataccttacc atctaaaatg   3000

tgtgattttt atagtctcgt tttaggaatt tcacagatct aaattatgta actgaaataa   3060

ggtgcttact caaagagtgt ccactattga ttgtattatg ctgctcactg atccttctgc   3120

atatttaaaa taaaatgtcc taaagggtta gtagacaaaa tgttagtctt ttgtatatta   3180

ggccaagtgc aattgacttc ccttttttaa tgtttcatga ccacccattg attgtattat   3240

aaccacttac agttgcttat attttttgtt ttaacttttg tttcttaaca tttagaatat   3300

tacattttgt attatacagt acctttctca gacattttgt ag                      3342
```

<210> SEQ ID NO 51
<211> LENGTH: 574
<212> TYPE: PRT
<213> ORGANISM: Homo sapiens
<220> FEATURE:
<223> OTHER INFORMATION: human frizzled7 (Fzd7)

<400> SEQUENCE: 51

```
Met Arg Asp Pro Gly Ala Ala Ala Pro Leu Ser Ser Leu Gly Leu Cys
  1               5                  10                  15

Ala Leu Val Leu Ala Leu Leu Gly Ala Leu Ser Ala Gly Ala Gly Ala
             20                  25                  30

Gln Pro Tyr His Gly Glu Lys Gly Ile Ser Val Pro Asp His Gly Phe
         35                  40                  45

Cys Gln Pro Ile Ser Ile Pro Leu Cys Thr Asp Ile Ala Tyr Asn Gln
     50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
                 85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125
```

-continued

```
Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Glu Arg Arg Phe Ala Arg Leu Trp
                245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val Ala His Val
    290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys
        355                 360                 365

Trp Gly His Glu Ala Ile Glu Ala Asn Ser Gln Tyr Phe His Leu Ala
    370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
                405                 410                 415

Ser Val Asp Ala Leu Arg Gly Phe Val Leu Ala Pro Leu Phe Val Tyr
            420                 425                 430

Leu Phe Ile Gly Thr Ser Phe Leu Leu Ala Gly Phe Val Ser Leu Phe
        435                 440                 445

Arg Ile Arg Thr Ile Met Lys His Asp Gly Thr Lys Thr Glu Lys Leu
    450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
        515                 520                 525

Val Phe Met Ile Lys Tyr Leu Met Thr Met Ile Val Gly Ile Thr Thr
    530                 535                 540
```

-continued

Gly Phe Trp Ile Trp Ser Gly Lys Thr Leu Gln Ser Trp Arg Arg Phe
545 550 555 560

Tyr His Arg Leu Ser His Ser Ser Lys Gly Glu Thr Ala Val
565 570

<210> SEQ ID NO 52
<211> LENGTH: 3851
<212> TYPE: DNA
<213> ORGANISM: Homo sapiens
<220> FEATURE:
<223> OTHER INFORMATION: human frizzled7 (Fzd7)

<400> SEQUENCE: 52
ctctcccaac cgcctcgtcg cactcctcag gctgagagca ccgctgcact cgcggccggc 60
gatgcgggac cccggcgcgg ccgctccgct ttcgtccctg ggcctctgtg ccctggtgct 120
ggcgctgctg ggcgcactgt ccgcgggcgc cggggcgcag ccgtaccacg gagagaaggg 180
catctccgtg ccggaccacg gcttctgcca gcccatctcc atcccgctgt gcacggacat 240
cgcctacaac cagaccatcc tgcccaacct gctgggccac acgaaccaag aggacgcggg 300
cctcgaggtg caccagttct acccgctggt gaaggtgcag tgttctcccg aactccgctt 360
tttcttatgc tccatgtatg cgcccgtgtg caccgtgctc gatcaggcca tcccgccgtg 420
tcgttctctg tgcgagcgcg cccgccaggg ctgcgaggcg ctcatgaaca agttcggctt 480
ccagtggccc gagcggctgc gctgcgagaa cttcccggtg cacggtgcgg gcgagatctg 540
cgtgggccag aacacgtcgg acggctccgg gggcccaggc ggcggcccca ctgcctaccc 600
taccgcgccc tacctgccgg acctgccctt caccgcgctg cccccggggg cctcagatgg 660
cagggggcgt cccgccttcc ccttctcatg cccccgtcag ctcaaggtgc ccccgtacct 720
gggctaccgc ttcctgggtg agcgcgattg tggcgccccg tgcgaaccgg gccgtgccaa 780
cggcctgatg tactttaagg aggaggagag gcgcttcgcc cgcctctggg tgggcgtgtg 840
gtccgtgctg tgctgcgcct cgacgctctt taccgttctc acctacctgg tggacatgcg 900
gcgcttcagc tacccagagc ggcccatcat cttcctgtcg ggctgctact tcatggtggc 960
cgtggcgcac gtggccggct tccttctaga ggaccgcgcc gtgtgcgtgg agcgcttctc 1020
ggacgatggc taccgcacgg tggcgcaggg caccaagaag gagggctgca ccatcctctt 1080
catggtgctc tacttcttcg gcatggccag ctccatctgg tgggtcattc tgtctctcac 1140
ttggttcctg gcggccggca tgaagtgggg ccacgaggcc atcgaggcca actcgcagta 1200
cttccacctg gccgcgtggg ccgtgcccgc cgtcaagacc atcactatcc tggccatggg 1260
ccaggtagac ggggacctgc tgagcggggt gtgctacgtt ggcctctcca gtgtggacgc 1320
gctgcggggc ttcgtgctgg cgcctctgtt cgtctacctc ttcataggca cgtccttctt 1380
gctggccggc ttcgtgtccc tcttccgtat ccgcaccatc atgaaacacg acggcaccaa 1440
gaccgagaag ctggagaagc tcatggtgcg catcggcgtc ttcagcgtgc tctacacagt 1500
gcccgccacc atcgtcctgg cctgctactt ctacgagcag gccttccgcg agcactggga 1560
gcgcacctgg ctcctgcaga cgtgcaagag ctatgccgtg ccctgcccgc ccggccactt 1620
cccgcccatg agccccgact tcaccgtctt catgatcaag tacctgatga ccatgatcgt 1680
cggcatcacc actggcttct ggatctggtc gggcaagacc ctgcagtcgt ggcgccgctt 1740
ctaccacaga cttagccaca gcagcaaggg ggagactgcg gtatgagccc cggcccctcc 1800
ccacctttcc caccccagcc ctcttgcaag aggagaggca cggtagggaa aagaactgct 1860
gggtgggggc ctgtttctgt aactttctcc ccctctactg agaagtgacc tggaagtgag 1920

-continued

```
aagttctttg cagatttggg gcgaggggtg atttggaaaa gaagacctgg gtggaaagcg   1980
gtttggatga aaagatttca ggcaaagact tgcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccgggaaagg tacagccctg tctgcggtgg   2220
ctgctttgtt ggaaagaggg agggcctcct gcggtgtgct tgtcaagcag tggtcaaacc   2280
ataatctctt ttcactgggg ccaaactgga gcccagatgg gttaatttcc agggtcagac   2340
attacggtct ctcctcccct gccccctccc gcctgttttt cctcccgtac tgctttcagg   2400
tcttgtaaaa taagcatttg gaagtcttgg gaggcctgcc tgctagaatc ctaatgtgag   2460
gatgcaaaag aaatgatgat aacattttga gataaggcca aggagacgtg gagtaggtat   2520
ttttgctact ttttcatttt ctggggaagg caggaggcag aaagacgggt gttttatttg   2580
gtctaatacc ctgaaaagaa gtgatgactt gttgcttttc aaaacaggaa tgcatttttc   2640
cccttgtctt tgttgtaaga gacaaaagag gaaacaaaag tgtctccctg tggaaaggca   2700
taactgtgac gaaagcaact tttataggca aagcagcgca aatctgaggt ttcccgttgg   2760
ttgttaattt ggttgagata aacattcctt tttaaggaaa agtgaagagc agtgtgctgt   2820
cacacaccgt taagccagag gttctgactt cgctaaagga aatgtaagag gttttgttgt   2880
ctgttttaaa taaatttaat tcggaacaca tgatccaaca gactatgtta aaatattcag   2940
ggaaatctct cccttcattt actttttctt gctataagcc tatatttagg tttcttttct   3000
atttttttct cccatttgga tcctttgagg taaaaaaaca taatgtcttc agcctcataa   3060
taaaggaaag ttaattaaaa aaaaaaagca aagagccatt ttgtcctgtt ttcttggttc   3120
catcaatctg tttattaaac atcatccata tgctgaccct gtctctgtgt ggttgggttg   3180
ggaggcgatc agcagatacc atagtgaacg aagaggaagg tttgaaccat gggccccatc   3240
tttaaagaaa gtcattaaaa gaaggtaaac ttcaaagtga ttctggagtt ctttgaaatg   3300
tgctggaaga cttaaattta ttaatcttaa atcatgtact ttttttctgt aatagaactc   3360
ggattctttt gcatgatggg gtaaagctta gcagagaatc atgggagcta acctttatcc   3420
cacctttgac actaccctcc aatcttgcaa cactatcctg tttctcagaa cagtttttaa   3480
atgccaatca tagagggtac tgtaaagtgt acaagttact ttatatatgt aatgttcact   3540
tgagtggaac tgctttttac attaaagtta aaatcgatct tgtgtttctt caaccttcaa   3600
aactatctca tctgtcagat ttttaaaact ccaacacagg ttttggcatc ttttgtgctg   3660
tatcttttaa gtgcatgtga aatttgtaaa atagagataa gtacagtatg tatattttgt   3720
aaatctccca tttttgtaag aaaatatata ttgtatttat acatttttac tttggatttt   3780
tgttttgttg gctttaaagg tctaccccac tttatcacat gtacagatca caaataaatt   3840
tttttaaata c                                                        3851
```

<210> SEQ ID NO 53
<211> LENGTH: 694
<212> TYPE: PRT
<213> ORGANISM: Homo sapiens
<220> FEATURE:
<223> OTHER INFORMATION: human frizzled8 (Fzd8)

<400> SEQUENCE: 53

```
Met Glu Trp Gly Tyr Leu Leu Glu Val Thr Ser Leu Leu Ala Ala Leu
  1               5                  10                  15
```

-continued

```
Ala Leu Leu Gln Arg Ser Ser Gly Ala Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Gly Asp Ala Ala Ala Pro Pro
        195                 200                 205

Ala Arg Gly Gly Gly Gly Gly Gly Lys Ala Arg Pro Pro Gly Gly Gly
    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
    290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Gly Ala Gly Gly
            340                 345                 350

Ala Gly Gly Ala Ala Ala Gly Ala Gly Ala Ala Gly Ala Gly Ala Gly
        355                 360                 365

Gly Pro Gly Gly Arg Gly Glu Tyr Glu Glu Leu Gly Ala Val Glu Gln
    370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430
```

-continued

```
Ala Ile Ala Gly Tyr Ser Gln Tyr Phe His Leu Ala Ala Trp Leu Val
        435                 440                 445

Pro Ser Val Lys Ser Ile Ala Val Leu Ala Leu Ser Ser Val Asp Gly
    450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
            500                 505                 510

Val Ile Lys Gln Gln Asp Gly Pro Thr Lys Thr His Lys Leu Glu Lys
        515                 520                 525

Leu Met Ile Arg Leu Gly Leu Phe Thr Val Leu Tyr Thr Val Pro Ala
    530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
                565                 570                 575

Gln Ala Arg Arg Pro Asp Tyr Ala Val Phe Met Leu Lys Tyr Phe Met
            580                 585                 590

Cys Leu Val Val Gly Ile Thr Ser Gly Val Trp Val Trp Ser Gly Lys
        595                 600                 605

Thr Leu Glu Ser Trp Arg Ser Leu Cys Thr Arg Cys Cys Trp Ala Ser
    610                 615                 620

Lys Gly Ala Ala Val Gly Gly Gly Ala Gly Ala Thr Ala Ala Gly Gly
625                 630                 635                 640

Gly Gly Gly Pro Gly Gly Gly Gly Gly Gly Gly Pro Gly Gly Gly Gly
                645                 650                 655

Gly Pro Gly Gly Gly Gly Gly Ser Leu Tyr Ser Asp Val Ser Thr Gly
            660                 665                 670

Leu Thr Trp Arg Ser Gly Thr Ala Ser Ser Val Ser Tyr Pro Lys Gln
        675                 680                 685

Met Pro Leu Ser Gln Val
    690
```

```
<210> SEQ ID NO 54
<211> LENGTH: 3195
<212> TYPE: DNA
<213> ORGANISM: Homo sapiens
<220> FEATURE:
<223> OTHER INFORMATION: human frizzled8 (Fzd8)

<400> SEQUENCE: 54

acagcatgga gtggggttac ctgttggaag tgacctcgct gctggccgcc ttggcgctgc      60

tgcagcgctc tagcggcgct gcggccgcct cggccaagga gctggcatgc caagagatca     120

ccgtgccgct gtgtaagggc atcggctaca actacaccta catgcccaat cagttcaacc     180

acgacacgca agacgaggcg ggcctggagg tgcaccagtt ctggccgctg gtggagatcc     240

agtgctcgcc cgatctcaag ttcttcctgt gcagcatgta cacgcccatc tgcctagagg     300

actacaagaa gccgctgccg ccctgccgct cggtgtgcga gcgcgccaag gccggctgcg     360

cgccgctcat gcgccagtac ggcttcgcct ggcccgaccg catgcgctgc gaccggctgc     420

ccgagcaagg caaccctgac acgctgtgca tggactacaa ccgcaccgac ctaaccaccg     480

ccgcgcccag cccgccgcgc cgcctgccgc cgccgccgcc cggcgagcag ccgccttcgg     540
```

-continued

```
gcagcggcca cggccgcccg ccgggggcca ggcccccgca ccgcggaggc ggcaggggcg    600
gtggcggcgg ggacgcggcg gcgcccccag ctcgcggcgg cggcggtggc gggaaggcgc    660
ggccccctgg cggcggcgcg gctccctgcg agcccgggtg ccagtgccgc gcgcctatgg    720
tgagcgtgtc cagcgagcgc cacccgctct acaaccgcgt caagacaggc cagatcgcta    780
actgcgcgct gccctgccac aaccccttttt tcagccagga cgagcgcgcc ttcaccgtct    840
tctggatcgg cctgtggtcg gtgctctgct tcgtgtccac cttcgccacc gtctccacct    900
tccttatcga catggagcgc ttcaagtacc cggagcggcc cattatcttc ctctcggcct    960
gctacctctt cgtgtcggtg ggctacctag tgcgcctggt ggcgggccac gagaaggtgg   1020
cgtgcagcgg tggcgcgccg ggcgcggggg gcgctggggg cgcgggcggc gcggcggcgg   1080
gcgcgggcgc ggcgggcgcg ggcgcgggcg gcccgggcgg gcgcggcgag tacgaggagc   1140
tgggcgcggt ggagcagcac gtgcgctacg agaccaccgg ccccgcgctg tgcaccgtgg   1200
tcttcttgct ggtctacttc ttcggcatgg ccagctccat ctggtgggtg atcttgtcgc   1260
tcacatggtt cctggcggcc ggtatgaagt ggggcaacga agccatcgcc ggctactcgc   1320
agtacttcca cctggccgcg tggcttgtgc ccagcgtcaa gtccatcgcg gtgctggcgc   1380
tcagctcggt ggacggcgac ccggtggcgg gcatctgcta cgtgggcaac cagagcctgg   1440
acaacctgcg cggcttcgtg ctggcgccgc tggtcatcta cctcttcatc ggcaccatgt   1500
tcctgctggc cggcttcgtg tccctgttcc gcatccgctc ggtcatcaag caacaggacg   1560
gccccaccaa gacgcacaag ctggagaagc tgatgatccg cctgggcctg ttcaccgtgc   1620
tctacaccgt gcccgccgcg gtggtggtcg cctgcctctt ctacgagcag cacaaccgcc   1680
cgcgctggga ggccacgcac aactgcccgt gcctgcggga cctgcagccc gaccaggcac   1740
gcaggcccga ctacgccgtc ttcatgctca agtacttcat gtgcctagtg gtgggcatca   1800
cctcgggcgt gtgggtctgg tccggcaaga cgctggagtc ctggcgctcc ctgtgcaccc   1860
gctgctgctg ggccagcaag ggcgccgcgg tgggcggggg cgcgggcgcc acggccgcgg   1920
ggggtggcgg cgggccgggg ggcggcggcg gcgggggacc cggcggcggc ggggggccgg   1980
gcggcggcgg gggctccctc tacagcgacg tcagcactgg cctgacgtgg cggtcgggca   2040
cggcgagctc cgtgtcttat ccaaagcaga tgccattgtc ccaggtctga gcggaggga   2100
gggggcgccc aggaggggtg gggagggggg cgaggagacc caagtgcagc gaagggacac   2160
ttgatgggct gaggttccca ccccttcaca gtgttgattg ctattagcat gataatgaac   2220
tcttaatggt atccattagc tgggacttaa atgactcact tagaacaaag tacctggcat   2280
tgaagcctcc cagacccagc cccttttcct ccattgatgt gcggggagct cctcccgcca   2340
cgcgttaatt tctgttggct gaggagggtg gactctgcgg cgtttccaga acccgagatt   2400
tggagccctc cctggctgca cttggctggg tttgcagtca gatacacaga tttcacctgg   2460
gagaacctct ttttctccct cgactcttcc tacgtaaact cccacccctg acttaccctg   2520
gaggaggggt gaccgccacc tgatgggatt gcacggtttg ggtattctta atgaccaggc   2580
aaatgcctta agtaaacaaa caagaaatgt cttaattata caccccacgt aaatacgggt   2640
ttcttacatt agaggatgta tttatataat tatttgttaa attgtaaaaa aaaaaagtgt   2700
aaaatatgta tatatccaaa gatatagtgt gtacattttt ttgtaaaaag tttagaggct   2760
tacccctgta agaacagata taagtattct attttgtcaa taaaatgact tttgataaat   2820
gatttaacca ttgccctctc ccccgcctct tctgagctgt cacctttaaa gtgcttgcta   2880
aggacgcatg ggaaaatgg acattttctg gcttgtcatt ctgtacactg accttaggca   2940
```

-continued

```
tggagaaaat tacttgttaa actctagttc ttaagttgtt agccaagtaa atatcattgt   3000

tgaactgaaa tcaaaattga gtttttgcac cttccccaaa gacggtgttt ttcatgggag   3060

ctcttttctg atccatggat aacaactctc actttagtgg atgtaaatgg aacttctgca   3120

aggcagtaat tcccccttagg ccttgttatt tatcctgcat ggtatcacta aaggtttcaa   3180

aaccctgaaa aaaaa                                                   3195


<210> SEQ ID NO 55
<211> LENGTH: 591
<212> TYPE: PRT
<213> ORGANISM: Homo sapiens
<220> FEATURE:
<223> OTHER INFORMATION: human frizzled9 (Fzd9)

<400> SEQUENCE: 55

Met Ala Val Ala Pro Leu Arg Gly Ala Leu Leu Leu Trp Gln Leu Leu
  1               5                  10                  15

Ala Ala Gly Gly Ala Ala Leu Glu Ile Gly Arg Phe Asp Pro Glu Arg
             20                  25                  30

Gly Arg Gly Ala Ala Pro Cys Gln Ala Val Glu Ile Pro Met Cys Arg
         35                  40                  45

Gly Ile Gly Tyr Asn Leu Thr Arg Met Pro Asn Leu Leu Gly His Thr
     50                  55                  60

Ser Gln Gly Glu Ala Ala Ala Glu Leu Ala Glu Phe Ala Pro Leu Val
 65                  70                  75                  80

Gln Tyr Gly Cys His Ser His Leu Arg Phe Phe Leu Cys Ser Leu Tyr
                 85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
    130                 135                 140

Arg Asn Asp Pro His Ala Leu Cys Met Glu Ala Pro Glu Asn Ala Thr
145                 150                 155                 160

Ala Gly Pro Ala Glu Pro His Lys Gly Leu Gly Met Leu Pro Val Ala
                165                 170                 175

Pro Arg Pro Ala Arg Pro Pro Gly Asp Leu Gly Pro Gly Ala Gly Gly
            180                 185                 190

Ser Gly Thr Cys Glu Asn Pro Glu Lys Phe Gln Tyr Val Glu Lys Ser
        195                 200                 205

Arg Ser Cys Ala Pro Arg Cys Gly Pro Gly Val Glu Val Phe Trp Ser
    210                 215                 220

Arg Arg Asp Lys Asp Phe Ala Leu Val Trp Met Ala Val Trp Ser Ala
225                 230                 235                 240

Leu Cys Phe Phe Ser Thr Ala Phe Thr Val Leu Thr Phe Leu Leu Glu
                245                 250                 255

Pro His Arg Phe Gln Tyr Pro Glu Arg Pro Ile Ile Phe Leu Ser Met
            260                 265                 270

Cys Tyr Asn Val Tyr Ser Leu Ala Phe Leu Ile Arg Ala Val Ala Gly
        275                 280                 285

Ala Gln Ser Val Ala Cys Asp Gln Glu Ala Gly Ala Leu Tyr Val Ile
    290                 295                 300

Gln Glu Gly Leu Glu Asn Thr Gly Cys Thr Leu Val Phe Leu Leu Leu
```

-continued

```
305                 310                 315                 320

Tyr Tyr Phe Gly Met Ala Ser Ser Leu Trp Trp Val Val Leu Thr Leu
                325                 330                 335

Thr Trp Phe Leu Ala Ala Gly Lys Lys Trp Gly His Glu Ala Ile Glu
            340                 345                 350

Ala His Gly Ser Tyr Phe His Met Ala Ala Trp Gly Leu Pro Ala Leu
        355                 360                 365

Lys Thr Ile Val Ile Leu Thr Leu Arg Lys Val Ala Gly Asp Glu Leu
    370                 375                 380

Thr Gly Leu Cys Tyr Val Ala Ser Thr Asp Ala Ala Ala Leu Thr Gly
385                 390                 395                 400

Phe Val Leu Val Pro Leu Ser Gly Tyr Leu Val Leu Gly Ser Ser Phe
                405                 410                 415

Leu Leu Thr Gly Phe Val Ala Leu Phe His Ile Arg Lys Ile Met Lys
            420                 425                 430

Thr Gly Gly Thr Asn Thr Glu Lys Leu Glu Lys Leu Met Val Lys Ile
        435                 440                 445

Gly Val Phe Ser Ile Leu Tyr Thr Val Pro Ala Thr Cys Val Ile Val
    450                 455                 460

Cys Tyr Val Tyr Glu Arg Leu Asn Met Asp Phe Trp Arg Leu Arg Ala
465                 470                 475                 480

Thr Glu Gln Pro Cys Ala Ala Ala Ala Gly Pro Gly Gly Arg Arg Asp
                485                 490                 495

Cys Ser Leu Pro Gly Gly Ser Val Pro Thr Val Ala Val Phe Met Leu
            500                 505                 510

Lys Ile Phe Met Ser Leu Val Val Gly Ile Thr Ser Gly Val Trp Val
        515                 520                 525

Trp Ser Ser Lys Thr Phe Gln Thr Trp Gln Ser Leu Cys Tyr Arg Lys
    530                 535                 540

Ile Ala Ala Gly Arg Ala Arg Ala Lys Ala Cys Arg Ala Pro Gly Ser
545                 550                 555                 560

Tyr Gly Arg Gly Thr His Cys His Tyr Lys Ala Pro Thr Val Val Leu
                565                 570                 575

His Met Thr Lys Thr Asp Pro Ser Leu Glu Asn Pro Thr His Leu
            580                 585                 590


<210> SEQ ID NO 56
<211> LENGTH: 2184
<212> TYPE: DNA
<213> ORGANISM: Homo sapiens
<220> FEATURE:
<223> OTHER INFORMATION: human frizzled9 (Fzd9)

<400> SEQUENCE: 56

ccgccttcgg cccgggcctc ccgggatggc cgtggcgcct ctgcgggggg cgctgctgct      60

gtggcagctg ctggcggcgg gcggcgcggc actggagatc ggccgcttcg acccggagcg     120

cgggcgcggg gctgcgccgt gccaggcggt ggagatcccc atgtgccgcg gcatcggcta     180

caacctgacc cgcatgccca acctgctggg ccacacgtcg cagggcgagg cggctgccga     240

gctagcggag ttcgcgccgc tggtgcagta cggctgccac agccacctgc gcttcttcct     300

gtgctcgctc tacgcgccca tgtgcaccga ccaggtctcg acgcccattc ccgcctgccg     360

gcccatgtgc gagcaggcgc gcctgcgctg cgcgcccatc atggagcagt tcaacttcgg     420

ctggccggac tcgctcgact gcgcccggct gcccacgcgc aacgacccgc acgcgctgtg     480
```

-continued

```
catggaggcg cccgagaacg ccacggccgg ccccgcggag ccccacaagg gcctgggcat    540

gctgcccgtg gcgccgcggc ccgcgcgccc tcccggagac ctgggcccgg gcgcgggcgg    600

cagtggcacc tgcgagaacc ccgagaagtt ccagtacgtg gagaagagcc gctcgtgcgc    660

accgcgctgc gggcccggcg tcgaggtgtt ctggtcccgg cgcgacaagg acttcgcgct    720

ggtctggatg gccgtgtggt cggcgctgtg cttcttctcc accgccttca ctgtgctcac    780

cttcttgctg gagccccacc gcttccagta ccccgagcgc cccatcatct tcctctccat    840

gtgctacaac gtctactcgc tggccttcct gatccgtgcg gtggccggag cgcagagcgt    900

ggcctgtgac caggaggcgg gcgcgctcta cgtgatccag gagggcctgg agaacacggg    960

ctgcacgctg gtcttcctac tgctctacta cttcggcatg gccagctcgc tctggtgggt   1020

ggtcctgacg ctcacctggt tcctggctgc cgggaagaaa tggggccacg aggccatcga   1080

ggcccacggc agctatttcc acatggctgc ctggggcctg cccgcgctca agaccatcgt   1140

catcctgacc ctgcgcaagg tggcgggtga tgagctgact gggctttgct acgtggccag   1200

cacggatgca gcagcgctca cgggcttcgt gctggtgccc ctctctggct acctggtgct   1260

gggcagtagt ttcctcctga ccggcttcgt ggccctcttc cacatccgca agatcatgaa   1320

gacgggcggc accaacacag agaagctgga gaagctcatg gtcaagatcg ggtcttctc    1380

catcctctac acggtgcccg ccacctgcgt catcgtttgc tatgtctacg aacgcctcaa   1440

catggacttc tggcgccttc gggccacaga gcagccatgc gcagcggccg cggggcccgg   1500

aggccggagg gactgctcgc tgccaggggg ctcggtgccc accgtggcgg tcttcatgct   1560

caaaatttc atgtcactgg tggtggggat caccagcggc gtctgggtgt ggagctccaa    1620

gactttccag acctggcaga gcctgtgcta ccgcaagata gcagctggcc gggcccgggc   1680

caaggcctgc cgcgcccccg ggagctacgg acgtggcacg cactgccact ataaggctcc   1740

caccgtggtc ttgcacatga ctaagacgga cccctctttg gagaacccca cacacctcta   1800

gccacacagg cctggcgcgg ggtggctgct gccccctcct tgccctccac gccctgcccc   1860

ctgcatcccc tagagacagc tgactagcag ctgcccagct gtcaaggtca ggcaagtgag   1920

caccggggac tgaggatcag ggcgggaccc cgtgaggctc attaggggag atgggggtct   1980

cccctaatgc gggggctgga ccaggctgag tccccacagg gtcctagtgg aggatgtgga   2040

ggggcggggc agaggggtcc agccggagtt tatttaatga tgtaatttat tgttgcgttc   2100

ctctggaagc tgtgactgga ataaaccccc gcgtggcact gctgatcctc tctggctggg   2160

aagggggaag gtaggaggtg aggc                                          2184
```

<210> SEQ ID NO 57
<211> LENGTH: 581
<212> TYPE: PRT
<213> ORGANISM: Homo sapiens
<220> FEATURE:
<223> OTHER INFORMATION: human frizzled10 (Fzd10)

<400> SEQUENCE: 57

```
Met Gln Arg Pro Gly Pro Arg Leu Trp Leu Val Leu Gln Val Met Gly
  1               5                  10                  15

Ser Cys Ala Ala Ile Ser Ser Met Asp Met Glu Arg Pro Gly Asp Gly
             20                  25                  30

Lys Cys Gln Pro Ile Glu Ile Pro Met Cys Lys Asp Ile Gly Tyr Asn
         35                  40                  45

Met Thr Arg Met Pro Asn Leu Met Gly His Glu Asn Gln Arg Glu Ala
     50                  55                  60
```

-continued

```
Ala Ile Gln Leu His Glu Phe Ala Pro Leu Val Glu Tyr Gly Cys His
 65                  70                  75                  80

Gly His Leu Arg Phe Phe Leu Cys Ser Leu Tyr Ala Pro Met Cys Thr
                 85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
    290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
        355                 360                 365

Ile Leu Val Met Arg Arg Val Ala Gly Asp Glu Leu Thr Gly Val Cys
    370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
        435                 440                 445

Val Leu Tyr Thr Val Pro Ala Thr Cys Val Ile Ala Cys Tyr Phe Tyr
    450                 455                 460

Glu Arg Leu Asn Met Asp Tyr Trp Lys Ile Leu Ala Ala Gln His Lys
465                 470                 475                 480
```

-continued

```
Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
        515                 520                 525

Gln Ser Trp Gln Gln Val Cys Ser Arg Arg Leu Lys Lys Lys Ser Arg
    530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
                565                 570                 575

Ser Pro Thr Cys Val
            580


<210> SEQ ID NO 58
<211> LENGTH: 3260
<212> TYPE: DNA
<213> ORGANISM: Homo sapiens
<220> FEATURE:
<223> OTHER INFORMATION: human frizzled10 (Fzd10)

<400> SEQUENCE: 58

tcgaaacagc tgccggctgg tcccggccga ggccggcgca gggagggagg agccgcccgg     60

gctgtggggg cgccgcgagc tgggccggcc tcggtgtgcc cgcgccgcca gcccgctcca    120

gacgcgccac ctgggcgctc caagaagagg ccgaagtttg ccgcggccgt gagttggagc    180

tcgcgccggg ccgctgcgcc gggagctccg ggggcttccc tcgcttcccg gtattgtttg    240

caaactttgc tgctctccgc cgcggccccc aactcggcgg acgccgggcg cggagagccg    300

agccgggggc gctgtgcgca gcgctcgggc caggccgggc gggcatgggc gggggcccga    360

gcaggggtgg agagccgggg ccagcagcag cccgtgcccg ggagcggcgg cgctgagggg    420

cgcggagctc cccgcgagga cacgtccaac gccagcatgc agcgcccggg cccccgcctg    480

tggctggtcc tgcaggtgat gggctcgtgc gccgccatca gctccatgga catggagcgc    540

ccgggcgacg gcaaatgcca gcccatcgag atcccgatgt gcaaggacat cggctacaac    600

atgactcgta tgcccaacct gatgggccac gagaaccagc gcgaggcagc catccagttg    660

cacgagttcg cgccgctggt ggagtacggc tgccacggcc acctccgctt cttcctgtgc    720

tcgctgtacg cgccgatgtg caccgagcag gtctctaccc ccatccccgc ctgccgggtc    780

atgtgcgagc aggcccggct caagtgctcc ccgattatgg agcagttcaa cttcaagtgg    840

cccgactccc tggactgccg gaaactcccc aacaagaacg accccaacta cctgtgcatg    900

gaggcgccca acaacggctc ggacgagccc acccggggct cgggcctgtt cccgccgctg    960

ttccggccgc agcggcccca cagcgcgcag gagcacccgc tgaaggacgg gggccccggg   1020

cgcggcggct gcgacaaccc gggcaagttc caccacgtgg agaagagcgc gtcgtgcgcg   1080

ccgctctgca cgcccggcgt ggacgtgtac tggagccgcg aggacaagcg cttcgcagtg   1140

gtctggctgg ccatctgggc ggtgctgtgc ttcttctcca gcgccttcac cgtgctcacc   1200

ttcctcatcg acccggcccg cttccgctac cccgagcgcc ccatcatctt cctctccatg   1260

tgctactgcg tctactccgt gggctacctc atccgcctct tcgccggcgc cgagagcatc   1320

gcctgcgacc gggacagcgg ccagctctat gtcatccagg agggactgga gagcaccggc   1380

tgcacgctgg tcttcctggt cctctactac ttcggcatgg ccagctcgct gtggtgggtg   1440
```

-continued

```
gtcctcacgc tcacctggtt cctggccgcc ggcaagaagt ggggccacga ggccatcgaa   1500

gccaacagca gctacttcca cctggcagcc tgggccatcc cggcggtgaa gaccatcctg   1560

atcctggtca tgcgcagggt ggcgggggac gagctcaccg ggtctgcta cgtgggcagc    1620

atggacgtca acgcgctcac cggcttcgtg ctcattcccc tggcctgcta cctggtcatc   1680

ggcacgtcct tcatcctctc gggcttcgtg gccctgttcc acatccggag ggtgatgaag   1740

acgggcggcg agaacacgga caagctggag aagctcatgg tgcgtatcgg gctcttctct   1800

gtgctgtaca ccgtgccggc cacctgtgtg atcgcctgct acttttacga acgcctcaac   1860

atggattact ggaagatcct ggcggcgcag cacaagtgca aaatgaacaa ccagactaaa   1920

acgctggact gcctgatggc cgcctccatc cccgccgtgg agatcttcat ggtgaagatc   1980

tttatgctgc tggtggtggg gatcaccagc gggatgtgga tttggacctc caagactctg   2040

cagtcctggc agcaggtgtg cagccgtagg ttaaagaaga agagccggag aaaaccggcc   2100

agcgtgatca ccagcggtgg gatttacaaa aaagcccagc atccccagaa aactcaccac   2160

gggaaatatg agatccctgc ccagtcgccc acctgcgtgt gaacagggct ggagggaagg   2220

gcacaggggc gcccggagct aagatgtggt gcttttcttg gttgtgtttt tctttcttct   2280

tcttcttttt ttttttttat aaaagcaaaa gagaaataca taaaaaagtg tttaccctga   2340

aattcaggat gctgtgatac actgaaagga aaaatgtact taaagggttt tgttttgttt   2400

tggttttcca gcgaagggaa gctcctccag tgaagtagcc tcttgtgtaa ctaatttgtg   2460

gtaaagtagt tgattcagcc ctcagaagaa aacttttgtt tagagccctc cctaaatata   2520

catctgtgta tttgagttgg ctttgctacc catttacaaa taagaggaca gataactgct   2580

ttgcaaattc aagagcctcc cctgggttaa caaatgagcc atccccaggg cccaccccca   2640

ggaaggccac agtgctgggc ggcatccctg cagaggaaag acaggacccg gggcccgcct   2700

cacaccccag tggatttgga gttgcttaaa atagactccg gccttcacca atagtctctc   2760

tgcaagacag aaacctccat caaacctcac atttgtgaac tcaaacgatg tgcaatacat   2820

ttttttctct ttccttgaaa ataaaaagag aaacaagtat tttgctatat ataaagacaa   2880

caaaagaaat ctcctaacaa aagaactaag aggcccagcc ctcagaaacc cttcagtgct   2940

acattttgtg gctttttaat ggaaaccaag ccaatgttat agacgtttgg actgatttgt   3000

ggaaaggagg ggggaagagg gagaaggatc attcaaaagt tacccaaagg gcttattgac   3060

tctttctatt gttaaacaaa tgatttccac aaacagatca ggaagcacta ggttggcaga   3120

gacactttgt ctagtgtatt ctcttcacag tgccaggaaa gagtggtttc tgcgtgtgta   3180

tatttgtaat atatgatatt tttcatgctc cactatttta ttaaaaataa aatatgttct   3240

ttagtttgct gctaaaaaaa                                               3260
```

<210> SEQ ID NO 59
<211> LENGTH: 49
<212> TYPE: PRT
<213> ORGANISM: Artificial Sequence
<220> FEATURE:
<223> OTHER INFORMATION: Description of Artificial Sequence:portion of first extracellular region of human frizzled1 (HFZ1)

<400> SEQUENCE: 59

```
Val Gly Gln Asn Thr Ser Asp Lys Gly Thr Pro Ser Leu Leu Pro Glu
  1               5                  10                  15

Phe Trp Thr Ser Asn Pro Gln His Gly Gly Gly Gly His Arg Gly Gly
             20                  25                  30
```

-continued

```
Phe Pro Gly Gly Ala Gly Ala Ser Glu Arg Gly Lys Phe Ser Cys Pro
         35                  40                  45

Arg


<210> SEQ ID NO 60
<211> LENGTH: 51
<212> TYPE: PRT
<213> ORGANISM: Artificial Sequence
<220> FEATURE:
<223> OTHER INFORMATION: Description of Artificial Sequence:portion of
      first extracellular region of human frizzled2
      (HFZ2)

<400> SEQUENCE: 60

Val Gly Gln Asn His Ser Glu Asp Gly Ala Pro Ala Leu Leu Thr Thr
  1               5                  10                  15

Ala Pro Pro Pro Gly Leu Gln Pro Gly Ala Gly Gly Thr Pro Gly Gly
             20                  25                  30

Pro Gly Gly Gly Gly Ala Pro Pro Arg Tyr Ala Thr Leu Glu His Pro
         35                  40                  45

Phe His Cys
     50


<210> SEQ ID NO 61
<211> LENGTH: 26
<212> TYPE: PRT
<213> ORGANISM: Artificial Sequence
<220> FEATURE:
<223> OTHER INFORMATION: Description of Artificial Sequence:portion of
      first extracellular region of human frizzled3
      (HFZ3)

<400> SEQUENCE: 61

Leu Val Asp Leu Asn Leu Ala Gly Glu Pro Thr Glu Gly Ala Pro Val
  1               5                  10                  15

Ala Val Gln Arg Asp Tyr Gly Phe Trp Cys
             20                  25


<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence:portion of
      first extracellular region of human frizzled4
      (HFZ4)

<400> SEQUENCE: 62

Cys Met Glu Gly Pro Gly Asp Glu Glu Val Pro Leu Pro His Lys Thr
  1               5                  10                  15

Pro Ile Gln Pro
             20


<210> SEQ ID NO 63
<211> LENGTH: 46
<212> TYPE: PRT
<213> ORGANISM: Artificial Sequence
<220> FEATURE:
<223> OTHER INFORMATION: Description of Artificial Sequence:portion of
      first extracellular region of human frizzled5
      (HFZ5)

<400> SEQUENCE: 63

Cys Met Asp Tyr Asn Arg Ser Glu Ala Thr Thr Ala Pro Pro Arg Pro
```

-continued

```
  1               5                  10                  15

Phe Pro Ala Lys Pro Thr Leu Pro Gly Pro Pro Gly Ala Pro Ala Ser
             20                  25                  30

Gly Gly Glu Cys Pro Ala Gly Gly Pro Phe Val Cys Lys Cys
         35                  40                  45


<210> SEQ ID NO 64
<211> LENGTH: 26
<212> TYPE: PRT
<213> ORGANISM: Artificial Sequence
<220> FEATURE:
<223> OTHER INFORMATION: Description of Artificial Sequence:portion of
      first extracellular region of human frizzled6
      (HFZ6)

<400> SEQUENCE: 64

Thr Phe Asp Pro His Thr Glu Phe Leu Gly Pro Gln Lys Lys Thr Glu
  1               5                  10                  15

Gln Val Gln Arg Asp Ile Gly Phe Trp Cys
             20                  25


<210> SEQ ID NO 65
<211> LENGTH: 50
<212> TYPE: PRT
<213> ORGANISM: Artificial Sequence
<220> FEATURE:
<223> OTHER INFORMATION: Description of Artificial Sequence:portion of
      first extracellular region of human frizzled7
      (HFZ7)

<400> SEQUENCE: 65

Val Gly Gln Asn Thr Ser Asp Gly Ser Gly Gly Pro Gly Gly Gly Pro
  1               5                  10                  15

Thr Ala Tyr Pro Thr Ala Pro Tyr Leu Pro Asp Leu Pro Phe Thr Ala
             20                  25                  30

Leu Pro Pro Gly Ala Ser Asp Gly Arg Gly Arg Pro Ala Phe Pro Phe
         35                  40                  45

Ser Cys
     50


<210> SEQ ID NO 66
<211> LENGTH: 87
<212> TYPE: PRT
<213> ORGANISM: Artificial Sequence
<220> FEATURE:
<223> OTHER INFORMATION: Description of Artificial Sequence:portion of
      first extracellular region of human frizzled8
      (HFZ8)

<400> SEQUENCE: 66

Cys Met Asp Tyr Asn Arg Thr Asp Leu Thr Thr Ala Ala Pro Ser Pro
  1               5                  10                  15

Pro Arg Arg Leu Pro Pro Pro Pro Pro Gly Glu Gln Pro Pro Ser Gly
             20                  25                  30

Ser Gly His Gly Arg Pro Pro Gly Ala Arg Pro Pro His Arg Gly Gly
         35                  40                  45

Gly Arg Gly Gly Gly Gly Gly Asp Ala Ala Ala Pro Pro Ala Arg Gly
     50                  55                  60

Gly Gly Gly Gly Gly Lys Ala Arg Pro Pro Gly Gly Gly Ala Ala Pro
 65                  70                  75                  80

Cys Glu Pro Gly Cys Gln Cys
                 85
```

-continued

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence:portion of first extracellular region of human frizzled9 (HFZ9)

<400> SEQUENCE: 67

Cys Met Glu Ala Pro Glu Asn Ala Thr Ala Gly Pro Ala Glu Pro His
1 5 10 15

Lys Gly Leu Gly Met Leu Pro Val Ala Pro Arg Pro Ala Arg Pro Pro
20 25 30

Gly Asp Leu Gly Pro
35

<210> SEQ ID NO 68
<211> LENGTH: 38
<212> TYPE: PRT
<213> ORGANISM: Artificial Sequence
<220> FEATURE:
<223> OTHER INFORMATION: Description of Artificial Sequence:portion of first extracellular region of human frizzled10 (HFZ10)

<400> SEQUENCE: 68

Asn Tyr Leu Cys Met Glu Ala Pro Asn Asn Gly Ser Asp Glu Pro Thr
1 5 10 15

Arg Gly Ser Gly Leu Phe Pro Pro Leu Phe Arg Pro Gln Arg Pro His
20 25 30

Ser Ala Gln Glu His Pro
35

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence:real-time PCR Wnt1 forward primer

<400> SEQUENCE: 69
cgaacctgct tacagactcc aa 22

<210> SEQ ID NO 70
<211> LENGTH: 17
<212> TYPE: DNA
<213> ORGANISM: Artificial Sequence
<220> FEATURE:
<223> OTHER INFORMATION: Description of Artificial Sequence:real-time PCR Wnt1 reverse primer

<400> SEQUENCE: 70
cagacgccgc tgtttgc 17

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:Wnt1 probe

<400> SEQUENCE: 71

-continued tgcaactggt actcgagccc agtctg 26

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence:real-time PCR Wnt2 forward primer

<400> SEQUENCE: 72
ggatgaccaa gtgtgggtgt aag 23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:real-time PCR Wnt2 reverse primer

<400> SEQUENCE: 73
gtgcacatcc agagcttcca 20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence:Wnt2 probe

<400> SEQUENCE: 74
cactggtgct gcgccgtgc 19

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence:real-time PCR Wnt2b forward primer

<400> SEQUENCE: 75
ggcacgagtg atctgtgaca ata 23

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:real-time PCR Wnt2b reverse primer

<400> SEQUENCE: 76
cgcatgatgt ctgggtaacg 20

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence:Wnt2b probe

<400> SEQUENCE: 77
tttggtgagc cggcagcgg 19

-continued

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt3 forward primer

<400> SEQUENCE: 78
ctgggccagc agtacacatc t 21

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence:real-time
PCR Wnt3 reverse primer

<400> SEQUENCE: 79
ggcatgatct cgatgtaatt gc 22

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:Wnt3 probe

<400> SEQUENCE: 80
tgctctgcgg ctccatccca 20

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt3a forward primer

<400> SEQUENCE: 81
cccgtgctgg acaaagct 18

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt3a reverse primer

<400> SEQUENCE: 82
tctgcacatg agcgtgtcac t 21

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence:Wnt3a probe

<400> SEQUENCE: 83
ttgtccacgc cattgcctca gc 22

<210> SEQ ID NO 84
<211> LENGTH: 20
<212> TYPE: DNA

-continued

<213> ORGANISM: Artificial Sequence
<220> FEATURE:
<223> OTHER INFORMATION: Description of Artificial Sequence:real-time
PCR Wnt4 forward primer

<400> SEQUENCE: 84
ggaggagacg tgcgagaaac 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:real-time
PCR Wnt4 reverse primer

<400> SEQUENCE: 85
caggttccgc ttgcacatct 20

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence:Wnt4 probe

<400> SEQUENCE: 86
caagggcctg atccagaggc agg 23

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:real-time
PCR Wnt5a forward primer

<400> SEQUENCE: 87
tctccttcgc ccaggttgta 20

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence:real-time
PCR Wnt5a reverse primer

<400> SEQUENCE: 88
cttctgacat ctgaacaggg ttattc 26

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence:Wnt5a probe

<400> SEQUENCE: 89
tgaagccaat tcttggtggt cgctagg 27

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence:real-time -continued PCR Wnt5b forward primer

<400> SEQUENCE: 90
ccaactcctg gtggtcatta gc 22

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt5b reverse primer

<400> SEQUENCE: 91
tgggcaccga tgataaacat c 21

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence:Wnt5b probe

<400> SEQUENCE: 92
ttgaacccgg tgcagagacc cg 22

<210> SEQ ID NO 93
<211> LENGTH: 16
<212> TYPE: DNA
<213> ORGANISM: Artificial Sequence
<220> FEATURE:
<223> OTHER INFORMATION: Description of Artificial Sequence:real-time
PCR Wnt6 forward primer

<400> SEQUENCE: 93
tccgccgctg gaattg 16

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt6 reverse primer

<400> SEQUENCE: 94
aggccgtctc ccgaatgt 18

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:Wnt6 probe

<400> SEQUENCE: 95
aggcctttgg acgcatcctg ca 22

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt7a forward primer

<400> SEQUENCE: 96

-continued

```
gacgccatca tcgtcatagg a                                             21


<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence:real-time
      PCR Wnt7a reverse primer

<400> SEQUENCE: 97

ggccattgcg gaactgaa                                                 18


<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence:Wnt7a probe

<400> SEQUENCE: 98

tcacaaatgg gcctggacga gtgtc                                         25


<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:real-time
      PCR Wnt7b forward primer

<400> SEQUENCE: 99

tgaagctcgg agcactgtca                                               20


<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence:real-time
      PCR Wnt7b reverse primer

<400> SEQUENCE: 100

ggccaggaat cttgttgca                                                19


<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:Wnt7b probe

<400> SEQUENCE: 101

tggtggccct gggagccaac                                               20


<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:real-time
      PCR Wnt8a forward primer

<400> SEQUENCE: 102

gcagaggcgg aactgatctt                                               20
```

-continued

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt8a reverse primer

<400> SEQUENCE: 103
cgaccctctg tgccatagat g 21

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence:Wnt8a probe

<400> SEQUENCE: 104
ccagattact gtacctgcaa ttccagcctg 30

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt8b forward primer

<400> SEQUENCE: 105
aatcgggaga cagcatttgt g 21

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence:real-time
PCR Wnt8b reverse primer

<400> SEQUENCE: 106
atctccaagg ctgcagtttc tagt 24

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence:Wnt8b probe

<400> SEQUENCE: 107
tgccatcagt tctgctggag tcatgtaca 29

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence:real-time
PCR Wnt10a forward primer

<400> SEQUENCE: 108
ctgggtgctc ctgttcttcc ta 22

<210> SEQ ID NO 109
<211> LENGTH: 19

-continued

<212> TYPE: DNA
<213> ORGANISM: Artificial Sequence
<220> FEATURE:
<223> OTHER INFORMATION: Description of Artificial Sequence:real-time
PCR Wnt10a reverse primer

<400> SEQUENCE: 109
gaggcggagg tccagaatg 19

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence:Wnt10a probe

<400> SEQUENCE: 110
ctgccatgcc caggtcagca cc 22

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt10b forward primer

<400> SEQUENCE: 111
cctcgcgggt ctcctgtt 18

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence:real-time
PCR Wnt10b reverse primer

<400> SEQUENCE: 112
aggcccagaa tctcattgct ta 22

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence:Wnt10b probe

<400> SEQUENCE: 113
ctggcgttgt gcagtcgggc t 21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt11 forward primer

<400> SEQUENCE: 114
cgtgtgctat ggcatcaagt g 21

<210> SEQ ID NO 115
<211> LENGTH: 20
<212> TYPE: DNA
<213> ORGANISM: Artificial Sequence
<220> FEATURE:

-continued

<223> OTHER INFORMATION: Description of Artificial Sequence:real-time
PCR Wnt11 reverse primer

<400> SEQUENCE: 115
gcagtgttgc gtctggttca 20

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence:Wnt11 probe

<400> SEQUENCE: 116
tgtccaagac accatcggcc ctg 23

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt14 forward primer

<400> SEQUENCE: 117
gggcagacgg tcaagcaa 18

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence:real-time
PCR Wnt14 reverse primer

<400> SEQUENCE: 118
ccagccttga tcaccttcac a 21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence:Wnt14 probe

<400> SEQUENCE: 119
ctgcgagccc gtgtggactt cc 22

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt16 forward primer

<400> SEQUENCE: 120
gccaatttgc cgctgaac 18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence:real-time
PCR Wnt16 reverse primer -continued

<400> SEQUENCE: 121
cggcagcagg tacggttt 18

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence:Wnt16 probe

<400> SEQUENCE: 122
ccgccagaag gagctgtgca aga 23

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence:real-time PCR Fzd1 forward primer

<400> SEQUENCE: 123
caccttgtga gccgaccaa 19

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence:real-time PCR Fzd1 reverse primer

<400> SEQUENCE: 124
cagcactgac caaatgccaa t 21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence:Fzd1 probe

<400> SEQUENCE: 125
aggagctgcg cttctcgcgc 20

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence:real-time PCR Fzd2 forward primer

<400> SEQUENCE: 126
tttctgggcg agcgtgat 18

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:real-time PCR Fzd2 reverse primer

<400> SEQUENCE: 127
aaacgcgtct cctcctgtga 20

-continued

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence:Fzd2 probe

<400> SEQUENCE: 128
tgcgaacctg cgcggcc 17

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence:real-time PCR Fzd3 forward primer

<400> SEQUENCE: 129
tggctatggt ggatgatcaa ag 22

<210> SEQ ID NO 130
<211> LENGTH: 17
<212> TYPE: DNA
<213> ORGANISM: Artificial Sequence
<220> FEATURE:
<223> OTHER INFORMATION: Description of Artificial Sequence:real-time PCR Fzd3 reverse primer

<400> SEQUENCE: 130
tggaggctgc cgtggta 17

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence:Fzd3 probe

<400> SEQUENCE: 131
aggaagcatc cacagcaaag tgagcag 27

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence:real-time PCR Fzd4 forward primer

<400> SEQUENCE: 132
ggcggcatgt gtctttcagt 20

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence:real-time PCR Fzd4 reverse primer

<400> SEQUENCE: 133
gaatttgctg cagttcagac tctct 25

<210> SEQ ID NO 134

-continued

<211> LENGTH: 26
<212> TYPE: DNA
<213> ORGANISM: Artificial Sequence
<220> FEATURE:
<223> OTHER INFORMATION: Description of Artificial Sequence:Fzd4 probe

<400> SEQUENCE: 134
agagacgctg tgaacccgtc ctgaag 26

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence:real-time PCR Fzd5 forward primer

<400> SEQUENCE: 135
cgcgagcaca accacatc 18

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence:real-time PCR Fzd5 reverse primer

<400> SEQUENCE: 136
agaagtagac caggaggaag acgat 25

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence:Fzd5 probe

<400> SEQUENCE: 137
tacgagacca cgggccctgc ac 22

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence:real-time PCR Fzd6 forward primer

<400> SEQUENCE: 138
acaagctgaa ggtcatttcc aaa 23

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence:real-time PCR Fzd6 reverse primer

<400> SEQUENCE: 139
gctactgcag aagtgccatg at 22

<210> SEQ ID NO 140
<211> LENGTH: 26
<212> TYPE: DNA
<213> ORGANISM: Artificial Sequence -continued
<220> FEATURE:
<223> OTHER INFORMATION: Description of Artificial Sequence:Fzd6 probe

<400> SEQUENCE: 140
atgggaacca gcacaggagc tacagc 26

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence:real-time
PCR Fzd7 forward primer

<400> SEQUENCE: 141
caacggcctg atgtacttta agg 23

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence:real-time
PCR Fzd7 reverse primer

<400> SEQUENCE: 142
catgtccacc aggtaggtga ga 22

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence:Fzd7 probe

<400> SEQUENCE: 143
ctgcgcctcg acgctcttta ccg 23

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:real-time
PCR Fzd8 forward primer

<400> SEQUENCE: 144
gctcggtcat caagcaacag 20

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence:real-time
PCR Fzd8 reverse primer

<400> SEQUENCE: 145
acggtgtaga gcacggtgaa c 21

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence:Fzd8 probe -continued

<400> SEQUENCE: 146
aagctgatga tccgcctggg cc 22

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence:real-time PCR Fzd9 forward primer

<400> SEQUENCE: 147
gcgctcaaga ccatcgtcat 20

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence:real-time PCR Fzd9 reverse primer

<400> SEQUENCE: 148
atccgtgctg gccacgta 18

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence:Fzd9 probe

<400> SEQUENCE: 149
tggcgggtga tgagctgact gg 22

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence:real-time PCR Fzd10 forward primer

<400> SEQUENCE: 150
gccgccatca gctccat 17

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence:real-time PCR Fzd10 reverse primer

<400> SEQUENCE: 151
tcatgttgta gccgatgtcc tt 22

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence:Fzd10 probe

<400> SEQUENCE: 152
atgccagccc atcgagatcc cg 22

-continued

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence:real-time
PCR Frp1 forward primer

<400> SEQUENCE: 153
agcgagtacg actacgtgag ctt 23

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence:real-time
PCR Frp1 reverse primer

<400> SEQUENCE: 154
gcactgaggt ggcttggtgt a 21

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence:Frp1 probe

<400> SEQUENCE: 155
agtcggacat cggcccgtac cag 23

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence:real-time
PCR Frp2 forward primer

<400> SEQUENCE: 156
agaccaagag caagaccatt taca 24

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence:real-time
PCR Frp2 reverse primer

<400> SEQUENCE: 157
ttgagccaca gcaccgatt 19

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence:Frp2 probe

<400> SEQUENCE: 158
cggtgtgtcc gaaagggacc tga 23

<210> SEQ ID NO 159

-continued

```
<211> LENGTH: 22
<212> TYPE: DNA
<213> ORGANISM: Artificial Sequence
<220> FEATURE:
<223> OTHER INFORMATION: Description of Artificial Sequence:real-time
      PCR Frp3 forward primer

<400> SEQUENCE: 159

gggctatgaa gatgaggaac gt                                             22


<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence:real-time
      PCR Frp3 reverse primer

<400> SEQUENCE: 160

ccgagtcgat ccttccactt c                                              21


<210> SEQ ID NO 161
<211> LENGTH: 34
<212> TYPE: DNA
<213> ORGANISM: Artificial Sequence
<220> FEATURE:
<223> OTHER INFORMATION: Description of Artificial Sequence:Frp3 probe

<400> SEQUENCE: 161

ccagattact cttggtggaa ggctctatag ctga                                34


<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence:real-time
      PCR Frp4 forward primer

<400> SEQUENCE: 162

cggaggatgt taagtggata gaca                                           24


<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence:real-time
      PCR Frp4 reverse primer

<400> SEQUENCE: 163

aggcgtttac agtcaacatc aaga                                           24


<210> SEQ ID NO 164
<211> LENGTH: 29
<212> TYPE: DNA
<213> ORGANISM: Artificial Sequence
<220> FEATURE:
<223> OTHER INFORMATION: Description of Artificial Sequence:Frp4 probe

<400> SEQUENCE: 164

cacaccagac atgatggtac aggaaaggc                                      29


<210> SEQ ID NO 165
<211> LENGTH: 20
<212> TYPE: DNA
<213> ORGANISM: Artificial Sequence
```

-continued

<220> FEATURE:
<223> OTHER INFORMATION: Description of Artificial Sequence:real-time
      PCR Frp5 forward primer

<400> SEQUENCE: 165
agctgattgg agcccagaaa                                              20

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence:real-time
      PCR Frp5 reverse primer

<400> SEQUENCE: 166
tggtgtcctt gcgcttca                                                18

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence:Frp5 probe

<400> SEQUENCE: 167
aagaagctgc tcaagccggg cc                                           22

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence:real-time
      PCR Wisp1 forward primer

<400> SEQUENCE: 168
cctgatgggc ttggcttct                                               19

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence:real-time
      PCR Wisp1 reverse primer

<400> SEQUENCE: 169
tgggattcct acagctcagg tt                                           22

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence:Wisp1 probe

<400> SEQUENCE: 170
ccgccaggtc ctatggatta atgcct                                       26

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence:real-time
      PCR Wisp2 forward primer -continued

<400> SEQUENCE: 171
acccacctcc tggccttct 19

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence:real-time
PCR Wisp2 reverse primer

<400> SEQUENCE: 172
agcagccaca gccatcca 18

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence:Wisp2 probe

<400> SEQUENCE: 173
tcctctgcct cctctcaaag gtgcgtac 28

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence:real-time
PCR Wisp3 forward primer

<400> SEQUENCE: 174
aaagctggct ggcagtcact 20

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence:real-time
PCR Wisp3 reverse primer

<400> SEQUENCE: 175
aatggttcca ggctacagtt tga 23

<210> SEQ ID NO 176
<211> LENGTH: 32
<212> TYPE: DNA
<213> ORGANISM: Artificial Sequence
<220> FEATURE:
<223> OTHER INFORMATION: Description of Artificial Sequence:Wisp3 probe

<400> SEQUENCE: 176
tctggagcta aaggtggaaa gaagtctgat ca 32

<210> SEQ ID NO 177
<211> LENGTH: 26
<212> TYPE: DNA
<213> ORGANISM: Artificial Sequence
<220> FEATURE:
<223> OTHER INFORMATION: Description of Artificial Sequence:real-time
PCR DKK1 forward primer

<400> SEQUENCE: 177

-continued

```
ggaataagta ccagaccatt gacaac                                          26


<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence:real-time
      PCR DKK1 reverse primer

<400> SEQUENCE: 178

gggactagcg cagtactcat ca                                              22


<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence:DKK1 probe

<400> SEQUENCE: 179

cagccgtacc cgtgcgcaga                                                 20


<210> SEQ ID NO 180
<211> LENGTH: 22
<212> TYPE: DNA
<213> ORGANISM: Artificial Sequence
<220> FEATURE:
<223> OTHER INFORMATION: Description of Artificial Sequence:real-time
      PCR DKK2 forward primer

<400> SEQUENCE: 180

ctgatggtgg agagctcaca ga                                              22


<210> SEQ ID NO 181
<211> LENGTH: 25
<212> TYPE: DNA
<213> ORGANISM: Artificial Sequence
<220> FEATURE:
<223> OTHER INFORMATION: Description of Artificial Sequence:real-time
      PCR DKK2 reverse primer

<400> SEQUENCE: 181

cagagaggac ttgatggagt tgagt                                           25


<210> SEQ ID NO 182
<211> LENGTH: 17
<212> TYPE: DNA
<213> ORGANISM: Artificial Sequence
<220> FEATURE:
<223> OTHER INFORMATION: Description of Artificial Sequence:DKK2 probe

<400> SEQUENCE: 182

cggcagttcg cgggcca                                                    17


<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence:real-time
      PCR DKK3 forward primer

<400> SEQUENCE: 183

ggaggacacg cagcacaaa                                                  19
```

-continued

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence:real-time
PCR DKK3 reverse primer

<400> SEQUENCE: 184
caggttcact tctgatgatg cttt 24

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence:DKK3 probe

<400> SEQUENCE: 185
tgcgcagcgc ggtggaag 18

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence:real-time
PCR DKK4 forward primer

<400> SEQUENCE: 186
ggcataaaga cactgctcaa gct 23

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence:real-time
PCR DKK4 reverse primer

<400> SEQUENCE: 187
gctggtcaat tggcttcga 19

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence:DKK4 probe

<400> SEQUENCE: 188
cgttgcgact gtggccctgg ac 22

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence:real-time
PCR IL-6 forward primer

<400> SEQUENCE: 189
cctgacccaa ccacaaatgc 20

<210> SEQ ID NO 190
<211> LENGTH: 22
<212> TYPE: DNA

-continued

```
<213> ORGANISM: Artificial Sequence
<220> FEATURE:
<223> OTHER INFORMATION: Description of Artificial Sequence:real-time
      PCR IL-6 reverse primer

<400> SEQUENCE: 190

gcgcagaatg agatgagttg tc                                           22


<210> SEQ ID NO 191
<211> LENGTH: 25
<212> TYPE: DNA
<213> ORGANISM: Artificial Sequence
<220> FEATURE:
<223> OTHER INFORMATION: Description of Artificial Sequence:IL-6 probe

<400> SEQUENCE: 191

ctgacgaagc tgcaggcaca gaacc                                        25


<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence:real-time
      PCR C-Myc forward primer

<400> SEQUENCE: 192

gccacgtctc cacacatcag                                              20


<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence:real-time
      PCR C-Myc reverse primer

<400> SEQUENCE: 193

tcttggcagc aggatagtcc tt                                           22


<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence:C-Myc probe

<400> SEQUENCE: 194

cgcagcgcct ccctccactc                                              20


<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence:real-time
      PCR Fibro forward primer

<400> SEQUENCE: 195

cacccaattc cttgctggta tc                                           22


<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence:real-time
```

-continued

PCR Fibro reverse primer

<400> SEQUENCE: 196
cccaggcttc tcatacttga tga 23

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence:Fibro probe

<400> SEQUENCE: 197
agccgccacg tgccaggatt ac 22

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence:real-time
PCR Cyc D1 forward primer

<400> SEQUENCE: 198
ggcggaggag aacaaacaga 20

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence:real-time
PCR Cyc D1 reverse primer

<400> SEQUENCE: 199
tggcacaaga ggcaacga 18

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence:Cyc D1 probe

<400> SEQUENCE: 200
tccgcaaaca cgcgcagacc 20

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence:real-time
PCR MMP3 forward primer

<400> SEQUENCE: 201
ccatcagagg aaatgaggta cga 23

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence:real-time
PCR MMP3 reverse primer

<400> SEQUENCE: 202
cctcacggtt ggagggaaa 19

<210> SEQ ID NO 203
<211> LENGTH: 26
<212> TYPE: DNA
<213> ORGANISM: Artificial Sequence
<220> FEATURE:
<223> OTHER INFORMATION: Description of Artificial Sequence:MMP3 probe

<400> SEQUENCE: 203
ctggataccc aagaggcatc cacacc 26

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence:real-time PCR LRP5 forward primer

<400> SEQUENCE: 204
cgtgattgcc gacgatctc 19

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence:real-time PCR LRP5 reverse primer

<400> SEQUENCE: 205
tccggccgct agtcttgtc 19

<210> SEQ ID NO 206
<211> LENGTH: 25
<212> TYPE: DNA
<213> ORGANISM: Artificial Sequence
<220> FEATURE:
<223> OTHER INFORMATION: Description of Artificial Sequence:LRP5 probe

<400> SEQUENCE: 206
acccgttcgg tctgacgcag tacag 25

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence:peptide linker

<400> SEQUENCE: 207

Gly Gly Gly Gly Ser
1 5

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence:Fzd-2 PCR amplification reverse primer

<400> SEQUENCE: 208
cagcgtcttg cccgaccaga tcca 24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence:Fzd-2 PCR amplification forward primer

<400> SEQUENCE: 209
ctagcgccgc tcttcgtgta cctg 24

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence:Fzd-5 PCR amplification forward primer

<400> SEQUENCE: 210
ttcatgtgcc tggtggtggg c 21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence:Fzd-5 PCR amplification reverse primer

<400> SEQUENCE: 211
tacacgtgcg acagggacac c 21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence:Wnt-1 PCR amplification forward primer

<400> SEQUENCE: 212
cacgacctcg tctacttcga c 21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence:Wnt-1 PCR amplification reverse primer

<400> SEQUENCE: 213
acagacactc gtgcagtacg c 21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence:Wnt-5a PCR amplification forward primer

<400> SEQUENCE: 214
acacctcttt ccaaacaggc c 21

-continued

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence:Wnt-5a PCR
amplification reverse primer

<400> SEQUENCE: 215
ggattgttaa actcaactct c 21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence:Wnt-7a PCR
amplification forward primer

<400> SEQUENCE: 216
cgcaacaagc ggcccacctt c 21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence:Wnt-7a PCR
amplification reverse primer

<400> SEQUENCE: 217
tccgtgcgct cgctgcacgt g 21

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence:Wnt-10b PCR
amplification forward primer

<400> SEQUENCE: 218
gaatgcgaat ccacaacaac ag 22

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence:Wnt-10b PCR
amplification reverse primer

<400> SEQUENCE: 219
ttgcggttgt gggtatcaat gaa 23

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence:Wnt-13 PCR
amplification forward primer

<400> SEQUENCE: 220
aagatggtgc caacttcacc g 21

-continued

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence:Wnt-13 PCR amplification reverse primer

<400> SEQUENCE: 221
ctgccttctt gggggctttg c 21

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence:G3PDH PCR amplification forward primer

<400> SEQUENCE: 222
accacagtcc atgccatcac 20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence:G3PDH PCR amplification reverse primer

<400> SEQUENCE: 223
tacagcaaca gggtggtgga 20

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence:short linker sequence

<400> SEQUENCE: 224

Gly Pro Ser Leu
1

<210> SEQ ID NO 225
<211> LENGTH: 75
<212> TYPE: PRT
<213> ORGANISM: Artificial Sequence
<220> FEATURE:
<223> OTHER INFORMATION: Description of Artificial Sequence:pFZD2-TT tetanus toxin epitope fused to frizzled domain

<400> SEQUENCE: 225

Met Cys Val Gly Gln Asn His Ser Glu Asp Gly Ala Pro Ala Leu Leu
1 5 10 15

Thr Thr Ala Pro Pro Pro Gly Leu Gln Pro Gly Ala Gly Gly Thr Pro
20 25 30

Gly Gly Pro Gly Gly Gly Gly Ala Pro Pro Arg Tyr Ala Thr Leu Glu
35 40 45

His Pro Phe His Cys Gly Pro Ser Leu Val Asp Asp Ala Leu Ile Asn
50 55 60

Ser Thr Lys Ile Tyr Ser Tyr Phe Pro Ser Val
65 70 75

-continued

<210> SEQ ID NO 226
<211> LENGTH: 228
<212> TYPE: DNA
<213> ORGANISM: Artificial Sequence
<220> FEATURE:
<223> OTHER INFORMATION: Description of Artificial Sequence:pFZD2-TT
tetanus toxin epitope fused to frizzled domain

<400> SEQUENCE: 226
atgtgcgtcg gccagaacca ctccgaggac ggagctcccg cgctactcac caccgcgccg 60
ccgccgggac tgcagccggg tgccgggggc accccgggtg gcccgggcgg cggcggcgct 120
cccccgcgct acgccacgct ggagcacccc ttccactgcg gccccagcct ggtggacgac 180
gccctgatca acagcaccaa gatctacagc tactttccca gcgtgtag 228

<210> SEQ ID NO 227
<211> LENGTH: 75
<212> TYPE: PRT
<213> ORGANISM: Artificial Sequence
<220> FEATURE:
<223> OTHER INFORMATION: Description of Artificial Sequence:pTT-FZD2
tetanus toxin epitope fused to frizzled domain

<400> SEQUENCE: 227

Met Val Asp Asp Ala Leu Ile Asn Ser Thr Lys Ile Tyr Ser Tyr Phe
1 5 10 15

Pro Ser Val Gly Pro Ser Leu Cys Val Gly Gln Asn His Ser Glu Asp
20 25 30

Gly Ala Pro Ala Leu Leu Thr Thr Ala Pro Pro Pro Gly Leu Gln Pro
35 40 45

Gly Ala Gly Gly Thr Pro Gly Gly Pro Gly Gly Gly Gly Ala Pro Pro
50 55 60

Arg Tyr Ala Thr Leu Glu His Pro Phe His Cys
65 70 75

<210> SEQ ID NO 228
<211> LENGTH: 228
<212> TYPE: DNA
<213> ORGANISM: Artificial Sequence
<220> FEATURE:
<223> OTHER INFORMATION: Description of Artificial Sequence:pTT-FZD2
tetanus toxin epitope fused to frizzled domain

<400> SEQUENCE: 228
atggtggacg acgccctgat caacagcacc aagatctaca gctactttcc cagcgtgggc 60
cccagcctgt gcgtcggcca gaaccactcc gaggacggag ctcccgcgct actcaccacc 120
gcgccgccgc cgggactgca gccgggtgcc gggggcaccc cgggtggccc gggcggcggc 180
ggcgctcccc cgcgctacgc cacgctggag caccccttcc actgctag 228

<210> SEQ ID NO 229
<211> LENGTH: 75
<212> TYPE: PRT
<213> ORGANISM: Artificial Sequence
<220> FEATURE:
<223> OTHER INFORMATION: Description of Artificial Sequence:PFZD2-MMVF
measles virus fusion (MVF) epitope fused to
frizzled domain

<400> SEQUENCE: 229

Met Cys Val Gly Gln Asn His Ser Glu Asp Gly Ala Pro Ala Leu Leu
1 5 10 15

Thr Thr Ala Pro Pro Pro Gly Leu Gln Pro Gly Ala Gly Gly Thr Pro

-continued

```
            20                  25                  30

Gly Gly Pro Gly Gly Gly Gly Ala Pro Pro Arg Tyr Ala Thr Leu Glu
        35                  40                  45

His Pro Phe His Cys Gly Pro Ser Leu Lys Leu Leu Ser Leu Ile Lys
    50                  55                  60

Gly Val Ile Val His Arg Leu Glu Gly Val Glu
 65                  70                  75


<210> SEQ ID NO 230
<211> LENGTH: 228
<212> TYPE: DNA
<213> ORGANISM: Artificial Sequence
<220> FEATURE:
<223> OTHER INFORMATION: Description of Artificial Sequence:PFZD2-MMVF
      measles virus fusion (MVF) epitope fused to
      frizzled domain

<400> SEQUENCE: 230

atgtgcgtcg gccagaacca ctccgaggac ggagctcccg cgctactcac caccgcgccg     60

ccgccgggac tgcagccggg tgccgggggc accccgggtg gcccgggcgg cggcggcgct    120

cccccgcgct acgccacgct ggagcacccc ttccactgcg gccccagcct gaagctgctg    180

agcctgatca agggcgtgat cgtgcaccgc ctggagggcg tggagtag                228


<210> SEQ ID NO 231
<211> LENGTH: 75
<212> TYPE: PRT
<213> ORGANISM: Artificial Sequence
<220> FEATURE:
<223> OTHER INFORMATION: Description of Artificial Sequence:PMMVF-ZD2
      measles virus fusion (MVF) epitope fused to
      frizzled domain

<400> SEQUENCE: 231

Met Lys Leu Leu Ser Leu Ile Lys Gly Val Ile Val His Arg Leu Glu
  1               5                  10                  15

Gly Val Glu Gly Pro Ser Leu Cys Val Gly Gln Asn His Ser Glu Asp
            20                  25                  30

Gly Ala Pro Ala Leu Leu Thr Thr Ala Pro Pro Pro Gly Leu Gln Pro
        35                  40                  45

Gly Ala Gly Gly Thr Pro Gly Gly Pro Gly Gly Gly Gly Ala Pro Pro
    50                  55                  60

Arg Tyr Ala Thr Leu Glu His Pro Phe His Cys
 65                  70                  75


<210> SEQ ID NO 232
<211> LENGTH: 228
<212> TYPE: DNA
<213> ORGANISM: Artificial Sequence
<220> FEATURE:
<223> OTHER INFORMATION: Description of Artificial Sequence:PMMVF-ZD2
      measles virus fusion (MVF) epitope fused to
      frizzled domain

<400> SEQUENCE: 232

atgaagctgc tgagcctgat caagggcgtg atcgtgcacc gcctggaggg cgtggagggc     60

cccagcctgt gcgtcggcca gaaccactcc gaggacggag ctcccgcgct actcaccacc    120

gcgccgccgc cgggactgca gccgggtgcc gggggcaccc cgggtggccc gggcggcggc    180

ggcgctcccc cgcgctacgc cacgctggag caccccttcc actgctag                228
```